US010377993B2

(12) United States Patent
Ohto et al.

(10) Patent No.: US 10,377,993 B2
(45) Date of Patent: Aug. 13, 2019

(54) RECOMBINANT MICROORGANISM AND METHOD FOR PRODUCING A SUBSTANCE USING THE SAME

(71) Applicants: TOYOTA JIDOSHA KABUSHIKI KAISHA, Toyota-shi, Aichi (JP); KYOTO UNIVERSITY, Kyoto-shi, Kyoto (JP)

(72) Inventors: Chikara Ohto, Toyota (JP); Masayoshi Muramatsu, Miyoshi (JP); Masakazu Ito, Toyota (JP); Jun Ogawa, Kyoto (JP); Shigenobu Kishino, Muko (JP)

(73) Assignees: TOYOTA JIDOSHA KABUSHIKI KAISHA, Toyota-shi (JP); KYOTO UNIVERSITY, Kyoto (JP)

( * ) Notice: Subject to any disclaimer, the term of this patent is extended or adjusted under 35 U.S.C. 154(b) by 357 days.

(21) Appl. No.: 14/716,973

(22) Filed: May 20, 2015

(65) Prior Publication Data

US 2015/0344851 A1 Dec. 3, 2015

(30) Foreign Application Priority Data

May 30, 2014 (JP) ................................ 2014-112538

(51) Int. Cl.

| | |
|---|---|
| ***C12N 9/00*** | (2006.01) |
| ***C12P 7/24*** | (2006.01) |
| ***C12P 7/04*** | (2006.01) |
| ***C12P 5/00*** | (2006.01) |
| ***C12N 9/02*** | (2006.01) |

(52) U.S. Cl.

CPC .............. *C12N 9/0008* (2013.01); *C12P 5/00* (2013.01); *C12P 7/04* (2013.01); *C12P 7/24* (2013.01); *C12Y 102/0105* (2013.01)

(58) Field of Classification Search

None

See application file for complete search history.

(56) References Cited

U.S. PATENT DOCUMENTS

2013/0130344 A1 5/2013 Lee et al.

FOREIGN PATENT DOCUMENTS

| | | | |
|---|---|---|---|
| CN | 102719467 | | * 10/2012 |
| JP | 2002-223788 | A | 8/2002 |
| JP | 2010-528627 | A | 8/2010 |
| JP | 2011-512848 | A | 4/2011 |
| JP | 2011067105 | A | 4/2011 |
| JP | 2011-520455 | A | 7/2011 |
| JP | 2012-506715 | A | 3/2012 |
| JP | 2012-511928 | A | 5/2012 |
| JP | 2013-528057 | A | 7/2013 |
| WO | 2008/151149 | A2 | 12/2008 |
| WO | 2009/111672 | A1 | 9/2009 |
| WO | 2009/140696 | A2 | 11/2009 |
| WO | 2010/062480 | A2 | 6/2010 |
| WO | 2010/071697 | A1 | 6/2010 |

OTHER PUBLICATIONS

Yesilirmak & Sayers, "Heterelogous Expression of Plant Genes", International Journal of Plant Genomics, vol. 2009, Article ID 296482, pp. 1-16. doi:10.1155/2009/296482.*

Vogel et al., "Genome sequencing and analysis of the model grass Brachypodium distachyon", Nature, 2010, vol. 463, pp. 763-768 . doi:10.1038/nature08747.*

Saski et al., "Complete chloroplast genome sequence of Glycine max and comparative analyses with other legume genomes", Plant Molecular Biology, 2005, vol. 59, pp. 309-322. DOI 10.1007/s11103-005-8882-0.*

Doan et al., "Functional expression of five *Arabidopsis* fatty acyl-CoA reductase genes in *Escherichia coli*", Journal of Plant Physiology, 2009, vol. 166, pp. 787-796.

Database GenBank, [online], Accession No. XP_003520320, <http://www.ncbi.nlm.nih.gov/protein/356503040?sat=4&satkey=105158316>, Jan. 7, 2014, Definition: Predicted: fatty acyl-CoA reductase 2-like [Glycine max].

Database GenBank, [online], Accession No. XP_003535102, <http://www.ncbi.nlm.nih.gov/protein/356533091?sat=4&satkey=105199172>, Jan. 7, 2014, Definition: Predicted: fatty acyl-CoA reductase 2-like [Glycine max].

Database GenBank, [online], Accession No. XP_004514155, <http://www.ncbi.nlm.nih.gov/protein/502167485?sat=21&satkey=12166004>, May 17, 2013, Definition: fatty acyl-CoA reductase 2-like isoform X1 [Cicer arietinum].

Database GenBank, [online], Accession No. XP_002323348, <http://www.ncbi.nlm.nih.gov/protein/566208984?report=genbank&log$=protalign&blast_rank=1&RID=RVPNFM44014>, Dec. 31, 2013, Definition: Male sterility protein 2 [Populus trichocarpa].

Database GenBank, [online], Accession No. CBI29968, <http://www.ncbi.nlm.nih.gov/protein/297739786?report=genbank&log$=protalign&blast_rank=1&RID=RVRFEU8C014>, Jun. 8, 2010, Definition: unnamed protein product, partial [Vitis vinifera].

Database GenBank, [online], Accession No. XP_004234754, <http://www.ncbi.nlm.nih.gov/protein/460377961?sat=18&satkey=25713136>, Mar. 12, 2013, Definition: Predicted: fatty acyl-CoA reductase 2-like [Solanum lycopersicum].

Database GenBank, [online], Accession No. XP_004144700, <http://www.ncbi.nlm.nih.gov/protein/449453912?sat=21&satkey=7893773>, Feb. 12, 2013, Definition: Predicted: Predicted: fatty acyl-CoA reductase 2-like [Cucumis sativus].

Database GenBank, [online], Accession No. XP_003562031, <http://www.ncbi.nlm.nih.gov/protein/357120636?sat=18&satkey=25545650>, Nov. 15, 2011, Definition: Predicted: fatty acyl-CoA reductase 2-like [Brachypodium distachyon].

(Continued)

*Primary Examiner* — Suzanne M Noakes

(74) *Attorney, Agent, or Firm* — Sughrue Mion, PLLC

(57) ABSTRACT

This invention provides a recombinant microorganism into which an acyl-CoA reductase exhibiting excellent activity in a reduction reaction using acyl-CoA as a substrate has been introduced. Such recombinant microorganism comprises a nucleic acid encoding an acyl-CoA reductase comprising any of characteristic Common sequences 1 to 3 introduced into a host microorganism.

11 Claims, 9 Drawing Sheets

Specification includes a Sequence Listing.

(56) References Cited

OTHER PUBLICATIONS

Database GenBank, [online], Accession No. XP_004987158, <http://www.ncbi.nlm.nih.gov/protein/514825002?sat=21&satkey=12772240>, Jun. 26, 2013, Definition: Predicted: fatty acyl-CoA reductase 2-like [Setaria italica].

Database GenBank, [online], Accession No. XP_002468445, <http://www.ncbi.nlm.nih.gov/protein/242042101?report=genbank&log8=protalign&blast_rank=28RID=RVSG27AE014>, Jul. 13, 2009, Definition: hypothetical protein SORBIDRAFT_01g046030 [Sorghum bicolor].

Database GenBank, [online], Accession No. EEC74588, <http://www.ncbi.nlm.nih.gov/protein/218192161?sat=21&satkey=9883729>, Dec. 17, 2008, Definition: hypothetical protein Osl_10168 [Oryza sativa Indica Group].

Dan Close, et al., "8-41: Biohydrocarbon fuel production in *Saccharomyces cerevisiae* using a synthetic production pathway: a proof in principle demonstration", 35th Symposium on Biotechnology for Fuels and Chemicals, Apr. 30, 2013,<https://sim.confex.com/sim/35th/webprogram/Paper24279.html>.

* cited by examiner

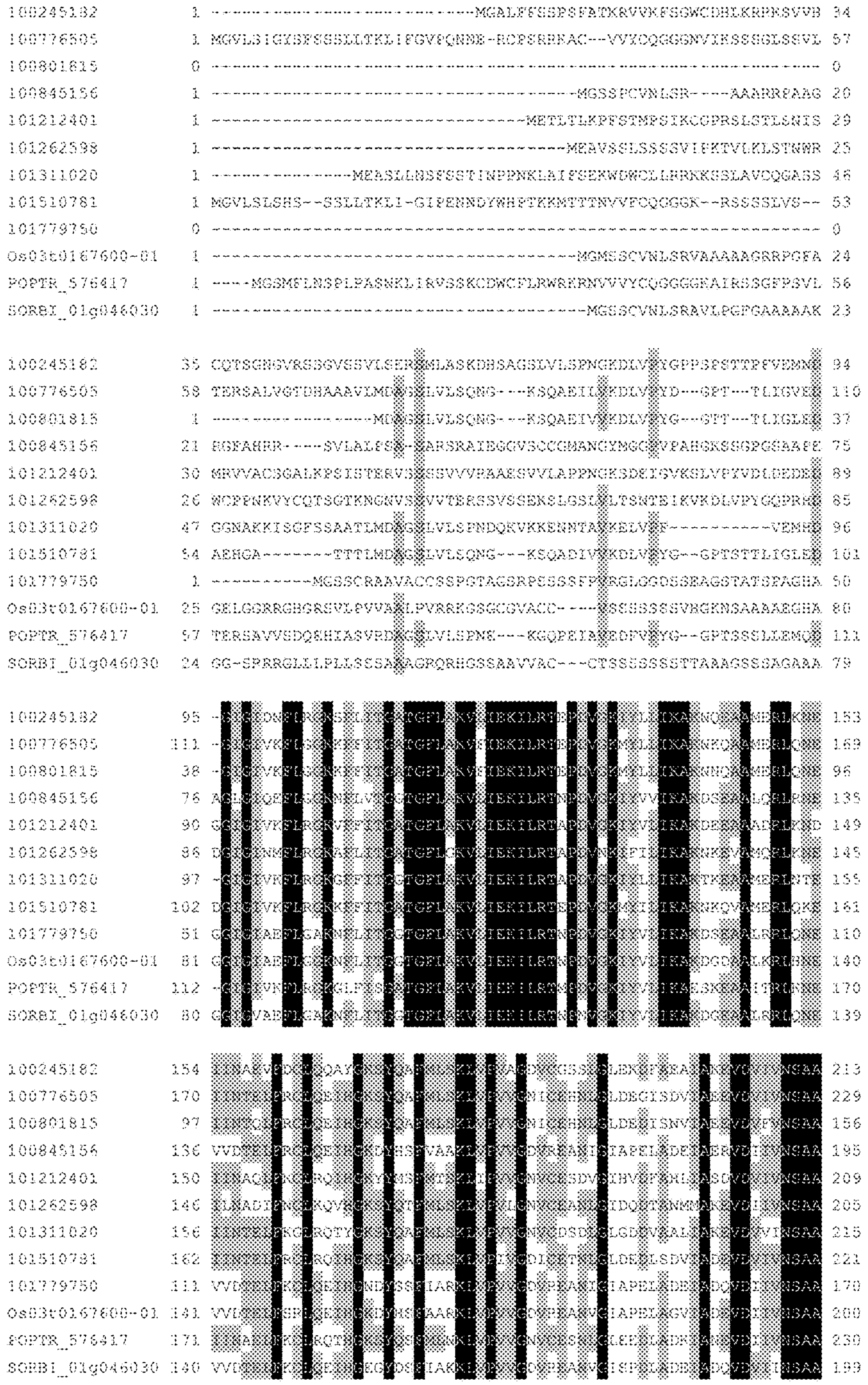

Fig. 2-1

```
100245182          1 ------------------------------MGALFFSSPSFATKRVVKFSGWCDHLKRPKSVVE  34
100776505          1 MGVLSIGYSFSSSLLTKLIFGVPQNEE-RCPSRHAC---VVYCQGGGNVIRSSSGLSSVL  57
100801815          0 -----------------------------------------------------------   0
100845156          1 ------------------------------MGSSPCVNLSR-----AAARRPAAG      20
101212401          1 ------------------------------METLTLKPFSTMPSIKCQPRSLSTLSNIS  29
101262598          1 ------------------------------MEAVSSLSSSGVIPKTVLKLSTNWR     25
101311020          1 -------------------MEASLLHSFSSTINPPNKLAIFSERWDWCLLHRKKSSLAVCQGASS 46
101510781          1 MGVLSLSHS--SSLLTKLI-GIPENNDYWHFTKKMTTTNVVFCQGGGK--RSSSSLVS--  53
101779750          0 -----------------------------------------------------------   0
Os03t0167600-01    1 -------------------------------MGMSSCVNLSRVAAAAAGRRPGFA     24
POPTR_576417       1 -----MGSMFLNSPLPASNKLIRVSSKCDWCFLRWRERNVVYCQGGGEAIRSSGFPSVL  56
SORBI_01g046030    1 -------------------------------MGSSCVNLSRAVLPGFGAAAAAK      23

100245182         35 CQTSGHSVRSSGVSSVLSER?MLASKDHSAGSLVLSPNGKDLV?YGPPSPSTTPFVEMN? 94
100776505         58 TERSALVGTDHAAAVLMD??LVLSQNG---KSQAEII?KDLV?YD---GPT---TLIGVE? 110
100801815          1 ------------MG?LVLSQNG---KSQAEIV?KDLV?YG---GPT---TLIGLE?  37
100845156         21 RGFAHRR----SVLALFSS-?ARSRAIEGGV?CCGHANCYMGC?VPAHSKSSGPGSAAEE  75
101212401         30 MRVVACSGALKPSISTERVS?SSVVVPAAESVVLAPPNGKSDEIGVKSLVPYVDLDEDE? 89
101262598         26 WCPPNKVYCQTSGTKNGNVS?VVTERSSVSSEKSLGSL?LTSNTEIKVKDLVPYGQPRH? 85
101311020         47 GGNAKKISGFSSAATLMD??LVLSPNDQKVKKENNTA?KELV?F---------VEMH?  96
101510781         54 AEHGA-------TTTLMD??LVLSQNG---KSQADIV?KDLV?YG--GPTSTTLIGLE? 101
101779750          1 ----------MGSSCRAAVACCSSPGTACSRPESSSFP?RGLGGDSSEAGSTATSPAGHA  50
Os03t0167600-01   25 GELGGRRGHGRSVLPVVA?LPVRRKGSGCGVACC-----?SSSSSSSVRGKNSAAAAEGHA  80
POPTR_576417      57 TERSAVVSDQEHIASVRDK??LVLSPNE---KGQPEIA?EDFV?YG--GPTSSSLLEMQ? 111
SORBI_01g046030   24 GG-SPRRGLLLPLLSCSA?AGRQRHGSSAAVVAC---CTSSSSSSSTTAAAGSSSAGAAA 79

100245182         95 -?-?DN?FRGN?LIG?TGFL?KV?IEKILRTEP?V?M?LLIKAN?Q?AMERLK??     153
100776505        111 -?-?KF?LRGN?FTG?TGFLAN?IEKILRTEP?V?M?LLIKAN?Q?AMERLQ??     169
100801815         38 -?-?KN?KKF?TG?TGFL?KV?IEKILRTEP?V?M?LLIKAN?Q?AMERLQ??       96
100845156         76 A?L?QEF?KNM?LVG?TGFL?KV?IEKILRIN?P?V?KVVIKAN?S?ALQSL??     135
101212401         90 G?-?VKF?KV?TGFL?KV?IEKILRTAP?V?KK?VIKAN?DE?AAEPL??           149
101262598         96 D?-?QNM?FRGN?AK?TGFL?RV?IERTLRTAD?V?KK?FIKAN?NK?AVMQEL??   145
101311020         97 -?-?DIVK?FLRGN?KF?TGFL?RV?IERILRTAD?V?KK?LLIKAN?TK?AMERL?T? 155
101510781        102 D?-?VKF?LRGN?KF?TGFL?KV?IERTLRTEP?V?KK?TIKAN?KQ?VMERLQK?S   161
101779750         51 G?-?AEF?KAN?LL?TGFL?KV?IEKTLRTN?P?V?KK?VVIKAN?DS?ALRPLQ??   110
Os03t0167600-01   81 G?-?AEF?KNS?LL?TGFL?KV?IEKILRTN?P?V?KK?VIKAN?GD?ALKR?E?     140
POPTR_576417     112 -?-?VKF?KGLF?SS?TGFL?KV?IEKTLRTN?P?V?KK?VIKA?SK?AITRK??     170
SORBI_01g046030   80 G?-?VAEF?KAN?LL?TGFL?KV?IERILRTN?P?V?KK?VIKA?DGD?ALRRLQE?   139

100245182        154 ??A?VPD??QAY?N?A?KI??V?AG??GSS?SLEK?F?REA??NK?V?C?NSAA       213
100776505        170 ??I??PR??F?N?A?KV??V?GVMI?HH?SLDEGISDV?AEKV??NSAA              229
100801815         97 ??HG?PR??E?N?A?KI??V?GVMI?HH?SLDE?ISNV?AEVV?P?NSAA             156
100845156        136 VVD??PR??E??L?YH?S?VAA?I??V?DR?AN?ISIAPEL?DE?A?RV??NSAA       195
101212401        130 ??AQ?KG?RQ??K?YN?A?KI??V?DV?SIHV?F?KLL?ASVV??NSAA              209
101262598        146 ??LNA?D?NKQV?KK?YT?A?KI??V?YI??IDQ?T?NMA?KV??NSAA             205
101311020        156 ??KG?RQTY?KY?AE?L??V?DV?GSD?LGD?V?AL?AK?V??NSAA                215
101510781        162 ??PR??QT??KY?ES?A??V?DDI?CN??GLDE?LSDV?AE?V??NSAA              221
101779750        111 VVD??PRE??N?DY?SS?IARKI??V??V?PRAN?V?IAPEL?DE?A?DV??H?SAA     170
Os03t0167600-01  141 VVD?? ?SHE??K?DY?HS?AARKI??V??V?PRAN?VGIAPEL?GV?A?DV??H?SAA   200
POPTR_576417     171 ??A??PR??DRQT??KY?N?NY??V?DV?CLEE?P?ADE?V??NSAA                230
SORBI_01g046030  140 VVD??G??GE??L?EGY?DS?IAKKI??V??V?PRAV?GISPE?L?ADE?DV??H?SAA   199
```

RECOMBINANT MICROORGANISM AND METHOD FOR PRODUCING A SUBSTANCE USING THE SAME

TECHNICAL FIELD

The present invention relates to a recombinant microorganism into which a gene associated with production of a target substance has been introduced and a method for producing a substance using such recombinant microorganism.

BACKGROUND ART

Microorganisms capable of synthesizing an aldehyde, an alcohol, or a hydrocarbon such as alkane, alkene, or alkyne, have been known. JP 2011-520455 A discloses an alkane synthase gene and an aldehyde synthase gene derived from *Synechococcus elongatus*, and it also discloses a method for producing an alkane or an aldehyde using such genes.

JP 2002-223788 A discloses the production of an alcohol using a transformed plant into which the acyl reductase gene has been introduced and, as a substrate, an aliphatic-acyl group bound to CoA and/or ACP. While JP 2002-223788 A describes that the acyl reductase gene is isolated from green algae, it does not disclose that a transformed plant is actually produced.

Further, JP 2013-528057 A discloses that aliphatic acyl-CoA reductase derived from *Clostridium kluyveri* is prepared and transformed into an *E. coli* strain together with another lipid synthesis-associated gene.

Furthermore, JP 2012-506715 A discloses a method for producing an aliphatic alcohol comprising expressing a gene encoding an aliphatic aldehyde biosynthetic polypeptide that reduces carboxylic acid into an aldehyde or a variant thereof in a host, so as to synthesize an aliphatic aldehyde, and producing an alcohol from an aliphatic aldehyde.

In addition, JP 2011-512848 A discloses a method for genetically engineering microorganisms capable of producing a primary alcohol using a malonyl-CoA-independent FAS metabolic pathway and an acyl reduction metabolic pathway.

Further, JP 2010-528627 A discloses a method for producing an oil component by introducing genes associated with oil and fat production into microalgae of *Chlorella.*

JP 2012-511928 A discloses microorganisms into which nucleic acids encoding isopropanol pathway enzymes such as succinyl-CoA:3-ketoacid-CoA transferase have been introduced and a method for producing isopropanol using such microorganisms.

SUMMARY OF THE INVENTION

Objects to be Attained by the Invention

There have been no acyl-CoA reductases known to exert excellent activity in microorganisms, and productivity has been disadvantageously low regarding an aldehyde generated via reduction from aliphatic acyl-CoA as a substrate or an alcohol or a hydrocarbon generated from such an aldehyde as a substrate.

Under the above circumstances, it is an object of the present invention to provide a recombinant microorganism into which an acyl-CoA reductase exerting excellent activity in a reduction reaction using acyl-CoA as a substrate has been introduced, and it is another object of the present invention to provide a method for producing a substance using such recombinant microorganism.

Means for Attaining the Objects

The present inventors have conducted concentrated studies in order to attain the above objects. As a result, they discovered that a group of acyl-CoA reductases having similar amino acid sequences is highly active in microorganisms. This has led to the completion of the present invention.

(1) A recombinant microorganism comprising a nucleic acid encoding an acyl-CoA reductase comprising common sequences including the following amino acid sequences: GxGxxxFLxxKxxxxxGxTGFLxKVxIEKILRTx-PxVxKxxxxIKAxxxxxAxxRLxxxxxxxxxFxx-LxxxxGxxYxxFxxxKLxPxxGxxxxxxxGxxxxxxxxx-AxxVDxxxNSAANTTFxERYDxAxxxNTxGxxxxMxxAx-xxxxLKLFLxxSTAYVNGQxQGxxxExPF (SEQ ID NO: 1), [26-57aa]GLxRAxxxGWQDTYVFT-KAMGEMxxxxxRxxxPVxxxRPSVIESTxxxPFPGW-MEGxRMMDPxxLxYGKGQLxGFxxDPxGVxDVVPAD-MVVNATLAxxAxHG (SEQ ID NO: 2), [9-18aa] YxxxSSxxNPLxFxxLxxxxxxHxxxxPxxDxxGxPIxVxxM (SEQ ID NO:3), and [39-48aa]VxQxxxLxxIYxPYT-FxxGRFDNxNxxxLxxxMxxxExxxFxFDVxxxxWxDYIx-NVHIPGLxxxVxKG (SEQ ID NO: 4) introduced into a host microorganism of.

(2) The recombinant microorganism according to (1), wherein the common sequences include the following amino acid sequences: G(I/L)G(I/V)xxFLx(G/A)Kx(F/L)x(I/V)(T/S)G(A/G)TGFL(A/G)KV(L/F)IEKILRTxP(D/N)V(G/N)K(I/M)(Y/F)x(L/V)IKA(K/E)xx(E/Q/D)(A/V)AxxRLx(N/I/K)(E/D)(I/V)(I/V/L)(N/D)(A/T)(E/Q/D)(V/L/I)Fx(O/G/R)L(Q/R/K)x(A/I/V/T)(Y/H)G(K/N/E)(S/D/Y/G)Y(Q/H /M/S/D)xF(M/V/I/A)(L/A/I)(S/A/R/N/K)KL(V/I)P(V/I)(A/L/V)Gx(V/I)(C/R)(G/E/D)x(S/N/D)(L/l/V)Gxxx(D/G/E)x(A/S)xx(I/M)Ax(E/R/D/Q)VD(V/I)(I/F/V)(V/I)NSAANTTF(D/H)ERYD(I/T/V)Ax(D/N)(I/V)NTxG(P/T)x(H/R/N)(L/I)Mx(F/I)A(K/H/Q)x(C/F)x(K/R/ N)LKLFL(Q/H)(V/I)STAYVNGQ(R/K/T)QG(R/V/L)(I/V)(M/L)E(K/R)PFxx(G/E)(D/E/L)x(I/V)(A/R/E/I)x(E/D) (SEQ ID NO: 5), [17-48aa]GL(E/Q)RAxxxGWQDTYVFTKAMGEM(V/M)(I/V)(D/N)x(M/L)R(G/D)(E/D)(I/L/V)PV(V/A)x(I/M)RPS-VIESTxx(E/D)PFPGWMEG(N/S)RMMDP(I/V)(V/I)L(Y/O/W)YGKGQL(T/S)GF(V/L)(A/V)DP(N/Y/E/D)GV(L/I)DVVPADMVVNATLA(A/S)(M/I)A(R/K/W)HG (SEQ ID NO: 6), [8-17aa](V/I)Y(Q/H)x(A/T/S)SS(V/T/A)(V/A)NPL(I/V/D/A)Fx(D/R/E)Lx(S/R/D/K/T)(H/L/M/F)(F/L)xxHxx(S/R/G)(S/O)PxxDxxG(N/R/Q/T)PIxV(P/S)xM(K/R/S)(L/F)(F/L)x(S/T)(T/I/M/V/S)(E/D)x(F/L)(S/A)x(H/Y)(L/V/I)(W/E)(R/I)(D/Y)(A/V)xx(R/K)(S/R/C/A) (SEQ ID NO: 7), and [18-26aa](K/R)(S/T)V(K/E)Q(A/T/L)(K/T/V)(Y/H)L(A/G)xIYxPYTF(Y/F)(G/P/N)GRFDN(S/G)N(T/V)(Q/E)xL(M/L/I/F)xxM(O/S/T)(E/A/K/V/P)(E/K/A/N)E(K/R)xxFxFDVx(S/N/G)(I/L/V)(D/E)WxDYI(S/T)NVHIPGL(R/K)(R/K)(H/Y)V(M/L)KG (SEQ ID NO: 8).

(3) The recombinant microorganism according to (1), wherein the acyl-CoA reductase is a protein (a) or (b) below:

(a) a protein comprising the amino acid sequence as shown in any of SEQ ID NOs: 14, 16, 18, 20, 22, 24, 26, 28, 30, 32, 34, and 36; or (b) a protein comprising an amino acid sequence having 70% or higher identity to the amino acid sequence as shown in any of SEQ ID NOs: 14, 16, 18, 20, 22, 24, 26, 28, 30, 32, 34, and 36 and having activity of an acyl-CoA reductase.

(4) The recombinant microorganism according to (1), wherein the common sequences include the following amino acid sequences: MDAGSLVLSQNGKSQA(E/D)I(L/V) VKDLVPY(D/G)G(P/T)T (SEQ ID NO: 9)[0-2aa]TLIG(V/L)ED (SEQ ID NO: 10), [0-1aa]GIGIVKFL(G/R)GKKF-FITGATGFLAKV(F/L)IEKILRTEPDVGKMY(L/I) LIKAKN(K/N)Q(A/V)AMERLQ(N/K)EIINT(E/Q)LFRCL (Q/R)(E/Q)IHGKSYQAFMLSKLVP(V/I)VG(N/D)ICE(H/T)NLGLDE(G/D)(I/L)S(D/N)VIA(E/D)EVDV(I/F) VNSAANTTFDERYDTAININT(I/R)GP(O/S)RLM(N/A) IAKKCK KLKLFLHVSTAYVNGQ(R/K) QGRIMERPFSIG(E/D)CIAREK(YL)IS (E/G)V(S/P) PKYLPTLDIE(G/N)EIN(L/M)V(S/L)(N/K)(Y/N)KG(D/N) (SEQ ID NO: 11), and [0-1 aa]IE(D/E)NLL(A/T)QKM(K/R)E(I/M)GLERA(R/K)RYGWQDTYVFTKAMGEMMID-KLR(G/D)DIPVV(V/I)(M/I)RPSVIEST(F/L)SEPFPGW-MEGNRMMDP(I/V)VL(C/W) YGKGQLTGFLVDPNGVLDVVPADMVVNATLAAMA (R/K)HG(V/M)(S/N/I)QK(P/A)DINVYQIASSVVNPL(V/A)FQDL(A/T)RLLYEHYSSSP(C/F)I DS(K/M)GRPIQVP (L/I)MK(L/F)FSS(T/S)EEFS GHLWRD(A/V)I(Q/N)K(R/S)G(L/I)T(A/S)(V/M)ASSK(G/A)KMSQKLEN(M/I) CRKS VEQAKYLA(N/K) IVEPYTFYGGRFDNSNTQRLME(S/I)MSE(K/E)EK(R/T)EF(G/D)FDVK(S/G)IDW(N/T)DYITNVHIPGLRR(H/Y)VMKGRGM(G/S)(S/N)Q (SEQ ID NO: 12).

(5) The recombinant microorganism according to (1), wherein the acyl-CoA reductase is the protein (a) or (b) below:

(a) a protein comprising the amino acid sequence as shown in any of SEQ ID NOs: 14, 16, and 18; or (b) a protein comprising an amino acid sequence having 70% or higher identity to the amino acid sequence as shown in any of SEQ ID NOs: 14, 16, and 18 and having activity of an acyl-CoA reductase.

(6) The recombinant microorganism according to (1), wherein the host microorganism is selected from the group consisting of *Escherichia coli, Corynebacterium*, and yeast.

(7) The recombinant microorganism according to (1), which has aldehyde decarbonylase activity for synthesizing a hydrocarbon using an aldehyde as a substrate.

(8) The recombinant microorganism according to (1), wherein the host microorganism comprises a nucleic acid encoding an aldehyde decarbonylase that synthesizes a hydrocarbon using an aldehyde as a substrate.

(9) The recombinant microorganism according to (1), which produces a hydrocarbon comprising a carbon chain of 13 to 15 carbon atoms.

(10) A recombinant microorganism comprising a nucleic acid encoding a protein (a) or (b) below introduced into a host microorganism:

(a) a protein comprising the amino acid sequence as shown in any of SEQ ID NOs: 14, 16, 18, 20, 22, 24, 26, 28, 30, 32, 34, and 36; or (b) a protein comprising an amino acid sequence having 70% or higher identity to the amino acid sequence as shown in any of SEQ ID NOs: 14, 16, 18, 20, 22, 24, 26, 28, 30, 32, 34, and 36 and having activity of an acyl-CoA reductase.

(11) The recombinant microorganism according to (10), wherein the host microorganism is selected from the group consisting of *Escherichia coli, Corynebacterium*, and yeast.

(12) The recombinant microorganism according to (10), which has aldehyde decarbonylase activity for synthesizing a hydrocarbon using an aldehyde as a substrate.

(13) The recombinant microorganism according to (10), wherein the host microorganism comprises a nucleic acid encoding an aldehyde decarbonylase that synthesizes a hydrocarbon using an aldehyde as a substrate.

(14) The recombinant microorganism according to (10), which produces a hydrocarbon comprising a carbon chain of 13 to 15 carbon atoms.

(15) A method for producing a substance comprising a step of culturing the recombinant microorganism according to any of (1) to (14) in a medium containing a carbon source and a step of recovering a target substance from the cultured recombinant microorganism.

(16) The method for producing a substance according to (15), wherein the target substance is at least one member selected from the group consisting of an aliphatic aldehyde, an aliphatic alcohol, and a hydrocarbon.

Effects of the Invention

The recombinant microorganism according to the present invention expresses an acyl-CoA reductase that exerts excellent activity in a reduction reaction from an aliphatic acyl-CoA as a substrate. Accordingly, such recombinant microorganism is excellent in terms of productivity of an aliphatic aldehyde caused by reduction of an aliphatic acyl-CoA with the aid of the acyl-CoA reductase, an aliphatic alcohol converted from the aliphatic aldehyde, and a hydrocarbon.

According to the method for producing a substance of the present invention, a recombinant microorganism that is excellent in terms of productivity of an aliphatic aldehyde caused by reduction of an aliphatic acyl-CoA with the aid of the acyl-CoA reductase, an aliphatic alcohol converted from the aliphatic aldehyde, and a hydrocarbon is used. Thus, productivity of substances, including an aliphatic aldehyde, an aliphatic alcohol, and a hydrocarbon, can be remarkably improved.

BRIEF DESCRIPTION OF THE DRAWINGS

FIG. 2-1 shows the results of multiple alignment analysis of the proteins included in the dendrogram shown in FIG. 1 (Gene ID No. 100245182 is SEQ ID NO: 24; Gene ID No. 100776505 is SEQ ID NO: 14; Gene ID No. 100801815 is SEQ ID NO: 16; Gene ID No. 100845156 is SEQ ID NO: 30; Gene ID No. 101212401 is SEQ ID NO: 28; Gene ID No. 101262598 is SEQ ID NO: 26; Gene ID No. 101311020 is SEQ ID NO: 20; Gene ID No. 101510781 is SEQ ID NO: 18; Gene ID No. 101779750 is SEQ ID NO: 32; Gene ID No. Os03t0167600-01 is SEQ ID NO: 36; Gene ID No. POPTR_576417 is SEQ ID NO: 22; Gene ID No. SORBI_01g046030 is SEQ ID NO: 34).

FIG. 2-2 is a continuation of FIG. 2-1, which shows the results of multiple alignment analysis of the proteins included in the dendrogram shown in FIG. 1.

FIG. 2-3 is a continuation of FIG. 2-2, which shows the results of multiple alignment analysis of the proteins included in the dendrogram shown in FIG. 1.

FIG. 3 shows the results of multiple alignment analysis of a protein having superior acyl-CoA reductase activity among the proteins included in the dendrogram shown in FIG. 1 (Gene ID No. 100776505 is SEQ ID NO: 14; Gene ID No. 100801815 is SEQ ID NO: 16; Gene ID No. 101510781 is SEQ ID NO: 18).

EMBODIMENTS FOR CARRYING OUT THE INVENTION

Figure 1:
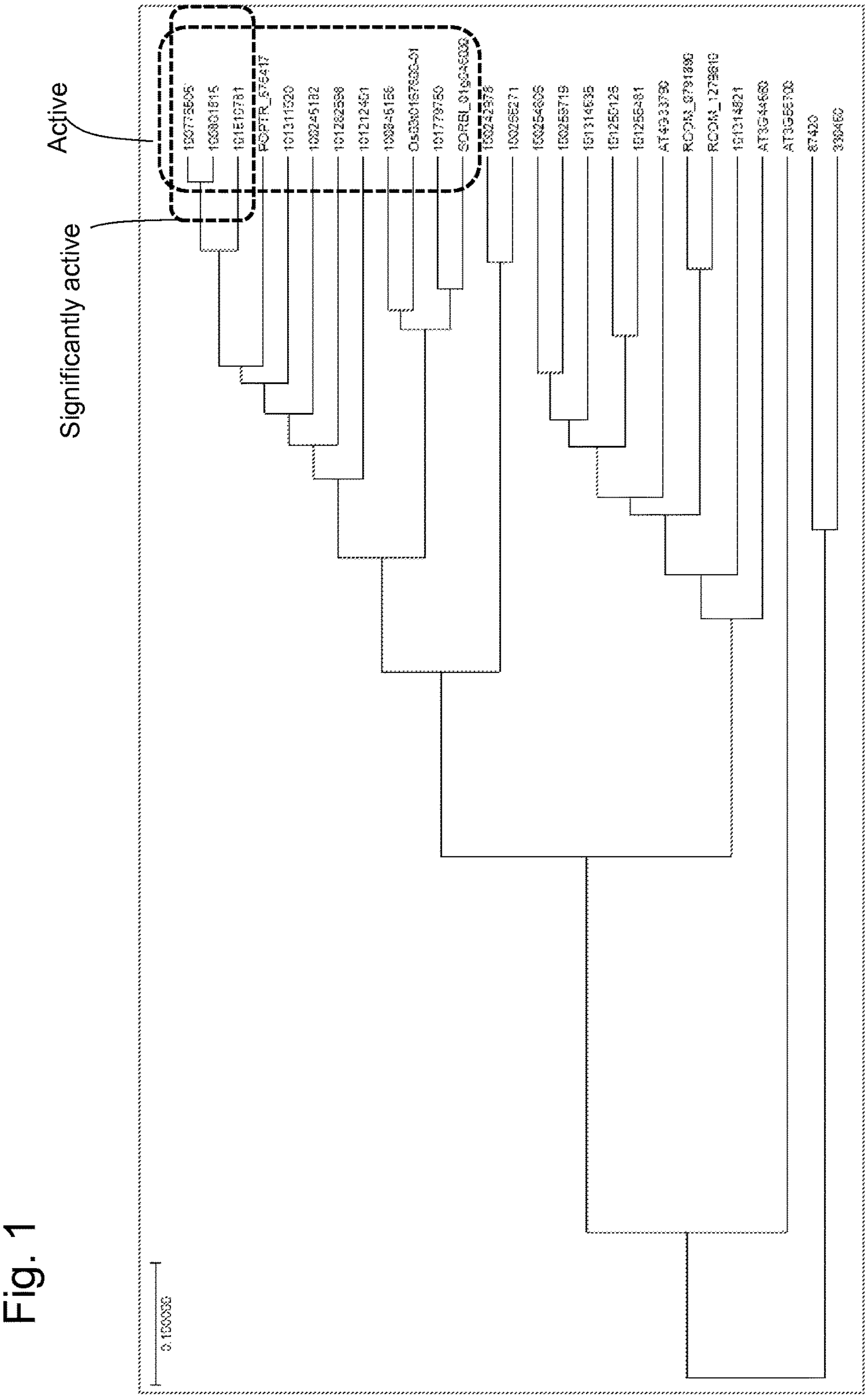
FIG. 1 shows a dendrogram prepared using ClustalW on the basis of amino acid sequence information regarding an acyl-CoA reductase with high-level activity for synthesizing an aldehyde using acyl-CoA as a substrate.

Hereafter, the present invention is described in more detail with reference to the drawings and the examples.

The recombinant microorganism according to the present invention comprises a nucleic acid encoding an acyl-CoA reductase having particular common sequences introduced thereinto. The recombinant microorganism according to the present invention expresses the acyl-CoA reductase to thereby reduce acyl-CoA (it is occasionally referred to as "aliphatic acyl-CoA"), which is a thioester compound of an aliphatic acid with CoA, and produce an aldehyde compound with high efficiency. The aldehyde compound produced is oxidized in the metabolic reaction within the microorganism and converted into an alcohol, or it is used as a substrate for hydrocarbon synthesis by an enzyme having hydrocarbon-synthesizing activity. Thus, the recombinant microorganism according to the present invention is not only capable of producing an aldehyde with high efficiency, but it is also capable of producing an alcohol and/or hydrocarbon from such aldehyde compound with high efficiency, through expression of the acyl-CoA reductase.

The term "nucleic acid" refers to a nucleic acid existing in nature, such as DNA or RNA, or an artificial nucleic acid, such as a nucleic acid molecule resulting from chemical modification to PNA (peptide nucleic acid), a nucleotide, a sugar, or a diester phosphate moiety. The term "a nucleic acid encoding an acyl-CoA reductase" refers both to a region comprising an expression regulatory region and a coding region in the genome and a region consisting of a coding region in the genome.

Acyl-CoA is synthesized from a sugar as a result of the metabolic reaction in a host microorganism. A sugar is a substance represented by a chemical formula $C_n(H_2O)_m$. Examples thereof include an aldehyde of a polyhydric alcohol, a ketone derivative of a polyhydric alcohol, and derivatives and condensates of substances related thereto, and specific examples include polysaccharides, oligosaccharides, disaccharides, and monosaccharides. Specific examples of monosaccharides include glucose, fructose, galactose, mannose, xylose, xylulose, ribose, erythrose, threose, erythrulose, glyceraldehyde, and dihydroxyacetone. Specific examples of disaccharides include sucrose (saccharose), lactose, maltose, trehalose, and cellobiose.

[Acyl-CoA Reductase]

An example of a common sequence in the acyl-CoA reductase described above is the amino acid sequence shown below:

```
GxGxxxFLxxKxxxxxGxTGFLxKVxIEKILRTxPxVxKxxxxIKAxxxx

xAxxRLxxxxxxxxxFxxLxxxxGxxYxxFxxxKLxPxxGxxxxxxxGxx

xxxxxxxAxxVDxxxNSAANTTFxERYDxAxxxNTxGxxxxMxxAxxxxx

LKLFLxxSTAYVNGQxQGxxxExPF(26-57aa)GLxRAxxxGWQDTYVF

TKAMGEMxxxxxRxxxPVxxxRPSVIESTxxxPFPGWMEGxRMMDPxxLx

YGKGQLxGFxxDPxGVxDVVPADMVVNATLAxxAxHG(9-18aa)YxxxS

SxxNPLxFxxLxxxxxxHxxxxPxxDxxGxPIxVxxM(39-48aa)VxQx

xxLxxIYxPYTFxxGRFDNxNxxxLxxxMxxxExxxFxFDVxxxxWxDYI

xNVHIPGLxxxVxKG (Common sequence 1).
```

In the amino acid sequence above, "x" represents an arbitrary amino acid residue. In the amino acid sequence above, a notation composed of two numbers separated by a hyphen (-) and "aa" indicates a region comprising an arbitrary number of intervening amino acid residues between two such numbers. In this description, amino acid sequences are represented in the manner described above.

In other words, the amino acid sequence of Common sequence 1 comprises the amino acid sequence of SEQ ID NO: 1, a region of 26 to 57 arbitrary amino acid residues, the amino acid sequence of SEQ ID NO: 2, a region of 9 to 18 arbitrary amino acid residues, the amino acid sequence of SEQ ID NO: 3, a region of 39 to 48 arbitrary amino acid residues, and the amino acid sequence of SEQ ID NO: 4 linked in that order from the N terminus to the C terminus.

Common sequence 1 is determined in the manner described below. That is, an acyl-CoA reductase having high-level activity for synthesizing an aldehyde compound using acyl-CoA as a substrate is identified from among various types of acyl-CoA reductases, a dendrogram is prepared using ClustalW on the basis of amino acid sequence information regarding the identified group of acyl-CoA reductases (FIG. 1), a multiple alignment is prepared (FIG. 2-1 to FIG. 2-3), and Common sequence 1 is then determined on the basis of the dendrogram and the multiple alignment prepared.

Specifically, Common sequence 1 is an amino acid sequence that characterizes a group of acyl-CoA reductases having high-level activity for synthesizing an aldehyde compound using acyl-CoA as a substrate among various types of acyl-CoA reductases. In other words, an acyl-CoA reductase that comprises Common sequence 1 has higher activity for synthesizing an aldehyde compound using acyl-CoA as a substrate than an acyl-CoA reductase that does not comprise Common sequence 1. Common sequence 1 can serve as an apparent standard for distinguishing a group of acyl-CoA reductases having high-level activity for synthesizing an aldehyde compound using acyl-CoA as a substrate from acyl-CoA reductases having no or low-level activity for synthesizing an aldehyde compound using acyl-CoA as a substrate.

Specific examples of acyl-CoA reductases each comprising Common sequence 1 include the 12 types of acyl-CoA reductases shown in Table 1.

TABLE 1

| Gene ID | Gene origin | Nucleotide sequence | Amino acid sequence |
|---|---|---|---|
| 101311020 | *Fragaria vesca* (woodland strawberry) | | SEQ ID NO: 20 |
| 100776505 | *Glycine max* (soybean) | SEQ ID NO: 13 | SEQ ID NO: 14 |
| 100801815 | | SEQ ID NO: 15 | SEQ ID NO: 16 |
| POPTR_576417 | *Populus trichocarpa* (black cottonwood) | SEQ ID NO: 21 | SEQ ID NO: 22 |
| 100245182 | *Vitis vinifera* (wine grape) | SEQ ID NO: 23 | SEQ ID NO: 24 |
| 101510781 | *Cicer arietinum* (chickpea) | SEQ ID NO: 17 | SEQ ID NO: 18 |
| 101262598 | *Solanum lycopersicum* (tomato) | SEQ ID NO: 25 | SEQ ID NO: 26 |
| 101212401 | *Cucumis sativus* (cucumber) | SEQ ID NO: 27 | SEQ ID NO: 28 |
| 100845156 | *Brachypodium distachyon* | SEQ ID NO: 29 | SEQ ID NO: 30 |
| 101779750 | *Setaria italica* (foxtail millet) | SEQ ID NO: 31 | SEQ ID NO: 32 |
| SORBI_01g046030 | *Sorghum bicolor* (sorghum) | SEQ ID NO: 33 | SEQ ID NO: 34 |
| Os03t0167600-01 | *Oryza sativa japonica* (Japanese rice) | SEQ ID NO: 35 | SEQ ID NO: 36 |

Specific examples of nucleic acids encoding acyl-CoA reductases comprising Common sequence 1 include the gene identified with Gene ID: 101311020 derived from *Fragaria vesca* (woodland strawberry), the gene identified with Gene ID: 100776505 derived from *Glycine max* (soybean), the gene identified with Gene ID: 100801815 derived from *Glycine max* (soybean), the gene identified with Gene ID: POPTR_576417 derived from *Populus trichocarpa* (black cottonwood), the gene identified with Gene ID: 100245182 derived from *Vitis vinifera* (wine grape), the gene identified with Gene ID: 101510781 derived from *Cicer arietinum* (chickpea), the gene identified with Gene ID: 101262598 derived from *Solanum lycopersicum* (tomato), the gene identified with Gene ID: 101212401 derived from *Cucumis sativus* (cucumber), the gene identified with Gene ID: 100845156 derived from *Brachypodium distachyon*, the gene identified with Gene ID: 101779750 derived from *Setaria italica* (foxtail millet), the gene identified with Gene ID: SORBI_01g046030 derived from *Sorghum bicolor* (sorghum), and the gene identified with Gene ID: Os03t0167600-01 derived from *Oryza sativa japonica* (Japanese rice).

Figure 2:
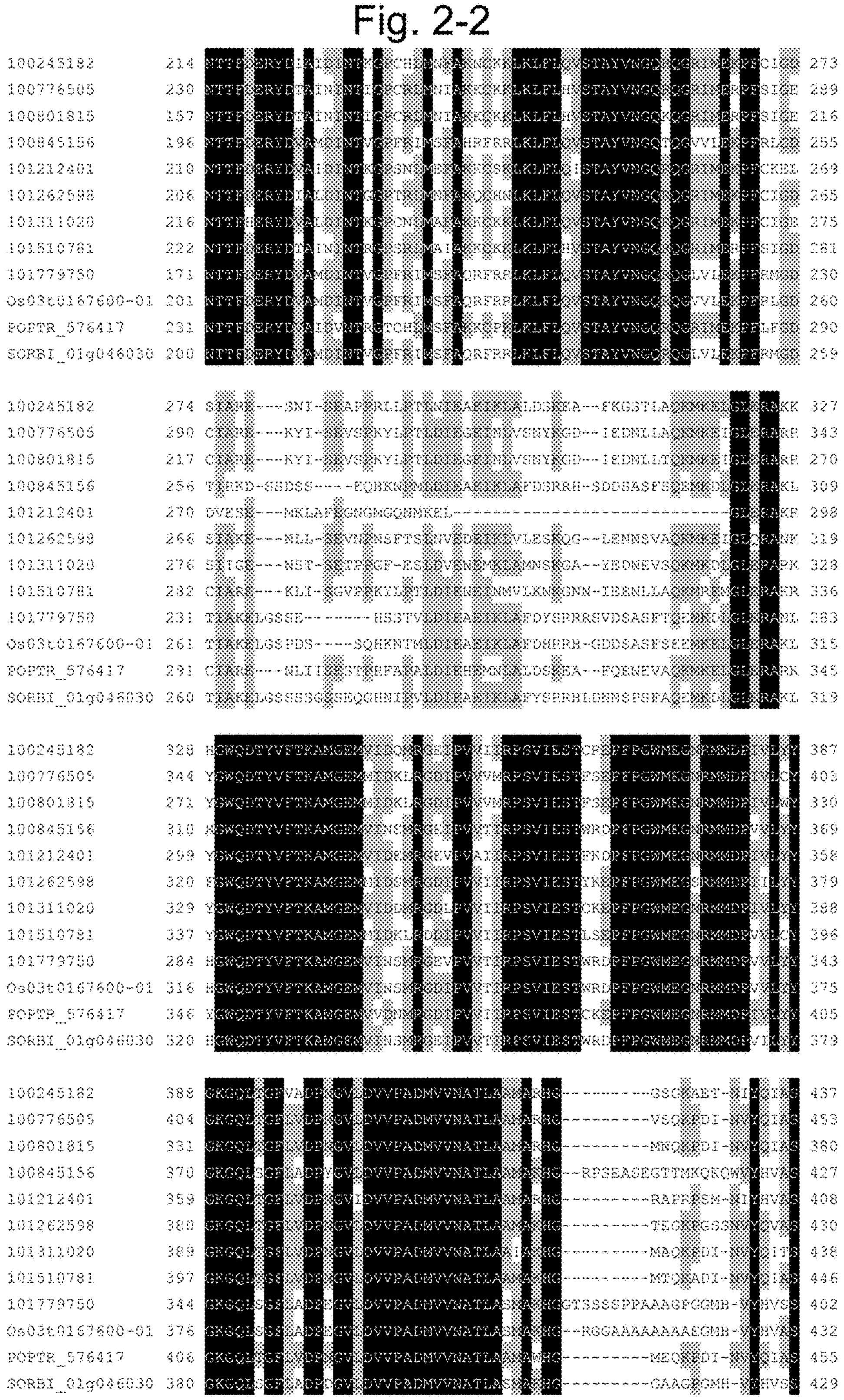
Figures 2, 3:
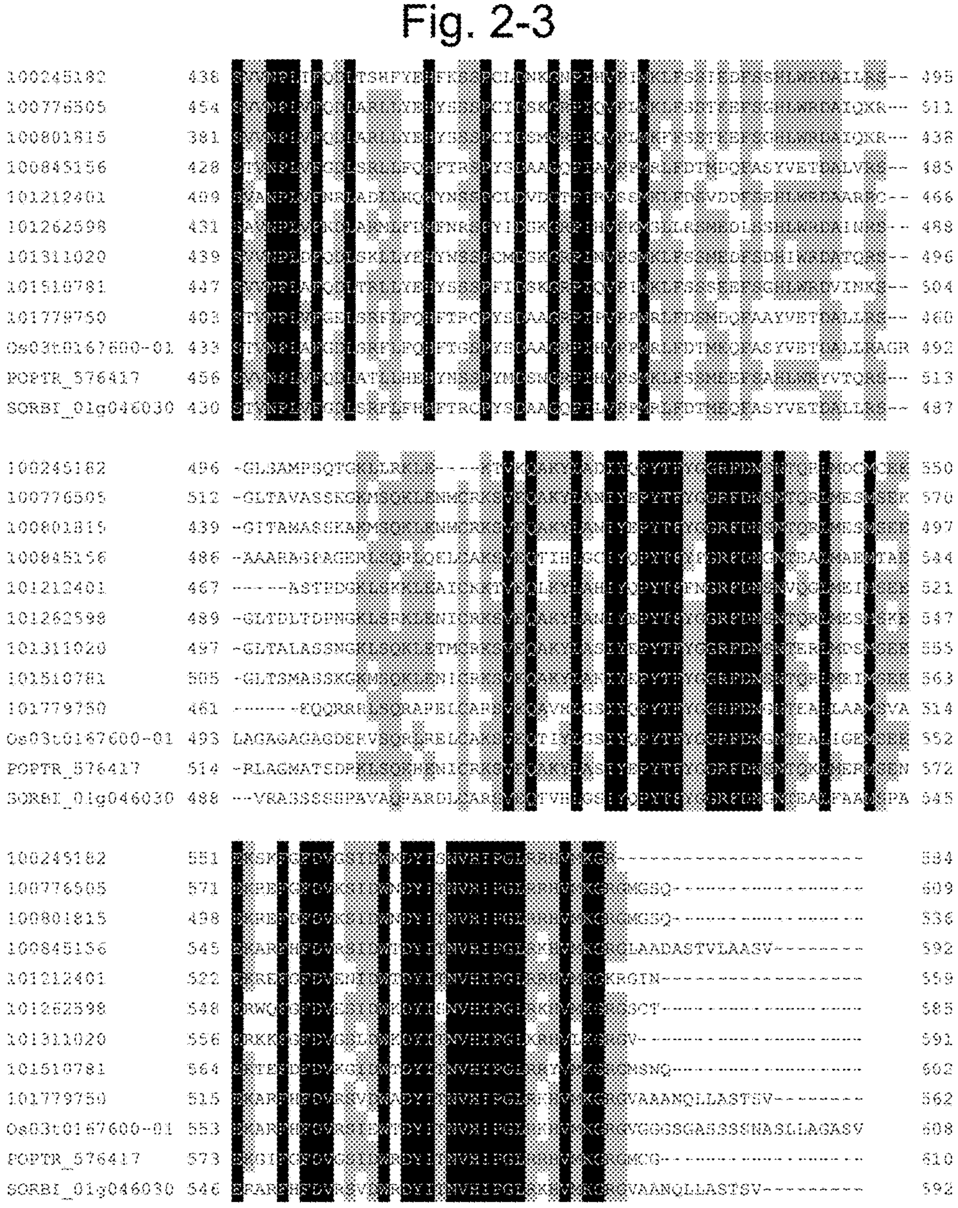
Figure 3:
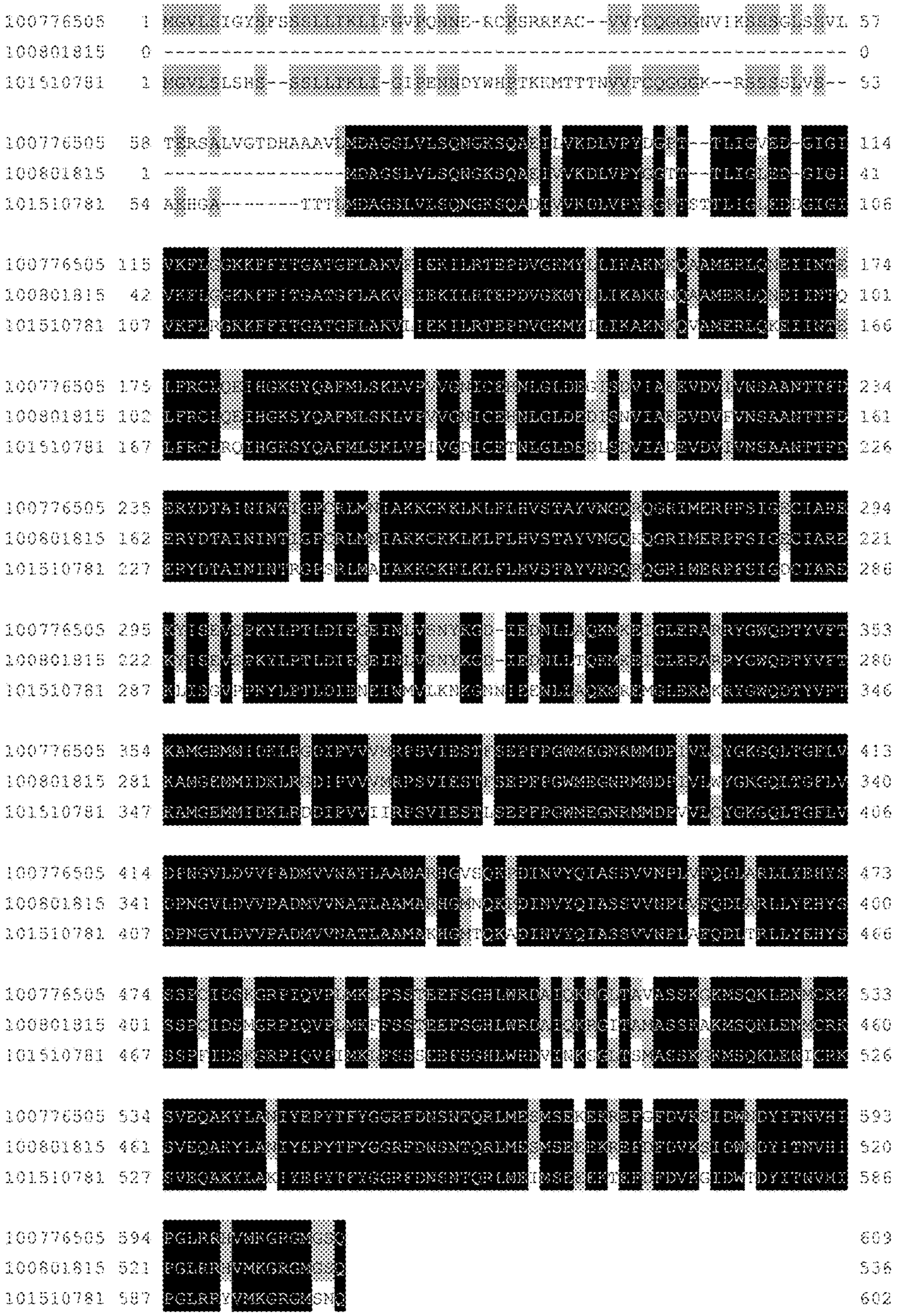

FIGS. 2-1 to 2-3 show the results of alignment analysis of amino acid sequences of acyl-CoA reductases derived from various plant species shown in Table 1 using the ClustalW multiple sequence alignment program, which is available on the DDBJ of the National Institute of Genetics. Versions and various parameters employed for analysis are described below.

ClustalW Version, 2.1
- Pairwise Alignment Parameters
  - Alignment Type, Slow
  - Slow Pairwise Alignment Options
    - Protein Weight Matrix, Gonnet
    - Gap Open, 10
    - Gap Extension, 0.1

Multiple Sequence Alignment Parameters
- Protein Weight Matrix, Gonnet
- Gap Open, 10
- Gap Extension, 0.20
- Gap Distances, 5
- No End Gaps, no
- Iteration, none
- Numiter, 1
- Clustering, NJ Output Options
- Format, Aln w/numbers
- Order, Aligned As is apparent from FIGS. 2-1 to 2-3, the acyl-CoA reductases shown in Table 1 comprise Common sequence 1 described above. As shown in FIGS. 2-1 to 2-3, Common sequence 1 is determined by extracting amino acid residues that are perfectly consistent among the amino acid sequences of the plurality of acyl-CoA reductases shown in Table 1 and substituting other amino acid residues with arbitrary amino acids (denoted as "X").

As shown in FIGS. 2-1 to 2-3, also, the amino acid sequences of the plurality of acyl-CoA reductases shown in Table 1 comprise amino acid residues that are not perfectly consistent with each other, but are similar to each other. Thus, Common sequence 2 comprising such similar amino acid residues instead of Common sequence 1 can be defined. Specifically, Common sequence 2, which is among the plurality of acyl-CoA reductases shown in Table 1, is an amino acid sequence comprising amino acid residues that are perfectly consistent among the plurality of acyl-CoA reductases shown in Table 1 and amino acid residues that are not perfectly consistent but are similar to each other.

Specifically, the amino acid sequence of Common sequence 2 is as shown below.

```
Common sequence 2:
G(I/L)G(I/V)xxFLx(G/A)Kx(F/L)x(I/V)(T/S)G(A/G)TGFL
(A/G)KV(L/F)IEKILRTxP(D/N)V(G/N)K(I/M)(Y/F)x(L/V)I
KA(K/E)xx(E/Q/D)(A/V)AxxRLx(N/I/K)(E/D)(I/V)(I/V/
L)(N/D)(A/T)(E/Q/D)(V/L/I)Fx(O/G/R)L(Q/R/K)x(A/I/
V/T)(Y/H)G(K/N/E)(S/D/Y/G)Y(Q/H/M/S/D)xF(M/V/I/A)
(L/A/I)(S/A/R/N/K)KL(V/I)P(V/I)(A/L/V)Gx(V/I)(C/R)
(G/E/D)x(S/N/D)(L/I/V)Gxxx(D/G/E)x(A/S)xx(I/M)Ax
(E/R/D/Q)VD(V/I)(I/F/V)(V/I)NSAANTTF(D/H)ERYD(I/
T/V)Ax(D/N)(I/V)NTxG(P/T)x(H/R/N)(L/I)Mx(F/I)A(K/
H/Q)x(C/F)x(K/R/N)LKLFL(Q/H)(V/I)STAYVNGQ(R/K/T)QG
(R/V/L)(I/V)(M/L)E(K/R)PFxx(G/E)(D/E/L)x(I/V)(A/R/
E/I)x(E/D)(17-48aa)GL(E/Q)RAxxxGWQDTYVFTKAMGEM(V/
M)(I/V)(D/N)x(M/L)R(G/D)(E/D)(I/L/V)PV(V/A)x(I/M)
RPSVIESTxx(E/D)PFPGWMEG(N/S)RMMDP(I/V)(V/I)L(Y/O/
W)YGKGQL(T/S)GF(V/L)(A/V)DP(N/Y/E/D)GV(L/I)DVVPAD
MVVNATLA(A/S)(M/I)A(R/K/W)HG(8-17aa)(V/I)Y(Q/H)x
(A/T/S)SS(V/T/A)(V/A)NPL(I/V/D/A)Fx(D/R/E)Lx(S/R/
```

-continued

```
D/K/T)(H/L/M/F)(F/L)xxHxx(S/R/G)(S/O)PxxDxxG(N/R/
Q/T)PIxV(P/S)xM(K/R/S)(L/F)(F/L)x(S/T)(T/I/M/V/S)
(E/D)x(F/L)(S/A)x(H/Y)(L/V/I)(W/E)(R/I)(D/Y)(A/V)
xx(R/K)(S/R/C/A)(18-26aa)(K/R)(S/T)V(K/E)Q(A/T/L)
(K/T/V)(Y/H)L(A/G)xIYxPYTF(Y/F)(G/P/N)GRFDN(S/G)N
(T/V)(Q/E)xL(M/L/I/F)xxM(O/S/T)(E/A/K/V/P)(E/K/A/
N)E(K/R)xxFxFDVx(S/N/G)(I/L/V)(D/E)WxDYI(S/T)NVHI
PGL(R/K)(R/K)(H/Y)V(M/L)KG
```

In the amino acid sequences described herein, a notation composed of a plurality of amino acids separated by slashes "I" in parentheses indicates that the position represented thereby is any of such plurality of amino acids.

In other words, the amino acid sequence of Common sequence 2 comprises the amino acid sequence of SEQ ID NO: 5, a region of 17 to 48 arbitrary amino acid residues, the amino acid sequence of SEQ ID NO: 6, a region of 8 to 17 arbitrary amino acid residues, the amino acid sequence of SEQ ID NO: 7, a region of 18 to 26 arbitrary amino acid residues, and the amino acid sequence of SEQ ID NO: 8 linked in that order from the N terminus to the C terminus.

The amino acid sequence of Common sequence 2 allows an acyl-CoA reductase having high-level activity for synthesizing an aldehyde compound using acyl-CoA as a substrate to be more precisely distinguished from an acyl-CoA reductase having no or low-level activity for synthesizing an aldehyde compound using acyl-CoA as a substrate among various types of acyl-CoA reductases.

Amino acid residues that can be present at given positions in Common sequence 2 vary for the following reasons. As described in Reference Document (1) (McKee Biochemistry, Third Edition, Chapter 5: Amino acids, Peptides, and Proteins, 5.1: Amino acids, Atsushi Ichikawa (supervising editor), Shinichi Fukuoka (supervising translator), Ryosuke Sone (publisher), Kagaku-Dojin Publishing Company, Inc., ISBN4-7598-0944-9), it is well known that amino acids are classified in accordance with side chains having similar properties (chemical properties or physical sizes). Also, it is well known that molecular evolutionary substitutions frequently occur between amino acid residues classified as members of a given group while maintaining protein activity. On the basis thereof, the amino acid substitution scoring matrix (BLOSUM) shown in FIG. 2 in Reference Document (2): Henikoff S., Henikoff J. G., Amino-acid substitution matrices from protein blocks, Proc. Natl. Acad. Sci. U.S.A., 89, 10915-10919, 1992 was proposed, and such technique has been extensively employed. Reference Document (2) is based on the finding such that substitution between amino acids having similar side-chain chemical properties would reduce changes in structures and functions occurring throughout a protein. According to Reference Documents (1) and (2), a group of side-chain amino acids to be taken into consideration for multiple alignment can be based on indicators such as chemical properties and physical sizes. According to the scoring matrix (BLOSUM) disclosed in Reference Document (2), such group of side-chain amino acids is indicated as a group of amino acids having a score of 0 or more, and preferably of 1 or more. Examples of representative groups include the 8 groups described below. Amino acids can be classified into more specific groups: for example, a group of amino acids having a score of 0 or more; a group of amino acids having a score of 1 or more; and a group of amino acids having a score of 2 or more.

1) Group of Aliphatic Hydrophobic Amino Acids (ILMV Group)

This group consists of amino acids comprising aliphatic hydrophobic side chains among the neutral non-polar amino acids described in Reference Document (1); i.e., V (Val, valine), L (Leu, leucine), I (Ile, isoleucine), and M (Met, methionine). Among the amino acids that are classified as the neutral non-polar amino acids according to Reference Document (1), FGACWP are not included in "the group of hydrophobic aliphatic amino acids" for the following reasons. That is, the size of G (Gly, glycine) or A (Ala, alanine) is less than or equal to that of a methyl group, and the effects of non-polar amino acids are weak. Also, C (Cys, cysteine) occasionally plays a key role in S—S bonding, and it forms a hydrogen bond with an oxygen or nitrogen atom. In addition, the side chain molecular weights of F (Phe, phenylalanine) and W (Trp, tryptophane) are particularly high, and the effects of aromatic amino acids are strong. Further, P (Pro, proline) fixes the angle of the polypeptide main chain because of its strong imino acid effects.

2) Group of Amino Acids Having Hydroxymethylene Groups (ST Group)

This group consists of amino acids having hydroxymethylene groups in the side chains among the neutral polar amino acids; i.e., S (Ser, serine) and T (Thr, threonine). Since sugars bind at the sites of hydroxyl groups existing in the S and T side chains, such sites of hydroxyl groups are often important for a given type of polypeptide (protein) to have particular activity.

3) Group of Acidic Amino Acids (DE Group)

This group consists of amino acids having acidic carboxyl groups in the side chains; i.e., D (Asp, aspartic acid) and E (Glu, glutamic acid).

4) Group of Basic Amino Acids (KR Group)

This group consists of basic amino acids; i.e., K (Lys, lysine) and R (Arg, arginine). K and R are positively charged over an extensive pH range and they have basic properties. In contrast, H (His, histidine), classified as a basic amino acid, is not substantially ionized at pH 7, and it is accordingly not classified as a member of this group.

5) Group of Amino Acids Comprising Methylene Group=Polar Group (DHN Group)

All amino acids classified as members of this group comprise methylene groups bound as side chains to carbon atoms at position a and polar groups at sites closer to the ends thereof. The amino acids of this group are very similar in terms of physical sizes of non-polar methylene groups, and the group consists of N (Asn, asparagine, with the polar group being an amide group), D (Asp, aspartic acid, with the polar group being a carboxyl group), and H (His, histidine, with the polar group being an imidazole group).

6) Group of Amino Acids Comprising Dimethylene Group=Polar Group (EKQR Group)

All amino acids classified as members of this group comprise linear hydrocarbons equal to or larger than dimethylene groups bound as side chains to carbon atoms at position a and polar groups at sites closer to the ends thereof. The amino acids of this group are very similar in terms of physical sizes of non-polar dimethylene groups, and the group consists of E (Glu, glutamic acid, with the polar group being a carboxyl group), K (Lys, lysine, with the polar group being an amino group), Q (Gln, glutamine, with the polar group being an amide group), and R (Arg, arginine, with the polar groups being imino and amino groups).

7) Group of Aromatic Amino Acids (FYW Group)

This group consists of aromatic amino acids comprising benzene nuclei in the side chains and having chemical properties peculiar to aromatic amino acids: i.e., F (Phe, phenylalanine), Y (Tyr, tyrosine), and W (Trp, tryptophane).

8) Group of Cyclic Polar Amino Acids (HY Group)

This group consists of amino acids having both cyclic structures and polar groups in the side chains; i.e., H (H, histidine, with both the cyclic structure and the polar group being imidazole groups) and Y (Tyr, tyrosine, with the cyclic structure being a benzene nucleus and the polar group being a hydroxyl group).

On the basis of the groups of amino acids described above, it can be easily deduced that novel proteins having the same functions are obtained by substituting an amino acid residue in the amino acid sequence of a protein having a given function with another amino acid residue of the same group. On the basis of "1) Group of aliphatic hydrophobic amino acids (ILMV group)" above, for example, it can be easily deduced that novel proteins having the same functions are obtained even if an isoleucine residue in the amino acid sequence of a protein having a particular function is substituted with a leucine residue. When there are a plurality of proteins having particular functions, amino acid sequences are occasionally described as consensus sequences. Even in such cases, it can be easily deduced that novel proteins having the same functions are obtained by substituting a particular amino acid residue with another amino acid residue of the same group. When there are a plurality of proteins having particular functions and the amino acid residue in the consensus sequence determined based thereon is isoleucine or leucine (L/I), for example, it can be easily deduced that novel proteins having the same functions are obtained even if the isoleucine or leucine residue is substituted with a methionine or valine residue on the basis of "1) Group of aliphatic hydrophobic amino acids (ILMV group)."

Among the acyl-CoA reductase genes shown in Table 1, the gene identified with Gene ID: 100776505 derived from *Glycine max* (soybean), the gene identified with Gene ID: 100801815 derived from *Glycine max* (soybean), and the gene identified with Gene ID: 101510781 derived from *Cicer arietinum* (chickpea) encode acyl-CoA reductases having significantly higher activity for synthesizing an aldehyde compound using acyl-CoA as a substrate than that of other acyl-CoA reductases. FIG. 3 shows the results of alignment analysis of three acyl-CoA reductases encoded by the gene identified with Gene ID: 100776505 derived from *Glycine max* (soybean), the gene identified with Gene ID: 100801815 derived from *Glycine max* (soybean), and the gene identified with Gene ID: 101510781 derived from *Cicer arietinum* (chickpea) using the ClustalW multiple sequence alignment program, which is available on the DDBJ of the National Institute of Genetics (the versions and various parameters employed for analysis are as described above).

As shown in FIG. 3, these 3 highly active acyl-CoA reductases have very similar amino acid sequences. Common sequence 3 can be defined as an amino acid sequence that characterizes such 3 acyl-CoA reductases.

Common sequence 3:
MDAGSLVLSQNGKSQA(E/D)I(L/V)VKDLVPY(D/G)G(P/T)T(0-
2aa)TLIG(V/L)ED(0-1aa)GIGIVKFL(G/R)GKKFFITGATGFLA -continued KV(F/L)IEKILRTEPDVGKMY(L/I)LIKAKN(K/N)Q(A/V)AMERL
Q(N/K)EIINT(E/Q)LFRCL(Q/R)(E/Q)IHGKSYQAFMLSKLVP
(V/I)VG(N/D)ICE(H/T)NLGLDE(G/D)(I/L)S(D/N)VIA(E/
D)EVDV(I/F)VNSAANTTFDERYDTAININT(I/R)GP(O/S)RLM
(N/A)IAKKCKKLKLFLHVSTAYVNGQ(R/K)QGRIMERPFSIG(E/D)
CIAREK(YL)IS(E/G)V(S/P)PKYLPTLDIE(G/N)EIN(L/M)V
(S/L)(N/K)(Y/N)KG(D/N)(0-1aa)IE(D/E)NLL(A/T)QKM
(K/R)E(I/M)GLERA(R/K)RYGWQDTYVFTKAMGEMMIDKLR(G/D)
DIPVV(V/I)(M/I)RPSVIEST(F/L)SEPFPGWMEGNRMMDP(I/V)
VL(C/W)YGKGQLTGFLVDPNGVLDVVPADMVVNATLAAMA(R/K)HG
(V/M)(S/N/I)QK(P/A)DINVYQIASSVVNPL(V/A)FQDL(A/T)
RLLYEHYSSSP(C/F)IDS(K/M)GRPIQVP(L/I)MK(L/F)FSS(T/
S)EEFSGHLWRD(A/V)I(Q/N)K(R/S)G(L/I)T(A/S)(V/M)ASS
K(G/A)KMSQKLEN(M/I)CRKSVEQAKYLA(N/K)IVEPYTFYGGRFD
NSNTQRLME(S/I)MSE(K/E)EK(R/T)EF(G/D)FDVK(S/G)IDW
(N/T)DYITNVHIPGLRR(H/Y)VMKGRGM(G/S)(S/N)Q The amino acid sequence of Common sequence 3 is represented in the same manner as in the cases of Common sequences 1 and 2. In other words, the amino acid sequence of Common sequence 3 comprises the amino acid sequence of SEQ ID NO: 9, a region of 0 to 2 arbitrary amino acid residues, the amino acid sequence of SEQ ID NO: 10, a region of 0 or 1 arbitrary amino acid residues, the amino acid sequence of SEQ ID NO: 11, a region of 0 or 1 arbitrary amino acid residues, and the amino acid sequence of SEQ ID NO: 12 linked in that order from the N terminus to the C terminus.

The amino acid sequence of Common sequence 3 allows an acyl-CoA reductase having particularly high-level activity for synthesizing an aldehyde compound using acyl-CoA as a substrate to be distinguished from an acyl-CoA reductase having no or low-level activity for synthesizing an aldehyde compound using acyl-CoA as a substrate among various types of acyl-CoA reductases.

When an acyl-CoA reductase comprising Common sequence 3 is expressed in a host microorganism, specifically, it reduces acyl-CoA to produce an aldehyde compound with higher efficiency. Thus, an alcohol and/or hydrocarbon can be produced from the aldehyde compound with higher efficiency.

As described above, a nucleic acid encoding an acyl-CoA reductase that can be used in the present invention is not particularly limited, provided that it encodes an acyl-CoA reductase comprising Common sequence 1, 2, or 3. In other words, such nucleic acid is not limited to the acyl-CoA reductase genes specifically exemplified in Table 1, and nucleic acids encoding acyl-CoA reductases derived from plant species that differ from those exemplified in Table 1 are also within the scope of such nucleic acid. For example, a nucleic acid encoding an acyl-CoA reductase derived from a plant species with sequence information that is not stored in GenBank or other databases and comprising Common sequence 1, 2, or 3 can be used.

Specific examples of acyl-CoA reductases that can be used in the present invention include proteins comprising amino acid sequences as shown in any of SEQ ID NOs: 14, 16, 18, 20, 22, 24, 26, 28, 30, 32, 34, and 36 shown in Table 1. A protein comprising an amino acid sequence as shown in any of SEQ ID NO: 14, 16, or 18 is particularly preferable as an acyl-CoA reductase.

Nucleic acids encoding acyl-CoA reductases that can be used in the present invention are not limited to the nucleic acids encoding acyl-CoA reductases identified with particular sequence identification numbers, as described above. Any nucleic acid can be used, provided that it encodes an acyl-CoA reductase comprising Common sequence 1, 2, or 3. A nucleic acid encoding an acyl-CoA reductase has activity such that a protein encoded thereby reduces acyl-CoA and generates an aldehyde compound.

Whether or not an acyl-CoA reductase that can be used in the present invention comprises Common sequence 1, 2, or 3 and whether or not a nucleic acid encoding such protein encodes a protein comprising Common sequence 1, 2, or 3 can be easily determined by comparing the amino acid sequence of the protein of interest or an amino acid sequence encoded by the nucleic acid with the amino acid sequence of Common sequence 1, 2, or 3.

For example, an acyl-CoA reductase comprising an amino acid sequence that is different from the amino acid sequence as shown in any of SEQ ID NOs: 14, 16, 18, 20, 22, 24, 26, 28, 30, 32, 34, and 36 and comprising Common sequence 1, 2, or 3 may encode a protein comprising an amino acid sequence derived from the amino acid sequence as shown in any of SEQ ID NOs: 14, 16, 18, 20, 22, 24, 26, 28, 30, 32, 34, and 36 by deletion, substitution, addition, or insertion of 1 or a plurality of amino acids and comprising Common sequence 1, 2, or 3 and having activity of an acyl-CoA reductase. A plurality of amino acids is, for example, 1 to 20, preferably 1 to 10, more preferably 1 to 7, further preferably 1 to 5, and particularly preferably 1 to 3 amino acids. Amino acid deletion, substitution, or addition can be performed by modifying the nucleotide sequence of the nucleic acid encoding the acyl-CoA reductase in accordance with a technique known in the art. A mutation can be introduced into a nucleotide sequence by conventional techniques, such as the Kunkel method or the Gapped duplex method, or a technique in accordance therewith. For example, a site-directed mutagenesis kit (e.g., Mutant-K or Mutant-G (trade names); manufactured by TAKARA Bio) may be used. Alternatively, a mutation may be introduced using the LA PCR in vitro Mutagenesis Series Kit (trade name: manufactured by TAKARA Bio). Further, mutagenesis may be carried out with the use of a chemical mutagen. Representative examples of chemical mutagens include EMS (ethylmethane sulfonate), 5-bromouracil, 2-aminopurine, hydroxylamine, N-methyl-N'-nitro-N-nitrosoguanidine, and other carcinogenic compounds. Also, it may be carried out by radiation application and ultraviolet processing with the use of x rays, $\alpha$ rays, $\beta$ rays, $\gamma$ rays, or ion beams.

For example, an acyl-CoA reductase comprising an amino acid sequence that is different from the amino acid sequence as shown in any of SEQ ID NOs: 14, 16, 18, 20, 22, 24, 26, 28, 30, 32, 34, and 36 and comprising Common sequence 1, 2, or 3 may encode a protein comprising an amino acid sequence having 70% or higher, preferably 80% or higher, more preferably 90% or higher, and most preferably 95% or higher similarity or identity to the amino acid sequence as shown in any of SEQ ID NOs: 14, 16, 18, 20, 22, 24, 26, 28, 30, 32, 34, and 36 and comprising Common sequence 1, 2, or 3 and having activity of an acyl-CoA reductase. The degree of similarity or identity is determined using a computer program equipped with the basic local alignment search tool (BLAST) program and a database storing gene sequence information by default.

A nucleic acid comprising an amino acid sequence that is different from the amino acid sequence as shown in any of SEQ ID NOs: 14, 16, 18, 20, 22, 24, 26, 28, 30, 32, 34, and 36 and encoding an acyl-CoA reductase comprising Common sequence 1, 2, or 3 can be identified by extracting nucleic acids from a target plant and isolating a nucleic acid hybridizing under stringent conditions to a nucleic acid encoding the amino acid sequence as shown in any of SEQ ID NOs: 14, 16, 18, 20, 22, 24, 26, 28, 30, 32, 34, and 36, when plant genome information is not apparent. Under stringent conditions, namely, a specific hybrid is formed, but a non-specific hybrid is not formed. For example, such conditions comprise hybridization at 45° C. with 6×SSC (sodium chloride/sodium citrate), followed by washing at 50° C. to 65° C. with 0.2 to 1×SSC and 0.1% SDS. Alternatively, such conditions comprise hybridization at 65° C. to 70° C. with 1×SSC, followed by washing at 65° C. to 70° C. with 0.3×SSC. Hybridization can be carried out by a conventional technique, such as the method described in J. Sambrook et al., Molecular Cloning: A Laboratory Manual, 2nd Ed., Cold Spring Harbor Laboratory, 1989.

Thus, the acyl-CoA reductase used in the present invention was defined as comprising Common sequence 1, 2, or 3, although it is not limited to a protein comprising Common sequence 1, 2, or 3.

Specifically, an acyl-CoA reductase used in the present invention may encode a protein comprising an amino acid sequence derived from the amino acid sequence as shown in any of SEQ ID NOs: 14, 16, 18, 20, 22, 24, 26, 28, 30, 32, 34, and 36 by deletion, substitution, addition, or insertion of one or a plurality of amino acids and having activity of an acyl-CoA reductase. A plurality of amino acids is, for example, 1 to 20, preferably 1 to 10, more preferably 1 to 7, further preferably 1 to 5, and particularly preferably 1 to 3 amino acids. Amino acid deletion, substitution, or addition can be performed by modifying the nucleotide sequence of the nucleic acid encoding the acyl-CoA reductase in accordance with a technique known in the art. A mutation can be introduced into a nucleotide sequence by the method described above.

An acyl-CoA reductase may encode, for example, a protein comprising an amino acid sequence having 70% or higher, preferably 80% or higher, more preferably 90% or higher, and most preferably 95% or higher similarity or identity to the amino acid sequence as shown in any of SEQ ID NOs: 14, 16, 18, 20, 22, 24, 26, 28, 30, 32, 34, and 36 and having activity of an acyl-CoA reductase. The degree of similarity or identity can be determined by the method described above.

Further, an acyl-CoA reductase may encode a protein encoded by a nucleic acid hybridizing under stringent conditions to, for example, a nucleic acid encoding the amino acid sequence as shown in any of SEQ ID NOs: 14, 16, 18, 20, 22, 24, 26, 28, 30, 32, 34, and 36 and having acyl-CoA reductase. Stringent conditions are as described above.

Whether or not a nucleic acid comprising a particular nucleotide sequence encodes the acyl-CoA reductase can be determined by preparing an expression vector comprising the nucleic acid incorporated into a site between an adequate promoter and a terminator, transforming an adequate host using the prepared expression vector, and assaying the acyl-CoA reductase activity of the protein expressed. Acyl-CoA reductase activity can be assayed by culturing the transformant in a medium containing a carbon source and analyzing the synthesized aldehyde compound or an alcohol derived from the aldehyde compound via gas chromatography, mass analysis, or other means. When culturing the transformant, acyl-CoA may be added to the medium.

[Expression Vector and Host Microorganism]

The nucleic acid encoding the acyl-CoA reductase described above is incorporated into an adequate expression vector and it is then introduced into a host microorganism. A host microorganism is not particularly limited, provided that it is capable of expressing an acyl-CoA reductase. Examples of host microorganisms include: bacteria of *Escherichia* such as *Escherichia coli, Corynebacterium* such as *Corynebacterium glutamicum, Bacillus* such as *Bacillus subtilis, Pseudomonas* such as *Pseudomonas putida*, and *Rhizobium* such as *Rhizobium meliloti*; and fungi including yeast and filamentous fungi, such as *Saccharomyces cerevisiae, Schizosaccharomyces pombe*, and *Pichia pastoris.*

When bacteria such as *Escherichia coli* are used for host microorganisms, it is preferable that an expression vector be capable of autonomous replication in such bacteria and be composed of a promoter, a ribosome binding sequence, the gene(s) described above, and a transcription terminator sequence. Also, an expression vector may comprise a gene that regulates promoter activity.

Any *Escherichia coli* strains that have heretofore been known can be used, and examples thereof include the *Escherichia coli* BL21 (DE3) strain, K12 strain, DH1 strain, and JM109 strain. As *Escherichia coli* strains, in particular, the K12 strains and strains prepared therefrom—that is, so-called K strains—can be used. An example of the *Bacillus subtilis* strain is the *Bacillus subtilis* 168 strain.

Any promoter can be used, provided that it allows a gene of interest to be expressed in a host such as *Escherichia coli*. Examples thereof include *Escherichia coli*-derived promoters, such as trp promoters, lac promoters, PL promoters, and PR promoters, and phage-derived promoters, such as T7 promoters. Artificially designed and/or modified promoters, such as tac promoters, may also be used.

An expression vector can be introduced by any method, provided that such method is intended to introduce DNA into bacteria. Examples thereof include a method involving the use of calcium ions (Cohen, S. N. et al., Proc. Natl. Acad. Sci., U.S.A., 69: 2110-2114, 1972) and electroporation.

Examples of yeast strains that can be used for host microorganisms include, but are not particularly limited to, *Candida* yeast strains, such as *Candida Shehatae, Pichia* yeast strains, such as *Pichia stipites, Pachysolen* yeast strains, such as *Pachysolen tannophilus, Saccharomyces* yeast strains, such as *Saccharomyces cerevisiae*, and *Schizosaccharomyces* yeast strains, such as *Schizosaccharomyces pombe*, with *Saccharomyces cerevisiae* being particularly preferable.

When the expression level of the acyl-CoA reductase is to be enhanced, an adequate promoter with high transcriptional activity is used. Examples of promoters that can be used include, but are not particularly limited to, glyceraldehyde-3-phosphate dehydrogenase gene (TDH3) promoters, 3-phosphoglycerate kinase gene (PGK1) promoters, and hyperosmolarity-responsive 7 gene (HOR7) promoters. Pyruvate decarboxylase gene (PDC1) promoters are particularly preferable because of their high capacity for enhancing the expression level of the target downstream genes. Also, gall promoters, gal10 promoters, heat shock protein promoters, MFα1 promoters, PHO5 promoters, GAP promoters, ADH promoters, or AOX1 promoters may be used, so that the expression level of the downstream genes can be enhanced.

As methods for introducing the genes described above, any conventional techniques that are known as yeast transformation techniques can be employed. Specific examples include, but are not limited to, the electroporation method (Meth. Enzym., 194, p. 182, 1990), the spheroplast method (Proc. Natl. Acad. Sci., U.S.A., 75, p. 1929, 1978), the lithium acetate method (J. Bacteriology, 153, p. 163, 1983), and methods described in Proc. Natl. Acad. Sci., U.S.A., 75, p. 1929, 1978 and Methods in Yeast Genetics, 2000 Edition: A Cold Spring Harbor Laboratory Course Manual.

The nucleic acid encoding the acyl-CoA reductase is preferably introduced into a microorganism capable of hydrocarbon synthesis with the use of an aldehyde compound as a substrate. In such a case, a recombinant microorganism expressing the acyl-CoA reductase can produce a hydrocarbon from an aldehyde compound with high efficiency. For example, a nucleic acid encoding an enzyme having decarbonylase activity (i.e., a decarbonylase) may be introduced into the microorganism, and a recombinant microorganism capable of hydrocarbon synthesis from an aldehyde compound can then be produced. The recombinant microorganism thus obtained or a microorganism that inherently has decarbonylase activity may be used as a host, the acyl-CoA reductase may be introduced into such host, and hydrocarbon synthesis can then be carried out with very high efficiency.

Enzymes having decarbonylase activity are not particularly limited, and conventional enzymes can be used. For example, WO 2006/109558 discloses a method in which novel microalgae, *Pseudochoricystis ellipsoidea*, capable of hydrocarbon production or microalgae of *Pseudochoricystis* or *Choricystis* capable of hydrocarbon production are cultured and a hydrocarbon is collected from the culture product. A nucleic acid encoding an enzyme having decarbonylase activity can be isolated from such an organism and used. Also, the gene converting an aldehyde into an alkane disclosed in JP 2010-528627 A and the alkane synthase gene or the aldehyde synthase gene derived from *Synechococcus elongatus* disclosed in JP 2011-520455 A can be used. In addition, a gene encoding a protein involved with aliphatic aldehyde decarbonylase activity derived from *Arabidopsis thaliana* disclosed in JP H09-322780 A (1997) can be used.

Further, WO 2013/129393 discloses a hydrocarbon synthase gene encoding an enzyme comprising a given motif sequence and having decarbonylase activity. With the use of the hydrocarbon synthase gene disclosed in WO 2013/129393, hydrocarbons as described above can be produced with high efficiency.

A recombinant microorganism that comprises an introduced nucleic acid encoding decarbonylase (e.g., recombinant *Escherichia coli* or recombinant yeast) would be capable of synthesizing a hydrocarbon from an aldehyde compound in the presence of an aldehyde compound and a coenzyme, such as NADH, through the expression of the decarbonylase.

Examples of hydrocarbons that can be synthesized include a hydrocarbon having a chain structure (i.e., a chain hydrocarbon) and a hydrocarbon having a cyclic structure (i.e., a cyclic hydrocarbon). A chain hydrocarbon may have one or more branches. Examples of branches include alkyl groups, such as methyl, ethyl, propyl, and butyl (including tert-butyl) groups, alkynyl groups, and alkenyl groups. Further examples of branches include chloromethyl, acetyl, 2-pyridyl, hydroxyphenyl, aminoacetyl, methoxy, phenoxy, methylthio, and phenylthio groups. Also, hydrocarbons to be synthesized may be saturated hydrocarbons (alkane) or unsaturated hydrocarbons (alkene and alkyne).

It is preferable that a hydrocarbon to be synthesized have about 5 to 20 carbon atoms, which is liquid at room temperature, although the number of carbon atoms is not limited thereto. A hydrocarbon to be synthesized is preferably a saturated hydrocarbon having 10 to 20 carbon atoms, more preferably 12 to 14 carbon atoms, and most preferably 13 carbon atoms, from the viewpoint of the application thereof for a diesel fuel. Specific examples of hydrocarbons to be synthesized include dodecane having 12 carbon atoms, tridecane having 13 carbon atoms, and tetradecane having 14 carbon atoms.

[Method for Substance Production]

As described above, the recombinant microorganism according to the present invention has excellent activity for synthesizing an aldehyde compound using acyl-CoA as a substrate. With the use of the recombinant microorganism according to the present invention, therefore, at least one compound selected from the group consisting of an aldehyde compound and an alcohol and a hydrocarbon synthesized from an aldehyde compound can be produced.

For example, the recombinant microorganism according to the present invention is cultured in a medium containing a carbon source, such as glucose, fructose, galactose, mannose, xylose, xylulose, ribose, erythrose, threose, erythrulose, glyceraldehyde, dihydroxyacetone, sucrose (saccharose), lactose, maltose, trehalose, or cellobiose. Thus, a target substance, such as the aldehyde compound, alcohol, or hydrocarbon as described above, can be produced.

The recombinant microorganism according to the present invention can also be used for a method for producing a target substance in vitro. For example, the recombinant microorganism according to the present invention is ground, the resulting solution containing the ground microorganism is used, and a target substance can then be synthesized in vitro. Specifically, acyl-CoA (a coenzyme such as NADH, if necessary) is added as a substrate to the solution, and a target substance can then be synthesized in vitro.

A target substance, such as a synthesized hydrocarbon, can be isolated in accordance with a conventional technique. For example, the recombinant yeast is cultured in a medium to produce a hydrocarbon. Since a hydrocarbon is synthesized in a medium, strains are separated from the medium via centrifugation or other means, and the target substance can then be isolated from the supernatant fraction. A hydrocarbon can be isolated from the supernatant fraction by, for example, adding an organic solvent, such as ethyl acetate or methanol, to the supernatant fraction and thoroughly agitating the solution. The aqueous phase is separated from the solvent phase, and a hydrocarbon can be extracted from the solvent phase.

EXAMPLES

Hereafter, the present invention is described in greater detail with reference to examples, although the technical scope of the present invention is not limited to these examples.

Example 1

In this example, an expression vector comprising the aldehyde decarbonylase gene (Gene ID: Npun R1711) derived from *Nostoc punctiform* and expression vectors comprising acyl-CoA reductase genes derived from various plant species were introduced into *Escherichia coli* strains, and the alkane productivity of the resulting recombinant *Escherichia coli* strains was evaluated. Table 2 shows the acyl-CoA reductase genes used in this example.

TABLE 2

| No. | Gene ID | Gene origin | Nucleotide sequence | Amino acid sequence | Transformant |
|---|---|---|---|---|---|
| 1 | AT4G33790 | *Arabidopsis thaliana* | SEQ ID NO: 37 | SEQ ID NO: 38 | At1 strain |
| 2 | AT3G56700 | | SEQ ID NO: 39 | SEQ ID NO: 40 | At2 strain |
| 3 | AT3G44560 | | SEQ ID NO: 41 | SEQ ID NO: 42 | At3 strain |
| 4 | 101311020 | *Fragaria vesca* (woodland strawberry) | | SEQ ID NO: 20 | Fv1 strain |
| 5 | 101314821 | | SEQ ID NO: 43 | SEQ ID NO: 44 | Fv2 strain |
| 6 | 101314535 | | SEQ ID NO: 45 | SEQ ID NO: 46 | Fv3 strain |
| 7 | 100776505 | *Glycine max* (soybean) | SEQ ID NO: 13 | SEQ ID NO: 14 | Gm1 strain |
| 8 | 100801815 | | SEQ ID NO: 15 | SEQ ID NO: 16 | Gm2 strain |
| 9 | POPTR_576417 | *Populus trichocarpa* (black cottonwood) | SEQ ID NO: 21 | SEQ ID NO: 22 | Pt1 strain |
| 10 | 101250126 | *Solanum lycopersicum* (tomato) | SEQ ID NO: 47 | SEQ ID NO: 48 | Sl1 strain |
| 11 | 101255461 | | SEQ ID NO: 49 | SEQ ID NO: 50 | Sl2 strain |
| 12 | RCOM_0791890 | *Ricinus communis* (castor bean) | SEQ ID NO: 51 | SEQ ID NO: 52 | Rc1 strain |
| 13 | RCOM_1279610 | | SEQ ID NO: 53 | SEQ ID NO: 54 | Rc2 strain |
| 14 | 100245182 | *Vitis vinifera* (wine grape) | SEQ ID NO: 23 | SEQ ID NO: 24 | Vv1 strain |
| 15 | 100242978 | | SEQ ID NO: 55 | SEQ ID NO: 56 | Vv2 strain |
| 16 | 100265271 | | SEQ ID NO: 57 | SEQ ID NO: 58 | Vv3 strain |
| 17 | 100259719 | | SEQ ID NO: 59 | SEQ ID NO: 60 | Vv4 strain |
| 18 | 100254606 | | SEQ ID NO: 61 | SEQ ID NO: 62 | Vv5 strain |
| 19 | 67420 | *Mus musculus* | SEQ ID NO: 63 | SEQ ID NO: 64 | Mm1 strain |
| 20 | 330450 | | SEQ ID NO: 65 | SEQ ID NO: 66 | Mm2 strain |
| 21 | 101510781 | *Cicer arietinum* (chickpea) | SEQ ID NO: 17 | SEQ ID NO: 18 | Ca1 strain |
| 22 | 101262598 | *Solanum lycopersicum* (tomato) | SEQ ID NO: 25 | SEQ ID NO: 26 | Sl3 strain |
| 23 | 101212401 | *Cucumis sativus* (cucumber) | SEQ ID NO: 27 | SEQ ID NO: 28 | Cc1 strain |
| 24 | 100845156 | *Brachypodium distachyon* | SEQ ID NO: 29 | SEQ ID NO: 30 | Bd1 strain |
| 25 | 101779750 | *Setaria italica* (foxtail millet) | SEQ ID NO: 31 | SEQ ID NO: 32 | Si1 strain |
| 26 | SORBI_01g046030 | *Sorghum bicolor* (sorghum) | SEQ ID NO: 33 | SEQ ID NO: 34 | Sb1 strain |
| 27 | Os03t0167600-01 | *Oryza sativa japonica* (Japanese rice) | SEQ ID NO: 35 | SEQ ID NO: 36 | Os1 strain |

The acyl-CoA reductase genes and the aldehyde decarbonylase genes used in this example were artificially synthesized on the basis of the nucleotide sequence information stored in the database. SEQ ID NOs: 67 and 68 show the nucleotide sequence and the amino acid sequence of the aldehyde decarbonylase gene (Gene ID: Npun R1711), respectively.

Figure 4:
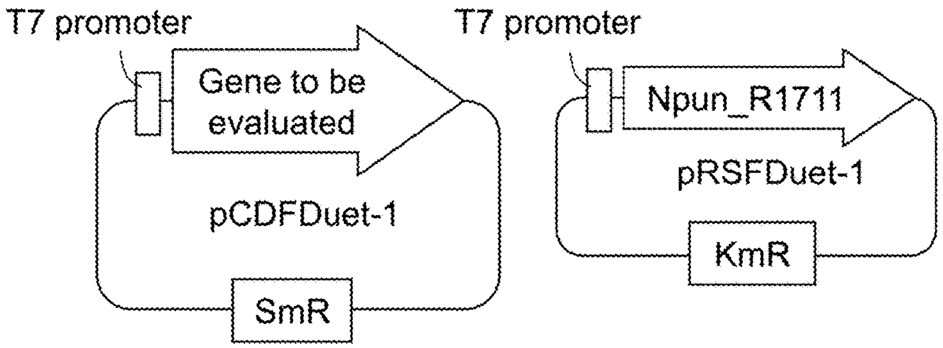
FIG. 4 schematically shows an expression vector containing the acyl-CoA reductase gene and an expression vector containing the aldehyde decarbonylase gene.

The artificially synthesized acyl-CoA reductase gene was inserted into the NdeI-XhoI site of the pCDFDuet-1 vector (Novagen), and the artificially synthesized aldehyde decarbonylase gene was inserted into the PstI site of the pRSF-Duet-1 vector (Novagen) (see FIG. 4). When artificially synthesizing the acyl-CoA reductase gene, the sequence: TACCATGGGCATACATATGGCCATCATAACGGT-TCTGGCAAATATTCTGAAATGA GCTGTTGACAAT-TAATCATCGGCTCGTATAATGTGTGGAATTGT-GAGCGGATAAC AATTTCACACAAGGAGATATACG (SEQ ID NO: 69) comprising the NdeI recognition sequence was added to the 5' terminus, and the sequence: TAAT-TAACCTAGGCTGCTGCCACCGCTGAG-CAATAACTAGCATAACCCCTTGGGG CCTCTAAACGGGTCTTGAGGGGTTTTTTGCCCTC-GAGTCCGGCCGCATGCGGCCGCAT (SEQ ID NO: 19) comprising the XhoI recognition sequence was added to the 3' terminus.

Subsequently, the two types of prepared expression vectors were transformed into the *E. coli* BL21 (DE3) strain. Transformation was carried out by preparing *E. coli* BL21 (DE3) competent cells with reference to User Protocol TB009 Rev. F0104 (Novagen).

Subsequently, the resulting transformant was subjected to shake culture in 0.5 ml of LB medium, which contains 30 mg/ml streptomycin and 50 mg/ml kanamycin, at 37° C. and 130 rpm overnight. The culture solution was inoculated into 2 ml of M9 medium, which contains 2% glucose, 0.1% yeast extract, 30 mg/ml streptomycin, and 50 mg/ml kanamycin, to an amount of 1% therein by volume, and shake culture was conducted at 37° C. and 130 rpm for about 4 hours (final absorption: OD 600 of 0.4 to 0.6). Isopropyl β-D-1-thiogalactopyranoside (IPTG) was added to the culture solution to a final concentration of 1 mM therein, and culture was conducted at 37° C. and 130 rpm for 3 days.

The culture solution (1 ml) was sampled in a 1.5-ml Eppendorf tube, the bacterial strains were collected using a centrifuge (6,000 rpm, 1 minute, room temperature), and the supernatant was removed. Ethyl acetate (100 ml) was added to the pellets, and a suspension was prepared via vortex for about 1 minute. The resultant was centrifuged at 10,000 rpm for 1 minute at room temperature, and the resulting supernatant was then subjected to GC/MS analysis. The conditions for GC/MS analysis are shown in Table 3.

TABLE 3

| [GC/MS analysis conditions] |
|---|
| Column: HP-5MS (Agilent: 19091S-433)<br>Inlet temperature: 260° C.<br>Detector temperature: 260° C.<br>Split ratio: 1/20<br>Carrier gas: He 1.0 ml/min<br>Oven heating conditions |
| 60° C., 1 min<br>Raised to 260° C. at 50° C./min<br>260° C., 1 min |

Figure 5:
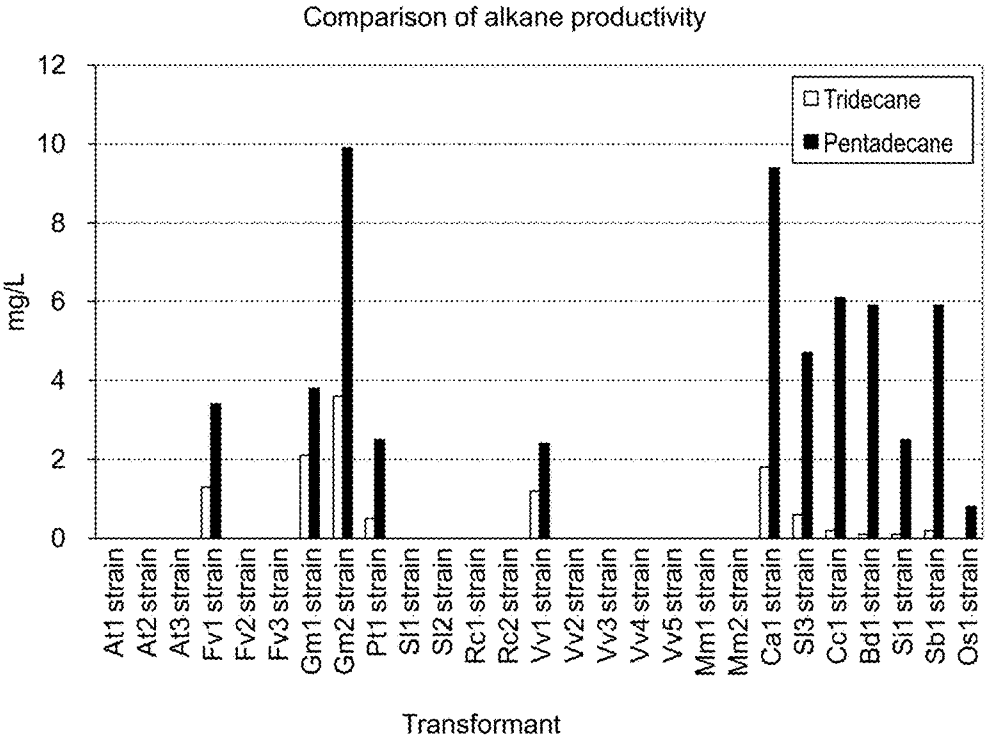
FIG. 5 shows a characteristic diagram showing the results of quantitative GC/MS analysis of tridecane and pentadecane of the recombinant *Escherichia coli* strains prepared in the example.
Figure 6:
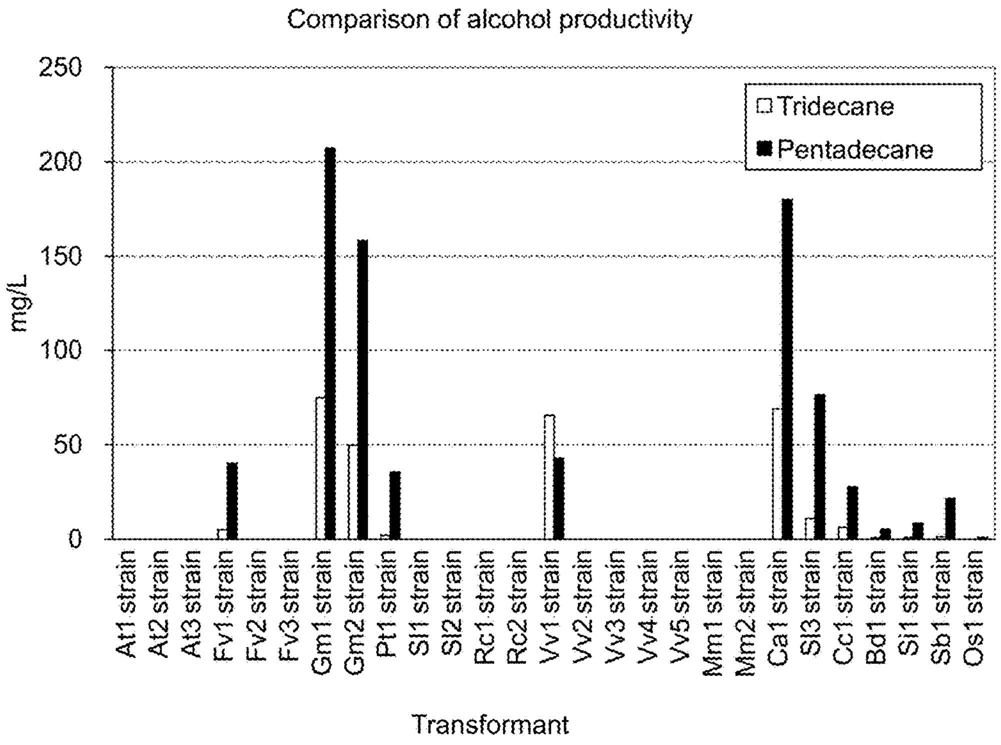
FIG. 6 shows a characteristic diagram showing the results of quantitative GC/MS analysis of tetradecanol and hexadecanol of the recombinant *Escherichia coli* strains prepared in the example.
Figure 7:
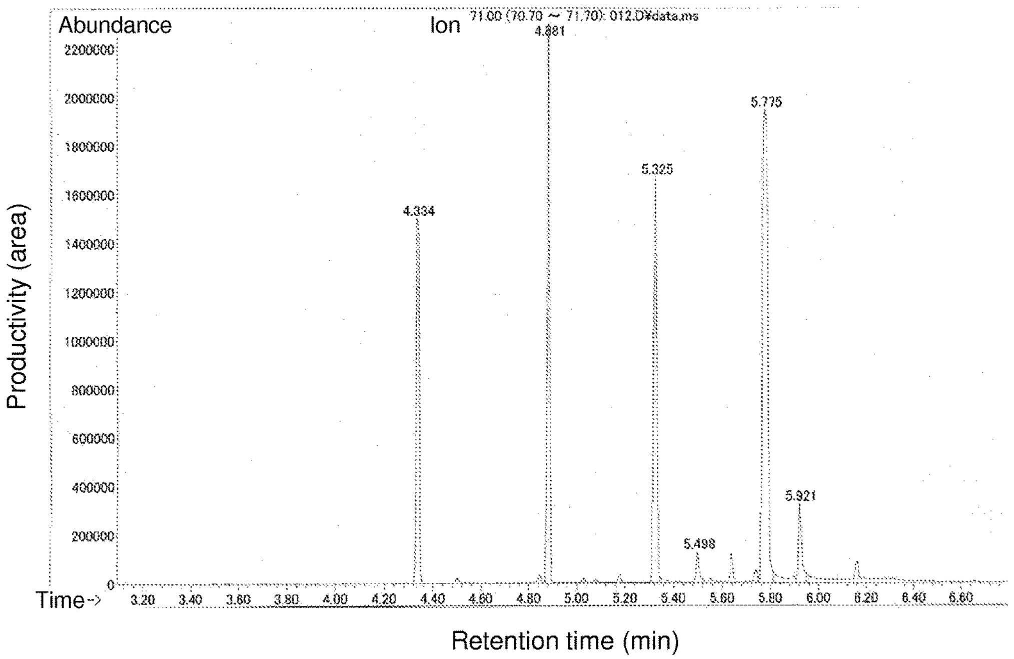
FIG. 7 shows a characteristic diagram showing a chart demonstrating the results of GC/MS analysis of the recombinant *Escherichia coli* strains prepared in the example (i.e., the Gm2 strain).

FIG. 5 shows the results of quantitative GC/MS analysis of tridecane and pentadecane of the 27 types of recombinant *Escherichia coli* strains prepared in this example, and FIG. 6 shows the results of quantitative GC/MS analysis of tetradecanol and hexadecanol thereof. FIG. 7 shows a chart showing the results of GC/MS analysis of the Gm2 strain among the 27 types of recombinant *Escherichia coli* strains. Table 4 shows a summary of the results of quantification shown in FIGS. 5 and 6.

TABLE 4

| | Concentration(mg/L) | | | |
|---|---|---|---|---|
| | Tridecane | Pentadecane | Tetradecanol | Hexadecanol |
| 1 At1 strain | 0.0 | 0.0 | 0.0 | 0.0 |
| 2 At2 strain | 0.0 | 0.0 | 0.0 | 0.0 |
| 3 At3 strain | 0.0 | 0.0 | 0.0 | 0.0 |
| 4 Fv1 strain | 1.3 | 3.4 | 5.0 | 40.2 |
| 5 Fv2 strain | 0.0 | 0.0 | 0.0 | 0.0 |
| 6 Fv3 strain | 0.0 | 0.0 | 0.0 | 0.0 |
| 7 Gm1 strain | 2.1 | 3.8 | 74.9 | 207.3 |
| 8 Gm2 strain | 3.6 | 9.9 | 49.7 | 158.3 |
| 9 Pt1 strain | 0.5 | 2.5 | 2.1 | 35.5 |
| 10 Sl1 strain | 0.0 | 0.0 | 0.0 | 0.0 |
| 11 Sl2 strain | 0.0 | 0.0 | 0.0 | 0.0 |
| 12 Rc1 strain | 0.0 | 0.0 | 0.0 | 0.0 |
| 13 Rc2 strain | 0.0 | 0.0 | 0.0 | 0.0 |
| 14 Vv1 strain | 1.2 | 2.4 | 65.6 | 42.8 |
| 15 Vv2 strain | 0.0 | 0.0 | 0.0 | 0.0 |
| 16 Vv3 strain | 0.0 | 0.0 | 0.0 | 0.0 |
| 17 Vv4 strain | 0.0 | 0.0 | 0.0 | 0.0 |
| 18 Vv5 strain | 0.0 | 0.0 | 0.0 | 0.0 |
| 19 Mm1 strain | 0.0 | 0.0 | 0.0 | 0.0 |
| 20 Mm2 strain | 0.0 | 0.0 | 0.0 | 0.0 |
| 21 Ca1 strain | 1.8 | 9.4 | 68.9 | 180.1 |
| 22 Sl3 strain | 0.6 | 4.7 | 11.0 | 76.4 |
| 23 Cc1 strain | 0.2 | 6.1 | 6.3 | 27.6 |
| 24 Bd1 strain | 0.1 | 5.9 | 0.8 | 5.3 |
| 25 Si1 strain | 0.1 | 2.5 | 0.9 | 8.4 |
| 26 Sb1 strain | 0.2 | 5.9 | 1.2 | 21.5 |
| 27 Os1 strain | 0.0 | 0.8 | 0.0 | 1.0 |

On the basis of the results shown in FIGS. 5 and 6 and Table 4, 12 types of recombinant *Escherichia coli* strains: i.e., the Fv1 strain, the Gm1 strain, the Gm2 strain, the Pt1 strain, the Vv1 strain, the Cal strain, the Sl3 strain, the Cc1 strain, the Bd1 strain, the Si1 strain, the Sb1 strain, and the Os1 strain, were found to have got alcohol and alkane production capacity. The results demonstrate that these 12 types of recombinant *Escherichia coli* strains had achieved the capacity to produce an aldehyde compound from acyl-CoA upon introduction of the acyl-CoA reductase gene. In other words, the acyl-CoA reductase genes in these 12 types of recombinant *Escherichia coli* strains were found to encode acyl-CoA reductases having activity for reducing acyl-CoA to generate an aldehyde compound in the host microorganisms.

In this example, more specifically, the gene identified with Gene ID: 101311020 derived from *Fragaria vesca* (woodland strawberry), the gene identified with Gene ID: 100776505 derived from *Glycine max* (soybean), the gene identified with Gene ID: 100801815 derived from *Glycine max* (soybean), the gene identified with Gene ID: POPTR_576417 derived from *Populus trichocarpa* (black cottonwood), the gene identified with Gene ID: 100245182 derived from *Vitis vinifera* (wine grape), the gene identified with Gene ID: 101510781 derived from *Cicer arietinum* (chickpea), the gene identified with Gene ID: 101262598 derived from *Solanum lycopersicum* (tomato), the gene identified with Gene ID: 101212401 derived from *Cucumis sativus* (cucumber), the gene identified with Gene ID: 100845156 derived from *Brachypodium distachyon*, the gene identified with Gene ID: 101779750 derived from *Setaria italica* (foxtail millet), the gene identified with Gene ID: SORBI_01g046030 derived from *Sorghum bicolor* (sorghum), and the gene identified with Gene ID: Os03t0167600-01 derived from *Oryza sativa japonica* (Japanese rice) were found to encode acyl-CoA reductases having activity for reducing acyl-CoA to generate an aldehyde compound in the host microorganisms. Common sequences 1 and 2 characterize the acyl-CoA reductases encoded by these 12 types of genes.

In particular, the results shown in FIGS. 5 and 6 and Table 4 demonstrate that the gene identified with Gene ID: 100776505 derived from *Glycine max* (soybean), the gene identified with Gene ID: 100801815 derived from *Glycine max* (soybean), and the gene identified with Gene ID: 101510781 derived from *Cicer arietinum* (chickpea) encode acyl-CoA reductases having the above-described activity, which is particularly remarkable. Common sequence 3 characterizes the acyl-CoA reductases encoded by these 3 types of genes.

All publications, patents, and patent applications cited herein are incorporated herein by reference in their entirety.

The invention claimed is:

1. A recombinant microorganism comprising a nucleic acid encoding an acyl-CoA reductase, wherein the acyl-CoA reductase is selected from (a) or (b) below:

(a) a protein comprising an amino acid sequence selected from the group consisting of SEQ ID NOs: 14, 16, 18, 20, 22, 24, 26, 28, 30, 32 and 34; or (b) an amino acid sequence having 80% or higher identity to an amino acid sequence selected from the group consisting of SEQ ID NOs: 14, 16, 18, 20, 22, 24, 26, 28, 30, 32 and 34, and having acyl-CoA reductase activity, wherein said recombinant microorganism further comprises aldehyde decarbonylase activity for synthesizing a hydrocarbon using an aldehyde as a substrate.

2. The recombinant microorganism according to claim 1, wherein the acyl-CoA reductase is the protein (a) or (b) below:

(a) a protein comprising an amino acid sequence selected from the group consisting of SEQ ID NOs: 14, 16, and 18; or (b) a protein comprising an amino acid sequence having 80% or higher identity to an amino acid sequence selected from the group consisting of SEQ ID NOs: 14, 16, and 18, and having acyl-CoA reductase activity.

3. The recombinant microorganism according to claim 1, wherein the host microorganism is selected from the group consisting of *Escherichia coli, Corynebacterium*, and yeast.

4. The recombinant microorganism according to claim 1, which produces a hydrocarbon comprising a carbon chain of 13 to 15 carbon atoms.

5. A recombinant microorganism comprising a nucleic acid encoding an acyl-CoA reductase, wherein the acyl-CoA reductase is selected from (a) or (b) below:

(a) a protein comprising an amino acid sequence selected from the group consisting of SEQ ID NOs: 14, 16, 18, 20, 22, 24, 26, 28, 30, 32 and 34; or (b) an amino acid sequence having 80% or higher identity to an amino acid sequence selected from the group consisting of SEQ ID NOs: 14, 16, 18, 20, 22, 24, 26, 28, 30, 32 and 34, and having acyl-CoA reductase activity, wherein said recombinant microorganism further comprises a nucleic acid encoding an aldehyde decarbonylase that synthesizes a hydrocarbon using an aldehyde as a substrate.

6. A recombinant microorganism comprising a nucleic acid encoding the protein (a) or (b) below introduced into a host microorganism:

(a) a protein comprising an amino acid sequence selected from the group consisting of SEQ ID NOs: 14, 16, 18, 20, 22, 24, 26, 28, 30, 32 and 34; or (b) a protein comprising an amino acid sequence having 80% or higher identity to an amino acid sequence selected from the group consisting of SEQ ID NOs: 14, 16, 18, 20, 22, 24, 26, 28, 30, 32 and 34, and having acyl-CoA reductase activity, wherein said recombinant microorganism further comprises aldehyde decarbonylase activity for synthesizing a hydrocarbon using an aldehyde as a substrate.

7. The recombinant microorganism according to claim 6, wherein the host microorganism is selected from the group consisting of *Escherichia coli, Corynebacterium*, and yeast.

8. The recombinant microorganism according to claim 6, which produces a hydrocarbon comprising a carbon chain of 13 to 15 carbon atoms.

9. A recombinant microorganism comprising a nucleic acid encoding the protein (a) or (b) below introduced into a host microorganism:

(a) a protein comprising an amino acid sequence selected from the group consisting of SEQ ID NOs: 14, 16, 18, 20, 22, 24, 26, 28, 30, 32 and 34; or (b) a protein comprising an amino acid sequence having 80% or higher identity to an amino acid sequence selected from the group consisting of SEQ ID NOs: 14, 16, 18, 20, 22, 24, 26, 28, 30, 32 and 34, and having acyl-CoA reductase activity, wherein said recombinant microorganism further comprises a nucleic acid encoding an aldehyde decarbonylase that synthesizes a hydrocarbon using an aldehyde as a substrate.

10. A method for producing a substance comprising a step of culturing the recombinant microorganism according to claim 1 in a medium containing a carbon source and a step of recovering a target substance from the cultured recombinant microorganism.

11. The method for producing a substance according to claim 10, wherein the target substance is at least one member selected from the group consisting of an aliphatic aldehyde, an aliphatic alcohol, and a hydrocarbon.

* * * * *

SEQUENCE LISTING

```
<160> NUMBER OF SEQ ID NOS: 69

<210> SEQ ID NO 1
<211> LENGTH: 175
<212> TYPE: PRT
<213> ORGANISM: Artificial Sequence
<220> FEATURE:
<223> OTHER INFORMATION: Synthetic sequence, part of consensus
      sequence 1
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(43)
<223> OTHER INFORMATION: Xaa can be any naturally occurring amino acid
<220> FEATURE:
<221> NAME/KEY: misc_feature
<222> LOCATION: (47)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (57)..(65)
<223> OTHER INFORMATION: Xaa can be any naturally occurring amino acid
<220> FEATURE:
<221> NAME/KEY: misc_feature
<222> LOCATION: (67)..(68)
```

<223> OTHER INFORMATION: Xaa can be any naturally occurring amino acid
<220> FEATURE:
<221> NAME/KEY: misc_feature
<222> LOCATION: (70)..(73)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (91)..(97)
<223> OTHER INFORMATION: Xaa can be any naturally occurring amino acid
<220> FEATURE:
<221> NAME/KEY: misc_feature
<222> LOCATION: (99)..(107)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (113)..(115)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(133)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (138)..(141)
<223> OTHER INFORMATION: Xaa can be any naturally occurring amino acid
<220> FEATURE:
<221> NAME/KEY: misc_feature
<222> LOCATION: (143)..(144)
<223> OTHER INFORMATION: Xaa can be any naturally occurring amino acid
<220> FEATURE:
<221> NAME/KEY: misc_feature
<222> LOCATION: (146)..(150)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(171)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid

<400> SEQUENCE: 1

```
Gly Xaa Gly Xaa Xaa Xaa Phe Leu Xaa Xaa Lys Xaa Xaa Xaa Xaa Xaa
1               5                   10                  15

Gly Xaa Thr Gly Phe Leu Xaa Lys Val Xaa Ile Glu Lys Ile Leu Arg
            20                  25                  30

Thr Xaa Pro Xaa Val Xaa Lys Xaa Xaa Xaa Xaa Ile Lys Ala Xaa Xaa
        35                  40                  45

Xaa Xaa Xaa Ala Xaa Xaa Arg Leu Xaa Xaa Xaa Xaa Xaa Xaa Xaa Xaa
    50                  55                  60

Xaa Phe Xaa Xaa Leu Xaa Xaa Xaa Xaa Gly Xaa Xaa Tyr Xaa Xaa Phe
65                  70                  75                  80

Xaa Xaa Xaa Lys Leu Xaa Pro Xaa Xaa Gly Xaa Xaa Xaa Xaa Xaa Xaa
                85                  90                  95

Xaa Gly Xaa Xaa Xaa Xaa Xaa Xaa Xaa Xaa Xaa Ala Xaa Xaa Val Asp
            100                 105                 110

Xaa Xaa Xaa Asn Ser Ala Ala Asn Thr Thr Phe Xaa Glu Arg Tyr Asp
        115                 120                 125

Xaa Ala Xaa Xaa Xaa Asn Thr Xaa Gly Xaa Xaa Xaa Xaa Met Xaa Xaa
    130                 135                 140

Ala Xaa Xaa Xaa Xaa Xaa Leu Lys Leu Phe Leu Xaa Xaa Ser Thr Ala
145                 150                 155                 160

Tyr Val Asn Gly Gln Xaa Gln Gly Xaa Xaa Xaa Glu Xaa Pro Phe
                165                 170                 175
```

<210> SEQ ID NO 2
<211> LENGTH: 103
<212> TYPE: PRT
<213> ORGANISM: Artificial Sequence
<220> FEATURE:
<223> OTHER INFORMATION: Synthetic sequence, part of consensus sequence 1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (35)..(37)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:

<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 2

```
Gly Leu Xaa Arg Ala Xaa Xaa Xaa Gly Trp Gln Asp Thr Tyr Val Phe
1               5                   10                  15

Thr Lys Ala Met Gly Glu Met Xaa Xaa Xaa Xaa Xaa Arg Xaa Xaa Xaa
            20                  25                  30

Pro Val Xaa Xaa Xaa Arg Pro Ser Val Ile Glu Ser Thr Xaa Xaa Xaa
        35                  40                  45

Pro Phe Pro Gly Trp Met Glu Gly Xaa Arg Met Met Asp Pro Xaa Xaa
    50                  55                  60

Leu Xaa Tyr Gly Lys Gly Gln Leu Xaa Gly Phe Xaa Xaa Asp Pro Xaa
65                  70                  75                  80

Gly Val Xaa Asp Val Val Pro Ala Asp Met Val Val Asn Ala Thr Leu
                85                  90                  95

Ala Xaa Xaa Ala Xaa His Gly
            100
```

<210> SEQ ID NO 3
<211> LENGTH: 42
<212> TYPE: PRT
<213> ORGANISM: Artificial Sequence
<220> FEATURE:
<223> OTHER INFORMATION: Synthetic sequence, part of consensus
      sequence 1
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

```
<220> FEATURE:
<221> NAME/KEY: misc_feature
<222> LOCATION: (17)..(22)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid

<400> SEQUENCE: 3

Tyr Xaa Xaa Xaa Ser Ser Xaa Xaa Asn Pro Leu Xaa Phe Xaa Xaa Leu
1               5                   10                  15

Xaa Xaa Xaa Xaa Xaa Xaa His Xaa Xaa Xaa Xaa Pro Xaa Xaa Asp Xaa
            20                  25                  30

Xaa Gly Xaa Pro Ile Xaa Val Xaa Xaa Met
        35                  40


<210> SEQ ID NO 4
<211> LENGTH: 69
<212> TYPE: PRT
<213> ORGANISM: Artificial Sequence
<220> FEATURE:
<223> OTHER INFORMATION: Synthetic sequence, part of consensus
      sequence 1
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (30)..(32)
```

<223> OTHER INFORMATION: Xaa can be any naturally occurring amino acid
<220> FEATURE:
<221> NAME/KEY: misc_feature
<222> LOCATION: (34)..(36)
<223> OTHER INFORMATION: Xaa can be any naturally occurring amino acid
<220> FEATURE:
<221> NAME/KEY: misc_feature
<222> LOCATION: (38)..(40)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (46)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid

<400> SEQUENCE: 4

```
Val Xaa Gln Xaa Xaa Xaa Leu Xaa Xaa Ile Tyr Xaa Pro Tyr Thr Phe
1               5                   10                  15

Xaa Xaa Gly Arg Phe Asp Asn Xaa Asn Xaa Xaa Xaa Leu Xaa Xaa Xaa
            20                  25                  30

Met Xaa Xaa Xaa Glu Xaa Xaa Xaa Phe Xaa Phe Asp Val Xaa Xaa Xaa
        35                  40                  45

Xaa Trp Xaa Asp Tyr Ile Xaa Asn Val His Ile Pro Gly Leu Xaa Xaa
    50                  55                  60

Xaa Val Xaa Lys Gly
65
```

<210> SEQ ID NO 5
<211> LENGTH: 184
<212> TYPE: PRT
<213> ORGANISM: Artificial Sequence
<220> FEATURE:
<223> OTHER INFORMATION: Synthetic sequence, part of consensus sequence 2
<220> FEATURE:
<221> NAME/KEY: misc_feature
<222> LOCATION: (2)..(2)
<223> OTHER INFORMATION: Xaa is I or L
<220> FEATURE:
<221> NAME/KEY: misc_feature
<222> LOCATION: (4)..(4)
<223> OTHER INFORMATION: Xaa is I or V
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa is G or A -continued
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is F or L
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa is I or V
<220> FEATURE:
<221> NAME/KEY: misc_feature
<222> LOCATION: (16)..(16)
<223> OTHER INFORMATION: Xaa is T or S
<220> FEATURE:
<221> NAME/KEY: misc_feature
<222> LOCATION: (18)..(18)
<223> OTHER INFORMATION: Xaa is A or G
<220> FEATURE:
<221> NAME/KEY: misc_feature
<222> LOCATION: (23)..(23)
<223> OTHER INFORMATION: Xaa is A or G
<220> FEATURE:
<221> NAME/KEY: misc_feature
<222> LOCATION: (26)..(26)
<223> OTHER INFORMATION: Xaa is L or F
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa is D or N
<220> FEATURE:
<221> NAME/KEY: misc_feature
<222> LOCATION: (38)..(38)
<223> OTHER INFORMATION: Xaa is G or N
<220> FEATURE:
<221> NAME/KEY: misc_feature
<222> LOCATION: (40)..(40)
<223> OTHER INFORMATION: Xaa is I or M
<220> FEATURE:
<221> NAME/KEY: misc_feature
<222> LOCATION: (41)..(41)
<223> OTHER INFORMATION: Xaa is Y or F
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa is L or V
<220> FEATURE:
<221> NAME/KEY: misc_feature
<222> LOCATION: (47)..(47)
<223> OTHER INFORMATION: Xaa is K or E
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa is E, Q or D
<220> FEATURE:
<221> NAME/KEY: misc_feature
<222> LOCATION: (51)..(51)
<223> OTHER INFORMATION: Xaa is A or V
<220> FEATURE:
<221> NAME/KEY: misc_feature
<222> LOCATION: (53)..(54)

<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa is N, I or K
<220> FEATURE:
<221> NAME/KEY: misc_feature
<222> LOCATION: (59)..(59)
<223> OTHER INFORMATION: Xaa is E or D
<220> FEATURE:
<221> NAME/KEY: misc_feature
<222> LOCATION: (60)..(60)
<223> OTHER INFORMATION: Xaa is I or V
<220> FEATURE:
<221> NAME/KEY: misc_feature
<222> LOCATION: (61)..(61)
<223> OTHER INFORMATION: Xaa is I, V or L
<220> FEATURE:
<221> NAME/KEY: misc_feature
<222> LOCATION: (62)..(62)
<223> OTHER INFORMATION: Xaa is N or D
<220> FEATURE:
<221> NAME/KEY: misc_feature
<222> LOCATION: (63)..(63)
<223> OTHER INFORMATION: Xaa is A or T
<220> FEATURE:
<221> NAME/KEY: misc_feature
<222> LOCATION: (64)..(64)
<223> OTHER INFORMATION: Xaa is E, Q or D
<220> FEATURE:
<221> NAME/KEY: misc_feature
<222> LOCATION: (65)..(65)
<223> OTHER INFORMATION: Xaa is V, L or I
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa is C, G or R
<220> FEATURE:
<221> NAME/KEY: misc_feature
<222> LOCATION: (70)..(70)
<223> OTHER INFORMATION: Xaa is Q, R or K
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa is A, I, V or T
<220> FEATURE:
<221> NAME/KEY: misc_feature
<222> LOCATION: (73)..(73)
<223> OTHER INFORMATION: Xaa is Y or H
<220> FEATURE:
<221> NAME/KEY: misc_feature
<222> LOCATION: (75)..(75)
<223> OTHER INFORMATION: Xaa is K, N or E
<220> FEATURE:
<221> NAME/KEY: misc_feature
<222> LOCATION: (76)..(76)
<223> OTHER INFORMATION: Xaa is S, D, Y or G
<220> FEATURE:
<221> NAME/KEY: misc_feature
<222> LOCATION: (78)..(78)
<223> OTHER INFORMATION: Xaa is Q, H, M, S or D
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa is M, V, I or A
<220> FEATURE:
<221> NAME/KEY: misc_feature
<222> LOCATION: (82)..(82)
<223> OTHER INFORMATION: Xaa is L, A or I
<220> FEATURE:
<221> NAME/KEY: misc_feature
<222> LOCATION: (83)..(83)
<223> OTHER INFORMATION: Xaa is S, A, R, N or K
<220> FEATURE:
<221> NAME/KEY: misc_feature
<222> LOCATION: (86)..(86)
<223> OTHER INFORMATION: Xaa is V or I
<220> FEATURE:
<221> NAME/KEY: misc_feature
<222> LOCATION: (88)..(88)
<223> OTHER INFORMATION: Xaa is V or I
<220> FEATURE:
<221> NAME/KEY: misc_feature
<222> LOCATION: (89)..(89)
<223> OTHER INFORMATION: Xaa is A, L or V
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa is V or I
<220> FEATURE:
<221> NAME/KEY: misc_feature
<222> LOCATION: (93)..(93)
<223> OTHER INFORMATION: Xaa is C or R
<220> FEATURE:
<221> NAME/KEY: misc_feature
<222> LOCATION: (94)..(94)
<223> OTHER INFORMATION: Xaa is G, E or D
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa is S, N or D
<220> FEATURE:
<221> NAME/KEY: misc_feature
<222> LOCATION: (97)..(97)
<223> OTHER INFORMATION: Xaa is L, I or V
<220> FEATURE:
<221> NAME/KEY: misc_feature
<222> LOCATION: (99)..(101)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa is D, G or E
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa is A or S
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa is I or M
<220> FEATURE:
<221> NAME/KEY: misc_feature
<222> LOCATION: (109)..(109)
<223> OTHER INFORMATION: Xaa can be any naturally occurring amino acid
<220> FEATURE:

<221> NAME/KEY: misc_feature
<222> LOCATION: (110)..(110)
<223> OTHER INFORMATION: Xaa is E, R, D or Q
<220> FEATURE:
<221> NAME/KEY: misc_feature
<222> LOCATION: (113)..(113)
<223> OTHER INFORMATION: Xaa is V or I
<220> FEATURE:
<221> NAME/KEY: misc_feature
<222> LOCATION: (114)..(114)
<223> OTHER INFORMATION: Xaa is I, F or V
<220> FEATURE:
<221> NAME/KEY: misc_feature
<222> LOCATION: (115)..(115)
<223> OTHER INFORMATION: Xaa is V or I
<220> FEATURE:
<221> NAME/KEY: misc_feature
<222> LOCATION: (124)..(124)
<223> OTHER INFORMATION: Xaa is D or H
<220> FEATURE:
<221> NAME/KEY: misc_feature
<222> LOCATION: (129)..(129)
<223> OTHER INFORMATION: Xaa is I, T or V
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa is D or N
<220> FEATURE:
<221> NAME/KEY: misc_feature
<222> LOCATION: (133)..(133)
<223> OTHER INFORMATION: Xaa is I or V
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa is P or T
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa is H, R or N
<220> FEATURE:
<221> NAME/KEY: misc_feature
<222> LOCATION: (141)..(141)
<223> OTHER INFORMATION: Xaa is L or I
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa is F or I
<220> FEATURE:
<221> NAME/KEY: misc_feature
<222> LOCATION: (146)..(146)
<223> OTHER INFORMATION: Xaa is K, H or Q
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa is C or F
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa is K, R or N
<220> FEATURE:
<221> NAME/KEY: misc_feature
<222> LOCATION: (156)..(156)
<223> OTHER INFORMATION: Xaa is Q or H
<220> FEATURE:
<221> NAME/KEY: misc_feature
<222> LOCATION: (157)..(157)
<223> OTHER INFORMATION: Xaa is V or I
<220> FEATURE:
<221> NAME/KEY: misc_feature
<222> LOCATION: (166)..(166)
<223> OTHER INFORMATION: Xaa is R, K or T
<220> FEATURE:
<221> NAME/KEY: misc_feature
<222> LOCATION: (169)..(169)
<223> OTHER INFORMATION: Xaa is R, V or L
<220> FEATURE:
<221> NAME/KEY: misc_feature
<222> LOCATION: (170)..(170)
<223> OTHER INFORMATION: Xaa is I or V
<220> FEATURE:
<221> NAME/KEY: misc_feature
<222> LOCATION: (171)..(171)
<223> OTHER INFORMATION: Xaa is M or L
<220> FEATURE:
<221> NAME/KEY: misc_feature
<222> LOCATION: (173)..(173)
<223> OTHER INFORMATION: Xaa is K or R
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa is G or E
<220> FEATURE:
<221> NAME/KEY: misc_feature
<222> LOCATION: (179)..(179)
<223> OTHER INFORMATION: Xaa is D, E or L
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa is I or V
<220> FEATURE:
<221> NAME/KEY: misc_feature
<222> LOCATION: (182)..(182)
<223> OTHER INFORMATION: Xaa is A, R, E or I
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa is E or D

<400> SEQUENCE: 5

```
Gly Xaa Gly Xaa Xaa Xaa Phe Leu Xaa Xaa Lys Xaa Xaa Xaa Xaa Xaa
1               5                   10                  15

Gly Xaa Thr Gly Phe Leu Xaa Lys Val Xaa Ile Glu Lys Ile Leu Arg
            20                  25                  30

Thr Xaa Pro Xaa Val Xaa Lys Xaa Xaa Xaa Xaa Ile Lys Ala Xaa Xaa
        35                  40                  45

Xaa Xaa Xaa Ala Xaa Xaa Arg Leu Xaa Xaa Xaa Xaa Xaa Xaa Xaa Xaa
    50                  55                  60
```

-continued

```
Xaa Phe Xaa Xaa Leu Xaa Xaa Xaa Xaa Gly Xaa Xaa Tyr Xaa Xaa Phe
65                  70                  75                  80

Xaa Xaa Xaa Lys Leu Xaa Pro Xaa Xaa Gly Xaa Xaa Xaa Xaa Xaa Xaa
                85                  90                  95

Xaa Gly Xaa Xaa Xaa Xaa Xaa Xaa Xaa Xaa Xaa Ala Xaa Xaa Val Asp
            100                 105                 110

Xaa Xaa Xaa Asn Ser Ala Ala Asn Thr Thr Phe Xaa Glu Arg Tyr Asp
        115                 120                 125

Xaa Ala Xaa Xaa Xaa Asn Thr Xaa Gly Xaa Xaa Xaa Xaa Met Xaa Xaa
    130                 135                 140

Ala Xaa Xaa Xaa Xaa Xaa Leu Lys Leu Phe Leu Xaa Xaa Ser Thr Ala
145                 150                 155                 160

Tyr Val Asn Gly Gln Xaa Gln Gly Xaa Xaa Xaa Glu Xaa Pro Phe Xaa
                165                 170                 175

Xaa Xaa Xaa Xaa Xaa Xaa Xaa Xaa
            180


<210> SEQ ID NO 6
<211> LENGTH: 103
<212> TYPE: PRT
<213> ORGANISM: Artificial Sequence
<220> FEATURE:
<223> OTHER INFORMATION: Synthetic sequence, part of consensus
      sequence 2
<220> FEATURE:
<221> NAME/KEY: misc_feature
<222> LOCATION: (3)..(3)
<223> OTHER INFORMATION: Xaa is E or Q
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is V or M
<220> FEATURE:
<221> NAME/KEY: misc_feature
<222> LOCATION: (25)..(25)
<223> OTHER INFORMATION: Xaa is I or V
<220> FEATURE:
<221> NAME/KEY: misc_feature
<222> LOCATION: (26)..(26)
<223> OTHER INFORMATION: Xaa is D or N
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa is M or L
<220> FEATURE:
<221> NAME/KEY: misc_feature
<222> LOCATION: (30)..(30)
<223> OTHER INFORMATION: Xaa is G or D
<220> FEATURE:
<221> NAME/KEY: misc_feature
<222> LOCATION: (31)..(31)
<223> OTHER INFORMATION: Xaa is E or D
<220> FEATURE:
<221> NAME/KEY: misc_feature
<222> LOCATION: (32)..(32)
<223> OTHER INFORMATION: Xaa is I, L or V
<220> FEATURE:
<221> NAME/KEY: misc_feature
<222> LOCATION: (35)..(35)
<223> OTHER INFORMATION: Xaa is V or A
<220> FEATURE:
<221> NAME/KEY: misc_feature
<222> LOCATION: (36)..(36)
```

<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa is I or M
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa is E or D
<220> FEATURE:
<221> NAME/KEY: misc_feature
<222> LOCATION: (57)..(57)
<223> OTHER INFORMATION: Xaa is N or S
<220> FEATURE:
<221> NAME/KEY: misc_feature
<222> LOCATION: (63)..(63)
<223> OTHER INFORMATION: Xaa is I or V
<220> FEATURE:
<221> NAME/KEY: misc_feature
<222> LOCATION: (64)..(64)
<223> OTHER INFORMATION: Xaa is V or I
<220> FEATURE:
<221> NAME/KEY: misc_feature
<222> LOCATION: (66)..(66)
<223> OTHER INFORMATION: Xaa is Y, C or W
<220> FEATURE:
<221> NAME/KEY: misc_feature
<222> LOCATION: (73)..(73)
<223> OTHER INFORMATION: Xaa is T or S
<220> FEATURE:
<221> NAME/KEY: misc_feature
<222> LOCATION: (76)..(76)
<223> OTHER INFORMATION: Xaa is V or L
<220> FEATURE:
<221> NAME/KEY: misc_feature
<222> LOCATION: (77)..(77)
<223> OTHER INFORMATION: Xaa is A or V
<220> FEATURE:
<221> NAME/KEY: misc_feature
<222> LOCATION: (80)..(80)
<223> OTHER INFORMATION: Xaa is N, Y, E or D
<220> FEATURE:
<221> NAME/KEY: misc_feature
<222> LOCATION: (83)..(83)
<223> OTHER INFORMATION: Xaa is L or I
<220> FEATURE:
<221> NAME/KEY: misc_feature
<222> LOCATION: (98)..(98)
<223> OTHER INFORMATION: Xaa is A or S
<220> FEATURE:
<221> NAME/KEY: misc_feature
<222> LOCATION: (99)..(99)
<223> OTHER INFORMATION: Xaa is M or I
<220> FEATURE:
<221> NAME/KEY: misc_feature
<222> LOCATION: (101)..(101)
<223> OTHER INFORMATION: Xaa is R, K or W

<400> SEQUENCE: 6

```
Gly Leu Xaa Arg Ala Xaa Xaa Xaa Gly Trp Gln Asp Thr Tyr Val Phe
1               5                   10                  15

Thr Lys Ala Met Gly Glu Met Xaa Xaa Xaa Xaa Xaa Arg Xaa Xaa Xaa
            20                  25                  30

Pro Val Xaa Xaa Xaa Arg Pro Ser Val Ile Glu Ser Thr Xaa Xaa Xaa
        35                  40                  45

Pro Phe Pro Gly Trp Met Glu Gly Xaa Arg Met Met Asp Pro Xaa Xaa
    50                  55                  60

Leu Xaa Tyr Gly Lys Gly Gln Leu Xaa Gly Phe Xaa Xaa Asp Pro Xaa
65                  70                  75                  80
```

Gly Val Xaa Asp Val Val Pro Ala Asp Met Val Val Asn Ala Thr Leu
85 90 95

Ala Xaa Xaa Ala Xaa His Gly
100

<210> SEQ ID NO 7
<211> LENGTH: 64
<212> TYPE: PRT
<213> ORGANISM: Artificial Sequence
<220> FEATURE:
<223> OTHER INFORMATION: Synthetic sequence, part of consensus sequence 2
<220> FEATURE:
<221> NAME/KEY: misc_feature
<222> LOCATION: (1)..(1)
<223> OTHER INFORMATION: Xaa is V or I
<220> FEATURE:
<221> NAME/KEY: misc_feature
<222> LOCATION: (3)..(3)
<223> OTHER INFORMATION: Xaa is Q or H
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is A, T or S
<220> FEATURE:
<221> NAME/KEY: misc_feature
<222> LOCATION: (8)..(8)
<223> OTHER INFORMATION: Xaa is V, T or A
<220> FEATURE:
<221> NAME/KEY: misc_feature
<222> LOCATION: (9)..(9)
<223> OTHER INFORMATION: Xaa is V or A
<220> FEATURE:
<221> NAME/KEY: misc_feature
<222> LOCATION: (13)..(13)
<223> OTHER INFORMATION: Xaa is I, V, D or A
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa is D, R or E
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is S, R, D, K or T
<220> FEATURE:
<221> NAME/KEY: misc_feature
<222> LOCATION: (20)..(20)
<223> OTHER INFORMATION: Xaa is H, L, M or F
<220> FEATURE:
<221> NAME/KEY: misc_feature
<222> LOCATION: (21)..(21)
<223> OTHER INFORMATION: Xaa is F or L
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa is S, R or G
<220> FEATURE:

<221> NAME/KEY: misc_feature
<222> LOCATION: (28)..(28)
<223> OTHER INFORMATION: Xaa is S or C
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa is N, R, Q or T
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa is P or S
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa is K, R or S
<220> FEATURE:
<221> NAME/KEY: misc_feature
<222> LOCATION: (45)..(45)
<223> OTHER INFORMATION: Xaa is L or F
<220> FEATURE:
<221> NAME/KEY: misc_feature
<222> LOCATION: (46)..(46)
<223> OTHER INFORMATION: Xaa is F or L
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa is S or T
<220> FEATURE:
<221> NAME/KEY: misc_feature
<222> LOCATION: (49)..(49)
<223> OTHER INFORMATION: Xaa is T, I, M, V or S
<220> FEATURE:
<221> NAME/KEY: misc_feature
<222> LOCATION: (50)..(50)
<223> OTHER INFORMATION: Xaa is E or D
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa is F or L
<220> FEATURE:
<221> NAME/KEY: misc_feature
<222> LOCATION: (53)..(53)
<223> OTHER INFORMATION: Xaa is S or A
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa is H or Y
<220> FEATURE:
<221> NAME/KEY: misc_feature
<222> LOCATION: (56)..(56)
<223> OTHER INFORMATION: Xaa is L, V or I
<220> FEATURE:
<221> NAME/KEY: misc_feature
<222> LOCATION: (57)..(57)
<223> OTHER INFORMATION: Xaa is W or E
<220> FEATURE:
<221> NAME/KEY: misc_feature
<222> LOCATION: (58)..(58)
<223> OTHER INFORMATION: Xaa is R or I
<220> FEATURE:
<221> NAME/KEY: misc_feature
<222> LOCATION: (59)..(59)
<223> OTHER INFORMATION: Xaa is D or Y
<220> FEATURE:
<221> NAME/KEY: misc_feature
<222> LOCATION: (60)..(60)
<223> OTHER INFORMATION: Xaa is A or V
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa is R or K
<220> FEATURE:
<221> NAME/KEY: misc_feature
<222> LOCATION: (64)..(64)
<223> OTHER INFORMATION: Xaa is S, R, C or A

<400> SEQUENCE: 7

```
Xaa Tyr Xaa Xaa Xaa Ser Ser Xaa Xaa Asn Pro Leu Xaa Phe Xaa Xaa
1               5                   10                  15

Leu Xaa Xaa Xaa Xaa Xaa Xaa His Xaa Xaa Xaa Xaa Pro Xaa Xaa Asp
            20                  25                  30

Xaa Xaa Gly Xaa Pro Ile Xaa Val Xaa Xaa Met Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

<210> SEQ ID NO 8
<211> LENGTH: 71
<212> TYPE: PRT
<213> ORGANISM: Artificial Sequence
<220> FEATURE:
<223> OTHER INFORMATION: Synthetic sequence, part of consensus sequence 2
<220> FEATURE:
<221> NAME/KEY: misc_feature
<222> LOCATION: (1)..(1)
<223> OTHER INFORMATION: Xaa is K or R
<220> FEATURE:
<221> NAME/KEY: misc_feature
<222> LOCATION: (2)..(2)
<223> OTHER INFORMATION: Xaa is S or T
<220> FEATURE:
<221> NAME/KEY: misc_feature
<222> LOCATION: (4)..(4)
<223> OTHER INFORMATION: Xaa is K or E
<220> FEATURE:
<221> NAME/KEY: misc_feature
<222> LOCATION: (6)..(6)
<223> OTHER INFORMATION: Xaa is A, T or L
<220> FEATURE:
<221> NAME/KEY: misc_feature
<222> LOCATION: (7)..(7)
<223> OTHER INFORMATION: Xaa is K, T or V
<220> FEATURE:
<221> NAME/KEY: misc_feature
<222> LOCATION: (8)..(8)
<223> OTHER INFORMATION: Xaa is Y or H
<220> FEATURE:
<221> NAME/KEY: misc_feature
<222> LOCATION: (10)..(10)
<223> OTHER INFORMATION: Xaa is A or G -continued
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa is Y or F
<220> FEATURE:
<221> NAME/KEY: misc_feature
<222> LOCATION: (20)..(20)
<223> OTHER INFORMATION: Xaa is G, P or N
<220> FEATURE:
<221> NAME/KEY: misc_feature
<222> LOCATION: (26)..(26)
<223> OTHER INFORMATION: Xaa is S or G
<220> FEATURE:
<221> NAME/KEY: misc_feature
<222> LOCATION: (28)..(28)
<223> OTHER INFORMATION: Xaa is T or V
<220> FEATURE:
<221> NAME/KEY: misc_feature
<222> LOCATION: (29)..(29)
<223> OTHER INFORMATION: Xaa is Q or E
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa is M, L, I or F
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa is C, S or T
<220> FEATURE:
<221> NAME/KEY: misc_feature
<222> LOCATION: (37)..(37)
<223> OTHER INFORMATION: Xaa is E, A, K, V or P
<220> FEATURE:
<221> NAME/KEY: misc_feature
<222> LOCATION: (38)..(38)
<223> OTHER INFORMATION: Xaa is E, K, A or N
<220> FEATURE:
<221> NAME/KEY: misc_feature
<222> LOCATION: (40)..(40)
<223> OTHER INFORMATION: Xaa is K or R
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa is S, N or G
<220> FEATURE:
<221> NAME/KEY: misc_feature
<222> LOCATION: (50)..(50)
<223> OTHER INFORMATION: Xaa is I, L or V
<220> FEATURE:
<221> NAME/KEY: misc_feature
<222> LOCATION: (51)..(51)

<223> OTHER INFORMATION: Xaa is D or E
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa is S or T
<220> FEATURE:
<221> NAME/KEY: misc_feature
<222> LOCATION: (65)..(65)
<223> OTHER INFORMATION: Xaa is R or K
<220> FEATURE:
<221> NAME/KEY: misc_feature
<222> LOCATION: (66)..(66)
<223> OTHER INFORMATION: Xaa is R or K
<220> FEATURE:
<221> NAME/KEY: misc_feature
<222> LOCATION: (67)..(67)
<223> OTHER INFORMATION: Xaa is H or Y
<220> FEATURE:
<221> NAME/KEY: misc_feature
<222> LOCATION: (69)..(69)
<223> OTHER INFORMATION: Xaa is M or L

<400> SEQUENCE: 8

```
Xaa Xaa Val Xaa Gln Xaa Xaa Xaa Leu Xaa Xaa Ile Tyr Xaa Pro Tyr
1               5                   10                  15

Thr Phe Xaa Xaa Gly Arg Phe Asp Asn Xaa Asn Xaa Xaa Xaa Leu Xaa
            20                  25                  30

Xaa Xaa Met Xaa Xaa Xaa Glu Xaa Xaa Xaa Phe Xaa Phe Asp Val Xaa
        35                  40                  45

Xaa Xaa Xaa Trp Xaa Asp Tyr Ile Xaa Asn Val His Ile Pro Gly Leu
    50                  55                  60

Xaa Xaa Xaa Val Xaa Lys Gly
65                  70
```

<210> SEQ ID NO 9
<211> LENGTH: 30
<212> TYPE: PRT
<213> ORGANISM: Artificial Sequence
<220> FEATURE:
<223> OTHER INFORMATION: Synthetic sequence, part of consensus sequence 3
<220> FEATURE:
<221> NAME/KEY: misc_feature
<222> LOCATION: (17)..(17)
<223> OTHER INFORMATION: Xaa is E or D
<220> FEATURE:
<221> NAME/KEY: misc_feature
<222> LOCATION: (19)..(19)
<223> OTHER INFORMATION: Xaa is L or V
<220> FEATURE:
<221> NAME/KEY: misc_feature
<222> LOCATION: (27)..(27)
<223> OTHER INFORMATION: Xaa is D or G
<220> FEATURE:
<221> NAME/KEY: misc_feature
<222> LOCATION: (29)..(29)
<223> OTHER INFORMATION: Xaa is P or T

<400> SEQUENCE: 9

```
Met Asp Ala Gly Ser Leu Val Leu Ser Gln Asn Gly Lys Ser Gln Ala
1               5                   10                  15

Xaa Ile Xaa Val Lys Asp Leu Val Pro Tyr Xaa Gly Xaa Thr
            20                  25                  30
```

<210> SEQ ID NO 10
<211> LENGTH: 7

<212> TYPE: PRT
<213> ORGANISM: Artificial Sequence
<220> FEATURE:
<223> OTHER INFORMATION: Synthetic sequence, part of consensus
sequence 3
<220> FEATURE:
<221> NAME/KEY: misc_feature
<222> LOCATION: (5)..(5)
<223> OTHER INFORMATION: Xaa is V or L

<400> SEQUENCE: 10

Thr Leu Ile Gly Xaa Glu Asp
1 5

<210> SEQ ID NO 11
<211> LENGTH: 213
<212> TYPE: PRT
<213> ORGANISM: Artificial Sequence
<220> FEATURE:
<223> OTHER INFORMATION: Synthetic sequence, part of consensus
sequence 3
<220> FEATURE:
<221> NAME/KEY: misc_feature
<222> LOCATION: (9)..(9)
<223> OTHER INFORMATION: Xaa is G or R
<220> FEATURE:
<221> NAME/KEY: misc_feature
<222> LOCATION: (26)..(26)
<223> OTHER INFORMATION: Xaa is F or L
<220> FEATURE:
<221> NAME/KEY: misc_feature
<222> LOCATION: (42)..(42)
<223> OTHER INFORMATION: Xaa is L or I
<220> FEATURE:
<221> NAME/KEY: misc_feature
<222> LOCATION: (49)..(49)
<223> OTHER INFORMATION: Xaa is K or N
<220> FEATURE:
<221> NAME/KEY: misc_feature
<222> LOCATION: (51)..(51)
<223> OTHER INFORMATION: Xaa is A or V
<220> FEATURE:
<221> NAME/KEY: misc_feature
<222> LOCATION: (58)..(58)
<223> OTHER INFORMATION: Xaa is N or K
<220> FEATURE:
<221> NAME/KEY: misc_feature
<222> LOCATION: (64)..(64)
<223> OTHER INFORMATION: Xaa is E or Q
<220> FEATURE:
<221> NAME/KEY: misc_feature
<222> LOCATION: (70)..(70)
<223> OTHER INFORMATION: Xaa is Q or R
<220> FEATURE:
<221> NAME/KEY: misc_feature
<222> LOCATION: (71)..(71)
<223> OTHER INFORMATION: Xaa is E or Q
<220> FEATURE:
<221> NAME/KEY: misc_feature
<222> LOCATION: (88)..(88)
<223> OTHER INFORMATION: Xaa is V or I
<220> FEATURE:
<221> NAME/KEY: misc_feature
<222> LOCATION: (91)..(91)
<223> OTHER INFORMATION: Xaa is N or D
<220> FEATURE:
<221> NAME/KEY: misc_feature
<222> LOCATION: (95)..(95)
<223> OTHER INFORMATION: Xaa is H or T
<220> FEATURE:
<221> NAME/KEY: misc_feature
<222> LOCATION: (102)..(102)
<223> OTHER INFORMATION: Xaa is G or D
<220> FEATURE:
<221> NAME/KEY: misc_feature
<222> LOCATION: (103)..(103)
<223> OTHER INFORMATION: Xaa is I or L
<220> FEATURE:
<221> NAME/KEY: misc_feature
<222> LOCATION: (105)..(105)
<223> OTHER INFORMATION: Xaa is D or N
<220> FEATURE:
<221> NAME/KEY: misc_feature
<222> LOCATION: (109)..(109)
<223> OTHER INFORMATION: Xaa is E or D
<220> FEATURE:
<221> NAME/KEY: misc_feature
<222> LOCATION: (114)..(114)
<223> OTHER INFORMATION: Xaa is I or F
<220> FEATURE:
<221> NAME/KEY: misc_feature
<222> LOCATION: (136)..(136)
<223> OTHER INFORMATION: Xaa is I or R
<220> FEATURE:
<221> NAME/KEY: misc_feature
<222> LOCATION: (139)..(139)
<223> OTHER INFORMATION: Xaa is C or S
<220> FEATURE:
<221> NAME/KEY: misc_feature
<222> LOCATION: (143)..(143)
<223> OTHER INFORMATION: Xaa is N or A
<220> FEATURE:
<221> NAME/KEY: misc_feature
<222> LOCATION: (166)..(166)
<223> OTHER INFORMATION: Xaa is R or K
<220> FEATURE:
<221> NAME/KEY: misc_feature
<222> LOCATION: (179)..(179)
<223> OTHER INFORMATION: Xaa is E or D
<220> FEATURE:
<221> NAME/KEY: misc_feature
<222> LOCATION: (186)..(186)
<223> OTHER INFORMATION: Xaa is Y or L
<220> FEATURE:
<221> NAME/KEY: misc_feature
<222> LOCATION: (189)..(189)
<223> OTHER INFORMATION: Xaa is E or G
<220> FEATURE:
<221> NAME/KEY: misc_feature
<222> LOCATION: (191)..(191)
<223> OTHER INFORMATION: Xaa is S or P
<220> FEATURE:
<221> NAME/KEY: misc_feature
<222> LOCATION: (202)..(202)
<223> OTHER INFORMATION: Xaa is G or N
<220> FEATURE:
<221> NAME/KEY: misc_feature
<222> LOCATION: (206)..(206)
<223> OTHER INFORMATION: Xaa is L or M
<220> FEATURE:
<221> NAME/KEY: misc_feature
<222> LOCATION: (208)..(208)
<223> OTHER INFORMATION: Xaa is S or L
<220> FEATURE:
<221> NAME/KEY: misc_feature
<222> LOCATION: (209)..(209)
<223> OTHER INFORMATION: Xaa is N or K
<220> FEATURE:
<221> NAME/KEY: misc_feature
<222> LOCATION: (210)..(210)
<223> OTHER INFORMATION: Xaa is Y or N
<220> FEATURE:
<221> NAME/KEY: misc_feature
<222> LOCATION: (213)..(213)
<223> OTHER INFORMATION: Xaa is D or N

<400> SEQUENCE: 11

Gly Ile Gly Ile Val Lys Phe Leu Xaa Gly Lys Lys Phe Phe Ile Thr
1               5                   10                  15

Gly Ala Thr Gly Phe Leu Ala Lys Val Xaa Ile Glu Lys Ile Leu Arg
            20                  25                  30

Thr Glu Pro Asp Val Gly Lys Met Tyr Xaa Leu Ile Lys Ala Lys Asn
        35                  40                  45

-continued

```
Xaa Gln Xaa Ala Met Glu Arg Leu Gln Xaa Glu Ile Ile Asn Thr Xaa
    50                  55                  60

Leu Phe Arg Cys Leu Xaa Xaa Ile His Gly Lys Ser Tyr Gln Ala Phe
65                  70                  75                  80

Met Leu Ser Lys Leu Val Pro Xaa Val Gly Xaa Ile Cys Glu Xaa Asn
                85                  90                  95

Leu Gly Leu Asp Glu Xaa Xaa Ser Xaa Val Ile Ala Xaa Glu Val Asp
            100                 105                 110

Val Xaa Val Asn Ser Ala Ala Asn Thr Thr Phe Asp Glu Arg Tyr Asp
        115                 120                 125

Thr Ala Ile Asn Ile Asn Thr Xaa Gly Pro Xaa Arg Leu Met Xaa Ile
    130                 135                 140

Ala Lys Lys Cys Lys Lys Leu Lys Leu Phe Leu His Val Ser Thr Ala
145                 150                 155                 160

Tyr Val Asn Gly Gln Xaa Gln Gly Arg Ile Met Glu Arg Pro Phe Ser
                165                 170                 175

Ile Gly Xaa Cys Ile Ala Arg Glu Lys Xaa Ile Ser Xaa Val Xaa Pro
            180                 185                 190

Lys Tyr Leu Pro Thr Leu Asp Ile Glu Xaa Glu Ile Asn Xaa Val Xaa
        195                 200                 205

Xaa Xaa Lys Gly Xaa
    210
```

<210> SEQ ID NO 12
<211> LENGTH: 286
<212> TYPE: PRT
<213> ORGANISM: Artificial Sequence
<220> FEATURE:
<223> OTHER INFORMATION: Synthetic sequence, part of consensus sequence 3
<220> FEATURE:
<221> NAME/KEY: misc_feature
<222> LOCATION: (3)..(3)
<223> OTHER INFORMATION: Xaa is D or E
<220> FEATURE:
<221> NAME/KEY: misc_feature
<222> LOCATION: (7)..(7)
<223> OTHER INFORMATION: Xaa is A or T
<220> FEATURE:
<221> NAME/KEY: misc_feature
<222> LOCATION: (11)..(11)
<223> OTHER INFORMATION: Xaa is K or R
<220> FEATURE:
<221> NAME/KEY: misc_feature
<222> LOCATION: (13)..(13)
<223> OTHER INFORMATION: Xaa is I or M
<220> FEATURE:
<221> NAME/KEY: misc_feature
<222> LOCATION: (19)..(19)
<223> OTHER INFORMATION: Xaa is R or K
<220> FEATURE:
<221> NAME/KEY: misc_feature
<222> LOCATION: (43)..(43)
<223> OTHER INFORMATION: Xaa is G or D
<220> FEATURE:
<221> NAME/KEY: misc_feature
<222> LOCATION: (49)..(49)
<223> OTHER INFORMATION: Xaa is V or I
<220> FEATURE:
<221> NAME/KEY: misc_feature
<222> LOCATION: (50)..(50)
<223> OTHER INFORMATION: Xaa is M or I
<220> FEATURE:
<221> NAME/KEY: misc_feature
<222> LOCATION: (59)..(59)
<223> OTHER INFORMATION: Xaa is F or L
<220> FEATURE:

-continued

<221> NAME/KEY: misc_feature
<222> LOCATION: (76)..(76)
<223> OTHER INFORMATION: Xaa is I or V
<220> FEATURE:
<221> NAME/KEY: misc_feature
<222> LOCATION: (79)..(79)
<223> OTHER INFORMATION: Xaa is C or W
<220> FEATURE:
<221> NAME/KEY: misc_feature
<222> LOCATION: (114)..(114)
<223> OTHER INFORMATION: Xaa is R or K
<220> FEATURE:
<221> NAME/KEY: misc_feature
<222> LOCATION: (117)..(117)
<223> OTHER INFORMATION: Xaa is V or M
<220> FEATURE:
<221> NAME/KEY: misc_feature
<222> LOCATION: (118)..(118)
<223> OTHER INFORMATION: Xaa is S, N or I
<220> FEATURE:
<221> NAME/KEY: misc_feature
<222> LOCATION: (121)..(121)
<223> OTHER INFORMATION: Xaa is P or A
<220> FEATURE:
<221> NAME/KEY: misc_feature
<222> LOCATION: (137)..(137)
<223> OTHER INFORMATION: Xaa is V or A
<220> FEATURE:
<221> NAME/KEY: misc_feature
<222> LOCATION: (142)..(142)
<223> OTHER INFORMATION: Xaa is A or T
<220> FEATURE:
<221> NAME/KEY: misc_feature
<222> LOCATION: (154)..(154)
<223> OTHER INFORMATION: Xaa is C or F
<220> FEATURE:
<221> NAME/KEY: misc_feature
<222> LOCATION: (158)..(158)
<223> OTHER INFORMATION: Xaa is K or M
<220> FEATURE:
<221> NAME/KEY: misc_feature
<222> LOCATION: (166)..(166)
<223> OTHER INFORMATION: Xaa is L or I
<220> FEATURE:
<221> NAME/KEY: misc_feature
<222> LOCATION: (169)..(169)
<223> OTHER INFORMATION: Xaa is L or F
<220> FEATURE:
<221> NAME/KEY: misc_feature
<222> LOCATION: (173)..(173)
<223> OTHER INFORMATION: Xaa is T or S
<220> FEATURE:
<221> NAME/KEY: misc_feature
<222> LOCATION: (184)..(184)
<223> OTHER INFORMATION: Xaa is A or V
<220> FEATURE:
<221> NAME/KEY: misc_feature
<222> LOCATION: (186)..(186)
<223> OTHER INFORMATION: Xaa is Q or N
<220> FEATURE:
<221> NAME/KEY: misc_feature
<222> LOCATION: (188)..(188)
<223> OTHER INFORMATION: Xaa is R or S
<220> FEATURE:
<221> NAME/KEY: misc_feature
<222> LOCATION: (190)..(190)
<223> OTHER INFORMATION: Xaa is L or I
<220> FEATURE:
<221> NAME/KEY: misc_feature
<222> LOCATION: (192)..(192)
<223> OTHER INFORMATION: Xaa is A or S
<220> FEATURE:
<221> NAME/KEY: misc_feature
<222> LOCATION: (193)..(193)
<223> OTHER INFORMATION: Xaa is V or M
<220> FEATURE:
<221> NAME/KEY: misc_feature
<222> LOCATION: (198)..(198)
<223> OTHER INFORMATION: Xaa is G or A

```
<220> FEATURE:
<221> NAME/KEY: misc_feature
<222> LOCATION: (207)..(207)
<223> OTHER INFORMATION: Xaa is M or I
<220> FEATURE:
<221> NAME/KEY: misc_feature
<222> LOCATION: (220)..(220)
<223> OTHER INFORMATION: Xaa is N or K
<220> FEATURE:
<221> NAME/KEY: misc_feature
<222> LOCATION: (243)..(243)
<223> OTHER INFORMATION: Xaa is S or I
<220> FEATURE:
<221> NAME/KEY: misc_feature
<222> LOCATION: (247)..(247)
<223> OTHER INFORMATION: Xaa is K or E
<220> FEATURE:
<221> NAME/KEY: misc_feature
<222> LOCATION: (250)..(250)
<223> OTHER INFORMATION: Xaa is R or T
<220> FEATURE:
<221> NAME/KEY: misc_feature
<222> LOCATION: (253)..(253)
<223> OTHER INFORMATION: Xaa is G or D
<220> FEATURE:
<221> NAME/KEY: misc_feature
<222> LOCATION: (258)..(258)
<223> OTHER INFORMATION: Xaa is S or G
<220> FEATURE:
<221> NAME/KEY: misc_feature
<222> LOCATION: (262)..(262)
<223> OTHER INFORMATION: Xaa is N or T
<220> FEATURE:
<221> NAME/KEY: misc_feature
<222> LOCATION: (276)..(276)
<223> OTHER INFORMATION: Xaa is H or Y
<220> FEATURE:
<221> NAME/KEY: misc_feature
<222> LOCATION: (284)..(284)
<223> OTHER INFORMATION: Xaa is G or S
<220> FEATURE:
<221> NAME/KEY: misc_feature
<222> LOCATION: (285)..(285)
<223> OTHER INFORMATION: Xaa is S or N

<400> SEQUENCE: 12

Ile Glu Xaa Asn Leu Leu Xaa Gln Lys Met Xaa Glu Xaa Gly Leu Glu
1               5                   10                  15

Arg Ala Xaa Arg Tyr Gly Trp Gln Asp Thr Tyr Val Phe Thr Lys Ala
            20                  25                  30

Met Gly Glu Met Met Ile Asp Lys Leu Arg Xaa Asp Ile Pro Val Val
        35                  40                  45

Xaa Xaa Arg Pro Ser Val Ile Glu Ser Thr Xaa Ser Glu Pro Phe Pro
    50                  55                  60

Gly Trp Met Glu Gly Asn Arg Met Met Asp Pro Xaa Val Leu Xaa Tyr
65                  70                  75                  80

Gly Lys Gly Gln Leu Thr Gly Phe Leu Val Asp Pro Asn Gly Val Leu
                85                  90                  95

Asp Val Val Pro Ala Asp Met Val Val Asn Ala Thr Leu Ala Ala Met
            100                 105                 110

Ala Xaa His Gly Xaa Xaa Gln Lys Xaa Asp Ile Asn Val Tyr Gln Ile
        115                 120                 125

Ala Ser Ser Val Val Asn Pro Leu Xaa Phe Gln Asp Leu Xaa Arg Leu
    130                 135                 140

Leu Tyr Glu His Tyr Ser Ser Ser Pro Xaa Ile Asp Ser Xaa Gly Arg
145                 150                 155                 160

Pro Ile Gln Val Pro Xaa Met Lys Xaa Phe Ser Ser Xaa Glu Glu Phe
                165                 170                 175
```

```
Ser Gly His Leu Trp Arg Asp Xaa Ile Xaa Lys Xaa Gly Xaa Thr Xaa
            180                 185                 190

Xaa Ala Ser Ser Lys Xaa Lys Met Ser Gln Lys Leu Glu Asn Xaa Cys
        195                 200                 205

Arg Lys Ser Val Glu Gln Ala Lys Tyr Leu Ala Xaa Ile Val Glu Pro
    210                 215                 220

Tyr Thr Phe Tyr Gly Gly Arg Phe Asp Asn Ser Asn Thr Gln Arg Leu
225                 230                 235                 240

Met Glu Xaa Met Ser Glu Xaa Glu Lys Xaa Glu Phe Xaa Phe Asp Val
                245                 250                 255

Lys Xaa Ile Asp Trp Xaa Asp Tyr Ile Thr Asn Val His Ile Pro Gly
            260                 265                 270

Leu Arg Arg Xaa Val Met Lys Gly Arg Gly Met Xaa Xaa Gln
        275                 280                 285


<210> SEQ ID NO 13
<211> LENGTH: 1827
<212> TYPE: DNA
<213> ORGANISM: Glycine max (soybean)
<220> FEATURE:
<221> NAME/KEY: CDS
<222> LOCATION: (1)..(1827)

<400> SEQUENCE: 13

atg ggc gtc ctg agc atc ggc tac tct ttc tcg tcg tcc ctg ctg acc       48
Met Gly Val Leu Ser Ile Gly Tyr Ser Phe Ser Ser Ser Leu Leu Thr
1               5                   10                  15

aaa ctg atc ttc ggc gtc cct caa aat aat gaa cgc tgt ccg tcc cgc       96
Lys Leu Ile Phe Gly Val Pro Gln Asn Asn Glu Arg Cys Pro Ser Arg
            20                  25                  30

cgt aag gct tgc gtg gtt tat tgt cag ggc ggt ggc aac gtg atc aaa      144
Arg Lys Ala Cys Val Val Tyr Cys Gln Gly Gly Gly Asn Val Ile Lys
        35                  40                  45

tcc agc tct ggt ctg tca tcg gtg ctg acc gaa cgt tcc gcg ctg gtt      192
Ser Ser Ser Gly Leu Ser Ser Val Leu Thr Glu Arg Ser Ala Leu Val
    50                  55                  60

ggc acc gat cac gcg gca gcc gtc ctg atg gac gct ggt tcc ctg gtg      240
Gly Thr Asp His Ala Ala Ala Val Leu Met Asp Ala Gly Ser Leu Val
65                  70                  75                  80

ctg agc cag aat ggc aag agc caa gca gaa atc ctg gtt aaa gat ctg      288
Leu Ser Gln Asn Gly Lys Ser Gln Ala Glu Ile Leu Val Lys Asp Leu
                85                  90                  95

gtc cct tac gac ggt ccg acc acc ctg att ggc gtt gag gat ggt atc      336
Val Pro Tyr Asp Gly Pro Thr Thr Leu Ile Gly Val Glu Asp Gly Ile
            100                 105                 110

ggc att gtc aag ttc ctg ggt ggc aaa aag ttc ttt atc acc ggt gca      384
Gly Ile Val Lys Phe Leu Gly Gly Lys Lys Phe Phe Ile Thr Gly Ala
        115                 120                 125

acc ggc ttc ctg gcc aag gtg ttt atc gaa aaa att ctg cgc acc gag      432
Thr Gly Phe Leu Ala Lys Val Phe Ile Glu Lys Ile Leu Arg Thr Glu
    130                 135                 140

cca gac gtt ggc aaa atg tat ctg ctg att aaa gca aag aac aaa cag      480
Pro Asp Val Gly Lys Met Tyr Leu Leu Ile Lys Ala Lys Asn Lys Gln
145                 150                 155                 160

gct gcg atg gaa cgc ctg caa aac gag atc att aat acc gaa ctg ttc      528
Ala Ala Met Glu Arg Leu Gln Asn Glu Ile Ile Asn Thr Glu Leu Phe
                165                 170                 175

cgt tgc ctg cag gaa atc cac ggt aaa tct tac caa gca ttt atg ctg      576
Arg Cys Leu Gln Glu Ile His Gly Lys Ser Tyr Gln Ala Phe Met Leu
```

-continued

```
            180                 185                 190

tca aaa ctg gtg cct gtc gtg ggc aac att tgt gaa cat aat ctg ggt      624
Ser Lys Leu Val Pro Val Val Gly Asn Ile Cys Glu His Asn Leu Gly
        195                 200                 205

ctg gat gag ggc atc agc gac gtt att gcc gaa gag gtt gat gtc atc      672
Leu Asp Glu Gly Ile Ser Asp Val Ile Ala Glu Glu Val Asp Val Ile
    210                 215                 220

gtg aac tct gca gcc aat acc acc ttt gat gaa cgc tat gac acc gcg      720
Val Asn Ser Ala Ala Asn Thr Thr Phe Asp Glu Arg Tyr Asp Thr Ala
225                 230                 235                 240

atc aac att aat acc atc ggt cct tgc cgt ctg atg aac atc gca aaa      768
Ile Asn Ile Asn Thr Ile Gly Pro Cys Arg Leu Met Asn Ile Ala Lys
                245                 250                 255

aag tgt aag aag ctg aag ctg ttc ctg cac gtg tca acc gcc tac gtt      816
Lys Cys Lys Lys Leu Lys Leu Phe Leu His Val Ser Thr Ala Tyr Val
            260                 265                 270

aat ggt cag cgc caa ggc cgt atc atg gaa cgc ccg ttt tcg atc ggc      864
Asn Gly Gln Arg Gln Gly Arg Ile Met Glu Arg Pro Phe Ser Ile Gly
        275                 280                 285

gag tgc att gct cgt gaa aag tat att agc gag gtc tct cca aaa tac      912
Glu Cys Ile Ala Arg Glu Lys Tyr Ile Ser Glu Val Ser Pro Lys Tyr
    290                 295                 300

ctg cct acc ctg gat atc gaa ggc gag att aac ctg gtg tcc aat tat      960
Leu Pro Thr Leu Asp Ile Glu Gly Glu Ile Asn Leu Val Ser Asn Tyr
305                 310                 315                 320

aaa ggc gat atc gaa gac aac ctg ctg gcc cag aag atg aaa gaa att     1008
Lys Gly Asp Ile Glu Asp Asn Leu Leu Ala Gln Lys Met Lys Glu Ile
                325                 330                 335

ggt ctg gag cgc gct cgc cgt tat ggc tgg caa gat acc tac gtg ttc     1056
Gly Leu Glu Arg Ala Arg Arg Tyr Gly Trp Gln Asp Thr Tyr Val Phe
            340                 345                 350

acc aag gcg atg ggc gag atg atg atc gat aaa ctg cgc ggc gac att     1104
Thr Lys Ala Met Gly Glu Met Met Ile Asp Lys Leu Arg Gly Asp Ile
        355                 360                 365

cct gtt gtc gtg atg cgt ccg agc gtc atc gaa tca acc ttc tcg gag     1152
Pro Val Val Val Met Arg Pro Ser Val Ile Glu Ser Thr Phe Ser Glu
    370                 375                 380

ccg ttt cca ggt tgg atg gaa ggc aac cgc atg atg gat cca att gtt     1200
Pro Phe Pro Gly Trp Met Glu Gly Asn Arg Met Met Asp Pro Ile Val
385                 390                 395                 400

ctg tgt tat ggt aaa ggc cag ctg acc ggt ttc ctg gtc gac cca aac     1248
Leu Cys Tyr Gly Lys Gly Gln Leu Thr Gly Phe Leu Val Asp Pro Asn
                405                 410                 415

ggc gtg ctg gat gtt gtc cct gct gac atg gtg gtt aat gcg acc ctg     1296
Gly Val Leu Asp Val Val Pro Ala Asp Met Val Val Asn Ala Thr Leu
            420                 425                 430

gct gcg atg gca cgt cat ggc gtt agc cag aaa ccg gat atc aac gtc     1344
Ala Ala Met Ala Arg His Gly Val Ser Gln Lys Pro Asp Ile Asn Val
        435                 440                 445

tac caa att gcc tcc agc gtc gtg aat cca ctg gtg ttt cag gat ctg     1392
Tyr Gln Ile Ala Ser Ser Val Val Asn Pro Leu Val Phe Gln Asp Leu
    450                 455                 460

gct cgc ctg ctg tac gaa cac tat tct tca tcg ccg tgc atc gac tct     1440
Ala Arg Leu Leu Tyr Glu His Tyr Ser Ser Ser Pro Cys Ile Asp Ser
465                 470                 475                 480

aag ggt cgt ccg att cag gtt cca ctg atg aaa ctg ttc tcc agc acc     1488
Lys Gly Arg Pro Ile Gln Val Pro Leu Met Lys Leu Phe Ser Ser Thr
                485                 490                 495

gaa gag ttt tca ggc cat ctg tgg cgc gat gcg atc caa aag cgt ggt     1536
```

-continued

```
Glu Glu Phe Ser Gly His Leu Trp Arg Asp Ala Ile Gln Lys Arg Gly
            500                 505                 510

ctg acc gca gtt gcc tct tca aag ggc aaa atg tcg cag aaa ctg gaa      1584
Leu Thr Ala Val Ala Ser Ser Lys Gly Lys Met Ser Gln Lys Leu Glu
        515                 520                 525

aac atg tgt cgc aag tcc gtc gag caa gct aaa tat ctg gcg aac att      1632
Asn Met Cys Arg Lys Ser Val Glu Gln Ala Lys Tyr Leu Ala Asn Ile
    530                 535                 540

tac gaa cca tat acc ttc tac ggt ggc cgc ttt gat aac tct aat acc      1680
Tyr Glu Pro Tyr Thr Phe Tyr Gly Gly Arg Phe Asp Asn Ser Asn Thr
545                 550                 555                 560

cag cgt ctg atg gaa tcg atg tcc gaa aag gag aag cgt gag ttc ggc      1728
Gln Arg Leu Met Glu Ser Met Ser Glu Lys Glu Lys Arg Glu Phe Gly
                565                 570                 575

ttt gac gtg aaa agc atc gat tgg aac gac tac att acc aac gtc cac      1776
Phe Asp Val Lys Ser Ile Asp Trp Asn Asp Tyr Ile Thr Asn Val His
            580                 585                 590

att cca ggt ctg cgt cgc cat gtg atg aaa ggt cgt ggt atg ggt agc      1824
Ile Pro Gly Leu Arg Arg His Val Met Lys Gly Arg Gly Met Gly Ser
        595                 600                 605

cag                                                                  1827
Gln


<210> SEQ ID NO 14
<211> LENGTH: 609
<212> TYPE: PRT
<213> ORGANISM: Glycine max (soybean)

<400> SEQUENCE: 14

Met Gly Val Leu Ser Ile Gly Tyr Ser Phe Ser Ser Ser Leu Leu Thr
1               5                   10                  15

Lys Leu Ile Phe Gly Val Pro Gln Asn Asn Glu Arg Cys Pro Ser Arg
            20                  25                  30

Arg Lys Ala Cys Val Val Tyr Cys Gln Gly Gly Gly Asn Val Ile Lys
        35                  40                  45

Ser Ser Ser Gly Leu Ser Ser Val Leu Thr Glu Arg Ser Ala Leu Val
    50                  55                  60

Gly Thr Asp His Ala Ala Ala Val Leu Met Asp Ala Gly Ser Leu Val
65                  70                  75                  80

Leu Ser Gln Asn Gly Lys Ser Gln Ala Glu Ile Leu Val Lys Asp Leu
                85                  90                  95

Val Pro Tyr Asp Gly Pro Thr Thr Leu Ile Gly Val Glu Asp Gly Ile
            100                 105                 110

Gly Ile Val Lys Phe Leu Gly Gly Lys Lys Phe Phe Ile Thr Gly Ala
        115                 120                 125

Thr Gly Phe Leu Ala Lys Val Phe Ile Glu Lys Ile Leu Arg Thr Glu
    130                 135                 140

Pro Asp Val Gly Lys Met Tyr Leu Leu Ile Lys Ala Lys Asn Lys Gln
145                 150                 155                 160

Ala Ala Met Glu Arg Leu Gln Asn Glu Ile Ile Asn Thr Glu Leu Phe
                165                 170                 175

Arg Cys Leu Gln Glu Ile His Gly Lys Ser Tyr Gln Ala Phe Met Leu
            180                 185                 190

Ser Lys Leu Val Pro Val Val Gly Asn Ile Cys Glu His Asn Leu Gly
        195                 200                 205

Leu Asp Glu Gly Ile Ser Asp Val Ile Ala Glu Glu Val Asp Val Ile
    210                 215                 220
```

```
Val Asn Ser Ala Ala Asn Thr Thr Phe Asp Glu Arg Tyr Asp Thr Ala
225                 230                 235                 240

Ile Asn Ile Asn Thr Ile Gly Pro Cys Arg Leu Met Asn Ile Ala Lys
                245                 250                 255

Lys Cys Lys Lys Leu Lys Leu Phe Leu His Val Ser Thr Ala Tyr Val
            260                 265                 270

Asn Gly Gln Arg Gln Gly Arg Ile Met Glu Arg Pro Phe Ser Ile Gly
        275                 280                 285

Glu Cys Ile Ala Arg Glu Lys Tyr Ile Ser Glu Val Ser Pro Lys Tyr
    290                 295                 300

Leu Pro Thr Leu Asp Ile Glu Gly Glu Ile Asn Leu Val Ser Asn Tyr
305                 310                 315                 320

Lys Gly Asp Ile Glu Asp Asn Leu Leu Ala Gln Lys Met Lys Glu Ile
                325                 330                 335

Gly Leu Glu Arg Ala Arg Arg Tyr Gly Trp Gln Asp Thr Tyr Val Phe
            340                 345                 350

Thr Lys Ala Met Gly Glu Met Met Ile Asp Lys Leu Arg Gly Asp Ile
        355                 360                 365

Pro Val Val Val Met Arg Pro Ser Val Ile Glu Ser Thr Phe Ser Glu
    370                 375                 380

Pro Phe Pro Gly Trp Met Glu Gly Asn Arg Met Met Asp Pro Ile Val
385                 390                 395                 400

Leu Cys Tyr Gly Lys Gly Gln Leu Thr Gly Phe Leu Val Asp Pro Asn
                405                 410                 415

Gly Val Leu Asp Val Val Pro Ala Asp Met Val Val Asn Ala Thr Leu
            420                 425                 430

Ala Ala Met Ala Arg His Gly Val Ser Gln Lys Pro Asp Ile Asn Val
        435                 440                 445

Tyr Gln Ile Ala Ser Ser Val Val Asn Pro Leu Val Phe Gln Asp Leu
    450                 455                 460

Ala Arg Leu Leu Tyr Glu His Tyr Ser Ser Ser Pro Cys Ile Asp Ser
465                 470                 475                 480

Lys Gly Arg Pro Ile Gln Val Pro Leu Met Lys Leu Phe Ser Ser Thr
                485                 490                 495

Glu Glu Phe Ser Gly His Leu Trp Arg Asp Ala Ile Gln Lys Arg Gly
            500                 505                 510

Leu Thr Ala Val Ala Ser Ser Lys Gly Lys Met Ser Gln Lys Leu Glu
        515                 520                 525

Asn Met Cys Arg Lys Ser Val Glu Gln Ala Lys Tyr Leu Ala Asn Ile
    530                 535                 540

Tyr Glu Pro Tyr Thr Phe Tyr Gly Gly Arg Phe Asp Asn Ser Asn Thr
545                 550                 555                 560

Gln Arg Leu Met Glu Ser Met Ser Glu Lys Glu Lys Arg Glu Phe Gly
                565                 570                 575

Phe Asp Val Lys Ser Ile Asp Trp Asn Asp Tyr Ile Thr Asn Val His
            580                 585                 590

Ile Pro Gly Leu Arg Arg His Val Met Lys Gly Arg Gly Met Gly Ser
        595                 600                 605

Gln
```

<210> SEQ ID NO 15
<211> LENGTH: 1608
<212> TYPE: DNA

```
<213> ORGANISM: Glycine max (soybean)
<220> FEATURE:
<221> NAME/KEY: CDS
<222> LOCATION: (1)..(1608)

<400> SEQUENCE: 15

atg gac gcg ggt tcg ctg gtt ctg tcg caa aac ggc aaa tcg cag gcg       48
Met Asp Ala Gly Ser Leu Val Leu Ser Gln Asn Gly Lys Ser Gln Ala
1               5                   10                  15

gag atc gtg gtt aaa gac ctg gtt cct tac ggc ggc acc acc acc ctg       96
Glu Ile Val Val Lys Asp Leu Val Pro Tyr Gly Gly Thr Thr Thr Leu
            20                  25                  30

atc ggc ctg gaa gat ggc atc ggt att gtg aaa ttc ctg ggc ggt aaa      144
Ile Gly Leu Glu Asp Gly Ile Gly Ile Val Lys Phe Leu Gly Gly Lys
        35                  40                  45

aag ttc ttt att acc ggc gcc acc ggt ttc ctg gct aaa gtg ttt atc      192
Lys Phe Phe Ile Thr Gly Ala Thr Gly Phe Leu Ala Lys Val Phe Ile
    50                  55                  60

gaa aag att ctg cgc acc gag cct gac gtt ggc aaa atg tat ctg ctg      240
Glu Lys Ile Leu Arg Thr Glu Pro Asp Val Gly Lys Met Tyr Leu Leu
65                  70                  75                  80

atc aaa gcc aag aac aat cag gcg gca atg gag cgc ctg caa aac gaa      288
Ile Lys Ala Lys Asn Asn Gln Ala Ala Met Glu Arg Leu Gln Asn Glu
                85                  90                  95

atc att aat acc cag ctg ttc cgt tgc ctg caa gaa atc cac ggt aaa      336
Ile Ile Asn Thr Gln Leu Phe Arg Cys Leu Gln Glu Ile His Gly Lys
            100                 105                 110

tcc tac cag gcg ttt atg ctg agc aag ctg gtg cca gtg gtt ggc aac      384
Ser Tyr Gln Ala Phe Met Leu Ser Lys Leu Val Pro Val Val Gly Asn
        115                 120                 125

att tgt gaa cat aat ctg ggt ctg gat gag gac atc tcg aac gtt att      432
Ile Cys Glu His Asn Leu Gly Leu Asp Glu Asp Ile Ser Asn Val Ile
    130                 135                 140

gca gaa gag gtc gat gtg ttc gtt aac tcc gcc gct aat acc acc ttt      480
Ala Glu Glu Val Asp Val Phe Val Asn Ser Ala Ala Asn Thr Thr Phe
145                 150                 155                 160

gat gaa cgc tat gac acc gca atc aac att aat acc atc ggc ccg tgc      528
Asp Glu Arg Tyr Asp Thr Ala Ile Asn Ile Asn Thr Ile Gly Pro Cys
                165                 170                 175

cgt ctg atg aac att gcc aaa aag tgt aaa aag ctg aaa ctg ttc ctg      576
Arg Leu Met Asn Ile Ala Lys Lys Cys Lys Lys Leu Lys Leu Phe Leu
            180                 185                 190

cac gtc agc acc gct tac gtg aat ggc cag aag caa ggt cgc atc atg      624
His Val Ser Thr Ala Tyr Val Asn Gly Gln Lys Gln Gly Arg Ile Met
        195                 200                 205

gaa cgt cca ttt tct atc ggc gag tgc att gcg cgc gaa aaa tat att      672
Glu Arg Pro Phe Ser Ile Gly Glu Cys Ile Ala Arg Glu Lys Tyr Ile
    210                 215                 220

agc gag gtt tct cct aag tac ctg ccg acc ctg gat atc gag ggc gaa      720
Ser Glu Val Ser Pro Lys Tyr Leu Pro Thr Leu Asp Ile Glu Gly Glu
225                 230                 235                 240

att aac ctg gtc tcc aat tat aaa ggt gat atc gaa gac aac ctg ctg      768
Ile Asn Leu Val Ser Asn Tyr Lys Gly Asp Ile Glu Asp Asn Leu Leu
                245                 250                 255

acc cag aaa atg aag gag att ggc ctg gaa cgc gca cgc cgt tat ggt      816
Thr Gln Lys Met Lys Glu Ile Gly Leu Glu Arg Ala Arg Arg Tyr Gly
            260                 265                 270

tgg caa gac acc tac gtg ttc acc aaa gcg atg ggc gag atg atg atc      864
Trp Gln Asp Thr Tyr Val Phe Thr Lys Ala Met Gly Glu Met Met Ile
        275                 280                 285
```

-continued

```
gat aag ctg cgc ggt gac att ccg gtc gtg gtt atg cgt cca agc gtc      912
Asp Lys Leu Arg Gly Asp Ile Pro Val Val Val Met Arg Pro Ser Val
    290                 295                 300

atc gaa tca acc ttc tcg gag ccg ttt cca ggc tgg atg gaa ggt aac      960
Ile Glu Ser Thr Phe Ser Glu Pro Phe Pro Gly Trp Met Glu Gly Asn
305                 310                 315                 320

cgc atg atg gat ccg att gtg ctg tgg tat ggc aag ggt cag ctg acc     1008
Arg Met Met Asp Pro Ile Val Leu Trp Tyr Gly Lys Gly Gln Leu Thr
                325                 330                 335

ggc ttt ctg gtt gac cct aac ggt gtc ctg gat gtc gtg ccg gcg gac     1056
Gly Phe Leu Val Asp Pro Asn Gly Val Leu Asp Val Val Pro Ala Asp
            340                 345                 350

atg gtt gtc aat gca acc ctg gcg gca atg gcc cgt cat ggc atg aac     1104
Met Val Val Asn Ala Thr Leu Ala Ala Met Ala Arg His Gly Met Asn
        355                 360                 365

cag aaa cca gat atc aat gtc tac caa att gct tcc agc gtg gtt aat     1152
Gln Lys Pro Asp Ile Asn Val Tyr Gln Ile Ala Ser Ser Val Val Asn
    370                 375                 380

cct ctg gtg ttc cag gat ctg gcg cgc ctg ctg tac gaa cac tat tct     1200
Pro Leu Val Phe Gln Asp Leu Ala Arg Leu Leu Tyr Glu His Tyr Ser
385                 390                 395                 400

tca tcg ccg tgc atc gac tca atg ggc cgt cca att cag gtt cct ctg     1248
Ser Ser Pro Cys Ile Asp Ser Met Gly Arg Pro Ile Gln Val Pro Leu
                405                 410                 415

atg aaa ttc ttt tcc agc acc gaa gag ttt tcc ggc cat ctg tgg cgc     1296
Met Lys Phe Phe Ser Ser Thr Glu Glu Phe Ser Gly His Leu Trp Arg
            420                 425                 430

gat gct atc caa aaa cgt ggt att acc gcg atg gcg tcc tcc aaa gcg     1344
Asp Ala Ile Gln Lys Arg Gly Ile Thr Ala Met Ala Ser Ser Lys Ala
        435                 440                 445

aag atg tct cag aag ctg gaa aac atg tgt cgc aaa tca gtt gag caa     1392
Lys Met Ser Gln Lys Leu Glu Asn Met Cys Arg Lys Ser Val Glu Gln
    450                 455                 460

gcg aag tat ctg gca aat atc tac gaa cca tat acc ttc tac ggc ggt     1440
Ala Lys Tyr Leu Ala Asn Ile Tyr Glu Pro Tyr Thr Phe Tyr Gly Gly
465                 470                 475                 480

cgc ttt gat aac agc aat acc cag cgt ctg atg gaa tcg atg tcc gaa     1488
Arg Phe Asp Asn Ser Asn Thr Gln Arg Leu Met Glu Ser Met Ser Glu
                485                 490                 495

gag gaa aag cgt gag ttc gat ttt gac gtc aag tct atc gat tgg aac     1536
Glu Glu Lys Arg Glu Phe Asp Phe Asp Val Lys Ser Ile Asp Trp Asn
            500                 505                 510

gac tac att acc aat gtc cat att cct ggt ctg cgt cgt cat gtg atg     1584
Asp Tyr Ile Thr Asn Val His Ile Pro Gly Leu Arg Arg His Val Met
        515                 520                 525

aaa ggt cgt ggt atg ggt agc caa                                     1608
Lys Gly Arg Gly Met Gly Ser Gln
    530                 535


<210> SEQ ID NO 16
<211> LENGTH: 536
<212> TYPE: PRT
<213> ORGANISM: Glycine max (soybean)

<400> SEQUENCE: 16

Met Asp Ala Gly Ser Leu Val Leu Ser Gln Asn Gly Lys Ser Gln Ala
1               5                   10                  15

Glu Ile Val Val Lys Asp Leu Val Pro Tyr Gly Gly Thr Thr Thr Leu
            20                  25                  30

Ile Gly Leu Glu Asp Gly Ile Gly Ile Val Lys Phe Leu Gly Gly Lys
```

```
        35                  40                  45

Lys Phe Phe Ile Thr Gly Ala Thr Gly Phe Leu Ala Lys Val Phe Ile
    50                  55                  60

Glu Lys Ile Leu Arg Thr Glu Pro Asp Val Gly Lys Met Tyr Leu Leu
65                  70                  75                  80

Ile Lys Ala Lys Asn Asn Gln Ala Ala Met Glu Arg Leu Gln Asn Glu
                85                  90                  95

Ile Ile Asn Thr Gln Leu Phe Arg Cys Leu Gln Glu Ile His Gly Lys
            100                 105                 110

Ser Tyr Gln Ala Phe Met Leu Ser Lys Leu Val Pro Val Val Gly Asn
        115                 120                 125

Ile Cys Glu His Asn Leu Gly Leu Asp Glu Asp Ile Ser Asn Val Ile
    130                 135                 140

Ala Glu Glu Val Asp Val Phe Val Asn Ser Ala Ala Asn Thr Thr Phe
145                 150                 155                 160

Asp Glu Arg Tyr Asp Thr Ala Ile Asn Ile Asn Thr Ile Gly Pro Cys
                165                 170                 175

Arg Leu Met Asn Ile Ala Lys Lys Cys Lys Lys Leu Lys Leu Phe Leu
            180                 185                 190

His Val Ser Thr Ala Tyr Val Asn Gly Gln Lys Gln Gly Arg Ile Met
        195                 200                 205

Glu Arg Pro Phe Ser Ile Gly Glu Cys Ile Ala Arg Glu Lys Tyr Ile
    210                 215                 220

Ser Glu Val Ser Pro Lys Tyr Leu Pro Thr Leu Asp Ile Glu Gly Glu
225                 230                 235                 240

Ile Asn Leu Val Ser Asn Tyr Lys Gly Asp Ile Glu Asp Asn Leu Leu
                245                 250                 255

Thr Gln Lys Met Lys Glu Ile Gly Leu Glu Arg Ala Arg Arg Tyr Gly
            260                 265                 270

Trp Gln Asp Thr Tyr Val Phe Thr Lys Ala Met Gly Glu Met Met Ile
        275                 280                 285

Asp Lys Leu Arg Gly Asp Ile Pro Val Val Val Met Arg Pro Ser Val
    290                 295                 300

Ile Glu Ser Thr Phe Ser Glu Pro Phe Pro Gly Trp Met Glu Gly Asn
305                 310                 315                 320

Arg Met Met Asp Pro Ile Val Leu Trp Tyr Gly Lys Gly Gln Leu Thr
                325                 330                 335

Gly Phe Leu Val Asp Pro Asn Gly Val Leu Asp Val Val Pro Ala Asp
            340                 345                 350

Met Val Val Asn Ala Thr Leu Ala Ala Met Ala Arg His Gly Met Asn
        355                 360                 365

Gln Lys Pro Asp Ile Asn Val Tyr Gln Ile Ala Ser Ser Val Val Asn
    370                 375                 380

Pro Leu Val Phe Gln Asp Leu Ala Arg Leu Leu Tyr Glu His Tyr Ser
385                 390                 395                 400

Ser Ser Pro Cys Ile Asp Ser Met Gly Arg Pro Ile Gln Val Pro Leu
                405                 410                 415

Met Lys Phe Phe Ser Ser Thr Glu Glu Phe Ser Gly His Leu Trp Arg
            420                 425                 430

Asp Ala Ile Gln Lys Arg Gly Ile Thr Ala Met Ala Ser Ser Lys Ala
        435                 440                 445

Lys Met Ser Gln Lys Leu Glu Asn Met Cys Arg Lys Ser Val Glu Gln
    450                 455                 460
```

-continued

```
Ala Lys Tyr Leu Ala Asn Ile Tyr Glu Pro Tyr Thr Phe Tyr Gly Gly
465                 470                 475                 480

Arg Phe Asp Asn Ser Asn Thr Gln Arg Leu Met Glu Ser Met Ser Glu
                485                 490                 495

Glu Glu Lys Arg Glu Phe Asp Phe Asp Val Lys Ser Ile Asp Trp Asn
            500                 505                 510

Asp Tyr Ile Thr Asn Val His Ile Pro Gly Leu Arg Arg His Val Met
        515                 520                 525

Lys Gly Arg Gly Met Gly Ser Gln
    530                 535


<210> SEQ ID NO 17
<211> LENGTH: 1806
<212> TYPE: DNA
<213> ORGANISM: Cicer arietinum (chickpea)
<220> FEATURE:
<221> NAME/KEY: CDS
<222> LOCATION: (1)..(1806)

<400> SEQUENCE: 17

atg ggc gtc ctg tcc ctg tcc cac tct tct tct ctg ttg acc aaa ctg       48
Met Gly Val Leu Ser Leu Ser His Ser Ser Ser Leu Leu Thr Lys Leu
1               5                   10                  15

atc ggc atc ccg gaa aat aac gac tac tgg cac cct acc aag aaa atg       96
Ile Gly Ile Pro Glu Asn Asn Asp Tyr Trp His Pro Thr Lys Lys Met
            20                  25                  30

acc acc acc aac gtg gtc ttc tgc cag ggc ggt ggc aag cgc tcc tct      144
Thr Thr Thr Asn Val Val Phe Cys Gln Gly Gly Gly Lys Arg Ser Ser
        35                  40                  45

tcc tct ctt gtg tcc gct gaa cac ggc gcg acc acc acc ctg atg gat      192
Ser Ser Leu Val Ser Ala Glu His Gly Ala Thr Thr Thr Leu Met Asp
    50                  55                  60

gct ggt tcc ctg gtc ctc tct cag aac ggc aaa tcc caa gcg gat atc      240
Ala Gly Ser Leu Val Leu Ser Gln Asn Gly Lys Ser Gln Ala Asp Ile
65                  70                  75                  80

gtt gtg aag gac ctt gtt cca tac ggt ggc cct acc tct acc acc ctt      288
Val Val Lys Asp Leu Val Pro Tyr Gly Gly Pro Thr Ser Thr Thr Leu
                85                  90                  95

att ggt ctg gaa gat gac ggt atc ggc att gtg aag ttc ctc cgc ggc      336
Ile Gly Leu Glu Asp Asp Gly Ile Gly Ile Val Lys Phe Leu Arg Gly
            100                 105                 110

aag aaa ttc ttt atc acc ggt gct acc ggc ttt ctc gcg aaa gtc ttg      384
Lys Lys Phe Phe Ile Thr Gly Ala Thr Gly Phe Leu Ala Lys Val Leu
        115                 120                 125

atc gaa aag att ctc cgt acc gag cca gat gtt ggc aag atg tac atc      432
Ile Glu Lys Ile Leu Arg Thr Glu Pro Asp Val Gly Lys Met Tyr Ile
    130                 135                 140

ttg atc aag gca aag aac aag cag gtg gca atg gaa cgc ctg caa aag      480
Leu Ile Lys Ala Lys Asn Lys Gln Val Ala Met Glu Arg Leu Gln Lys
145                 150                 155                 160

gaa atc att aat acc gag ctt ttc cgc tgc ctg cgt cag atc cac ggc      528
Glu Ile Ile Asn Thr Glu Leu Phe Arg Cys Leu Arg Gln Ile His Gly
                165                 170                 175

aaa tcc tat caa gca ttt atg ctc tct aag ttg gtt ccg atc gtg ggt      576
Lys Ser Tyr Gln Ala Phe Met Leu Ser Lys Leu Val Pro Ile Val Gly
            180                 185                 190

gat att tgt gaa acc aac ttg ggc ctt gat gag gac ctc tcc gac gtg      624
Asp Ile Cys Glu Thr Asn Leu Gly Leu Asp Glu Asp Leu Ser Asp Val
        195                 200                 205
```

-continued

```
atc gca gat gaa gtt gac gtg att gtc aac tcc gca gcc aat acc acc      672
Ile Ala Asp Glu Val Asp Val Ile Val Asn Ser Ala Ala Asn Thr Thr
    210                 215                 220

ttc gat gag cgc tac gac acc gcc atc aac att aat acc cgc ggc cct      720
Phe Asp Glu Arg Tyr Asp Thr Ala Ile Asn Ile Asn Thr Arg Gly Pro
225                 230                 235                 240

tcc cgt ttg atg gca atc gcc aag aaa tgc aag aaa ctg aag ctc ttc      768
Ser Arg Leu Met Ala Ile Ala Lys Lys Cys Lys Lys Leu Lys Leu Phe
                245                 250                 255

ttg cac gtc tcc acc gct tat gtt aac ggt cag cgc caa ggc cgt atc      816
Leu His Val Ser Thr Ala Tyr Val Asn Gly Gln Arg Gln Gly Arg Ile
            260                 265                 270

atg gaa cgc ccg ttt tcc atc ggt gat tgt att gcg cgt gag aaa ctg      864
Met Glu Arg Pro Phe Ser Ile Gly Asp Cys Ile Ala Arg Glu Lys Leu
        275                 280                 285

atc tct ggc gtg cca cct aag tac ctt ccc acc ctg gac atc gag aac      912
Ile Ser Gly Val Pro Pro Lys Tyr Leu Pro Thr Leu Asp Ile Glu Asn
    290                 295                 300

gaa att aat atg gtc ctc aaa aac aag ggc aac aat atc gaa gag aat      960
Glu Ile Asn Met Val Leu Lys Asn Lys Gly Asn Asn Ile Glu Glu Asn
305                 310                 315                 320

ctg ctc gca cag aaa atg cgc gag atg ggt ttg gaa cgc gcc aag cgt     1008
Leu Leu Ala Gln Lys Met Arg Glu Met Gly Leu Glu Arg Ala Lys Arg
                325                 330                 335

tat ggc tgg caa gat acc tac gtc ttc acc aaa gca atg ggc gaa atg     1056
Tyr Gly Trp Gln Asp Thr Tyr Val Phe Thr Lys Ala Met Gly Glu Met
            340                 345                 350

atg atc gac aag ctt cgc gat gac att cca gtc gtt atc att cgt cct     1104
Met Ile Asp Lys Leu Arg Asp Asp Ile Pro Val Val Ile Ile Arg Pro
        355                 360                 365

tcc gtt atc gaa tcc acc ctg tct gag ccg ttc ccc ggt tgg atg gag     1152
Ser Val Ile Glu Ser Thr Leu Ser Glu Pro Phe Pro Gly Trp Met Glu
    370                 375                 380

ggc aac cgc atg atg gat cca gtg gtc ctc tgc tat ggc aag ggc cag     1200
Gly Asn Arg Met Met Asp Pro Val Val Leu Cys Tyr Gly Lys Gly Gln
385                 390                 395                 400

ctc acc ggt ttc ttg gtg gac ccg aac ggc gtc ctt gat gtt gtg ccc     1248
Leu Thr Gly Phe Leu Val Asp Pro Asn Gly Val Leu Asp Val Val Pro
                405                 410                 415

gct gac atg gtc gtt aat gcg acc ctg gct gcg atg gca aaa cac ggc     1296
Ala Asp Met Val Val Asn Ala Thr Leu Ala Ala Met Ala Lys His Gly
            420                 425                 430

atg acc cag aag gcc gat atc aac gtg tac caa att gct tcc tct gtg     1344
Met Thr Gln Lys Ala Asp Ile Asn Val Tyr Gln Ile Ala Ser Ser Val
        435                 440                 445

gtc aat cca ctt gcg ttc cag gat ctg acc cgc ttg ctt tac gaa cac     1392
Val Asn Pro Leu Ala Phe Gln Asp Leu Thr Arg Leu Leu Tyr Glu His
    450                 455                 460

tat tcc tct tcc cct ttt atc gac tcc aaa ggt cgt ccg atc caa gtt     1440
Tyr Ser Ser Ser Pro Phe Ile Asp Ser Lys Gly Arg Pro Ile Gln Val
465                 470                 475                 480

ccc att atg aag ctg ttc tct tcc tct gaa gag ttt tcc ggc cac ctc     1488
Pro Ile Met Lys Leu Phe Ser Ser Ser Glu Glu Phe Ser Gly His Leu
                485                 490                 495

tgg cgc gat gtg atc aac aag tcc ggt ttg acc tct atg gca tcc tct     1536
Trp Arg Asp Val Ile Asn Lys Ser Gly Leu Thr Ser Met Ala Ser Ser
            500                 505                 510

aaa ggc aag atg tcc cag aaa ctc gaa aac atc tgt cgc aag tct gtg     1584
Lys Gly Lys Met Ser Gln Lys Leu Glu Asn Ile Cys Arg Lys Ser Val
        515                 520                 525
```

```
gag caa gca aaa tac ttg gcc aag att tac gaa cca tat acc ttc tac     1632
Glu Gln Ala Lys Tyr Leu Ala Lys Ile Tyr Glu Pro Tyr Thr Phe Tyr
    530                 535                 540

ggt ggc cgc ttt gac aac tcc aat acc cag cgt ttg atg gaa atc atg     1680
Gly Gly Arg Phe Asp Asn Ser Asn Thr Gln Arg Leu Met Glu Ile Met
545                 550                 555                 560

tct gaa gag gaa aaa acc gag ttc gat ttt gac gtc aag ggt att gat     1728
Ser Glu Glu Glu Lys Thr Glu Phe Asp Phe Asp Val Lys Gly Ile Asp
                565                 570                 575

tgg acc gac tat atc acc aac gtt cac att cct ggc ctg cgc cgt tac     1776
Trp Thr Asp Tyr Ile Thr Asn Val His Ile Pro Gly Leu Arg Arg Tyr
            580                 585                 590

gtg atg aag ggt cgc ggc atg tcc aat cag                             1806
Val Met Lys Gly Arg Gly Met Ser Asn Gln
        595                 600


<210> SEQ ID NO 18
<211> LENGTH: 602
<212> TYPE: PRT
<213> ORGANISM: Cicer arietinum (chickpea)

<400> SEQUENCE: 18

Met Gly Val Leu Ser Leu Ser His Ser Ser Ser Leu Leu Thr Lys Leu
1               5                   10                  15

Ile Gly Ile Pro Glu Asn Asn Asp Tyr Trp His Pro Thr Lys Lys Met
            20                  25                  30

Thr Thr Thr Asn Val Val Phe Cys Gln Gly Gly Gly Lys Arg Ser Ser
        35                  40                  45

Ser Ser Leu Val Ser Ala Glu His Gly Ala Thr Thr Thr Leu Met Asp
    50                  55                  60

Ala Gly Ser Leu Val Leu Ser Gln Asn Gly Lys Ser Gln Ala Asp Ile
65                  70                  75                  80

Val Val Lys Asp Leu Val Pro Tyr Gly Gly Pro Thr Ser Thr Thr Leu
                85                  90                  95

Ile Gly Leu Glu Asp Asp Gly Ile Gly Ile Val Lys Phe Leu Arg Gly
            100                 105                 110

Lys Lys Phe Phe Ile Thr Gly Ala Thr Gly Phe Leu Ala Lys Val Leu
        115                 120                 125

Ile Glu Lys Ile Leu Arg Thr Glu Pro Asp Val Gly Lys Met Tyr Ile
    130                 135                 140

Leu Ile Lys Ala Lys Asn Lys Gln Val Ala Met Glu Arg Leu Gln Lys
145                 150                 155                 160

Glu Ile Ile Asn Thr Glu Leu Phe Arg Cys Leu Arg Gln Ile His Gly
                165                 170                 175

Lys Ser Tyr Gln Ala Phe Met Leu Ser Lys Leu Val Pro Ile Val Gly
            180                 185                 190

Asp Ile Cys Glu Thr Asn Leu Gly Leu Asp Glu Asp Leu Ser Asp Val
        195                 200                 205

Ile Ala Asp Glu Val Asp Val Ile Val Asn Ser Ala Ala Asn Thr Thr
    210                 215                 220

Phe Asp Glu Arg Tyr Asp Thr Ala Ile Asn Ile Asn Thr Arg Gly Pro
225                 230                 235                 240

Ser Arg Leu Met Ala Ile Ala Lys Lys Cys Lys Lys Leu Lys Leu Phe
                245                 250                 255

Leu His Val Ser Thr Ala Tyr Val Asn Gly Gln Arg Gln Gly Arg Ile
            260                 265                 270
```

-continued

Met Glu Arg Pro Phe Ser Ile Gly Asp Cys Ile Ala Arg Glu Lys Leu
275 280 285

Ile Ser Gly Val Pro Pro Lys Tyr Leu Pro Thr Leu Asp Ile Glu Asn
290 295 300

Glu Ile Asn Met Val Leu Lys Asn Lys Gly Asn Asn Ile Glu Glu Asn
305 310 315 320

Leu Leu Ala Gln Lys Met Arg Glu Met Gly Leu Glu Arg Ala Lys Arg
325 330 335

Tyr Gly Trp Gln Asp Thr Tyr Val Phe Thr Lys Ala Met Gly Glu Met
340 345 350

Met Ile Asp Lys Leu Arg Asp Asp Ile Pro Val Val Ile Ile Arg Pro
355 360 365

Ser Val Ile Glu Ser Thr Leu Ser Glu Pro Phe Pro Gly Trp Met Glu
370 375 380

Gly Asn Arg Met Met Asp Pro Val Val Leu Cys Tyr Gly Lys Gly Gln
385 390 395 400

Leu Thr Gly Phe Leu Val Asp Pro Asn Gly Val Leu Asp Val Val Pro
405 410 415

Ala Asp Met Val Val Asn Ala Thr Leu Ala Ala Met Ala Lys His Gly
420 425 430

Met Thr Gln Lys Ala Asp Ile Asn Val Tyr Gln Ile Ala Ser Ser Val
435 440 445

Val Asn Pro Leu Ala Phe Gln Asp Leu Thr Arg Leu Leu Tyr Glu His
450 455 460

Tyr Ser Ser Ser Pro Phe Ile Asp Ser Lys Gly Arg Pro Ile Gln Val
465 470 475 480

Pro Ile Met Lys Leu Phe Ser Ser Ser Glu Glu Phe Ser Gly His Leu
485 490 495

Trp Arg Asp Val Ile Asn Lys Ser Gly Leu Thr Ser Met Ala Ser Ser
500 505 510

Lys Gly Lys Met Ser Gln Lys Leu Glu Asn Ile Cys Arg Lys Ser Val
515 520 525

Glu Gln Ala Lys Tyr Leu Ala Lys Ile Tyr Glu Pro Tyr Thr Phe Tyr
530 535 540

Gly Gly Arg Phe Asp Asn Ser Asn Thr Gln Arg Leu Met Glu Ile Met
545 550 555 560

Ser Glu Glu Glu Lys Thr Glu Phe Asp Phe Asp Val Lys Gly Ile Asp
565 570 575

Trp Thr Asp Tyr Ile Thr Asn Val His Ile Pro Gly Leu Arg Arg Tyr
580 585 590

Val Met Lys Gly Arg Gly Met Ser Asn Gln
595 600

<210> SEQ ID NO 19
<211> LENGTH: 113
<212> TYPE: DNA
<213> ORGANISM: Artificial Sequence
<220> FEATURE:
<223> OTHER INFORMATION: Synthetic DNA

<400> SEQUENCE: 19
taattaacct aggctgctgc caccgctgag caataactag cataacccct tggggcctct 60
aaacgggtct tgaggggttt tttgccctcg agtccggccg catgcggccg cat 113

<210> SEQ ID NO 20
<211> LENGTH: 591
<212> TYPE: PRT
<213> ORGANISM: Fragaria vesca (woodland strawberry)

<400> SEQUENCE: 20

```
Met Glu Ala Ser Leu Leu Asn Ser Phe Ser Ser Thr Ile Asn Pro Pro
1               5                   10                  15

Asn Lys Leu Ala Ile Phe Ser Glu Lys Trp Asp Trp Cys Leu Leu Arg
            20                  25                  30

Arg Lys Lys Ser Ser Leu Ala Val Cys Gln Gly Ala Ser Ser Gly Gly
        35                  40                  45

Asn Ala Lys Lys Ile Ser Gly Phe Ser Ser Ala Ala Thr Leu Met Asp
    50                  55                  60

Ala Gly Ser Leu Val Leu Ser Pro Asn Asp Gln Lys Val Lys Lys Glu
65                  70                  75                  80

Asn Asn Thr Ala Val Lys Glu Leu Val Pro Phe Val Glu Met His Asp
                85                  90                  95

Gly Ile Gly Ile Val Lys Phe Leu Arg Gly Lys Gly Phe Phe Ile Thr
            100                 105                 110

Gly Gly Thr Gly Phe Leu Ala Lys Val Leu Ile Glu Lys Ile Leu Arg
        115                 120                 125

Thr Ala Pro Asp Val Gly Lys Ile Tyr Leu Leu Ile Lys Ala Lys Thr
    130                 135                 140

Lys Glu Ala Ala Met Glu Arg Leu Asn Thr Glu Ile Ile Asn Thr Glu
145                 150                 155                 160

Leu Phe Lys Gly Leu Arg Gln Thr Tyr Gly Lys Ser Tyr Gln Ala Phe
                165                 170                 175

Met Leu Ser Lys Leu Val Pro Val Val Gly Asn Val Cys Asp Ser Asp
            180                 185                 190

Leu Gly Leu Gly Asp Asp Val Ala Ala Leu Ile Ala Lys Glu Val Asp
        195                 200                 205

Val Val Ile Asn Ser Ala Ala Asn Thr Thr Phe His Glu Arg Tyr Asp
    210                 215                 220

Val Ala Leu Asp Ile Asn Thr Lys Gly Pro Cys Asn Leu Met Ala Phe
225                 230                 235                 240

Ala Lys Lys Cys Lys Lys Leu Lys Leu Phe Leu Gln Val Ser Thr Ala
                245                 250                 255

Tyr Val Asn Gly Gln Arg Gln Gly Arg Ile Met Glu Lys Pro Phe Cys
            260                 265                 270

Ile Gly Glu Ser Ile Ile Gly Glu Asn Ser Thr Ser Glu Thr Pro Pro
        275                 280                 285

Gly Phe Glu Ser Leu Asp Val Glu Asn Glu Met Lys Leu Ala Met Asn
    290                 295                 300

Ser Lys Gly Ala Tyr Glu Asp Asn Glu Val Ser Gln Lys Met Lys Asp
305                 310                 315                 320

Leu Gly Leu Glu Arg Ala Arg Lys Tyr Gly Trp Gln Asp Thr Tyr Val
                325                 330                 335

Phe Thr Lys Ala Met Gly Glu Met Val Ile Asp Asp Met Arg Gly Asp
            340                 345                 350

Leu Pro Val Val Ile Ile Arg Pro Ser Val Ile Glu Ser Thr Cys Lys
        355                 360                 365

Glu Pro Phe Pro Gly Trp Met Glu Gly Asn Arg Met Met Asp Pro Ile
    370                 375                 380
```

Val Leu Tyr Tyr Gly Lys Gly Gln Leu Thr Gly Phe Leu Val Asp Pro
385 390 395 400

Asn Gly Val Leu Asp Val Val Pro Ala Asp Met Val Val Asn Ala Thr
405 410 415

Leu Ala Ala Ile Ala Lys His Gly Met Ala Gln Lys Pro Asp Ile Asn
420 425 430

Val Tyr Gln Ile Thr Ser Ser Val Val Asn Pro Leu Asp Phe Gln Asp
435 440 445

Leu Ser Lys Leu Leu Tyr Glu His Tyr Asn Ser Ser Pro Cys Met Asp
450 455 460

Ser Lys Gly Arg Pro Ile Asn Val Pro Ser Met Lys Leu Phe Ser Ser
465 470 475 480

Met Glu Asp Phe Ser Asp His Ile Trp Arg Asp Ala Thr Gln Arg Ser
485 490 495

Gly Leu Thr Ala Leu Ala Ser Ser Asn Gly Lys Leu Ser Gln Lys Leu
500 505 510

Glu Thr Met Cys Arg Lys Ser Val Glu Gln Ala Lys Tyr Leu Ala Ser
515 520 525

Ile Tyr Glu Pro Tyr Thr Phe Tyr Gly Gly Arg Phe Asp Asn Ser Asn
530 535 540

Thr Glu Arg Leu Met Asp Ser Met Ser Glu Glu Glu Arg Lys Lys Phe
545 550 555 560

Gly Phe Asp Val Gly Ser Leu Asp Trp Lys Asp Tyr Ile Thr Asn Val
565 570 575

His Ile Pro Gly Leu Lys Arg His Val Leu Lys Gly Arg Gly Val
580 585 590

<210> SEQ ID NO 21
<211> LENGTH: 1830
<212> TYPE: DNA
<213> ORGANISM: Populus trichocarpa (black cottonwood)
<220> FEATURE:
<221> NAME/KEY: CDS
<222> LOCATION: (1)..(1830)

<400> SEQUENCE: 21 atg ggt agc atg ttt ctg aac tcc cct ctg cct gcg tct aat aaa ctg 48
Met Gly Ser Met Phe Leu Asn Ser Pro Leu Pro Ala Ser Asn Lys Leu
1 5 10 15 atc cgt gtt tcg tct aag tgc gac tgg tgc ttt ctg cgt tgg cgc aaa 96
Ile Arg Val Ser Ser Lys Cys Asp Trp Cys Phe Leu Arg Trp Arg Lys
20 25 30 cgt aac gtg gtt gtc tat tgc cag ggc ggt ggc ggt aaa gct atc cgc 144
Arg Asn Val Val Val Tyr Cys Gln Gly Gly Gly Gly Lys Ala Ile Arg
35 40 45 tcc agc ggc ttt ccg agc gtg ctg acc gaa cgt tcc gcg gtg gtt agc 192
Ser Ser Gly Phe Pro Ser Val Leu Thr Glu Arg Ser Ala Val Val Ser
50 55 60 gac cag gag cac atc gcc tcc gtt cgc gat gct ggc tct ctg gtc ctg 240
Asp Gln Glu His Ile Ala Ser Val Arg Asp Ala Gly Ser Leu Val Leu
65 70 75 80 tca cct aac gaa aaa ggt caa ccg gaa att gcg gtc gag gac ttc gtg 288
Ser Pro Asn Glu Lys Gly Gln Pro Glu Ile Ala Val Glu Asp Phe Val
85 90 95 cct tac ggc ggt ccg acc tct tca tcg ctg ctg gag atg cag gat ggc 336
Pro Tyr Gly Gly Pro Thr Ser Ser Ser Leu Leu Glu Met Gln Asp Gly
100 105 110 atc ggt att gtc aaa ttc ctg cgc ggc aag ggt ctg ttt atc agc ggc 384

-continued

```
Ile Gly Ile Val Lys Phe Leu Arg Gly Lys Gly Leu Phe Ile Ser Gly
        115                 120                 125

gcg acc ggt ttc ctg gca aaa gtg ctg atc gaa aag att ctg cgt acc      432
Ala Thr Gly Phe Leu Ala Lys Val Leu Ile Glu Lys Ile Leu Arg Thr
    130                 135                 140

atg ccg gat gtc ggc aaa atc tat gtg ctg att aaa gcg gaa tcc aaa      480
Met Pro Asp Val Gly Lys Ile Tyr Val Leu Ile Lys Ala Glu Ser Lys
145                 150                 155                 160

gaa gcg gca att acc cgc ctg aag aac gaa atc att aat gca gag ctg      528
Glu Ala Ala Ile Thr Arg Leu Lys Asn Glu Ile Ile Asn Ala Glu Leu
                165                 170                 175

ttt aaa tgc ctg cgt cag acc cac ggc aag tca tac caa tcg ttc atg      576
Phe Lys Cys Leu Arg Gln Thr His Gly Lys Ser Tyr Gln Ser Phe Met
            180                 185                 190

ctg aac aaa ctg gtc cca gtc gtg ggc aac gtg tgt gaa agc aat ctg      624
Leu Asn Lys Leu Val Pro Val Val Gly Asn Val Cys Glu Ser Asn Leu
        195                 200                 205

ggt ctg gaa gag gat ctg gcc gac aag atc gct aac gaa gtt gat atc      672
Gly Leu Glu Glu Asp Leu Ala Asp Lys Ile Ala Asn Glu Val Asp Ile
    210                 215                 220

att gtc aac tcc gcc gct aat acc acc ttt gat gag cgc tat gac gtg      720
Ile Val Asn Ser Ala Ala Asn Thr Thr Phe Asp Glu Arg Tyr Asp Val
225                 230                 235                 240

gca att gat gtt aat acc cgt ggc acc tgc cac ctg atg tca ttt gcc      768
Ala Ile Asp Val Asn Thr Arg Gly Thr Cys His Leu Met Ser Phe Ala
                245                 250                 255

aaa aag tgt cca aaa ctg aag ctg ttc ctg cag gtt tct acc gct tac      816
Lys Lys Cys Pro Lys Leu Lys Leu Phe Leu Gln Val Ser Thr Ala Tyr
            260                 265                 270

gtc aac ggc cag cgc caa ggt cgt atc atg gaa aaa cct ttc ctg ttt      864
Val Asn Gly Gln Arg Gln Gly Arg Ile Met Glu Lys Pro Phe Leu Phe
        275                 280                 285

ggt gac tgc att gcc cgc gaa aat ctg atc att agc gag tct acc cca      912
Gly Asp Cys Ile Ala Arg Glu Asn Leu Ile Ile Ser Glu Ser Thr Pro
    290                 295                 300

cgt ttt gcc cct gct ctg gac atc gaa cat gag atg aac ctg gcc ctg      960
Arg Phe Ala Pro Ala Leu Asp Ile Glu His Glu Met Asn Leu Ala Leu
305                 310                 315                 320

gat agc aaa gaa gct ttc cag gaa aat gag gtt gct caa aaa atg aag     1008
Asp Ser Lys Glu Ala Phe Gln Glu Asn Glu Val Ala Gln Lys Met Lys
                325                 330                 335

gaa ctg ggc ctg gag cgc gcg cgt aaa tat ggt tgg cag gat acc tac     1056
Glu Leu Gly Leu Glu Arg Ala Arg Lys Tyr Gly Trp Gln Asp Thr Tyr
            340                 345                 350

gtg ttt acc aag gct atg ggc gaa atg gtt gtc gac aac atg cgc ggt     1104
Val Phe Thr Lys Ala Met Gly Glu Met Val Val Asp Asn Met Arg Gly
        355                 360                 365

gat atc cca gtg gtt atc att cgt cct tcg gtt att gaa tcc acc tgt     1152
Asp Ile Pro Val Val Ile Ile Arg Pro Ser Val Ile Glu Ser Thr Cys
    370                 375                 380

aaa gag ccg ttt cca ggc tgg atg gaa ggt aat cgc atg atg gac cca     1200
Lys Glu Pro Phe Pro Gly Trp Met Glu Gly Asn Arg Met Met Asp Pro
385                 390                 395                 400

atc gtg ctg tac tat ggc aag ggt caa ctg acc ggc ttc ctg gtg gat     1248
Ile Val Leu Tyr Tyr Gly Lys Gly Gln Leu Thr Gly Phe Leu Val Asp
                405                 410                 415

ccg aac ggt gtt ctg gac gtc gtg cca gcg gat atg gtt gtc aat gca     1296
Pro Asn Gly Val Leu Asp Val Val Pro Ala Asp Met Val Val Asn Ala
            420                 425                 430
```

-continued

```
acc ctg gct gca atg gcc tgg cac ggt atg gaa cag aaa cct gat atc      1344
Thr Leu Ala Ala Met Ala Trp His Gly Met Glu Gln Lys Pro Asp Ile
        435                 440                 445

aac gtg tat caa att gca tcc agc gtg gtt aat ccg ctg gtt ttc cag      1392
Asn Val Tyr Gln Ile Ala Ser Ser Val Val Asn Pro Leu Val Phe Gln
    450                 455                 460

gac ctg gcc acc ctg ctg cac gaa cat tat aac tct tca ccg tac atg      1440
Asp Leu Ala Thr Leu Leu His Glu His Tyr Asn Ser Ser Pro Tyr Met
465                 470                 475                 480

gat tca aat ggc cgc ccg att cac gtt cca tcg atg aaa ctg ttc tcc      1488
Asp Ser Asn Gly Arg Pro Ile His Val Pro Ser Met Lys Leu Phe Ser
                485                 490                 495

agc atg gaa gag ttt tcg gca cat ctg tgg cgt tat gtc acc caa cgc      1536
Ser Met Glu Glu Phe Ser Ala His Leu Trp Arg Tyr Val Thr Gln Arg
            500                 505                 510

tct cgt ctg gcg ggt atg gca acc agc gat cgc aaa ctg tct cag aag      1584
Ser Arg Leu Ala Gly Met Ala Thr Ser Asp Arg Lys Leu Ser Gln Lys
        515                 520                 525

cat gaa aac atc tgt cgt aaa tcc gtg gag caa gcg aag tac ctg gca      1632
His Glu Asn Ile Cys Arg Lys Ser Val Glu Gln Ala Lys Tyr Leu Ala
    530                 535                 540

agc att tac gaa cca tat acc ttc tac ggc ggt cgc ttt gac aac tct      1680
Ser Ile Tyr Glu Pro Tyr Thr Phe Tyr Gly Gly Arg Phe Asp Asn Ser
545                 550                 555                 560

aat acc cag aaa ctg atg gag cgt atg tca gaa aat gag aag ggc att      1728
Asn Thr Gln Lys Leu Met Glu Arg Met Ser Glu Asn Glu Lys Gly Ile
                565                 570                 575

ttc ggt ttt gat gtg ggc tcc atc gat tgg cgc gac tac att acc aat      1776
Phe Gly Phe Asp Val Gly Ser Ile Asp Trp Arg Asp Tyr Ile Thr Asn
            580                 585                 590

gtc cat att cca ggt ctg cgt cgt cac gtg atg aaa ggt cgt ggc atg      1824
Val His Ile Pro Gly Leu Arg Arg His Val Met Lys Gly Arg Gly Met
        595                 600                 605

tgt ggc                                                               1830
Cys Gly
    610


<210> SEQ ID NO 22
<211> LENGTH: 610
<212> TYPE: PRT
<213> ORGANISM: Populus trichocarpa (black cottonwood)

<400> SEQUENCE: 22

Met Gly Ser Met Phe Leu Asn Ser Pro Leu Pro Ala Ser Asn Lys Leu
1               5                   10                  15

Ile Arg Val Ser Ser Lys Cys Asp Trp Cys Phe Leu Arg Trp Arg Lys
            20                  25                  30

Arg Asn Val Val Val Tyr Cys Gln Gly Gly Gly Gly Lys Ala Ile Arg
        35                  40                  45

Ser Ser Gly Phe Pro Ser Val Leu Thr Glu Arg Ser Ala Val Val Ser
    50                  55                  60

Asp Gln Glu His Ile Ala Ser Val Arg Asp Ala Gly Ser Leu Val Leu
65                  70                  75                  80

Ser Pro Asn Glu Lys Gly Gln Pro Glu Ile Ala Val Glu Asp Phe Val
                85                  90                  95

Pro Tyr Gly Gly Pro Thr Ser Ser Ser Leu Leu Glu Met Gln Asp Gly
            100                 105                 110

Ile Gly Ile Val Lys Phe Leu Arg Gly Lys Gly Leu Phe Ile Ser Gly
        115                 120                 125
```

-continued

```
Ala Thr Gly Phe Leu Ala Lys Val Leu Ile Glu Lys Ile Leu Arg Thr
    130                 135                 140

Met Pro Asp Val Gly Lys Ile Tyr Val Leu Ile Lys Ala Glu Ser Lys
145                 150                 155                 160

Glu Ala Ala Ile Thr Arg Leu Lys Asn Glu Ile Ile Asn Ala Glu Leu
                165                 170                 175

Phe Lys Cys Leu Arg Gln Thr His Gly Lys Ser Tyr Gln Ser Phe Met
            180                 185                 190

Leu Asn Lys Leu Val Pro Val Val Gly Asn Val Cys Glu Ser Asn Leu
        195                 200                 205

Gly Leu Glu Glu Asp Leu Ala Asp Lys Ile Ala Asn Glu Val Asp Ile
    210                 215                 220

Ile Val Asn Ser Ala Ala Asn Thr Thr Phe Asp Glu Arg Tyr Asp Val
225                 230                 235                 240

Ala Ile Asp Val Asn Thr Arg Gly Thr Cys His Leu Met Ser Phe Ala
                245                 250                 255

Lys Lys Cys Pro Lys Leu Lys Leu Phe Leu Gln Val Ser Thr Ala Tyr
            260                 265                 270

Val Asn Gly Gln Arg Gln Gly Arg Ile Met Glu Lys Pro Phe Leu Phe
        275                 280                 285

Gly Asp Cys Ile Ala Arg Glu Asn Leu Ile Ile Ser Glu Ser Thr Pro
    290                 295                 300

Arg Phe Ala Pro Ala Leu Asp Ile Glu His Glu Met Asn Leu Ala Leu
305                 310                 315                 320

Asp Ser Lys Glu Ala Phe Gln Glu Asn Glu Val Ala Gln Lys Met Lys
                325                 330                 335

Glu Leu Gly Leu Glu Arg Ala Arg Lys Tyr Gly Trp Gln Asp Thr Tyr
            340                 345                 350

Val Phe Thr Lys Ala Met Gly Glu Met Val Val Asp Asn Met Arg Gly
        355                 360                 365

Asp Ile Pro Val Val Ile Ile Arg Pro Ser Val Ile Glu Ser Thr Cys
    370                 375                 380

Lys Glu Pro Phe Pro Gly Trp Met Glu Gly Asn Arg Met Met Asp Pro
385                 390                 395                 400

Ile Val Leu Tyr Tyr Gly Lys Gly Gln Leu Thr Gly Phe Leu Val Asp
                405                 410                 415

Pro Asn Gly Val Leu Asp Val Val Pro Ala Asp Met Val Val Asn Ala
            420                 425                 430

Thr Leu Ala Ala Met Ala Trp His Gly Met Glu Gln Lys Pro Asp Ile
        435                 440                 445

Asn Val Tyr Gln Ile Ala Ser Ser Val Val Asn Pro Leu Val Phe Gln
    450                 455                 460

Asp Leu Ala Thr Leu Leu His Glu His Tyr Asn Ser Ser Pro Tyr Met
465                 470                 475                 480

Asp Ser Asn Gly Arg Pro Ile His Val Pro Ser Met Lys Leu Phe Ser
                485                 490                 495

Ser Met Glu Glu Phe Ser Ala His Leu Trp Arg Tyr Val Thr Gln Arg
            500                 505                 510

Ser Arg Leu Ala Gly Met Ala Thr Ser Asp Arg Lys Leu Ser Gln Lys
        515                 520                 525

His Glu Asn Ile Cys Arg Lys Ser Val Glu Gln Ala Lys Tyr Leu Ala
    530                 535                 540
```

-continued

```
Ser Ile Tyr Glu Pro Tyr Thr Phe Tyr Gly Gly Arg Phe Asp Asn Ser
545                 550                 555                 560

Asn Thr Gln Lys Leu Met Glu Arg Met Ser Glu Asn Glu Lys Gly Ile
                565                 570                 575

Phe Gly Phe Asp Val Gly Ser Ile Asp Trp Arg Asp Tyr Ile Thr Asn
            580                 585                 590

Val His Ile Pro Gly Leu Arg Arg His Val Met Lys Gly Arg Gly Met
        595                 600                 605

Cys Gly
    610


<210> SEQ ID NO 23
<211> LENGTH: 1752
<212> TYPE: DNA
<213> ORGANISM: Vitis vinifera (wine grape)
<220> FEATURE:
<221> NAME/KEY: CDS
<222> LOCATION: (1)..(1752)

<400> SEQUENCE: 23

atg ggc gca ctg ttc ttt tcg tcc ccg tct ttc gca acc aag cgt gtc       48
Met Gly Ala Leu Phe Phe Ser Ser Pro Ser Phe Ala Thr Lys Arg Val
1               5                   10                  15

gtg aag ttt agc ggc tgg tgt gat cat ctg aag cgt cgt aaa agc gtg       96
Val Lys Phe Ser Gly Trp Cys Asp His Leu Lys Arg Arg Lys Ser Val
            20                  25                  30

gtt cac tgc cag acc tct ggc aac ggt gtg cgt tcc agc ggt gtg tct      144
Val His Cys Gln Thr Ser Gly Asn Gly Val Arg Ser Ser Gly Val Ser
        35                  40                  45

tca gtt ctg agc gaa cgc tct atg ctg gct tct aaa gac cat tca gcg      192
Ser Val Leu Ser Glu Arg Ser Met Leu Ala Ser Lys Asp His Ser Ala
    50                  55                  60

ggc tcg ctg gtg ctg tcc ccg aat ggc aag gat ctg gtt ccg tac ggc      240
Gly Ser Leu Val Leu Ser Pro Asn Gly Lys Asp Leu Val Pro Tyr Gly
65                  70                  75                  80

ccg ccg tcg cct tcc acc acc cca ttc gtg gaa atg aac gac ggc atc      288
Pro Pro Ser Pro Ser Thr Thr Pro Phe Val Glu Met Asn Asp Gly Ile
                85                  90                  95

ggt att gat aat ttc ctg cgt ggt aaa tcc ttt ctg att acc ggc gct      336
Gly Ile Asp Asn Phe Leu Arg Gly Lys Ser Phe Leu Ile Thr Gly Ala
            100                 105                 110

acc ggt ttt ctg gcg aaa gtt ctg att gaa aag atc ctg cgc acc gag      384
Thr Gly Phe Leu Ala Lys Val Leu Ile Glu Lys Ile Leu Arg Thr Glu
        115                 120                 125

ccg gat gtc ggc aaa att tac ctg ctg atc aaa gct aag aac caa gag      432
Pro Asp Val Gly Lys Ile Tyr Leu Leu Ile Lys Ala Lys Asn Gln Glu
    130                 135                 140

gcg gca atg gaa cgt ctg aag aac gag atc att aat gcg gaa gtc ttc      480
Ala Ala Met Glu Arg Leu Lys Asn Glu Ile Ile Asn Ala Glu Val Phe
145                 150                 155                 160

gac tgc ctg cag caa gcg tat ggc aaa tca tac cag gca ttt atg ctg      528
Asp Cys Leu Gln Gln Ala Tyr Gly Lys Ser Tyr Gln Ala Phe Met Leu
                165                 170                 175

tcg aag ctg gtt ccg gtc gca ggc gat gtg tgt ggt tcg tcc ctg ggc      576
Ser Lys Leu Val Pro Val Ala Gly Asp Val Cys Gly Ser Ser Leu Gly
            180                 185                 190

ctg gag aaa gac ttc gcc gaa gct att gcg aaa gaa gtg gat gtt atc      624
Leu Glu Lys Asp Phe Ala Glu Ala Ile Ala Lys Glu Val Asp Val Ile
        195                 200                 205

gtc aac agc gcc gct aat acc acc ttt gat gaa cgc tat gac atc gcg      672
```

-continued

```
Val Asn Ser Ala Ala Asn Thr Thr Phe Asp Glu Arg Tyr Asp Ile Ala
    210                 215                 220

att gat atc aac acc aaa ggc cca tgc cac ctg atg aac ttc gca aag      720
Ile Asp Ile Asn Thr Lys Gly Pro Cys His Leu Met Asn Phe Ala Lys
225                 230                 235                 240

aac tgt aag aag ctg aag ctg ttt ctg cag gtc tcc acc gcc tac gtg      768
Asn Cys Lys Lys Leu Lys Leu Phe Leu Gln Val Ser Thr Ala Tyr Val
                245                 250                 255

aat ggt cag cgc caa ggc cgt att atg gaa aaa ccg ttc tgt att ggt      816
Asn Gly Gln Arg Gln Gly Arg Ile Met Glu Lys Pro Phe Cys Ile Gly
            260                 265                 270

gat agc atc gcg cgt gaa tcc aac atc agc gag gca ccg ccg cgt ctg      864
Asp Ser Ile Ala Arg Glu Ser Asn Ile Ser Glu Ala Pro Pro Arg Leu
        275                 280                 285

ctg cca acc ctg aat att gag gca gaa atc aag ctg gcc ctg gat tcc      912
Leu Pro Thr Leu Asn Ile Glu Ala Glu Ile Lys Leu Ala Leu Asp Ser
    290                 295                 300

aaa gaa gcc ttc aag ggc agc acc ctg gct cag aaa atg aag gag ctg      960
Lys Glu Ala Phe Lys Gly Ser Thr Leu Ala Gln Lys Met Lys Glu Leu
305                 310                 315                 320

ggt ctg gaa cgt gcc aaa aag cat ggc tgg caa gac acc tat gtc ttt     1008
Gly Leu Glu Arg Ala Lys Lys His Gly Trp Gln Asp Thr Tyr Val Phe
                325                 330                 335

acc aaa gct atg ggt gaa atg gtg att gat cag atg cgc ggc gag atc     1056
Thr Lys Ala Met Gly Glu Met Val Ile Asp Gln Met Arg Gly Glu Ile
            340                 345                 350

cca gtc gtg atc att cgt cct tcg gtg att gaa tcc acc tgc cgc gag     1104
Pro Val Val Ile Ile Arg Pro Ser Val Ile Glu Ser Thr Cys Arg Glu
        355                 360                 365

cca ttc cct ggt tgg atg gaa ggc aac cgc atg atg gac ccg atc gtt     1152
Pro Phe Pro Gly Trp Met Glu Gly Asn Arg Met Met Asp Pro Ile Val
    370                 375                 380

ctg tac tat ggc aag ggt cag ctg acc ggt ttt gtt gcc gat cct aac     1200
Leu Tyr Tyr Gly Lys Gly Gln Leu Thr Gly Phe Val Ala Asp Pro Asn
385                 390                 395                 400

ggc gtc ctg gac gtt gtc ccg gca gat atg gtg gtt aat gct acc ctg     1248
Gly Val Leu Asp Val Val Pro Ala Asp Met Val Val Asn Ala Thr Leu
                405                 410                 415

gct gca atg gct cgt cac ggc ggt tct ggt aaa gcc gaa acc aac att     1296
Ala Ala Met Ala Arg His Gly Gly Ser Gly Lys Ala Glu Thr Asn Ile
            420                 425                 430

tat cag atc gct agc tct gtc gtg aat cca ctg atc ttt caa gac ctg     1344
Tyr Gln Ile Ala Ser Ser Val Val Asn Pro Leu Ile Phe Gln Asp Leu
        435                 440                 445

acc agc cac ttc tac gag cat ttt aaa tca tcg cct tgt ctg gat aac     1392
Thr Ser His Phe Tyr Glu His Phe Lys Ser Ser Pro Cys Leu Asp Asn
    450                 455                 460

aag ggc aat cct att cac gtt ccg atc atg aaa ctg ttc tcc agc att     1440
Lys Gly Asn Pro Ile His Val Pro Ile Met Lys Leu Phe Ser Ser Ile
465                 470                 475                 480

gaa gac ttt tct tca cat ctg tgg cgc gat gcg atc ctg cgt tct ggt     1488
Glu Asp Phe Ser Ser His Leu Trp Arg Asp Ala Ile Leu Arg Ser Gly
                485                 490                 495

ctg tca gca atg cct agc caa acc ggc aag ctg ctg cgc aaa ctg gag     1536
Leu Ser Ala Met Pro Ser Gln Thr Gly Lys Leu Leu Arg Lys Leu Glu
            500                 505                 510

aag acc gtc aaa cag gca aag tac ctg gcc gat att tac caa cca tat     1584
Lys Thr Val Lys Gln Ala Lys Tyr Leu Ala Asp Ile Tyr Gln Pro Tyr
        515                 520                 525
```

```
acc ttc tac ggc ggt cgc ttt gac aac tcc aat acc cag cgt ctg atg      1632
Thr Phe Tyr Gly Gly Arg Phe Asp Asn Ser Asn Thr Gln Arg Leu Met
    530                 535                 540

gat tgc atg tgt gaa gag gaa aaa tct aag ttc ggt ttt gac gtt ggc      1680
Asp Cys Met Cys Glu Glu Glu Lys Ser Lys Phe Gly Phe Asp Val Gly
545                 550                 555                 560

tca atc gat tgg aaa gat tac att tct aac gtc cat atc cct ggt ctg      1728
Ser Ile Asp Trp Lys Asp Tyr Ile Ser Asn Val His Ile Pro Gly Leu
                565                 570                 575

cgt cgc cat gtg atg aaa ggt cgc                                      1752
Arg Arg His Val Met Lys Gly Arg
            580


<210> SEQ ID NO 24
<211> LENGTH: 584
<212> TYPE: PRT
<213> ORGANISM: Vitis vinifera (wine grape)

<400> SEQUENCE: 24

Met Gly Ala Leu Phe Phe Ser Ser Pro Ser Phe Ala Thr Lys Arg Val
1               5                   10                  15

Val Lys Phe Ser Gly Trp Cys Asp His Leu Lys Arg Arg Lys Ser Val
            20                  25                  30

Val His Cys Gln Thr Ser Gly Asn Gly Val Arg Ser Ser Gly Val Ser
        35                  40                  45

Ser Val Leu Ser Glu Arg Ser Met Leu Ala Ser Lys Asp His Ser Ala
    50                  55                  60

Gly Ser Leu Val Leu Ser Pro Asn Gly Lys Asp Leu Val Pro Tyr Gly
65                  70                  75                  80

Pro Pro Ser Pro Ser Thr Thr Pro Phe Val Glu Met Asn Asp Gly Ile
                85                  90                  95

Gly Ile Asp Asn Phe Leu Arg Gly Lys Ser Phe Leu Ile Thr Gly Ala
            100                 105                 110

Thr Gly Phe Leu Ala Lys Val Leu Ile Glu Lys Ile Leu Arg Thr Glu
        115                 120                 125

Pro Asp Val Gly Lys Ile Tyr Leu Leu Ile Lys Ala Lys Asn Gln Glu
    130                 135                 140

Ala Ala Met Glu Arg Leu Lys Asn Glu Ile Ile Asn Ala Glu Val Phe
145                 150                 155                 160

Asp Cys Leu Gln Gln Ala Tyr Gly Lys Ser Tyr Gln Ala Phe Met Leu
                165                 170                 175

Ser Lys Leu Val Pro Val Ala Gly Asp Val Cys Gly Ser Ser Leu Gly
            180                 185                 190

Leu Glu Lys Asp Phe Ala Glu Ala Ile Ala Lys Glu Val Asp Val Ile
        195                 200                 205

Val Asn Ser Ala Ala Asn Thr Thr Phe Asp Glu Arg Tyr Asp Ile Ala
    210                 215                 220

Ile Asp Ile Asn Thr Lys Gly Pro Cys His Leu Met Asn Phe Ala Lys
225                 230                 235                 240

Asn Cys Lys Lys Leu Lys Leu Phe Leu Gln Val Ser Thr Ala Tyr Val
                245                 250                 255

Asn Gly Gln Arg Gln Gly Arg Ile Met Glu Lys Pro Phe Cys Ile Gly
            260                 265                 270

Asp Ser Ile Ala Arg Glu Ser Asn Ile Ser Glu Ala Pro Pro Arg Leu
        275                 280                 285

Leu Pro Thr Leu Asn Ile Glu Ala Glu Ile Lys Leu Ala Leu Asp Ser
```

```
    290                 295                 300

Lys Glu Ala Phe Lys Gly Ser Thr Leu Ala Gln Lys Met Lys Glu Leu
305                 310                 315                 320

Gly Leu Glu Arg Ala Lys Lys His Gly Trp Gln Asp Thr Tyr Val Phe
                325                 330                 335

Thr Lys Ala Met Gly Glu Met Val Ile Asp Gln Met Arg Gly Glu Ile
            340                 345                 350

Pro Val Val Ile Ile Arg Pro Ser Val Ile Glu Ser Thr Cys Arg Glu
        355                 360                 365

Pro Phe Pro Gly Trp Met Glu Gly Asn Arg Met Met Asp Pro Ile Val
    370                 375                 380

Leu Tyr Tyr Gly Lys Gly Gln Leu Thr Gly Phe Val Ala Asp Pro Asn
385                 390                 395                 400

Gly Val Leu Asp Val Val Pro Ala Asp Met Val Val Asn Ala Thr Leu
                405                 410                 415

Ala Ala Met Ala Arg His Gly Gly Ser Gly Lys Ala Glu Thr Asn Ile
            420                 425                 430

Tyr Gln Ile Ala Ser Ser Val Val Asn Pro Leu Ile Phe Gln Asp Leu
        435                 440                 445

Thr Ser His Phe Tyr Glu His Phe Lys Ser Ser Pro Cys Leu Asp Asn
    450                 455                 460

Lys Gly Asn Pro Ile His Val Pro Ile Met Lys Leu Phe Ser Ser Ile
465                 470                 475                 480

Glu Asp Phe Ser Ser His Leu Trp Arg Asp Ala Ile Leu Arg Ser Gly
                485                 490                 495

Leu Ser Ala Met Pro Ser Gln Thr Gly Lys Leu Leu Arg Lys Leu Glu
            500                 505                 510

Lys Thr Val Lys Gln Ala Lys Tyr Leu Ala Asp Ile Tyr Gln Pro Tyr
        515                 520                 525

Thr Phe Tyr Gly Gly Arg Phe Asp Asn Ser Asn Thr Gln Arg Leu Met
    530                 535                 540

Asp Cys Met Cys Glu Glu Glu Lys Ser Lys Phe Gly Phe Asp Val Gly
545                 550                 555                 560

Ser Ile Asp Trp Lys Asp Tyr Ile Ser Asn Val His Ile Pro Gly Leu
                565                 570                 575

Arg Arg His Val Met Lys Gly Arg
            580


<210> SEQ ID NO 25
<211> LENGTH: 1755
<212> TYPE: DNA
<213> ORGANISM: Solanum lycopersicum (tomato)
<220> FEATURE:
<221> NAME/KEY: CDS
<222> LOCATION: (1)..(1755)

<400> SEQUENCE: 25

atg gaa gca gtg tcc tct ctg tcc tct tct tct gtc atc cct aaa acc       48
Met Glu Ala Val Ser Ser Leu Ser Ser Ser Ser Val Ile Pro Lys Thr
1               5                   10                  15

gtc ctc aaa ctt tct acc aac tgg cgc tgg tgt ccc ccc aac aaa gtg       96
Val Leu Lys Leu Ser Thr Asn Trp Arg Trp Cys Pro Pro Asn Lys Val
            20                  25                  30

tat tgc caa acc tct ggc acc aag aac ggt aat gtt tcc tct gtg gtc      144
Tyr Cys Gln Thr Ser Gly Thr Lys Asn Gly Asn Val Ser Ser Val Val
        35                  40                  45
```

-continued

```
acc gaa cgc tcc tct gtg tcc tct gag aag tcc ctt ggc tct ctg gtc      192
Thr Glu Arg Ser Ser Val Ser Ser Glu Lys Ser Leu Gly Ser Leu Val
    50                  55                  60

ctc acc tct aac acc gaa att aag gtg aaa gac ctc gtc ccg tac ggc      240
Leu Thr Ser Asn Thr Glu Ile Lys Val Lys Asp Leu Val Pro Tyr Gly
65                  70                  75                  80

cag cct cgt cac gat gac ggt atc ggt att aac atg ttc ctt cgt ggc      288
Gln Pro Arg His Asp Asp Gly Ile Gly Ile Asn Met Phe Leu Arg Gly
                85                  90                  95

aag gct ttt ctg atc acc ggc gcg acc ggt ttc ctt ggc aaa gtt ctg      336
Lys Ala Phe Leu Ile Thr Gly Ala Thr Gly Phe Leu Gly Lys Val Leu
            100                 105                 110

att gag aag atc ctc cgc acc gct cca gac gtg aac aag atc ttc atc      384
Ile Glu Lys Ile Leu Arg Thr Ala Pro Asp Val Asn Lys Ile Phe Ile
        115                 120                 125

ttg atc aag gca aag aac aag gaa gtg gcc atg caa cgc ctc aag aac      432
Leu Ile Lys Ala Lys Asn Lys Glu Val Ala Met Gln Arg Leu Lys Asn
    130                 135                 140

gag att ttg aat gcg gat atc ttc aac tgc ctc aaa cag gtc cac ggc      480
Glu Ile Leu Asn Ala Asp Ile Phe Asn Cys Leu Lys Gln Val His Gly
145                 150                 155                 160

aag tcc tac caa acc ttt atg ctt tct aag ctg gtt cca gtg ctc ggc      528
Lys Ser Tyr Gln Thr Phe Met Leu Ser Lys Leu Val Pro Val Leu Gly
                165                 170                 175

aac gtt tgt gaa gcc aat ttg ggt atc gat cag gac acc gct aac atg      576
Asn Val Cys Glu Ala Asn Leu Gly Ile Asp Gln Asp Thr Ala Asn Met
            180                 185                 190

atg gcg aag gaa gtt gat atc att gtg aac tcc gca gcc aat acc acc      624
Met Ala Lys Glu Val Asp Ile Ile Val Asn Ser Ala Ala Asn Thr Thr
        195                 200                 205

ttc gat gag cgc tat gac att gcg ctt gat atc aac acc ggc ggt cct      672
Phe Asp Glu Arg Tyr Asp Ile Ala Leu Asp Ile Asn Thr Gly Gly Pro
    210                 215                 220

acc cgt ctg atg aac ttc gca aaa caa tgc cac aat ttg aag ctt ttt      720
Thr Arg Leu Met Asn Phe Ala Lys Gln Cys His Asn Leu Lys Leu Phe
225                 230                 235                 240

ctg cag gtg tcc acc gcc tac gtc aac ggc cag cgc caa ggt cgt atc      768
Leu Gln Val Ser Thr Ala Tyr Val Asn Gly Gln Arg Gln Gly Arg Ile
                245                 250                 255

atg gaa aaa cca ttc tgt att ggc gac tcc atc gct aag gaa aac ctg      816
Met Glu Lys Pro Phe Cys Ile Gly Asp Ser Ile Ala Lys Glu Asn Leu
            260                 265                 270

ctc tct gag gtc aac cct aat tcc ttt acc tct ctg aat gtc gaa gat      864
Leu Ser Glu Val Asn Pro Asn Ser Phe Thr Ser Leu Asn Val Glu Asp
        275                 280                 285

gag att aaa ctc gtt ttg gaa tcc aag cag ggc ctg gaa aac aat tct      912
Glu Ile Lys Leu Val Leu Glu Ser Lys Gln Gly Leu Glu Asn Asn Ser
    290                 295                 300

gtg gcc cag aaa atg aag gaa atc ggc ttg caa cgc gct aac aaa ttc      960
Val Ala Gln Lys Met Lys Glu Ile Gly Leu Gln Arg Ala Asn Lys Phe
305                 310                 315                 320

ggt tgg cag gat acc tat gtc ttt acc aag gca atg ggc gag atg atg     1008
Gly Trp Gln Asp Thr Tyr Val Phe Thr Lys Ala Met Gly Glu Met Met
                325                 330                 335

att gac tcc atg cgc ggt gat atc ccg gtt gtg atc att cgt ccc tcc     1056
Ile Asp Ser Met Arg Gly Asp Ile Pro Val Val Ile Ile Arg Pro Ser
            340                 345                 350

gtg atc gaa tct acc tac aag gag cca ttc cct ggc tgg atg gaa ggt     1104
Val Ile Glu Ser Thr Tyr Lys Glu Pro Phe Pro Gly Trp Met Glu Gly
        355                 360                 365
```

```
tcc cgc atg atg gac ccg atc att ctc tac tat ggc aag ggt caa ctc     1152
Ser Arg Met Met Asp Pro Ile Ile Leu Tyr Tyr Gly Lys Gly Gln Leu
    370                 375                 380

acc ggc ttc ttg gtt gat cca aac ggt gtg ctt gac gtc gtt cct gct     1200
Thr Gly Phe Leu Val Asp Pro Asn Gly Val Leu Asp Val Val Pro Ala
385                 390                 395                 400

gat atg gtg gtc aat gcg acc ctg gct gcg atg gca aaa cac ggt acc     1248
Asp Met Val Val Asn Ala Thr Leu Ala Ala Met Ala Lys His Gly Thr
                405                 410                 415

gag ggc aag ccg ggt tcc tct aac gtc tat cag gtt gca tcc tct gcc     1296
Glu Gly Lys Pro Gly Ser Ser Asn Val Tyr Gln Val Ala Ser Ser Ala
            420                 425                 430

gtc aat ccc ctg gtt ttc aag gac ctt gca cgc atg ctg ttc gat cac     1344
Val Asn Pro Leu Val Phe Lys Asp Leu Ala Arg Met Leu Phe Asp His
        435                 440                 445

ttt aac cgt tcc cct tac att gat tct aaa ggc cgc cca atc cac gtg     1392
Phe Asn Arg Ser Pro Tyr Ile Asp Ser Lys Gly Arg Pro Ile His Val
    450                 455                 460

cct aag atg tcc ttg ctt cgt tct atg gaa gac ctc tcc tct cac ttg     1440
Pro Lys Met Ser Leu Leu Arg Ser Met Glu Asp Leu Ser Ser His Leu
465                 470                 475                 480

tgg cgc gat gcc atc aac cgt tcc ggc ctc acc gat ttg acc gac ccg     1488
Trp Arg Asp Ala Ile Asn Arg Ser Gly Leu Thr Asp Leu Thr Asp Pro
                485                 490                 495

aac ggt aaa ctt tcc cgc aag ctg gaa aat att tgc cgt aaa tcc gtt     1536
Asn Gly Lys Leu Ser Arg Lys Leu Glu Asn Ile Cys Arg Lys Ser Val
            500                 505                 510

gag cag gca aag tac ttg gcc aac atc tac gag ccc tat acc ttc tac     1584
Glu Gln Ala Lys Tyr Leu Ala Asn Ile Tyr Glu Pro Tyr Thr Phe Tyr
        515                 520                 525

ggc ggt cgc ttt gac aac tcc aat acc caa cgt ctg atg gaa tcc atg     1632
Gly Gly Arg Phe Asp Asn Ser Asn Thr Gln Arg Leu Met Glu Ser Met
    530                 535                 540

tct aaa gaa gag cgc tgg cag ttc ggc ttt gat gtg gag tcc atc gat     1680
Ser Lys Glu Glu Arg Trp Gln Phe Gly Phe Asp Val Glu Ser Ile Asp
545                 550                 555                 560

tgg aag gac tac att tcc aac gtg cac atc cca ggt ctg cgc aaa cac     1728
Trp Lys Asp Tyr Ile Ser Asn Val His Ile Pro Gly Leu Arg Lys His
                565                 570                 575

gtc atg aag ggc cgt ggt tcc tgt acc                                 1755
Val Met Lys Gly Arg Gly Ser Cys Thr
            580                 585


<210> SEQ ID NO 26
<211> LENGTH: 585
<212> TYPE: PRT
<213> ORGANISM: Solanum lycopersicum (tomato)

<400> SEQUENCE: 26

Met Glu Ala Val Ser Ser Leu Ser Ser Ser Ser Val Ile Pro Lys Thr
1               5                   10                  15

Val Leu Lys Leu Ser Thr Asn Trp Arg Trp Cys Pro Pro Asn Lys Val
            20                  25                  30

Tyr Cys Gln Thr Ser Gly Thr Lys Asn Gly Asn Val Ser Ser Val Val
        35                  40                  45

Thr Glu Arg Ser Ser Val Ser Ser Glu Lys Ser Leu Gly Ser Leu Val
    50                  55                  60

Leu Thr Ser Asn Thr Glu Ile Lys Val Lys Asp Leu Val Pro Tyr Gly
65                  70                  75                  80
```

-continued

```
Gln Pro Arg His Asp Asp Gly Ile Gly Ile Asn Met Phe Leu Arg Gly
                85                  90                  95

Lys Ala Phe Leu Ile Thr Gly Ala Thr Gly Phe Leu Gly Lys Val Leu
            100                 105                 110

Ile Glu Lys Ile Leu Arg Thr Ala Pro Asp Val Asn Lys Ile Phe Ile
        115                 120                 125

Leu Ile Lys Ala Lys Asn Lys Glu Val Ala Met Gln Arg Leu Lys Asn
    130                 135                 140

Glu Ile Leu Asn Ala Asp Ile Phe Asn Cys Leu Lys Gln Val His Gly
145                 150                 155                 160

Lys Ser Tyr Gln Thr Phe Met Leu Ser Lys Leu Val Pro Val Leu Gly
                165                 170                 175

Asn Val Cys Glu Ala Asn Leu Gly Ile Asp Gln Asp Thr Ala Asn Met
            180                 185                 190

Met Ala Lys Glu Val Asp Ile Ile Val Asn Ser Ala Ala Asn Thr Thr
        195                 200                 205

Phe Asp Glu Arg Tyr Asp Ile Ala Leu Asp Ile Asn Thr Gly Gly Pro
    210                 215                 220

Thr Arg Leu Met Asn Phe Ala Lys Gln Cys His Asn Leu Lys Leu Phe
225                 230                 235                 240

Leu Gln Val Ser Thr Ala Tyr Val Asn Gly Gln Arg Gln Gly Arg Ile
                245                 250                 255

Met Glu Lys Pro Phe Cys Ile Gly Asp Ser Ile Ala Lys Glu Asn Leu
            260                 265                 270

Leu Ser Glu Val Asn Pro Asn Ser Phe Thr Ser Leu Asn Val Glu Asp
        275                 280                 285

Glu Ile Lys Leu Val Leu Glu Ser Lys Gln Gly Leu Glu Asn Asn Ser
    290                 295                 300

Val Ala Gln Lys Met Lys Glu Ile Gly Leu Gln Arg Ala Asn Lys Phe
305                 310                 315                 320

Gly Trp Gln Asp Thr Tyr Val Phe Thr Lys Ala Met Gly Glu Met Met
                325                 330                 335

Ile Asp Ser Met Arg Gly Asp Ile Pro Val Val Ile Ile Arg Pro Ser
            340                 345                 350

Val Ile Glu Ser Thr Tyr Lys Glu Pro Phe Pro Gly Trp Met Glu Gly
        355                 360                 365

Ser Arg Met Met Asp Pro Ile Ile Leu Tyr Tyr Gly Lys Gly Gln Leu
    370                 375                 380

Thr Gly Phe Leu Val Asp Pro Asn Gly Val Leu Asp Val Val Pro Ala
385                 390                 395                 400

Asp Met Val Val Asn Ala Thr Leu Ala Ala Met Ala Lys His Gly Thr
                405                 410                 415

Glu Gly Lys Pro Gly Ser Ser Asn Val Tyr Gln Val Ala Ser Ser Ala
            420                 425                 430

Val Asn Pro Leu Val Phe Lys Asp Leu Ala Arg Met Leu Phe Asp His
        435                 440                 445

Phe Asn Arg Ser Pro Tyr Ile Asp Ser Lys Gly Arg Pro Ile His Val
    450                 455                 460

Pro Lys Met Ser Leu Leu Arg Ser Met Glu Asp Leu Ser Ser His Leu
465                 470                 475                 480

Trp Arg Asp Ala Ile Asn Arg Ser Gly Leu Thr Asp Leu Thr Asp Pro
                485                 490                 495
```

-continued

```
Asn Gly Lys Leu Ser Arg Lys Leu Glu Asn Ile Cys Arg Lys Ser Val
            500                 505                 510

Glu Gln Ala Lys Tyr Leu Ala Asn Ile Tyr Glu Pro Tyr Thr Phe Tyr
        515                 520                 525

Gly Gly Arg Phe Asp Asn Ser Asn Thr Gln Arg Leu Met Glu Ser Met
    530                 535                 540

Ser Lys Glu Glu Arg Trp Gln Phe Gly Phe Asp Val Glu Ser Ile Asp
545                 550                 555                 560

Trp Lys Asp Tyr Ile Ser Asn Val His Ile Pro Gly Leu Arg Lys His
                565                 570                 575

Val Met Lys Gly Arg Gly Ser Cys Thr
            580                 585


<210> SEQ ID NO 27
<211> LENGTH: 1677
<212> TYPE: DNA
<213> ORGANISM: Cucumis sativus (cucumber)
<220> FEATURE:
<221> NAME/KEY: CDS
<222> LOCATION: (1)..(1677)

<400> SEQUENCE: 27

atg gaa acc ctg acc ctg aaa ccc ttc tct acc atg cct tct atc aag       48
Met Glu Thr Leu Thr Leu Lys Pro Phe Ser Thr Met Pro Ser Ile Lys
1               5                   10                  15

tgc ggc cct cgc tct ctg tct acc ctc tct aac atc tct atg cgt gtg       96
Cys Gly Pro Arg Ser Leu Ser Thr Leu Ser Asn Ile Ser Met Arg Val
            20                  25                  30

gtc gca tgc tcc ggt gca ctc aag cca tcc atc tct acc gag cgt gtg      144
Val Ala Cys Ser Gly Ala Leu Lys Pro Ser Ile Ser Thr Glu Arg Val
        35                  40                  45

tcc tct tcc tct gtt gtg gtc cgc gca gcc gaa tcc gtt gtg ttg gcg      192
Ser Ser Ser Ser Val Val Val Arg Ala Ala Glu Ser Val Val Leu Ala
    50                  55                  60

cca cct aac ggc aag tcc gat gag atc ggc gtc aaa tct ctt gtg cct      240
Pro Pro Asn Gly Lys Ser Asp Glu Ile Gly Val Lys Ser Leu Val Pro
65                  70                  75                  80

tac gtc gat ctg gac gag gat gaa gac ggc ggt atc ggt att gtc aag      288
Tyr Val Asp Leu Asp Glu Asp Glu Asp Gly Gly Ile Gly Ile Val Lys
                85                  90                  95

ttc ctc cgc ggc aaa gtt ttc ttt atc acc ggt gcc acc ggc ttt ctc      336
Phe Leu Arg Gly Lys Val Phe Phe Ile Thr Gly Ala Thr Gly Phe Leu
            100                 105                 110

gct aag gtg ttg atc gaa aaa att ctc cgt acc gca cct gac gtg ggc      384
Ala Lys Val Leu Ile Glu Lys Ile Leu Arg Thr Ala Pro Asp Val Gly
        115                 120                 125

aag atc tac gtc ttg att aag gca aaa gat gaa gag gct gcg gca gac      432
Lys Ile Tyr Val Leu Ile Lys Ala Lys Asp Glu Glu Ala Ala Ala Asp
    130                 135                 140

cgt ctg aaa aac gat atc att aat gca cag ctt ttc aag tgc ctg cgc      480
Arg Leu Lys Asn Asp Ile Ile Asn Ala Gln Leu Phe Lys Cys Leu Arg
145                 150                 155                 160

caa atc cac ggc aaa tac tat atg tcc ttt atg acc tct aag ctt atc      528
Gln Ile His Gly Lys Tyr Tyr Met Ser Phe Met Thr Ser Lys Leu Ile
                165                 170                 175

cct gtc gtt ggt aac gtg tgt gaa tcc gac gtt ggc att cac gtg gat      576
Pro Val Val Gly Asn Val Cys Glu Ser Asp Val Gly Ile His Val Asp
            180                 185                 190

ttc gcc cac ctg atc gct tcc gat gtc gac gtt att gtg aac tct gcc      624
Phe Ala His Leu Ile Ala Ser Asp Val Asp Val Ile Val Asn Ser Ala
```

```
        195                 200                 205

gct aat acc acc ttc gat gaa cgc tac gac gtg gct atc gat att aac      672
Ala Asn Thr Thr Phe Asp Glu Arg Tyr Asp Val Ala Ile Asp Ile Asn
    210                 215                 220

acc aag ggc ccg tcc aat ctg atg gag ttc gcg aag aaa tgc tcc aag      720
Thr Lys Gly Pro Ser Asn Leu Met Glu Phe Ala Lys Lys Cys Ser Lys
225                 230                 235                 240

ttg aaa ctt ttt ctg cag atc tcc acc gca tac gtg aac ggt cag cgc      768
Leu Lys Leu Phe Leu Gln Ile Ser Thr Ala Tyr Val Asn Gly Gln Arg
                245                 250                 255

caa ggc cgt att atg gag aag ccc ttc tgt aaa gaa ctc gac gtc gag      816
Gln Gly Arg Ile Met Glu Lys Pro Phe Cys Lys Glu Leu Asp Val Glu
            260                 265                 270

tcc gaa atg aag ttg gcc ttt gaa ggc aac ggt atg ggc cag aat atg      864
Ser Glu Met Lys Leu Ala Phe Glu Gly Asn Gly Met Gly Gln Asn Met
        275                 280                 285

aag gag ctc ggt ttg gaa cgc gca aaa cgt tac ggc tgg caa gac acc      912
Lys Glu Leu Gly Leu Glu Arg Ala Lys Arg Tyr Gly Trp Gln Asp Thr
    290                 295                 300

tat gtt ttc acc aag gca atg ggc gag atg gtg atc gat gag atg cgt      960
Tyr Val Phe Thr Lys Ala Met Gly Glu Met Val Ile Asp Glu Met Arg
305                 310                 315                 320

ggc gaa gtc ccg gtt gct atc att cgc ccc tcc gtc att gag tct acc     1008
Gly Glu Val Pro Val Ala Ile Ile Arg Pro Ser Val Ile Glu Ser Thr
                325                 330                 335

ttc aag gac ccg ttt ccc ggt tgg atg gaa ggc aac cgc atg atg gat     1056
Phe Lys Asp Pro Phe Pro Gly Trp Met Glu Gly Asn Arg Met Met Asp
            340                 345                 350

cca atc gtt ctt tac tat ggt aaa ggc cag ctc acc ggt ttc ttg gtt     1104
Pro Ile Val Leu Tyr Tyr Gly Lys Gly Gln Leu Thr Gly Phe Leu Val
        355                 360                 365

gat cca aac ggc gtg att gac gtg gtc cct gcc gat atg gtt gtg aat     1152
Asp Pro Asn Gly Val Ile Asp Val Val Pro Ala Asp Met Val Val Asn
    370                 375                 380

gct acc ttg gca gca atg gcg cgc cac ggc cgt gca cca cgc cct tcc     1200
Ala Thr Leu Ala Ala Met Ala Arg His Gly Arg Ala Pro Arg Pro Ser
385                 390                 395                 400

atg aac atc tac cac gtc gcg tcc tct gtt gca aac cca ctc gtg ttc     1248
Met Asn Ile Tyr His Val Ala Ser Ser Val Ala Asn Pro Leu Val Phe
                405                 410                 415

aat cgc ttg gcc gac ctg ctc cac caa cac tat aat tcc tct ccg tgc     1296
Asn Arg Leu Ala Asp Leu Leu His Gln His Tyr Asn Ser Ser Pro Cys
            420                 425                 430

ctg gat gtg gac ggt acc cca atc cgt gtc tcc tct atg aag ctt ttc     1344
Leu Asp Val Asp Gly Thr Pro Ile Arg Val Ser Ser Met Lys Leu Phe
        435                 440                 445

gat tcc gtt gat gac ttt tct gaa cac ctg tgg cgt gac gca gct cgc     1392
Asp Ser Val Asp Asp Phe Ser Glu His Leu Trp Arg Asp Ala Ala Arg
    450                 455                 460

cgt tgc gcc tcc acc cca gat ggc aag ctt tct aag aaa ctg gag gct     1440
Arg Cys Ala Ser Thr Pro Asp Gly Lys Leu Ser Lys Lys Leu Glu Ala
465                 470                 475                 480

atc tgt aag aaa acc gtc gaa cag ctt aaa tac ctg gcg cac att tac     1488
Ile Cys Lys Lys Thr Val Glu Gln Leu Lys Tyr Leu Ala His Ile Tyr
                485                 490                 495

caa cct tat acc ttc ttt aac ggt cgt ttc gac aac tcc aat gtt cag     1536
Gln Pro Tyr Thr Phe Phe Asn Gly Arg Phe Asp Asn Ser Asn Val Gln
            500                 505                 510

ggc ctc atg gaa atc atg tcc gaa gag gaa aag cgc gag ttc ggt ttt     1584
```

```
Gly Leu Met Glu Ile Met Ser Glu Glu Glu Lys Arg Glu Phe Gly Phe
        515                 520                 525

gat gtg gaa aac att gat tgg acc gac tac atc acc aat gtc cac att      1632
Asp Val Glu Asn Ile Asp Trp Thr Asp Tyr Ile Thr Asn Val His Ile
    530                 535                 540

cca ggc ctg cgc cgt cac gtt atg aag ggt aaa cgc ggc atc aac          1677
Pro Gly Leu Arg Arg His Val Met Lys Gly Lys Arg Gly Ile Asn
545                 550                 555


<210> SEQ ID NO 28
<211> LENGTH: 559
<212> TYPE: PRT
<213> ORGANISM: Cucumis sativus (cucumber)

<400> SEQUENCE: 28

Met Glu Thr Leu Thr Leu Lys Pro Phe Ser Thr Met Pro Ser Ile Lys
1               5                   10                  15

Cys Gly Pro Arg Ser Leu Ser Thr Leu Ser Asn Ile Ser Met Arg Val
            20                  25                  30

Val Ala Cys Ser Gly Ala Leu Lys Pro Ser Ile Ser Thr Glu Arg Val
        35                  40                  45

Ser Ser Ser Ser Val Val Val Arg Ala Ala Glu Ser Val Val Leu Ala
    50                  55                  60

Pro Pro Asn Gly Lys Ser Asp Glu Ile Gly Val Lys Ser Leu Val Pro
65                  70                  75                  80

Tyr Val Asp Leu Asp Glu Asp Glu Asp Gly Gly Ile Gly Ile Val Lys
                85                  90                  95

Phe Leu Arg Gly Lys Val Phe Phe Ile Thr Gly Ala Thr Gly Phe Leu
            100                 105                 110

Ala Lys Val Leu Ile Glu Lys Ile Leu Arg Thr Ala Pro Asp Val Gly
        115                 120                 125

Lys Ile Tyr Val Leu Ile Lys Ala Lys Asp Glu Glu Ala Ala Ala Asp
    130                 135                 140

Arg Leu Lys Asn Asp Ile Ile Asn Ala Gln Leu Phe Lys Cys Leu Arg
145                 150                 155                 160

Gln Ile His Gly Lys Tyr Tyr Met Ser Phe Met Thr Ser Lys Leu Ile
                165                 170                 175

Pro Val Val Gly Asn Val Cys Glu Ser Asp Val Gly Ile His Val Asp
            180                 185                 190

Phe Ala His Leu Ile Ala Ser Asp Val Asp Val Ile Val Asn Ser Ala
        195                 200                 205

Ala Asn Thr Thr Phe Asp Glu Arg Tyr Asp Val Ala Ile Asp Ile Asn
    210                 215                 220

Thr Lys Gly Pro Ser Asn Leu Met Glu Phe Ala Lys Lys Cys Ser Lys
225                 230                 235                 240

Leu Lys Leu Phe Leu Gln Ile Ser Thr Ala Tyr Val Asn Gly Gln Arg
                245                 250                 255

Gln Gly Arg Ile Met Glu Lys Pro Phe Cys Lys Glu Leu Asp Val Glu
            260                 265                 270

Ser Glu Met Lys Leu Ala Phe Glu Gly Asn Gly Met Gly Gln Asn Met
        275                 280                 285

Lys Glu Leu Gly Leu Glu Arg Ala Lys Arg Tyr Gly Trp Gln Asp Thr
    290                 295                 300

Tyr Val Phe Thr Lys Ala Met Gly Glu Met Val Ile Asp Glu Met Arg
305                 310                 315                 320
```

```
Gly Glu Val Pro Val Ala Ile Ile Arg Pro Ser Val Ile Glu Ser Thr
                325                 330                 335

Phe Lys Asp Pro Phe Pro Gly Trp Met Glu Gly Asn Arg Met Met Asp
            340                 345                 350

Pro Ile Val Leu Tyr Tyr Gly Lys Gly Gln Leu Thr Gly Phe Leu Val
        355                 360                 365

Asp Pro Asn Gly Val Ile Asp Val Val Pro Ala Asp Met Val Val Asn
    370                 375                 380

Ala Thr Leu Ala Ala Met Ala Arg His Gly Arg Ala Pro Arg Pro Ser
385                 390                 395                 400

Met Asn Ile Tyr His Val Ala Ser Ser Val Ala Asn Pro Leu Val Phe
                405                 410                 415

Asn Arg Leu Ala Asp Leu Leu His Gln His Tyr Asn Ser Ser Pro Cys
            420                 425                 430

Leu Asp Val Asp Gly Thr Pro Ile Arg Val Ser Ser Met Lys Leu Phe
        435                 440                 445

Asp Ser Val Asp Asp Phe Ser Glu His Leu Trp Arg Asp Ala Ala Arg
    450                 455                 460

Arg Cys Ala Ser Thr Pro Asp Gly Lys Leu Ser Lys Lys Leu Glu Ala
465                 470                 475                 480

Ile Cys Lys Lys Thr Val Glu Gln Leu Lys Tyr Leu Ala His Ile Tyr
                485                 490                 495

Gln Pro Tyr Thr Phe Phe Asn Gly Arg Phe Asp Asn Ser Asn Val Gln
            500                 505                 510

Gly Leu Met Glu Ile Met Ser Glu Glu Glu Lys Arg Glu Phe Gly Phe
        515                 520                 525

Asp Val Glu Asn Ile Asp Trp Thr Asp Tyr Ile Thr Asn Val His Ile
    530                 535                 540

Pro Gly Leu Arg Arg His Val Met Lys Gly Lys Arg Gly Ile Asn
545                 550                 555


<210> SEQ ID NO 29
<211> LENGTH: 1776
<212> TYPE: DNA
<213> ORGANISM: Brachypodium distachyon
<220> FEATURE:
<221> NAME/KEY: CDS
<222> LOCATION: (1)..(1776)

<400> SEQUENCE: 29

atg ggt tct tcc ccc tgc gtg aat ctt tct cgt gct gct gcc cgt cgt       48
Met Gly Ser Ser Pro Cys Val Asn Leu Ser Arg Ala Ala Ala Arg Arg
1               5                   10                  15

ccg gct gct ggt cgc ggc ttc gcc cac cgt cgt tcc gtg ttg gcc ctt       96
Pro Ala Ala Gly Arg Gly Phe Ala His Arg Arg Ser Val Leu Ala Leu
            20                  25                  30

cca tcc gcg tct gca cgc tct cgt gct att gaa ggc ggt gtt tcc tgc      144
Pro Ser Ala Ser Ala Arg Ser Arg Ala Ile Glu Gly Gly Val Ser Cys
        35                  40                  45

tgt ggc atg gcg aac ggt tac atg ggc ggt cct gtg cct gca cac ggc      192
Cys Gly Met Ala Asn Gly Tyr Met Gly Gly Pro Val Pro Ala His Gly
    50                  55                  60

aaa tcc tct ggt cct ggt tcc gca gca cct gaa gca ggt ctc ggt atc      240
Lys Ser Ser Gly Pro Gly Ser Ala Ala Pro Glu Ala Gly Leu Gly Ile
65                  70                  75                  80

cag gag ttc ttg ggc ggt aaa aac ttt ctt gtg acc ggc ggt acc ggc      288
Gln Glu Phe Leu Gly Gly Lys Asn Phe Leu Val Thr Gly Gly Thr Gly
                85                  90                  95
```

-continued

```
ttc ctc gct aag gtc ttg atc gaa aaa att ctg cgc acc aat cct gac      336
Phe Leu Ala Lys Val Leu Ile Glu Lys Ile Leu Arg Thr Asn Pro Asp
            100                 105                 110

gtg ggc aag atc tat gtg gtc att aag gcg aaa gat tcc gaa gct gcg      384
Val Gly Lys Ile Tyr Val Val Ile Lys Ala Lys Asp Ser Glu Ala Ala
        115                 120                 125

ctc cag cgc ttg cgt aac gaa gtt gtg gac acc gag ctt ttc cgc tgc      432
Leu Gln Arg Leu Arg Asn Glu Val Val Asp Thr Glu Leu Phe Arg Cys
    130                 135                 140

ctg caa gag att cac ggc aag gat tac cac tcc ttt gtc gca gcc aaa      480
Leu Gln Glu Ile His Gly Lys Asp Tyr His Ser Phe Val Ala Ala Lys
145                 150                 155                 160

ttg gtt cca gtc gtt ggc gac gtg cgc gaa gca aac atc ggt att gcc      528
Leu Val Pro Val Val Gly Asp Val Arg Glu Ala Asn Ile Gly Ile Ala
                165                 170                 175

cct gag ctt gct gac gaa atc gcg gag cgt gtg gat atc att gtc aac      576
Pro Glu Leu Ala Asp Glu Ile Ala Glu Arg Val Asp Ile Ile Val Asn
            180                 185                 190

tcc gct gcg aat acc acc ttc gat gaa cgc tat gac gtg gca atg gat      624
Ser Ala Ala Asn Thr Thr Phe Asp Glu Arg Tyr Asp Val Ala Met Asp
        195                 200                 205

att aac acc gtc ggc cca ttc cgc atc atg tcc ttc gcc cac cgt ttt      672
Ile Asn Thr Val Gly Pro Phe Arg Ile Met Ser Phe Ala His Arg Phe
    210                 215                 220

cgc cgt ctg aag ctc ttt ttg cag gtg tcc acc gct tac gtc aat ggc      720
Arg Arg Leu Lys Leu Phe Leu Gln Val Ser Thr Ala Tyr Val Asn Gly
225                 230                 235                 240

cag acc caa ggt gtg gtc ctg gaa aag ccg ttc cgc ctc ggc gat acc      768
Gln Thr Gln Gly Val Val Leu Glu Lys Pro Phe Arg Leu Gly Asp Thr
                245                 250                 255

atc cgt aaa gat tcc tct gac tcc tct gag caa cac aag aac ccc atg      816
Ile Arg Lys Asp Ser Ser Asp Ser Ser Glu Gln His Lys Asn Pro Met
            260                 265                 270

ttg gac atc gaa gct gag att aag ctt gcg ttc gat tct cgc cgt cac      864
Leu Asp Ile Glu Ala Glu Ile Lys Leu Ala Phe Asp Ser Arg Arg His
        275                 280                 285

tcc gat gac tcc gcc tct ttt tcc cag gaa atg aag gac ctt ggc ctg      912
Ser Asp Asp Ser Ala Ser Phe Ser Gln Glu Met Lys Asp Leu Gly Leu
    290                 295                 300

gag cgc gct aaa ttg cac ggt tgg caa gat acc tac gtt ttc acc aag      960
Glu Arg Ala Lys Leu His Gly Trp Gln Asp Thr Tyr Val Phe Thr Lys
305                 310                 315                 320

gcg atg ggc gaa atg gtg atc aac tcc atg cgc ggc gag atc ccg gtt     1008
Ala Met Gly Glu Met Val Ile Asn Ser Met Arg Gly Glu Ile Pro Val
                325                 330                 335

gtg acc att cgt ccc tct gtc atc gaa tcc acc tgg cgc gac cca ttc     1056
Val Thr Ile Arg Pro Ser Val Ile Glu Ser Thr Trp Arg Asp Pro Phe
            340                 345                 350

cct ggc tgg atg gag ggt aat cgc atg atg gat cca gtc gtt ctc tac     1104
Pro Gly Trp Met Glu Gly Asn Arg Met Met Asp Pro Val Val Leu Tyr
        355                 360                 365

tat ggc aag ggt cag ctc tcc ggc ttt ttg gca gac cca tac ggc gtt     1152
Tyr Gly Lys Gly Gln Leu Ser Gly Phe Leu Ala Asp Pro Tyr Gly Val
    370                 375                 380

ttg gac gtg gtc cct gca gat atg gtt gtg aac gcc acc ctt gca gca     1200
Leu Asp Val Val Pro Ala Asp Met Val Val Asn Ala Thr Leu Ala Ala
385                 390                 395                 400

atg gca aag cac ggt cgt cca tct gaa gca tcc gag ggt acc acc atg     1248
Met Ala Lys His Gly Arg Pro Ser Glu Ala Ser Glu Gly Thr Thr Met
```

```
                405                 410                 415

aag cag aaa caa tgg gtc tac cac gtt gca tcc tct acc gtt aat cct     1296
Lys Gln Lys Gln Trp Val Tyr His Val Ala Ser Ser Thr Val Asn Pro
            420                 425                 430

ctt gtg ttc ggc gac ctg tcc cgc ctg ctc ttc cag cac ttt acc cgt     1344
Leu Val Phe Gly Asp Leu Ser Arg Leu Leu Phe Gln His Phe Thr Arg
        435                 440                 445

tct ccg tat tcc gat gct gcg ggt caa ccc atc gcc gtg cca cct atg     1392
Ser Pro Tyr Ser Asp Ala Ala Gly Gln Pro Ile Ala Val Pro Pro Met
    450                 455                 460

cgc ctg ttc gat act atg gat cag ttt gcg tct tac gtc gaa acc gat     1440
Arg Leu Phe Asp Thr Met Asp Gln Phe Ala Ser Tyr Val Glu Thr Asp
465                 470                 475                 480

gca ctg gtt cgt tcc gca gcc gct cgt gcc ggt cct gct ggc gag cgc     1488
Ala Leu Val Arg Ser Ala Ala Ala Arg Ala Gly Pro Ala Gly Glu Arg
                485                 490                 495

ctc tct cag cgt ctt caa gaa ctg tgc gct aaa tcc gtg gag cag acc     1536
Leu Ser Gln Arg Leu Gln Glu Leu Cys Ala Lys Ser Val Glu Gln Thr
            500                 505                 510

att cac ctg ggc tgt atc tac caa cca tat acc ttc tac cct ggc cgc     1584
Ile His Leu Gly Cys Ile Tyr Gln Pro Tyr Thr Phe Tyr Pro Gly Arg
        515                 520                 525

ttt gac aac ggt aat acc gaa gcg ctc atg gca gag atg acc gca gaa     1632
Phe Asp Asn Gly Asn Thr Glu Ala Leu Met Ala Glu Met Thr Ala Glu
    530                 535                 540

gag aag gcc cgc ttc cac ttt gat gtc cgt tcc atc gat tgg acc gac     1680
Glu Lys Ala Arg Phe His Phe Asp Val Arg Ser Ile Asp Trp Thr Asp
545                 550                 555                 560

tac att acc aac gtc cac atc ccc ggc ctg cgc aag cac gtt atg aaa     1728
Tyr Ile Thr Asn Val His Ile Pro Gly Leu Arg Lys His Val Met Lys
                565                 570                 575

ggc cgt ggt ctg gcg gca gat gcc tct acc gtt ctc gcc gct tcc gtg     1776
Gly Arg Gly Leu Ala Ala Asp Ala Ser Thr Val Leu Ala Ala Ser Val
            580                 585                 590


<210> SEQ ID NO 30
<211> LENGTH: 592
<212> TYPE: PRT
<213> ORGANISM: Brachypodium distachyon

<400> SEQUENCE: 30

Met Gly Ser Ser Pro Cys Val Asn Leu Ser Arg Ala Ala Ala Arg Arg
1               5                   10                  15

Pro Ala Ala Gly Arg Gly Phe Ala His Arg Arg Ser Val Leu Ala Leu
            20                  25                  30

Pro Ser Ala Ser Ala Arg Ser Arg Ala Ile Glu Gly Gly Val Ser Cys
        35                  40                  45

Cys Gly Met Ala Asn Gly Tyr Met Gly Gly Pro Val Pro Ala His Gly
    50                  55                  60

Lys Ser Ser Gly Pro Gly Ser Ala Ala Pro Glu Ala Gly Leu Gly Ile
65                  70                  75                  80

Gln Glu Phe Leu Gly Gly Lys Asn Phe Leu Val Thr Gly Gly Thr Gly
                85                  90                  95

Phe Leu Ala Lys Val Leu Ile Glu Lys Ile Leu Arg Thr Asn Pro Asp
            100                 105                 110

Val Gly Lys Ile Tyr Val Val Ile Lys Ala Lys Asp Ser Glu Ala Ala
        115                 120                 125

Leu Gln Arg Leu Arg Asn Glu Val Val Asp Thr Glu Leu Phe Arg Cys
```

-continued

```
    130                 135                 140

Leu Gln Glu Ile His Gly Lys Asp Tyr His Ser Phe Val Ala Ala Lys
145                 150                 155                 160

Leu Val Pro Val Val Gly Asp Val Arg Glu Ala Asn Ile Gly Ile Ala
                165                 170                 175

Pro Glu Leu Ala Asp Glu Ile Ala Glu Arg Val Asp Ile Ile Val Asn
            180                 185                 190

Ser Ala Ala Asn Thr Thr Phe Asp Glu Arg Tyr Asp Val Ala Met Asp
        195                 200                 205

Ile Asn Thr Val Gly Pro Phe Arg Ile Met Ser Phe Ala His Arg Phe
    210                 215                 220

Arg Arg Leu Lys Leu Phe Leu Gln Val Ser Thr Ala Tyr Val Asn Gly
225                 230                 235                 240

Gln Thr Gln Gly Val Val Leu Glu Lys Pro Phe Arg Leu Gly Asp Thr
                245                 250                 255

Ile Arg Lys Asp Ser Ser Asp Ser Ser Glu Gln His Lys Asn Pro Met
            260                 265                 270

Leu Asp Ile Glu Ala Glu Ile Lys Leu Ala Phe Asp Ser Arg Arg His
        275                 280                 285

Ser Asp Asp Ser Ala Ser Phe Ser Gln Glu Met Lys Asp Leu Gly Leu
    290                 295                 300

Glu Arg Ala Lys Leu His Gly Trp Gln Asp Thr Tyr Val Phe Thr Lys
305                 310                 315                 320

Ala Met Gly Glu Met Val Ile Asn Ser Met Arg Gly Glu Ile Pro Val
                325                 330                 335

Val Thr Ile Arg Pro Ser Val Ile Glu Ser Thr Trp Arg Asp Pro Phe
            340                 345                 350

Pro Gly Trp Met Glu Gly Asn Arg Met Met Asp Pro Val Val Leu Tyr
        355                 360                 365

Tyr Gly Lys Gly Gln Leu Ser Gly Phe Leu Ala Asp Pro Tyr Gly Val
    370                 375                 380

Leu Asp Val Val Pro Ala Asp Met Val Val Asn Ala Thr Leu Ala Ala
385                 390                 395                 400

Met Ala Lys His Gly Arg Pro Ser Glu Ala Ser Glu Gly Thr Thr Met
                405                 410                 415

Lys Gln Lys Gln Trp Val Tyr His Val Ala Ser Ser Thr Val Asn Pro
            420                 425                 430

Leu Val Phe Gly Asp Leu Ser Arg Leu Leu Phe Gln His Phe Thr Arg
        435                 440                 445

Ser Pro Tyr Ser Asp Ala Ala Gly Gln Pro Ile Ala Val Pro Pro Met
    450                 455                 460

Arg Leu Phe Asp Thr Met Asp Gln Phe Ala Ser Tyr Val Glu Thr Asp
465                 470                 475                 480

Ala Leu Val Arg Ser Ala Ala Ala Arg Ala Gly Pro Ala Gly Glu Arg
                485                 490                 495

Leu Ser Gln Arg Leu Gln Glu Leu Cys Ala Lys Ser Val Glu Gln Thr
            500                 505                 510

Ile His Leu Gly Cys Ile Tyr Gln Pro Tyr Thr Phe Tyr Pro Gly Arg
        515                 520                 525

Phe Asp Asn Gly Asn Thr Glu Ala Leu Met Ala Glu Met Thr Ala Glu
    530                 535                 540

Glu Lys Ala Arg Phe His Phe Asp Val Arg Ser Ile Asp Trp Thr Asp
545                 550                 555                 560
```

```
Tyr Ile Thr Asn Val His Ile Pro Gly Leu Arg Lys His Val Met Lys
                565                 570                 575

Gly Arg Gly Leu Ala Ala Asp Ala Ser Thr Val Leu Ala Ala Ser Val
            580                 585                 590


<210> SEQ ID NO 31
<211> LENGTH: 1686
<212> TYPE: DNA
<213> ORGANISM: Setaria italica (foxtail millet)
<220> FEATURE:
<221> NAME/KEY: CDS
<222> LOCATION: (1)..(1686)

<400> SEQUENCE: 31

atg ggt tct tct tgt cgt gct gct gtc gcg tgc tgt tct tcc ccc ggc       48
Met Gly Ser Ser Cys Arg Ala Ala Val Ala Cys Cys Ser Ser Pro Gly
1               5                   10                  15

acc gca ggt tct cgt ccc tct tct tct tct ttc ccc gtg cgc ggt ctg       96
Thr Ala Gly Ser Arg Pro Ser Ser Ser Ser Phe Pro Val Arg Gly Leu
            20                  25                  30

ggc ggt gat tcc tct gaa gca ggt tct acc gca acc tct cct gca ggt      144
Gly Gly Asp Ser Ser Glu Ala Gly Ser Thr Ala Thr Ser Pro Ala Gly
        35                  40                  45

cac gcc ggc ggt atc ggt att gca gag ttc ctt ggc gcc aag aac ttt      192
His Ala Gly Gly Ile Gly Ile Ala Glu Phe Leu Gly Ala Lys Asn Phe
    50                  55                  60

ctg atc acc ggc ggt acc ggt ttc ctt gca aag gtg ctg atc gaa aaa      240
Leu Ile Thr Gly Gly Thr Gly Phe Leu Ala Lys Val Leu Ile Glu Lys
65                  70                  75                  80

att ctc cgc acc aat ccc gac gtc ggc aag atc tac gtt ttg atc aag      288
Ile Leu Arg Thr Asn Pro Asp Val Gly Lys Ile Tyr Val Leu Ile Lys
                85                  90                  95

gcc aag gat tcc gaa gca gcc ctc cgc cgt ttg cag aac gaa gtg gtc      336
Ala Lys Asp Ser Glu Ala Ala Leu Arg Arg Leu Gln Asn Glu Val Val
            100                 105                 110

gac acc gag ctc ttc aag tgc ttg caa gag atc cac ggc aat gat tac      384
Asp Thr Glu Leu Phe Lys Cys Leu Gln Glu Ile His Gly Asn Asp Tyr
        115                 120                 125

tcc tct ttt att gca cgt aaa ctc gtt cca gtt gtg ggt gac gtg cgc      432
Ser Ser Phe Ile Ala Arg Lys Leu Val Pro Val Val Gly Asp Val Arg
    130                 135                 140

gaa gcc aac atc ggc att gcc cct gaa ttg gct gat gag atc gcg gat      480
Glu Ala Asn Ile Gly Ile Ala Pro Glu Leu Ala Asp Glu Ile Ala Asp
145                 150                 155                 160

cag gtc gac atc att gtt aac tcc gct gcg aat acc acc ttc gat gag      528
Gln Val Asp Ile Ile Val Asn Ser Ala Ala Asn Thr Thr Phe Asp Glu
                165                 170                 175

cgc tat gac gtg gca atg gat atc aac acc gtc ggc cca ttc cgc att      576
Arg Tyr Asp Val Ala Met Asp Ile Asn Thr Val Gly Pro Phe Arg Ile
            180                 185                 190

atg tcc ttc gct cag cgt ttc cgc cgt ttg aag ctt ttt ctg caa gtg      624
Met Ser Phe Ala Gln Arg Phe Arg Arg Leu Lys Leu Phe Leu Gln Val
        195                 200                 205

tcc acc gcg tac gtc aat ggc cag cgt caa ggt ctc gtg ttg gaa aag      672
Ser Thr Ala Tyr Val Asn Gly Gln Arg Gln Gly Leu Val Leu Glu Lys
    210                 215                 220

cct ttc cgc atg ggt gac acc atc gct aaa gaa ctc ggc tcc tct gag      720
Pro Phe Arg Met Gly Asp Thr Ile Ala Lys Glu Leu Gly Ser Ser Glu
225                 230                 235                 240

cac tcc tct acc gtg ctt gat atc gaa gct gag att aag ctg gcg ttc      768
```

-continued

```
His Ser Ser Thr Val Leu Asp Ile Glu Ala Glu Ile Lys Leu Ala Phe
                245                 250                 255

gac tat tct cgc cgt cgc tcc gtc gat tct gct tcc ttt acc cag gaa      816
Asp Tyr Ser Arg Arg Arg Ser Val Asp Ser Ala Ser Phe Thr Gln Glu
            260                 265                 270

atg aag gac ctt ggt ctg gag cgc gcg aac ttg cac ggc tgg caa gat      864
Met Lys Asp Leu Gly Leu Glu Arg Ala Asn Leu His Gly Trp Gln Asp
        275                 280                 285

acc tac gtc ttc acc aaa gca atg ggt gaa atg gtt atc aat tcc atg      912
Thr Tyr Val Phe Thr Lys Ala Met Gly Glu Met Val Ile Asn Ser Met
    290                 295                 300

cgc ggc gag gtg cca gtc gtt acc atc cgt cct tct gtt att gaa tcc      960
Arg Gly Glu Val Pro Val Val Thr Ile Arg Pro Ser Val Ile Glu Ser
305                 310                 315                 320

acc tgg cgc gac cca ttc cct ggc tgg atg gag ggt aac cgc atg atg     1008
Thr Trp Arg Asp Pro Phe Pro Gly Trp Met Glu Gly Asn Arg Met Met
                325                 330                 335

gat cca gtg gtc ctg tac tat ggc aag ggt cag ctt tcc ggt ttc ctg     1056
Asp Pro Val Val Leu Tyr Tyr Gly Lys Gly Gln Leu Ser Gly Phe Leu
            340                 345                 350

gct gat ccg gaa ggc gtc ctt gac gtt gtg ccc gcg gat atg gtc gtt     1104
Ala Asp Pro Glu Gly Val Leu Asp Val Val Pro Ala Asp Met Val Val
        355                 360                 365

aac gct acc ctg gcg tct atg gca aaa cac ggc ggt acc tct tcc tcc     1152
Asn Ala Thr Leu Ala Ser Met Ala Lys His Gly Gly Thr Ser Ser Ser
    370                 375                 380

tcc cca cca gca gcc gct ggt ccg ggc ggt atg cac gtg tac cac gtc     1200
Ser Pro Pro Ala Ala Ala Gly Pro Gly Gly Met His Val Tyr His Val
385                 390                 395                 400

tcc tct tcc acc gtg aac cca ctg gtc ttc ggc gag ctc tcc cgc ttc     1248
Ser Ser Ser Thr Val Asn Pro Leu Val Phe Gly Glu Leu Ser Arg Phe
                405                 410                 415

ttg ttt cag cac ttt acc cgt tgc cca tat tcc gac gca gca ggt cgt     1296
Leu Phe Gln His Phe Thr Arg Cys Pro Tyr Ser Asp Ala Ala Gly Arg
            420                 425                 430

cct atc cct gtc ccg ccc atg cgt ctg ttc gat tct atg gat cag ttt     1344
Pro Ile Pro Val Pro Pro Met Arg Leu Phe Asp Ser Met Asp Gln Phe
        435                 440                 445

gcc gct tac gtt gaa acc gat gca ctg ctc cgc tct gag cag caa cgt     1392
Ala Ala Tyr Val Glu Thr Asp Ala Leu Leu Arg Ser Glu Gln Gln Arg
    450                 455                 460

cgc cgt ctc tcc caa cgc gca cgt gaa ttg tgt gcc cgc tct gtt gag     1440
Arg Arg Leu Ser Gln Arg Ala Arg Glu Leu Cys Ala Arg Ser Val Glu
465                 470                 475                 480

cag gcc gtg cac ctc ggt tcc att tac caa ccg tat acc ttc tac ggc     1488
Gln Ala Val His Leu Gly Ser Ile Tyr Gln Pro Tyr Thr Phe Tyr Gly
                485                 490                 495

ggt cgc ttt gac aac ggc aat acc gaa gct ttg ctt gcg gca atg tcc     1536
Gly Arg Phe Asp Asn Gly Asn Thr Glu Ala Leu Leu Ala Ala Met Ser
            500                 505                 510

gtt gcc gag aag gct cgc ttc cac ttt gat gtt cgt tcc gtg gat tgg     1584
Val Ala Glu Lys Ala Arg Phe His Phe Asp Val Arg Ser Val Asp Trp
        515                 520                 525

gcg gac tac atc acc aac gtg cac att cct ggc ctg cgc aag cac gtc     1632
Ala Asp Tyr Ile Thr Asn Val His Ile Pro Gly Leu Arg Lys His Val
    530                 535                 540

atg aaa ggc cgt ggt gtt gcc gct gcg aat cag ctg ctc gcc tct acc     1680
Met Lys Gly Arg Gly Val Ala Ala Ala Asn Gln Leu Leu Ala Ser Thr
545                 550                 555                 560
```

-continued

```
tct gtg                                                             1686
Ser Val


<210> SEQ ID NO 32
<211> LENGTH: 562
<212> TYPE: PRT
<213> ORGANISM: Setaria italica (foxtail millet)

<400> SEQUENCE: 32

Met Gly Ser Ser Cys Arg Ala Ala Val Ala Cys Cys Ser Ser Pro Gly
1               5                   10                  15

Thr Ala Gly Ser Arg Pro Ser Ser Ser Ser Phe Pro Val Arg Gly Leu
            20                  25                  30

Gly Gly Asp Ser Ser Glu Ala Gly Ser Thr Ala Thr Ser Pro Ala Gly
        35                  40                  45

His Ala Gly Gly Ile Gly Ile Ala Glu Phe Leu Gly Ala Lys Asn Phe
    50                  55                  60

Leu Ile Thr Gly Gly Thr Gly Phe Leu Ala Lys Val Leu Ile Glu Lys
65                  70                  75                  80

Ile Leu Arg Thr Asn Pro Asp Val Gly Lys Ile Tyr Val Leu Ile Lys
                85                  90                  95

Ala Lys Asp Ser Glu Ala Ala Leu Arg Arg Leu Gln Asn Glu Val Val
            100                 105                 110

Asp Thr Glu Leu Phe Lys Cys Leu Gln Glu Ile His Gly Asn Asp Tyr
        115                 120                 125

Ser Ser Phe Ile Ala Arg Lys Leu Val Pro Val Val Gly Asp Val Arg
    130                 135                 140

Glu Ala Asn Ile Gly Ile Ala Pro Glu Leu Ala Asp Glu Ile Ala Asp
145                 150                 155                 160

Gln Val Asp Ile Ile Val Asn Ser Ala Ala Asn Thr Thr Phe Asp Glu
                165                 170                 175

Arg Tyr Asp Val Ala Met Asp Ile Asn Thr Val Gly Pro Phe Arg Ile
            180                 185                 190

Met Ser Phe Ala Gln Arg Phe Arg Arg Leu Lys Leu Phe Leu Gln Val
        195                 200                 205

Ser Thr Ala Tyr Val Asn Gly Gln Arg Gln Gly Leu Val Leu Glu Lys
    210                 215                 220

Pro Phe Arg Met Gly Asp Thr Ile Ala Lys Glu Leu Gly Ser Ser Glu
225                 230                 235                 240

His Ser Ser Thr Val Leu Asp Ile Glu Ala Glu Ile Lys Leu Ala Phe
                245                 250                 255

Asp Tyr Ser Arg Arg Arg Ser Val Asp Ser Ala Ser Phe Thr Gln Glu
            260                 265                 270

Met Lys Asp Leu Gly Leu Glu Arg Ala Asn Leu His Gly Trp Gln Asp
        275                 280                 285

Thr Tyr Val Phe Thr Lys Ala Met Gly Glu Met Val Ile Asn Ser Met
    290                 295                 300

Arg Gly Glu Val Pro Val Val Thr Ile Arg Pro Ser Val Ile Glu Ser
305                 310                 315                 320

Thr Trp Arg Asp Pro Phe Pro Gly Trp Met Glu Gly Asn Arg Met Met
                325                 330                 335

Asp Pro Val Val Leu Tyr Tyr Gly Lys Gly Gln Leu Ser Gly Phe Leu
            340                 345                 350

Ala Asp Pro Glu Gly Val Leu Asp Val Val Pro Ala Asp Met Val Val
        355                 360                 365
```

-continued

```
Asn Ala Thr Leu Ala Ser Met Ala Lys His Gly Gly Thr Ser Ser Ser
    370                 375                 380

Ser Pro Pro Ala Ala Ala Gly Pro Gly Gly Met His Val Tyr His Val
385                 390                 395                 400

Ser Ser Ser Thr Val Asn Pro Leu Val Phe Gly Glu Leu Ser Arg Phe
                405                 410                 415

Leu Phe Gln His Phe Thr Arg Cys Pro Tyr Ser Asp Ala Ala Gly Arg
            420                 425                 430

Pro Ile Pro Val Pro Pro Met Arg Leu Phe Asp Ser Met Asp Gln Phe
        435                 440                 445

Ala Ala Tyr Val Glu Thr Asp Ala Leu Leu Arg Ser Glu Gln Gln Arg
    450                 455                 460

Arg Arg Leu Ser Gln Arg Ala Arg Glu Leu Cys Ala Arg Ser Val Glu
465                 470                 475                 480

Gln Ala Val His Leu Gly Ser Ile Tyr Gln Pro Tyr Thr Phe Tyr Gly
                485                 490                 495

Gly Arg Phe Asp Asn Gly Asn Thr Glu Ala Leu Leu Ala Ala Met Ser
            500                 505                 510

Val Ala Glu Lys Ala Arg Phe His Phe Asp Val Arg Ser Val Asp Trp
        515                 520                 525

Ala Asp Tyr Ile Thr Asn Val His Ile Pro Gly Leu Arg Lys His Val
    530                 535                 540

Met Lys Gly Arg Gly Val Ala Ala Ala Asn Gln Leu Leu Ala Ser Thr
545                 550                 555                 560

Ser Val


<210> SEQ ID NO 33
<211> LENGTH: 1776
<212> TYPE: DNA
<213> ORGANISM: Sorghum bicolor (sorghum)
<220> FEATURE:
<221> NAME/KEY: CDS
<222> LOCATION: (1)..(1776)

<400> SEQUENCE: 33

atg ggt tct tct tgc gtg aat ctt tct cgt gcg gtc ctc ccc ggt ttc       48
Met Gly Ser Ser Cys Val Asn Leu Ser Arg Ala Val Leu Pro Gly Phe
1               5                   10                  15

ggt gcg gcg gct gcg gct aag ggt ggt tct cgt cgt cgc ggc ctg ctc       96
Gly Ala Ala Ala Ala Ala Lys Gly Gly Ser Arg Arg Arg Gly Leu Leu
            20                  25                  30

ttg cca ctt ctg tcc tct tcc gca gcc gct ggt cgt cag cgt cac ggt      144
Leu Pro Leu Leu Ser Ser Ser Ala Ala Ala Gly Arg Gln Arg His Gly
        35                  40                  45

tct tcc gcg gca gtg gtc gct tgc tgt acc tct tcc tct tcc tct tcc      192
Ser Ser Ala Ala Val Val Ala Cys Cys Thr Ser Ser Ser Ser Ser Ser
    50                  55                  60

tct acc acc gcc gct gcg ggc tcc tct tcc gca ggt gca gcc gct ggc      240
Ser Thr Thr Ala Ala Ala Gly Ser Ser Ser Ala Gly Ala Ala Ala Gly
65                  70                  75                  80

ggt att ggt gtt gca gaa ttc ttg ggc gcc aag aac ttt ctt atc acc      288
Gly Ile Gly Val Ala Glu Phe Leu Gly Ala Lys Asn Phe Leu Ile Thr
                85                  90                  95

ggc ggt acc ggc ttc ttg gcc aag gtg ctt atc gag aaa att ctt cgc      336
Gly Gly Thr Gly Phe Leu Ala Lys Val Leu Ile Glu Lys Ile Leu Arg
            100                 105                 110

acc aac ccg aat gtc ggc aag atc tac gtt ctg atc aag gct aag gac      384
```

-continued

```
Thr Asn Pro Asn Val Gly Lys Ile Tyr Val Leu Ile Lys Ala Lys Asp
        115                 120                 125

ggt gaa gca gca ctg cgc cgt ctc cag aac gaa gtt gtg gat acc gag      432
Gly Glu Ala Ala Leu Arg Arg Leu Gln Asn Glu Val Val Asp Thr Glu
    130                 135                 140

ctg ttc aag tgc ctc caa gaa att cac ggc gag ggt tac gac tcc ttt      480
Leu Phe Lys Cys Leu Gln Glu Ile His Gly Glu Gly Tyr Asp Ser Phe
145                 150                 155                 160

atc gcc aag aaa ctt gtg ccg gtc gtt ggt gat gtg cgc gaa gct aac      528
Ile Ala Lys Lys Leu Val Pro Val Val Gly Asp Val Arg Glu Ala Asn
                165                 170                 175

gtc ggc att tcc ccc gat ctc gct gac gag atc gcg gat cag gtg gac      576
Val Gly Ile Ser Pro Asp Leu Ala Asp Glu Ile Ala Asp Gln Val Asp
            180                 185                 190

gtc atc att aac tcc gcc gct aat acc acc ttc gat gag cgc tat gac      624
Val Ile Ile Asn Ser Ala Ala Asn Thr Thr Phe Asp Glu Arg Tyr Asp
        195                 200                 205

gtg gcg atg gat att aac acc gtc ggc ccg ttc cgc atc atg tcc ttc      672
Val Ala Met Asp Ile Asn Thr Val Gly Pro Phe Arg Ile Met Ser Phe
    210                 215                 220

gca cag cgt ttt cgc cgt ctc aag ttg ttt ctt caa gtt tcc acc gcc      720
Ala Gln Arg Phe Arg Arg Leu Lys Leu Phe Leu Gln Val Ser Thr Ala
225                 230                 235                 240

tac gtg aat ggc cag cgt caa ggt ctg gtg ctc gaa aag ccc ttc cgc      768
Tyr Val Asn Gly Gln Arg Gln Gly Leu Val Leu Glu Lys Pro Phe Arg
                245                 250                 255

atg ggc gac acc att gca aaa gaa ctc ggc tct tcc tct tcc ggt tct      816
Met Gly Asp Thr Ile Ala Lys Glu Leu Gly Ser Ser Ser Ser Gly Ser
            260                 265                 270

tcc gag caa ggc cac aac atc cca gtc ttg gat atc gaa gct gag att      864
Ser Glu Gln Gly His Asn Ile Pro Val Leu Asp Ile Glu Ala Glu Ile
        275                 280                 285

aag ctt gcg ttc tat tcc cgc cgt cac ctg gac aac aat tct cct tcc      912
Lys Leu Ala Phe Tyr Ser Arg Arg His Leu Asp Asn Asn Ser Pro Ser
    290                 295                 300

ttt gcc cag gaa atg aag gat ttg ggt ctt gag cgc gct aaa ctg cac      960
Phe Ala Gln Glu Met Lys Asp Leu Gly Leu Glu Arg Ala Lys Leu His
305                 310                 315                 320

ggc tgg caa gat acc tac gtt ttc acc aag gca atg ggt gaa atg gtg     1008
Gly Trp Gln Asp Thr Tyr Val Phe Thr Lys Ala Met Gly Glu Met Val
                325                 330                 335

atc aac tcc atg cgc ggc gag atc cca gtg gtc acc att cgt cct tct     1056
Ile Asn Ser Met Arg Gly Glu Ile Pro Val Val Thr Ile Arg Pro Ser
            340                 345                 350

gtg atc gaa tcc acc tgg cgt gac cct ttc cct ggt tgg atg gag ggt     1104
Val Ile Glu Ser Thr Trp Arg Asp Pro Phe Pro Gly Trp Met Glu Gly
        355                 360                 365

aac cgc atg atg gat cca gtg atc ctg tac tat ggc aaa ggc cag ttg     1152
Asn Arg Met Met Asp Pro Val Ile Leu Tyr Tyr Gly Lys Gly Gln Leu
    370                 375                 380

tcc ggt ttc ctt gcg gat cct gac ggt gtc ctc gac gtt gtg cct gca     1200
Ser Gly Phe Leu Ala Asp Pro Asp Gly Val Leu Asp Val Val Pro Ala
385                 390                 395                 400

gat atg gtc gtt aac gcc acc ttg gct tct atg gca aag cac ggc ggt     1248
Asp Met Val Val Asn Ala Thr Leu Ala Ser Met Ala Lys His Gly Gly
                405                 410                 415

gca gca ggt cct ggt atg cac gtt tac cac gtg tct tcc tct acc gtg     1296
Ala Ala Gly Pro Gly Met His Val Tyr His Val Ser Ser Ser Thr Val
            420                 425                 430
```

```
aat cct ctg gtc ttc ggc gac ctg tcc cgc ttc ctc ttt cac cac ttt      1344
Asn Pro Leu Val Phe Gly Asp Leu Ser Arg Phe Leu Phe His His Phe
        435                 440                 445

acc cgt tgc cca tat tcc gat gcc gct ggc cag cct atc ctg gtg cca      1392
Thr Arg Cys Pro Tyr Ser Asp Ala Ala Gly Gln Pro Ile Leu Val Pro
    450                 455                 460

cct atg cgc ctc ttc gac act atg gaa caa ttt gct tcc tac gtc gag      1440
Pro Met Arg Leu Phe Asp Thr Met Glu Gln Phe Ala Ser Tyr Val Glu
465                 470                 475                 480

acc gat gcg ctc ttg cgc tcc gtt cgt gca tcc tct tcc tct tcc cca      1488
Thr Asp Ala Leu Leu Arg Ser Val Arg Ala Ser Ser Ser Ser Ser Pro
                485                 490                 495

gca gtg gca cag cgt gca cgt gat ctc tgt gcc cgc tct gtt gaa cag      1536
Ala Val Ala Gln Arg Ala Arg Asp Leu Cys Ala Arg Ser Val Glu Gln
            500                 505                 510

acc gtg cac ttg ggt tcc atc tac caa ccg tat acc ttc tac ggc ggt      1584
Thr Val His Leu Gly Ser Ile Tyr Gln Pro Tyr Thr Phe Tyr Gly Gly
        515                 520                 525

cgc ttt gac aac ggc aat acc gaa gca ttg ttc gca gca atg tcc cct      1632
Arg Phe Asp Asn Gly Asn Thr Glu Ala Leu Phe Ala Ala Met Ser Pro
    530                 535                 540

gca gag cgt gca cgt ttc cac ttt gat gtc cgc tcc gtt gat tgg cgt      1680
Ala Glu Arg Ala Arg Phe His Phe Asp Val Arg Ser Val Asp Trp Arg
545                 550                 555                 560

gac tac att acc aac gtc cac atc cct ggc ctg cgc aag cac gtc atg      1728
Asp Tyr Ile Thr Asn Val His Ile Pro Gly Leu Arg Lys His Val Met
                565                 570                 575

aaa ggc cgt ggt gtt gcc gct aat cag ctt ctg gcc tct acc tct gtg      1776
Lys Gly Arg Gly Val Ala Ala Asn Gln Leu Leu Ala Ser Thr Ser Val
            580                 585                 590


<210> SEQ ID NO 34
<211> LENGTH: 592
<212> TYPE: PRT
<213> ORGANISM: Sorghum bicolor (sorghum)

<400> SEQUENCE: 34

Met Gly Ser Ser Cys Val Asn Leu Ser Arg Ala Val Leu Pro Gly Phe
1               5                   10                  15

Gly Ala Ala Ala Ala Ala Lys Gly Gly Ser Arg Arg Arg Gly Leu Leu
            20                  25                  30

Leu Pro Leu Leu Ser Ser Ser Ala Ala Ala Gly Arg Gln Arg His Gly
        35                  40                  45

Ser Ser Ala Ala Val Val Ala Cys Cys Thr Ser Ser Ser Ser Ser Ser
    50                  55                  60

Ser Thr Thr Ala Ala Ala Gly Ser Ser Ser Ala Gly Ala Ala Ala Gly
65                  70                  75                  80

Gly Ile Gly Val Ala Glu Phe Leu Gly Ala Lys Asn Phe Leu Ile Thr
                85                  90                  95

Gly Gly Thr Gly Phe Leu Ala Lys Val Leu Ile Glu Lys Ile Leu Arg
            100                 105                 110

Thr Asn Pro Asn Val Gly Lys Ile Tyr Val Leu Ile Lys Ala Lys Asp
        115                 120                 125

Gly Glu Ala Ala Leu Arg Arg Leu Gln Asn Glu Val Val Asp Thr Glu
    130                 135                 140

Leu Phe Lys Cys Leu Gln Glu Ile His Gly Glu Gly Tyr Asp Ser Phe
145                 150                 155                 160

Ile Ala Lys Lys Leu Val Pro Val Val Gly Asp Val Arg Glu Ala Asn
```

-continued

```
                165                 170                 175

Val Gly Ile Ser Pro Asp Leu Ala Asp Glu Ile Ala Asp Gln Val Asp
            180                 185                 190

Val Ile Ile Asn Ser Ala Ala Asn Thr Thr Phe Asp Glu Arg Tyr Asp
        195                 200                 205

Val Ala Met Asp Ile Asn Thr Val Gly Pro Phe Arg Ile Met Ser Phe
    210                 215                 220

Ala Gln Arg Phe Arg Arg Leu Lys Leu Phe Leu Gln Val Ser Thr Ala
225                 230                 235                 240

Tyr Val Asn Gly Gln Arg Gln Gly Leu Val Leu Glu Lys Pro Phe Arg
                245                 250                 255

Met Gly Asp Thr Ile Ala Lys Glu Leu Gly Ser Ser Ser Ser Gly Ser
            260                 265                 270

Ser Glu Gln Gly His Asn Ile Pro Val Leu Asp Ile Glu Ala Glu Ile
        275                 280                 285

Lys Leu Ala Phe Tyr Ser Arg Arg His Leu Asp Asn Asn Ser Pro Ser
    290                 295                 300

Phe Ala Gln Glu Met Lys Asp Leu Gly Leu Glu Arg Ala Lys Leu His
305                 310                 315                 320

Gly Trp Gln Asp Thr Tyr Val Phe Thr Lys Ala Met Gly Glu Met Val
                325                 330                 335

Ile Asn Ser Met Arg Gly Glu Ile Pro Val Val Thr Ile Arg Pro Ser
            340                 345                 350

Val Ile Glu Ser Thr Trp Arg Asp Pro Phe Pro Gly Trp Met Glu Gly
        355                 360                 365

Asn Arg Met Met Asp Pro Val Ile Leu Tyr Tyr Gly Lys Gly Gln Leu
    370                 375                 380

Ser Gly Phe Leu Ala Asp Pro Asp Gly Val Leu Asp Val Val Pro Ala
385                 390                 395                 400

Asp Met Val Val Asn Ala Thr Leu Ala Ser Met Ala Lys His Gly Gly
                405                 410                 415

Ala Ala Gly Pro Gly Met His Val Tyr His Val Ser Ser Ser Thr Val
            420                 425                 430

Asn Pro Leu Val Phe Gly Asp Leu Ser Arg Phe Leu Phe His His Phe
        435                 440                 445

Thr Arg Cys Pro Tyr Ser Asp Ala Ala Gly Gln Pro Ile Leu Val Pro
    450                 455                 460

Pro Met Arg Leu Phe Asp Thr Met Glu Gln Phe Ala Ser Tyr Val Glu
465                 470                 475                 480

Thr Asp Ala Leu Leu Arg Ser Val Arg Ala Ser Ser Ser Ser Ser Pro
                485                 490                 495

Ala Val Ala Gln Arg Ala Arg Asp Leu Cys Ala Arg Ser Val Glu Gln
            500                 505                 510

Thr Val His Leu Gly Ser Ile Tyr Gln Pro Tyr Thr Phe Tyr Gly Gly
        515                 520                 525

Arg Phe Asp Asn Gly Asn Thr Glu Ala Leu Phe Ala Ala Met Ser Pro
    530                 535                 540

Ala Glu Arg Ala Arg Phe His Phe Asp Val Arg Ser Val Asp Trp Arg
545                 550                 555                 560

Asp Tyr Ile Thr Asn Val His Ile Pro Gly Leu Arg Lys His Val Met
                565                 570                 575

Lys Gly Arg Gly Val Ala Ala Asn Gln Leu Leu Ala Ser Thr Ser Val
            580                 585                 590
```

```
<210> SEQ ID NO 35
<211> LENGTH: 1824
<212> TYPE: DNA
<213> ORGANISM: Oryza sativa japonica (Japanese rice)
<220> FEATURE:
<221> NAME/KEY: CDS
<222> LOCATION: (1)..(1824)

<400> SEQUENCE: 35

atg ggc atg tct tcc tgc gtc aat ctt tct cgc gtc gct gct gcg gcg       48
Met Gly Met Ser Ser Cys Val Asn Leu Ser Arg Val Ala Ala Ala Ala
1               5                   10                  15

gct ggt cgt cgt ccc ggc ttc gct ggt gaa ctg ggc ggc cgc cgt ggt       96
Ala Gly Arg Arg Pro Gly Phe Ala Gly Glu Leu Gly Gly Arg Arg Gly
            20                  25                  30

cac ggc cgc tcc gtt ctc cca gtg gtc gca gca ttg cct gtg cgc cgt      144
His Gly Arg Ser Val Leu Pro Val Val Ala Ala Leu Pro Val Arg Arg
        35                  40                  45

aag ggt tcc ggt tgc ggt gtg gca tgc tgt gtc tcc tct tcc tct tcc      192
Lys Gly Ser Gly Cys Gly Val Ala Cys Cys Val Ser Ser Ser Ser Ser
    50                  55                  60

tct tcc gtt cac ggc aaa aac tcc gct gcg gca gcc gaa ggt cac gct      240
Ser Ser Val His Gly Lys Asn Ser Ala Ala Ala Ala Glu Gly His Ala
65                  70                  75                  80

ggc ggt atc ggt att gcg gag ttc ctt ggc ggt aaa aat ttt ctg atc      288
Gly Gly Ile Gly Ile Ala Glu Phe Leu Gly Gly Lys Asn Phe Leu Ile
                85                  90                  95

acc ggc ggt acc ggc ttc ctc gct aag gtc ttg atc gaa aaa att ctc      336
Thr Gly Gly Thr Gly Phe Leu Ala Lys Val Leu Ile Glu Lys Ile Leu
            100                 105                 110

cgc acc aac cca gac gtc ggc aag atc tat gtt ttg att aag gcg aaa      384
Arg Thr Asn Pro Asp Val Gly Lys Ile Tyr Val Leu Ile Lys Ala Lys
        115                 120                 125

gat ggt gac gct gcg ctc aaa cgt ttg cac aac gag gtt gtg gac acc      432
Asp Gly Asp Ala Ala Leu Lys Arg Leu His Asn Glu Val Val Asp Thr
    130                 135                 140

gaa ctt ttc tcc cgc ctg cag gag atc cac ggc aag gat tac cac tct      480
Glu Leu Phe Ser Arg Leu Gln Glu Ile His Gly Lys Asp Tyr His Ser
145                 150                 155                 160

ttt gca gcc cgt aaa ctc gtg cca gtc gtt ggc gat gtg cgc gag gca      528
Phe Ala Ala Arg Lys Leu Val Pro Val Val Gly Asp Val Arg Glu Ala
                165                 170                 175

aac gtc ggc att gcg cct gaa ttg gca ggt gtc atc gcc gat gag gtt      576
Asn Val Gly Ile Ala Pro Glu Leu Ala Gly Val Ile Ala Asp Glu Val
            180                 185                 190

gac atc att gtg aac tcc gct gcg aat acc acc ttc gat gaa cgc tat      624
Asp Ile Ile Val Asn Ser Ala Ala Asn Thr Thr Phe Asp Glu Arg Tyr
        195                 200                 205

gac gtg gcg atg gat att aat acc gtc ggc cca ttc cgc atc atg tcc      672
Asp Val Ala Met Asp Ile Asn Thr Val Gly Pro Phe Arg Ile Met Ser
    210                 215                 220

ttc gca cag cgt ttt cgc cgt ctg aag ctc ttt ttg caa gtt tcc acc      720
Phe Ala Gln Arg Phe Arg Arg Leu Lys Leu Phe Leu Gln Val Ser Thr
225                 230                 235                 240

gcc tac gtg aac ggc cag cgt caa ggt gtg gtc ctc gaa aag ccg ttc      768
Ala Tyr Val Asn Gly Gln Arg Gln Gly Val Val Leu Glu Lys Pro Phe
                245                 250                 255

cgc ttg ggc gac acc atc gcc aaa gag ctg ggt tcc ccc gat tct tcc      816
Arg Leu Gly Asp Thr Ile Ala Lys Glu Leu Gly Ser Pro Asp Ser Ser
            260                 265                 270
```

-continued

```
cag cac aag aac acc atg ctt gac atc gag gca gaa att aaa ctg gcc      864
Gln His Lys Asn Thr Met Leu Asp Ile Glu Ala Glu Ile Lys Leu Ala
        275                 280                 285

ttc gat cac cgc cgt cac ggc gat gac tct gca tcc ttt tct gaa gag      912
Phe Asp His Arg Arg His Gly Asp Asp Ser Ala Ser Phe Ser Glu Glu
    290                 295                 300

atg aag gag ctt ggc ctg gaa cgc gcc aaa ctc cac ggt tgg caa gac      960
Met Lys Glu Leu Gly Leu Glu Arg Ala Lys Leu His Gly Trp Gln Asp
305                 310                 315                 320

acc tac gtc ttc acc aag gct atg ggc gaa atg gtt atc aat tcc atg     1008
Thr Tyr Val Phe Thr Lys Ala Met Gly Glu Met Val Ile Asn Ser Met
                325                 330                 335

cgc ggt gat atc ccg gtt gtg acc att cgt ccc tcc gtg atc gaa tct     1056
Arg Gly Asp Ile Pro Val Val Thr Ile Arg Pro Ser Val Ile Glu Ser
            340                 345                 350

acc tgg cgt gac cct ttc cct ggt tgg atg gag ggt aac cgc atg atg     1104
Thr Trp Arg Asp Pro Phe Pro Gly Trp Met Glu Gly Asn Arg Met Met
        355                 360                 365

gat ccg gtc gtt ttg tac tat ggc aag ggt cag ctc tcc ggc ttc ttg     1152
Asp Pro Val Val Leu Tyr Tyr Gly Lys Gly Gln Leu Ser Gly Phe Leu
    370                 375                 380

gca gat cca gaa ggt gtg ctt gac gtg gtc cct gcc gat atg gtt gtg     1200
Ala Asp Pro Glu Gly Val Leu Asp Val Val Pro Ala Asp Met Val Val
385                 390                 395                 400

aat gca acc ctg gcc tct atg gca aaa cac ggt cgc ggc ggt gca gcc     1248
Asn Ala Thr Leu Ala Ser Met Ala Lys His Gly Arg Gly Gly Ala Ala
                405                 410                 415

gct gcg gca gcc gct gcg gag ggt atg cac gtc tac cac gtt gct tct     1296
Ala Ala Ala Ala Ala Ala Glu Gly Met His Val Tyr His Val Ala Ser
            420                 425                 430

tcc acc gtg aac cct ctg gcg ttc ggc gac ctt tcc cgc ttc ctg ttt     1344
Ser Thr Val Asn Pro Leu Ala Phe Gly Asp Leu Ser Arg Phe Leu Phe
        435                 440                 445

cag cac ttt acc ggc tcc ccg tat tct gat gca gca ggt cgt cct atc     1392
Gln His Phe Thr Gly Ser Pro Tyr Ser Asp Ala Ala Gly Arg Pro Ile
    450                 455                 460

cac gtc cca cct atg cgt ctt ttc gac act atg gaa caa ttt gct tcc     1440
His Val Pro Pro Met Arg Leu Phe Asp Thr Met Glu Gln Phe Ala Ser
465                 470                 475                 480

tac gtt gaa acc gat gct ctg ctc cgt gca ggc cgt ctg gct ggt gca     1488
Tyr Val Glu Thr Asp Ala Leu Leu Arg Ala Gly Arg Leu Ala Gly Ala
                485                 490                 495

ggt gca ggt gca ggt gac gaa cgt gtg tcc caa cgt ctt cgt gag ctg     1536
Gly Ala Gly Ala Gly Asp Glu Arg Val Ser Gln Arg Leu Arg Glu Leu
            500                 505                 510

tgt gcc aag tcc gtc gaa cag acc att tat ctc ggc tct atc tac caa     1584
Cys Ala Lys Ser Val Glu Gln Thr Ile Tyr Leu Gly Ser Ile Tyr Gln
        515                 520                 525

cca tat acc ttc tac ggc ggt cgc ttt gat aac ggc aat acc gag gct     1632
Pro Tyr Thr Phe Tyr Gly Gly Arg Phe Asp Asn Gly Asn Thr Glu Ala
    530                 535                 540

ttg att ggt gaa atg tcc gaa gag gaa aag gcg cgc ttc cac ttt gac     1680
Leu Ile Gly Glu Met Ser Glu Glu Glu Lys Ala Arg Phe His Phe Asp
545                 550                 555                 560

gtt cgt tct atc gaa tgg acc gat tac att acc aat gtg cac atc cct     1728
Val Arg Ser Ile Glu Trp Thr Asp Tyr Ile Thr Asn Val His Ile Pro
                565                 570                 575

ggc ctc cgc aag cac gtc atg aaa ggt cgt ggt gtt ggc ggt ggc tcc     1776
Gly Leu Arg Lys His Val Met Lys Gly Arg Gly Val Gly Gly Gly Ser
```

```
            580                 585                 590

ggt gca tct tcc tct tcc aac gcc tcc ttg ctt gct ggt gcg tct gtg     1824
Gly Ala Ser Ser Ser Ser Asn Ala Ser Leu Leu Ala Gly Ala Ser Val
        595                 600                 605


<210> SEQ ID NO 36
<211> LENGTH: 608
<212> TYPE: PRT
<213> ORGANISM: Oryza sativa japonica (Japanese rice)

<400> SEQUENCE: 36

Met Gly Met Ser Ser Cys Val Asn Leu Ser Arg Val Ala Ala Ala Ala
1               5                   10                  15

Ala Gly Arg Arg Pro Gly Phe Ala Gly Glu Leu Gly Gly Arg Arg Gly
            20                  25                  30

His Gly Arg Ser Val Leu Pro Val Val Ala Ala Leu Pro Val Arg Arg
        35                  40                  45

Lys Gly Ser Gly Cys Gly Val Ala Cys Cys Val Ser Ser Ser Ser Ser
    50                  55                  60

Ser Ser Val His Gly Lys Asn Ser Ala Ala Ala Ala Glu Gly His Ala
65                  70                  75                  80

Gly Gly Ile Gly Ile Ala Glu Phe Leu Gly Gly Lys Asn Phe Leu Ile
                85                  90                  95

Thr Gly Gly Thr Gly Phe Leu Ala Lys Val Leu Ile Glu Lys Ile Leu
            100                 105                 110

Arg Thr Asn Pro Asp Val Gly Lys Ile Tyr Val Leu Ile Lys Ala Lys
        115                 120                 125

Asp Gly Asp Ala Ala Leu Lys Arg Leu His Asn Glu Val Val Asp Thr
    130                 135                 140

Glu Leu Phe Ser Arg Leu Gln Glu Ile His Gly Lys Asp Tyr His Ser
145                 150                 155                 160

Phe Ala Ala Arg Lys Leu Val Pro Val Val Gly Asp Val Arg Glu Ala
                165                 170                 175

Asn Val Gly Ile Ala Pro Glu Leu Ala Gly Val Ile Ala Asp Glu Val
            180                 185                 190

Asp Ile Ile Val Asn Ser Ala Ala Asn Thr Thr Phe Asp Glu Arg Tyr
        195                 200                 205

Asp Val Ala Met Asp Ile Asn Thr Val Gly Pro Phe Arg Ile Met Ser
    210                 215                 220

Phe Ala Gln Arg Phe Arg Arg Leu Lys Leu Phe Leu Gln Val Ser Thr
225                 230                 235                 240

Ala Tyr Val Asn Gly Gln Arg Gln Gly Val Val Leu Glu Lys Pro Phe
                245                 250                 255

Arg Leu Gly Asp Thr Ile Ala Lys Glu Leu Gly Ser Pro Asp Ser Ser
            260                 265                 270

Gln His Lys Asn Thr Met Leu Asp Ile Glu Ala Glu Ile Lys Leu Ala
        275                 280                 285

Phe Asp His Arg Arg His Gly Asp Asp Ser Ala Ser Phe Ser Glu Glu
    290                 295                 300

Met Lys Glu Leu Gly Leu Glu Arg Ala Lys Leu His Gly Trp Gln Asp
305                 310                 315                 320

Thr Tyr Val Phe Thr Lys Ala Met Gly Glu Met Val Ile Asn Ser Met
                325                 330                 335

Arg Gly Asp Ile Pro Val Val Thr Ile Arg Pro Ser Val Ile Glu Ser
            340                 345                 350
```

-continued

```
Thr Trp Arg Asp Pro Phe Pro Gly Trp Met Glu Gly Asn Arg Met Met
        355                 360                 365

Asp Pro Val Val Leu Tyr Tyr Gly Lys Gly Gln Leu Ser Gly Phe Leu
    370                 375                 380

Ala Asp Pro Glu Gly Val Leu Asp Val Val Pro Ala Asp Met Val Val
385                 390                 395                 400

Asn Ala Thr Leu Ala Ser Met Ala Lys His Gly Arg Gly Gly Ala Ala
                405                 410                 415

Ala Ala Ala Ala Ala Ala Glu Gly Met His Val Tyr His Val Ala Ser
            420                 425                 430

Ser Thr Val Asn Pro Leu Ala Phe Gly Asp Leu Ser Arg Phe Leu Phe
        435                 440                 445

Gln His Phe Thr Gly Ser Pro Tyr Ser Asp Ala Ala Gly Arg Pro Ile
    450                 455                 460

His Val Pro Pro Met Arg Leu Phe Asp Thr Met Glu Gln Phe Ala Ser
465                 470                 475                 480

Tyr Val Glu Thr Asp Ala Leu Leu Arg Ala Gly Arg Leu Ala Gly Ala
                485                 490                 495

Gly Ala Gly Ala Gly Asp Glu Arg Val Ser Gln Arg Leu Arg Glu Leu
            500                 505                 510

Cys Ala Lys Ser Val Glu Gln Thr Ile Tyr Leu Gly Ser Ile Tyr Gln
        515                 520                 525

Pro Tyr Thr Phe Tyr Gly Gly Arg Phe Asp Asn Gly Asn Thr Glu Ala
    530                 535                 540

Leu Ile Gly Glu Met Ser Glu Glu Glu Lys Ala Arg Phe His Phe Asp
545                 550                 555                 560

Val Arg Ser Ile Glu Trp Thr Asp Tyr Ile Thr Asn Val His Ile Pro
                565                 570                 575

Gly Leu Arg Lys His Val Met Lys Gly Arg Gly Val Gly Gly Gly Ser
            580                 585                 590

Gly Ala Ser Ser Ser Ser Asn Ala Ser Leu Leu Ala Gly Ala Ser Val
        595                 600                 605


<210> SEQ ID NO 37
<211> LENGTH: 1581
<212> TYPE: DNA
<213> ORGANISM: Arabidopsis thaliana
<220> FEATURE:
<221> NAME/KEY: CDS
<222> LOCATION: (1)..(1581)

<400> SEQUENCE: 37

atg gca acc acc aac gtc ctg gca acc tcg cac gcc ttc aaa ctg aac       48
Met Ala Thr Thr Asn Val Leu Ala Thr Ser His Ala Phe Lys Leu Asn
1               5                   10                  15

ggc gtc tcg tac ttt tct tct ttc cct cgc aaa cct aac cac tac atg       96
Gly Val Ser Tyr Phe Ser Ser Phe Pro Arg Lys Pro Asn His Tyr Met
            20                  25                  30

cca cgc cgt cgc ctg tct cat acc acc cgt cgc gtg cag acc tca tgc      144
Pro Arg Arg Arg Leu Ser His Thr Thr Arg Arg Val Gln Thr Ser Cys
        35                  40                  45

ttc tat ggt gaa acc tcg ttt gag gcc gtt acc agc ctg gtc acc cct      192
Phe Tyr Gly Glu Thr Ser Phe Glu Ala Val Thr Ser Leu Val Thr Pro
    50                  55                  60

aag acc gaa acc agc cgt aac tct gat ggt atc ggc att gtc cgc ttc      240
Lys Thr Glu Thr Ser Arg Asn Ser Asp Gly Ile Gly Ile Val Arg Phe
65                  70                  75                  80
```

-continued

```
ctg gag ggt aaa tcc tac ctg gtg acc ggt gcg acc ggc ttt ctg gca      288
Leu Glu Gly Lys Ser Tyr Leu Val Thr Gly Ala Thr Gly Phe Leu Ala
                85                  90                  95

aag gtt ctg atc gaa aaa ctg ctg cgt gaa agc ctg gag atc ggc aaa      336
Lys Val Leu Ile Glu Lys Leu Leu Arg Glu Ser Leu Glu Ile Gly Lys
            100                 105                 110

att ttt ctg ctg atg cgt tct aag gac cag gaa tca gcg aat aaa cgc      384
Ile Phe Leu Leu Met Arg Ser Lys Asp Gln Glu Ser Ala Asn Lys Arg
        115                 120                 125

ctg tac gat gag atc att tcc agc gac ctg ttc aag ctg ctg aaa caa      432
Leu Tyr Asp Glu Ile Ile Ser Ser Asp Leu Phe Lys Leu Leu Lys Gln
    130                 135                 140

atg cac ggc tcc tcc tac gaa gcg ttt atg aaa cgc aag ctg atc ccg      480
Met His Gly Ser Ser Tyr Glu Ala Phe Met Lys Arg Lys Leu Ile Pro
145                 150                 155                 160

gtt att ggt gat atc gaa gag gac aac ctg ggc atc aag agc gaa atc      528
Val Ile Gly Asp Ile Glu Glu Asp Asn Leu Gly Ile Lys Ser Glu Ile
                165                 170                 175

gca aac atg atc tct gaa gag atc gat gtc atc att tcc tgc ggc ggt      576
Ala Asn Met Ile Ser Glu Glu Ile Asp Val Ile Ile Ser Cys Gly Gly
            180                 185                 190

cgt acc acc ttc gat gac cgc tac gac tca gct ctg tcg gtc aac gct      624
Arg Thr Thr Phe Asp Asp Arg Tyr Asp Ser Ala Leu Ser Val Asn Ala
        195                 200                 205

ctg ggt cct gcg tac gtg acc ggt aaa cgc gaa ggc acc gtt ctg gag      672
Leu Gly Pro Ala Tyr Val Thr Gly Lys Arg Glu Gly Thr Val Leu Glu
    210                 215                 220

acc cca ctg tgt att ggc gaa aac atc acc agc gat ctg aat att aag      720
Thr Pro Leu Cys Ile Gly Glu Asn Ile Thr Ser Asp Leu Asn Ile Lys
225                 230                 235                 240

tct gaa ctg aaa ctg gcc tca gag gct gtc cgt aag ttc cgt ggc cgc      768
Ser Glu Leu Lys Leu Ala Ser Glu Ala Val Arg Lys Phe Arg Gly Arg
                245                 250                 255

gaa gag atc aaa aag ctg aaa gaa ctg ggt ttt gag cgc gca cag cac      816
Glu Glu Ile Lys Lys Leu Lys Glu Leu Gly Phe Glu Arg Ala Gln His
            260                 265                 270

tac ggc tgg gaa aat agc tat acc ttc acc aag gcc att ggc gag gct      864
Tyr Gly Trp Glu Asn Ser Tyr Thr Phe Thr Lys Ala Ile Gly Glu Ala
        275                 280                 285

gtt atc cat tcc aaa cgt ggc aac ctg cct gtg gtt atc att cgc ccg      912
Val Ile His Ser Lys Arg Gly Asn Leu Pro Val Val Ile Ile Arg Pro
    290                 295                 300

agc atc att gaa tcg tcc tac aat gag ccg ttt cca ggt tgg att cag      960
Ser Ile Ile Glu Ser Ser Tyr Asn Glu Pro Phe Pro Gly Trp Ile Gln
305                 310                 315                 320

ggc acc cgt atg gcc gat cca atc att ctg gcg tat gca aag ggt cag     1008
Gly Thr Arg Met Ala Asp Pro Ile Ile Leu Ala Tyr Ala Lys Gly Gln
                325                 330                 335

atc tca gat ttc tgg gct gac cca caa tcg ctg atg gat atc att cct     1056
Ile Ser Asp Phe Trp Ala Asp Pro Gln Ser Leu Met Asp Ile Ile Pro
            340                 345                 350

gtc gac atg gtg gcc aac gcg gca att gcc gct atg gct aag cac ggt     1104
Val Asp Met Val Ala Asn Ala Ala Ile Ala Ala Met Ala Lys His Gly
        355                 360                 365

tgc ggc gtg cct gaa ttt aaa gtt tat aac ctg acc agc tct tca cat     1152
Cys Gly Val Pro Glu Phe Lys Val Tyr Asn Leu Thr Ser Ser Ser His
    370                 375                 380

gtg aat ccg atg cgc gcc ggc aaa ctg atc gat ctg tcc cac cag cat     1200
Val Asn Pro Met Arg Ala Gly Lys Leu Ile Asp Leu Ser His Gln His
```

```
385                 390                 395                 400

ctg tgt gac ttt ccg ctg gaa gag acc gtt att gat ctg gaa cac atg     1248
Leu Cys Asp Phe Pro Leu Glu Glu Thr Val Ile Asp Leu Glu His Met
                405                 410                 415

aag atc cat tcg tcc ctg gag ggt ttc acc agc gct ctg agc aac acc     1296
Lys Ile His Ser Ser Leu Glu Gly Phe Thr Ser Ala Leu Ser Asn Thr
            420                 425                 430

atc att aaa caa gaa cgt gtc att gac aat gag ggc ggt ggc ctg tct     1344
Ile Ile Lys Gln Glu Arg Val Ile Asp Asn Glu Gly Gly Gly Leu Ser
        435                 440                 445

acc aaa ggc aag cgc aaa ctg aac tac ttt gtg agc ctg gcg aag acc     1392
Thr Lys Gly Lys Arg Lys Leu Asn Tyr Phe Val Ser Leu Ala Lys Thr
    450                 455                 460

tac gaa cca tat acc ttc ttt cag gca cgc ttc gat aac acc aat acc     1440
Tyr Glu Pro Tyr Thr Phe Phe Gln Ala Arg Phe Asp Asn Thr Asn Thr
465                 470                 475                 480

acc tcg ctg atc caa gaa atg agc atg gaa gag aaa aag acc ttc ggt     1488
Thr Ser Leu Ile Gln Glu Met Ser Met Glu Glu Lys Lys Thr Phe Gly
                485                 490                 495

ttt gat att aaa ggc atc gac tgg gaa cat tat atc gtg aat gtc cat     1536
Phe Asp Ile Lys Gly Ile Asp Trp Glu His Tyr Ile Val Asn Val His
            500                 505                 510

ctg cct ggt ctg aag aaa gag ttc ctg tcg aag aag aaa acc gaa         1581
Leu Pro Gly Leu Lys Lys Glu Phe Leu Ser Lys Lys Lys Thr Glu
        515                 520                 525


<210> SEQ ID NO 38
<211> LENGTH: 527
<212> TYPE: PRT
<213> ORGANISM: Arabidopsis thaliana

<400> SEQUENCE: 38

Met Ala Thr Thr Asn Val Leu Ala Thr Ser His Ala Phe Lys Leu Asn
1               5                   10                  15

Gly Val Ser Tyr Phe Ser Ser Phe Pro Arg Lys Pro Asn His Tyr Met
            20                  25                  30

Pro Arg Arg Arg Leu Ser His Thr Thr Arg Arg Val Gln Thr Ser Cys
        35                  40                  45

Phe Tyr Gly Glu Thr Ser Phe Glu Ala Val Thr Ser Leu Val Thr Pro
    50                  55                  60

Lys Thr Glu Thr Ser Arg Asn Ser Asp Gly Ile Gly Ile Val Arg Phe
65                  70                  75                  80

Leu Glu Gly Lys Ser Tyr Leu Val Thr Gly Ala Thr Gly Phe Leu Ala
                85                  90                  95

Lys Val Leu Ile Glu Lys Leu Leu Arg Glu Ser Leu Glu Ile Gly Lys
            100                 105                 110

Ile Phe Leu Leu Met Arg Ser Lys Asp Gln Glu Ser Ala Asn Lys Arg
        115                 120                 125

Leu Tyr Asp Glu Ile Ile Ser Ser Asp Leu Phe Lys Leu Leu Lys Gln
    130                 135                 140

Met His Gly Ser Ser Tyr Glu Ala Phe Met Lys Arg Lys Leu Ile Pro
145                 150                 155                 160

Val Ile Gly Asp Ile Glu Glu Asp Asn Leu Gly Ile Lys Ser Glu Ile
                165                 170                 175

Ala Asn Met Ile Ser Glu Glu Ile Asp Val Ile Ile Ser Cys Gly Gly
            180                 185                 190

Arg Thr Thr Phe Asp Asp Arg Tyr Asp Ser Ala Leu Ser Val Asn Ala
```

```
        195                 200                 205

Leu Gly Pro Ala Tyr Val Thr Gly Lys Arg Glu Gly Thr Val Leu Glu
    210                 215                 220

Thr Pro Leu Cys Ile Gly Glu Asn Ile Thr Ser Asp Leu Asn Ile Lys
225                 230                 235                 240

Ser Glu Leu Lys Leu Ala Ser Glu Ala Val Arg Lys Phe Arg Gly Arg
            245                 250                 255

Glu Glu Ile Lys Lys Leu Lys Glu Leu Gly Phe Glu Arg Ala Gln His
            260                 265                 270

Tyr Gly Trp Glu Asn Ser Tyr Thr Phe Thr Lys Ala Ile Gly Glu Ala
        275                 280                 285

Val Ile His Ser Lys Arg Gly Asn Leu Pro Val Val Ile Ile Arg Pro
    290                 295                 300

Ser Ile Ile Glu Ser Ser Tyr Asn Glu Pro Phe Pro Gly Trp Ile Gln
305                 310                 315                 320

Gly Thr Arg Met Ala Asp Pro Ile Ile Leu Ala Tyr Ala Lys Gly Gln
            325                 330                 335

Ile Ser Asp Phe Trp Ala Asp Pro Gln Ser Leu Met Asp Ile Ile Pro
            340                 345                 350

Val Asp Met Val Ala Asn Ala Ala Ile Ala Ala Met Ala Lys His Gly
        355                 360                 365

Cys Gly Val Pro Glu Phe Lys Val Tyr Asn Leu Thr Ser Ser Ser His
    370                 375                 380

Val Asn Pro Met Arg Ala Gly Lys Leu Ile Asp Leu Ser His Gln His
385                 390                 395                 400

Leu Cys Asp Phe Pro Leu Glu Glu Thr Val Ile Asp Leu Glu His Met
            405                 410                 415

Lys Ile His Ser Ser Leu Glu Gly Phe Thr Ser Ala Leu Ser Asn Thr
            420                 425                 430

Ile Ile Lys Gln Glu Arg Val Ile Asp Asn Glu Gly Gly Gly Leu Ser
        435                 440                 445

Thr Lys Gly Lys Arg Lys Leu Asn Tyr Phe Val Ser Leu Ala Lys Thr
    450                 455                 460

Tyr Glu Pro Tyr Thr Phe Phe Gln Ala Arg Phe Asp Asn Thr Asn Thr
465                 470                 475                 480

Thr Ser Leu Ile Gln Glu Met Ser Met Glu Glu Lys Lys Thr Phe Gly
            485                 490                 495

Phe Asp Ile Lys Gly Ile Asp Trp Glu His Tyr Ile Val Asn Val His
            500                 505                 510

Leu Pro Gly Leu Lys Lys Glu Phe Leu Ser Lys Lys Lys Thr Glu
        515                 520                 525


<210> SEQ ID NO 39
<211> LENGTH: 1581
<212> TYPE: DNA
<213> ORGANISM: Arabidopsis thaliana
<220> FEATURE:
<221> NAME/KEY: CDS
<222> LOCATION: (1)..(1581)

<400> SEQUENCE: 39

atg gca acc acc aac gtc ctg gca acc tcg cac gcc ttc aaa ctg aac       48
Met Ala Thr Thr Asn Val Leu Ala Thr Ser His Ala Phe Lys Leu Asn
1               5                   10                  15

ggc gtc tcg tac ttt tct tct ttc cct cgc aaa cct aac cac tac atg       96
Gly Val Ser Tyr Phe Ser Ser Phe Pro Arg Lys Pro Asn His Tyr Met
```

-continued

```
            20                  25                  30

cca cgc cgt cgc ctg tct cat acc acc cgt cgc gtg cag acc tca tgc      144
Pro Arg Arg Arg Leu Ser His Thr Thr Arg Arg Val Gln Thr Ser Cys
        35                  40                  45

ttc tat ggt gaa acc tcg ttt gag gcc gtt acc agc ctg gtc acc cct      192
Phe Tyr Gly Glu Thr Ser Phe Glu Ala Val Thr Ser Leu Val Thr Pro
    50                  55                  60

aag acc gaa acc agc cgt aac tct gat ggt atc ggc att gtc cgc ttc      240
Lys Thr Glu Thr Ser Arg Asn Ser Asp Gly Ile Gly Ile Val Arg Phe
65                  70                  75                  80

ctg gag ggt aaa tcc tac ctg gtg acc ggt gcg acc ggc ttt ctg gca      288
Leu Glu Gly Lys Ser Tyr Leu Val Thr Gly Ala Thr Gly Phe Leu Ala
                85                  90                  95

aag gtt ctg atc gaa aaa ctg ctg cgt gaa agc ctg gag atc ggc aaa      336
Lys Val Leu Ile Glu Lys Leu Leu Arg Glu Ser Leu Glu Ile Gly Lys
            100                 105                 110

att ttt ctg ctg atg cgt tct aag gac cag gaa tca gcg aat aaa cgc      384
Ile Phe Leu Leu Met Arg Ser Lys Asp Gln Glu Ser Ala Asn Lys Arg
        115                 120                 125

ctg tac gat gag atc att tcc agc gac ctg ttc aag ctg ctg aaa caa      432
Leu Tyr Asp Glu Ile Ile Ser Ser Asp Leu Phe Lys Leu Leu Lys Gln
    130                 135                 140

atg cac ggc tcc tcc tac gaa gcg ttt atg aaa cgc aag ctg atc ccg      480
Met His Gly Ser Ser Tyr Glu Ala Phe Met Lys Arg Lys Leu Ile Pro
145                 150                 155                 160

gtt att ggt gat atc gaa gag gac aac ctg ggc atc aag agc gaa atc      528
Val Ile Gly Asp Ile Glu Glu Asp Asn Leu Gly Ile Lys Ser Glu Ile
                165                 170                 175

gca aac atg atc tct gaa gag atc gat gtc atc att tcc tgc ggc ggt      576
Ala Asn Met Ile Ser Glu Glu Ile Asp Val Ile Ile Ser Cys Gly Gly
            180                 185                 190

cgt acc acc ttc gat gac cgc tac gac tca gct ctg tcg gtc aac gct      624
Arg Thr Thr Phe Asp Asp Arg Tyr Asp Ser Ala Leu Ser Val Asn Ala
        195                 200                 205

ctg ggt cct gcg tac gtg acc ggt aaa cgc gaa ggc acc gtt ctg gag      672
Leu Gly Pro Ala Tyr Val Thr Gly Lys Arg Glu Gly Thr Val Leu Glu
    210                 215                 220

acc cca ctg tgt att ggc gaa aac atc acc agc gat ctg aat att aag      720
Thr Pro Leu Cys Ile Gly Glu Asn Ile Thr Ser Asp Leu Asn Ile Lys
225                 230                 235                 240

tct gaa ctg aaa ctg gcc tca gag gct gtc cgt aag ttc cgt ggc cgc      768
Ser Glu Leu Lys Leu Ala Ser Glu Ala Val Arg Lys Phe Arg Gly Arg
                245                 250                 255

gaa gag atc aaa aag ctg aaa gaa ctg ggt ttt gag cgc gca cag cac      816
Glu Glu Ile Lys Lys Leu Lys Glu Leu Gly Phe Glu Arg Ala Gln His
            260                 265                 270

tac ggc tgg gaa aat agc tat acc ttc acc aag gcc att ggc gag gct      864
Tyr Gly Trp Glu Asn Ser Tyr Thr Phe Thr Lys Ala Ile Gly Glu Ala
        275                 280                 285

gtt atc cat tcc aaa cgt ggc aac ctg cct gtg gtt atc att cgc ccg      912
Val Ile His Ser Lys Arg Gly Asn Leu Pro Val Val Ile Ile Arg Pro
    290                 295                 300

agc atc att gaa tcg tcc tac aat gag ccg ttt cca ggt tgg att cag      960
Ser Ile Ile Glu Ser Ser Tyr Asn Glu Pro Phe Pro Gly Trp Ile Gln
305                 310                 315                 320

ggc acc cgt atg gcc gat cca atc att ctg gcg tat gca aag ggt cag     1008
Gly Thr Arg Met Ala Asp Pro Ile Ile Leu Ala Tyr Ala Lys Gly Gln
                325                 330                 335

atc tca gat ttc tgg gct gac cca caa tcg ctg atg gat atc att cct     1056
```

```
Ile Ser Asp Phe Trp Ala Asp Pro Gln Ser Leu Met Asp Ile Ile Pro
            340                 345                 350

gtc gac atg gtg gcc aac gcg gca att gcc gct atg gct aag cac ggt     1104
Val Asp Met Val Ala Asn Ala Ala Ile Ala Ala Met Ala Lys His Gly
        355                 360                 365

tgc ggc gtg cct gaa ttt aaa gtt tat aac ctg acc agc tct tca cat     1152
Cys Gly Val Pro Glu Phe Lys Val Tyr Asn Leu Thr Ser Ser Ser His
    370                 375                 380

gtg aat ccg atg cgc gcc ggc aaa ctg atc gat ctg tcc cac cag cat     1200
Val Asn Pro Met Arg Ala Gly Lys Leu Ile Asp Leu Ser His Gln His
385                 390                 395                 400

ctg tgt gac ttt ccg ctg gaa gag acc gtt att gat ctg gaa cac atg     1248
Leu Cys Asp Phe Pro Leu Glu Glu Thr Val Ile Asp Leu Glu His Met
                405                 410                 415

aag atc cat tcg tcc ctg gag ggt ttc acc agc gct ctg agc aac acc     1296
Lys Ile His Ser Ser Leu Glu Gly Phe Thr Ser Ala Leu Ser Asn Thr
            420                 425                 430

atc att aaa caa gaa cgt gtc att gac aat gag ggc ggt ggc ctg tct     1344
Ile Ile Lys Gln Glu Arg Val Ile Asp Asn Glu Gly Gly Gly Leu Ser
        435                 440                 445

acc aaa ggc aag cgc aaa ctg aac tac ttt gtg agc ctg gcg aag acc     1392
Thr Lys Gly Lys Arg Lys Leu Asn Tyr Phe Val Ser Leu Ala Lys Thr
    450                 455                 460

tac gaa cca tat acc ttc ttt cag gca cgc ttc gat aac acc aat acc     1440
Tyr Glu Pro Tyr Thr Phe Phe Gln Ala Arg Phe Asp Asn Thr Asn Thr
465                 470                 475                 480

acc tcg ctg atc caa gaa atg agc atg gaa gag aaa aag acc ttc ggt     1488
Thr Ser Leu Ile Gln Glu Met Ser Met Glu Glu Lys Lys Thr Phe Gly
                485                 490                 495

ttt gat att aaa ggc atc gac tgg gaa cat tat atc gtg aat gtc cat     1536
Phe Asp Ile Lys Gly Ile Asp Trp Glu His Tyr Ile Val Asn Val His
            500                 505                 510

ctg cct ggt ctg aag aaa gag ttc ctg tcg aag aag aaa acc gaa         1581
Leu Pro Gly Leu Lys Lys Glu Phe Leu Ser Lys Lys Lys Thr Glu
        515                 520                 525


<210> SEQ ID NO 40
<211> LENGTH: 527
<212> TYPE: PRT
<213> ORGANISM: Arabidopsis thaliana

<400> SEQUENCE: 40

Met Ala Thr Thr Asn Val Leu Ala Thr Ser His Ala Phe Lys Leu Asn
1               5                   10                  15

Gly Val Ser Tyr Phe Ser Ser Phe Pro Arg Lys Pro Asn His Tyr Met
            20                  25                  30

Pro Arg Arg Arg Leu Ser His Thr Thr Arg Arg Val Gln Thr Ser Cys
        35                  40                  45

Phe Tyr Gly Glu Thr Ser Phe Glu Ala Val Thr Ser Leu Val Thr Pro
    50                  55                  60

Lys Thr Glu Thr Ser Arg Asn Ser Asp Gly Ile Gly Ile Val Arg Phe
65                  70                  75                  80

Leu Glu Gly Lys Ser Tyr Leu Val Thr Gly Ala Thr Gly Phe Leu Ala
                85                  90                  95

Lys Val Leu Ile Glu Lys Leu Leu Arg Glu Ser Leu Glu Ile Gly Lys
            100                 105                 110

Ile Phe Leu Leu Met Arg Ser Lys Asp Gln Glu Ser Ala Asn Lys Arg
        115                 120                 125
```

```
Leu Tyr Asp Glu Ile Ile Ser Ser Asp Leu Phe Lys Leu Leu Lys Gln
    130                 135                 140

Met His Gly Ser Ser Tyr Glu Ala Phe Met Lys Arg Lys Leu Ile Pro
145                 150                 155                 160

Val Ile Gly Asp Ile Glu Glu Asp Asn Leu Gly Ile Lys Ser Glu Ile
                165                 170                 175

Ala Asn Met Ile Ser Glu Glu Ile Asp Val Ile Ile Ser Cys Gly Gly
            180                 185                 190

Arg Thr Thr Phe Asp Asp Arg Tyr Asp Ser Ala Leu Ser Val Asn Ala
        195                 200                 205

Leu Gly Pro Ala Tyr Val Thr Gly Lys Arg Glu Gly Thr Val Leu Glu
    210                 215                 220

Thr Pro Leu Cys Ile Gly Glu Asn Ile Thr Ser Asp Leu Asn Ile Lys
225                 230                 235                 240

Ser Glu Leu Lys Leu Ala Ser Glu Ala Val Arg Lys Phe Arg Gly Arg
                245                 250                 255

Glu Glu Ile Lys Lys Leu Lys Glu Leu Gly Phe Glu Arg Ala Gln His
            260                 265                 270

Tyr Gly Trp Glu Asn Ser Tyr Thr Phe Thr Lys Ala Ile Gly Glu Ala
        275                 280                 285

Val Ile His Ser Lys Arg Gly Asn Leu Pro Val Val Ile Ile Arg Pro
    290                 295                 300

Ser Ile Ile Glu Ser Ser Tyr Asn Glu Pro Phe Pro Gly Trp Ile Gln
305                 310                 315                 320

Gly Thr Arg Met Ala Asp Pro Ile Ile Leu Ala Tyr Ala Lys Gly Gln
                325                 330                 335

Ile Ser Asp Phe Trp Ala Asp Pro Gln Ser Leu Met Asp Ile Ile Pro
            340                 345                 350

Val Asp Met Val Ala Asn Ala Ala Ile Ala Ala Met Ala Lys His Gly
        355                 360                 365

Cys Gly Val Pro Glu Phe Lys Val Tyr Asn Leu Thr Ser Ser Ser His
    370                 375                 380

Val Asn Pro Met Arg Ala Gly Lys Leu Ile Asp Leu Ser His Gln His
385                 390                 395                 400

Leu Cys Asp Phe Pro Leu Glu Glu Thr Val Ile Asp Leu Glu His Met
                405                 410                 415

Lys Ile His Ser Ser Leu Glu Gly Phe Thr Ser Ala Leu Ser Asn Thr
            420                 425                 430

Ile Ile Lys Gln Glu Arg Val Ile Asp Asn Glu Gly Gly Gly Leu Ser
        435                 440                 445

Thr Lys Gly Lys Arg Lys Leu Asn Tyr Phe Val Ser Leu Ala Lys Thr
    450                 455                 460

Tyr Glu Pro Tyr Thr Phe Phe Gln Ala Arg Phe Asp Asn Thr Asn Thr
465                 470                 475                 480

Thr Ser Leu Ile Gln Glu Met Ser Met Glu Glu Lys Lys Thr Phe Gly
                485                 490                 495

Phe Asp Ile Lys Gly Ile Asp Trp Glu His Tyr Ile Val Asn Val His
            500                 505                 510

Leu Pro Gly Leu Lys Lys Glu Phe Leu Ser Lys Lys Lys Thr Glu
        515                 520                 525
```

<210> SEQ ID NO 41
<211> LENGTH: 1488
<212> TYPE: DNA

```
<213> ORGANISM: Arabidopsis thaliana
<220> FEATURE:
<221> NAME/KEY: CDS
<222> LOCATION: (1)..(1488)

<400> SEQUENCE: 41

atg gag ttc tcg tgc gtt cac ttt ctg caa aat aag acc atc ctg gtt       48
Met Glu Phe Ser Cys Val His Phe Leu Gln Asn Lys Thr Ile Leu Val
1               5                   10                  15

acc ggc gcg acc ggc ttt ctg gct aag gtg ttc gtg gag aaa atc ctg       96
Thr Gly Ala Thr Gly Phe Leu Ala Lys Val Phe Val Glu Lys Ile Leu
            20                  25                  30

cgc gtt cag ccg aac gtc aat aag ctg tac ctg gtg gtt cgt gcc agc      144
Arg Val Gln Pro Asn Val Asn Lys Leu Tyr Leu Val Val Arg Ala Ser
        35                  40                  45

gat aac gaa gcg gca acc aaa cgc ctg cgt acc gaa gct ttt gag aaa      192
Asp Asn Glu Ala Ala Thr Lys Arg Leu Arg Thr Glu Ala Phe Glu Lys
    50                  55                  60

gac ctg ttc aag gtg ctg cgc gat aac ctg ggc gac gaa aaa ctg aat      240
Asp Leu Phe Lys Val Leu Arg Asp Asn Leu Gly Asp Glu Lys Leu Asn
65                  70                  75                  80

acc ctg ctg tca gag aag gtc gtg cca gtt gcc ggc gat att gct atg      288
Thr Leu Leu Ser Glu Lys Val Val Pro Val Ala Gly Asp Ile Ala Met
                85                  90                  95

gac cac ctg ggt atg aaa gat tcg aac ctg cgc gaa cgt atg cag aag      336
Asp His Leu Gly Met Lys Asp Ser Asn Leu Arg Glu Arg Met Gln Lys
            100                 105                 110

gag atc gac att gtt gtc aac gtc gcc gct acc acc aat ttt gat gaa      384
Glu Ile Asp Ile Val Val Asn Val Ala Ala Thr Thr Asn Phe Asp Glu
        115                 120                 125

cgt tac gac atc ggc ctg ggt att aat acc ttt ggc gcc ctg aac gtg      432
Arg Tyr Asp Ile Gly Leu Gly Ile Asn Thr Phe Gly Ala Leu Asn Val
    130                 135                 140

ctg aat ttc gcg aaa aag tgc gtt aaa gca cag ctg ctg ctg cat gtc      480
Leu Asn Phe Ala Lys Lys Cys Val Lys Ala Gln Leu Leu Leu His Val
145                 150                 155                 160

tcc acc gct tat gtg tgt ggc gaa aaa cct ggt ctg ctg cct gag aag      528
Ser Thr Ala Tyr Val Cys Gly Glu Lys Pro Gly Leu Leu Pro Glu Lys
                165                 170                 175

ccg ttc gtg atg gaa gag atc tgc aac gaa aat ggt ctg caa ctg gat      576
Pro Phe Val Met Glu Glu Ile Cys Asn Glu Asn Gly Leu Gln Leu Asp
            180                 185                 190

att aac ctg gaa cgc gag ctg atg aaa cag cgt ctg aag gaa ctg aat      624
Ile Asn Leu Glu Arg Glu Leu Met Lys Gln Arg Leu Lys Glu Leu Asn
        195                 200                 205

gag caa ggc tgt tct gaa gag ggt acc acc ttt tac atg aaa gaa ctg      672
Glu Gln Gly Cys Ser Glu Glu Gly Thr Thr Phe Tyr Met Lys Glu Leu
    210                 215                 220

ggc atg gag cgc gcg aag ctg cac ggt tgg cca aac acc tat gtt ttc      720
Gly Met Glu Arg Ala Lys Leu His Gly Trp Pro Asn Thr Tyr Val Phe
225                 230                 235                 240

acc aaa agc atg ggc gaa atg ctg ctg ggt aac cat aaa gaa aat ctg      768
Thr Lys Ser Met Gly Glu Met Leu Leu Gly Asn His Lys Glu Asn Leu
                245                 250                 255

cca ctg gtc atc att cgc cct acc atg atc acc agc acc ctg ttt gaa      816
Pro Leu Val Ile Ile Arg Pro Thr Met Ile Thr Ser Thr Leu Phe Glu
            260                 265                 270

ccg ttc cca ggc tgg att gag ggt ctg cgt acc gtc gat tct gtg atc      864
Pro Phe Pro Gly Trp Ile Glu Gly Leu Arg Thr Val Asp Ser Val Ile
        275                 280                 285
```

-continued

```
att gca tac ggc aaa ggt gtg ctg aag tgc ttt ctg gtg gac gtt aac      912
Ile Ala Tyr Gly Lys Gly Val Leu Lys Cys Phe Leu Val Asp Val Asn
    290                 295                 300

tct gtc tgt gat atg atc cct gcg gac atg gtg gcg aat gca atg att      960
Ser Val Cys Asp Met Ile Pro Ala Asp Met Val Ala Asn Ala Met Ile
305                 310                 315                 320

gcg gca gcc gct acc cac gca ggc ggt tca aaa gtt cac atg gtc tat     1008
Ala Ala Ala Ala Thr His Ala Gly Gly Ser Lys Val His Met Val Tyr
                325                 330                 335

caa gtg ggc tcc agc cac caa aac ccg atc att tac ggt gaa atc cgc     1056
Gln Val Gly Ser Ser His Gln Asn Pro Ile Ile Tyr Gly Glu Ile Arg
            340                 345                 350

gag att ctg ttt tgc tat ttc acc aaa aac tct ctg cgc tca cgt aat     1104
Glu Ile Leu Phe Cys Tyr Phe Thr Lys Asn Ser Leu Arg Ser Arg Asn
        355                 360                 365

ggc tcg atg atc acc gtt tcc aaa atg aag ctg att ccg acc ctg gcc     1152
Gly Ser Met Ile Thr Val Ser Lys Met Lys Leu Ile Pro Thr Leu Ala
    370                 375                 380

ctg ttc tcc ctg tac atg acc atc cgc tat aaa ctg ccg gtt cag ctg     1200
Leu Phe Ser Leu Tyr Met Thr Ile Arg Tyr Lys Leu Pro Val Gln Leu
385                 390                 395                 400

ctg aag ctg gtc gat atc att tac cca agc cgt gaa ggc gac gag tac     1248
Leu Lys Leu Val Asp Ile Ile Tyr Pro Ser Arg Glu Gly Asp Glu Tyr
                405                 410                 415

aag aac aag aac cgc aag atc gat atg gtg atg cgt ctg gtt aag ctg     1296
Lys Asn Lys Asn Arg Lys Ile Asp Met Val Met Arg Leu Val Lys Leu
            420                 425                 430

tac gaa ccg tac gtg ctg ttt aaa ggt att ttc gat gac cgc aac acc     1344
Tyr Glu Pro Tyr Val Leu Phe Lys Gly Ile Phe Asp Asp Arg Asn Thr
        435                 440                 445

aag aat ctg tgt gct aaa caa aag gaa gag gat aac cgt aat tcc gaa     1392
Lys Asn Leu Cys Ala Lys Gln Lys Glu Glu Asp Asn Arg Asn Ser Glu
    450                 455                 460

aac ttc atg ttt gat ttc gac cct aaa atc att aag tgg aaa gat tac     1440
Asn Phe Met Phe Asp Phe Asp Pro Lys Ile Ile Lys Trp Lys Asp Tyr
465                 470                 475                 480

ctg att aac gtc cat atc cct ggt ctg att acc cat gtc ctg aag aag     1488
Leu Ile Asn Val His Ile Pro Gly Leu Ile Thr His Val Leu Lys Lys
                485                 490                 495


<210> SEQ ID NO 42
<211> LENGTH: 496
<212> TYPE: PRT
<213> ORGANISM: Arabidopsis thaliana

<400> SEQUENCE: 42

Met Glu Phe Ser Cys Val His Phe Leu Gln Asn Lys Thr Ile Leu Val
1               5                   10                  15

Thr Gly Ala Thr Gly Phe Leu Ala Lys Val Phe Val Glu Lys Ile Leu
            20                  25                  30

Arg Val Gln Pro Asn Val Asn Lys Leu Tyr Leu Val Val Arg Ala Ser
        35                  40                  45

Asp Asn Glu Ala Ala Thr Lys Arg Leu Arg Thr Glu Ala Phe Glu Lys
    50                  55                  60

Asp Leu Phe Lys Val Leu Arg Asp Asn Leu Gly Asp Glu Lys Leu Asn
65                  70                  75                  80

Thr Leu Leu Ser Glu Lys Val Val Pro Val Ala Gly Asp Ile Ala Met
                85                  90                  95

Asp His Leu Gly Met Lys Asp Ser Asn Leu Arg Glu Arg Met Gln Lys
```

```
            100                 105                 110

Glu Ile Asp Ile Val Val Asn Val Ala Ala Thr Thr Asn Phe Asp Glu
        115                 120                 125

Arg Tyr Asp Ile Gly Leu Gly Ile Asn Thr Phe Gly Ala Leu Asn Val
    130                 135                 140

Leu Asn Phe Ala Lys Lys Cys Val Lys Ala Gln Leu Leu Leu His Val
145                 150                 155                 160

Ser Thr Ala Tyr Val Cys Gly Glu Lys Pro Gly Leu Leu Pro Glu Lys
                165                 170                 175

Pro Phe Val Met Glu Glu Ile Cys Asn Glu Asn Gly Leu Gln Leu Asp
            180                 185                 190

Ile Asn Leu Glu Arg Glu Leu Met Lys Gln Arg Leu Lys Glu Leu Asn
        195                 200                 205

Glu Gln Gly Cys Ser Glu Glu Gly Thr Thr Phe Tyr Met Lys Glu Leu
    210                 215                 220

Gly Met Glu Arg Ala Lys Leu His Gly Trp Pro Asn Thr Tyr Val Phe
225                 230                 235                 240

Thr Lys Ser Met Gly Glu Met Leu Leu Gly Asn His Lys Glu Asn Leu
                245                 250                 255

Pro Leu Val Ile Ile Arg Pro Thr Met Ile Thr Ser Thr Leu Phe Glu
            260                 265                 270

Pro Phe Pro Gly Trp Ile Glu Gly Leu Arg Thr Val Asp Ser Val Ile
        275                 280                 285

Ile Ala Tyr Gly Lys Gly Val Leu Lys Cys Phe Leu Val Asp Val Asn
    290                 295                 300

Ser Val Cys Asp Met Ile Pro Ala Asp Met Val Ala Asn Ala Met Ile
305                 310                 315                 320

Ala Ala Ala Ala Thr His Ala Gly Gly Ser Lys Val His Met Val Tyr
                325                 330                 335

Gln Val Gly Ser Ser His Gln Asn Pro Ile Ile Tyr Gly Glu Ile Arg
            340                 345                 350

Glu Ile Leu Phe Cys Tyr Phe Thr Lys Asn Ser Leu Arg Ser Arg Asn
        355                 360                 365

Gly Ser Met Ile Thr Val Ser Lys Met Lys Leu Ile Pro Thr Leu Ala
    370                 375                 380

Leu Phe Ser Leu Tyr Met Thr Ile Arg Tyr Lys Leu Pro Val Gln Leu
385                 390                 395                 400

Leu Lys Leu Val Asp Ile Ile Tyr Pro Ser Arg Glu Gly Asp Glu Tyr
                405                 410                 415

Lys Asn Lys Asn Arg Lys Ile Asp Met Val Met Arg Leu Val Lys Leu
            420                 425                 430

Tyr Glu Pro Tyr Val Leu Phe Lys Gly Ile Phe Asp Asp Arg Asn Thr
        435                 440                 445

Lys Asn Leu Cys Ala Lys Gln Lys Glu Glu Asp Asn Arg Asn Ser Glu
    450                 455                 460

Asn Phe Met Phe Asp Phe Asp Pro Lys Ile Ile Lys Trp Lys Asp Tyr
465                 470                 475                 480

Leu Ile Asn Val His Ile Pro Gly Leu Ile Thr His Val Leu Lys Lys
                485                 490                 495
```

<210> SEQ ID NO 43
<211> LENGTH: 1479
<212> TYPE: DNA
<213> ORGANISM: Fragaria vesca (woodland strawberry)

```
<220> FEATURE:
<221> NAME/KEY: CDS
<222> LOCATION: (1)..(1479)

<400> SEQUENCE: 43

atg ggt ctg gac tct gtt ctg ggc tac ctg caa aat aaa acc atc ctg       48
Met Gly Leu Asp Ser Val Leu Gly Tyr Leu Gln Asn Lys Thr Ile Leu
1               5                   10                  15

att acc ggc gct acc ggc ttt ctg ggc atg gtc ttc gtc gaa aaa atc       96
Ile Thr Gly Ala Thr Gly Phe Leu Gly Met Val Phe Val Glu Lys Ile
            20                  25                  30

ctg cgc gtg cag ccg aac ctg aaa aag ctg tac ctg ctg gtt cgc gcg      144
Leu Arg Val Gln Pro Asn Leu Lys Lys Leu Tyr Leu Leu Val Arg Ala
        35                  40                  45

tcc gat acc aag agc gca acc cac cgt atg cat gac gaa atc att ggc      192
Ser Asp Thr Lys Ser Ala Thr His Arg Met His Asp Glu Ile Ile Gly
    50                  55                  60

aaa gag ctg ttc cgc gtg ctg cgt caa aag tgg ggt acc gat ttc gac      240
Lys Glu Leu Phe Arg Val Leu Arg Gln Lys Trp Gly Thr Asp Phe Asp
65                  70                  75                  80

tca ttt atc tcg gaa aaa gtg gtt gcc ctg cct ggc gat gtc acc att      288
Ser Phe Ile Ser Glu Lys Val Val Ala Leu Pro Gly Asp Val Thr Ile
                85                  90                  95

gaa aac ctg ggt gtg tct gag ccg cgc ctg atg gaa gag ctg tgc tcg      336
Glu Asn Leu Gly Val Ser Glu Pro Arg Leu Met Glu Glu Leu Cys Ser
            100                 105                 110

gaa atc cag atc att ttc aac tcc gcg gca acc acc aat ttt gat gag      384
Glu Ile Gln Ile Ile Phe Asn Ser Ala Ala Thr Thr Asn Phe Asp Glu
        115                 120                 125

cgc tac gac att tca ctg gcc gtt aat acc ttc ggc acc ctg cgt gtc      432
Arg Tyr Asp Ile Ser Leu Ala Val Asn Thr Phe Gly Thr Leu Arg Val
    130                 135                 140

ctg tcg ttt gct aaa aag tgc ctg aaa ctg cag atg ctg ctg cac gtc      480
Leu Ser Phe Ala Lys Lys Cys Leu Lys Leu Gln Met Leu Leu His Val
145                 150                 155                 160

tct acc gcc tat gtg tgt ggc gaa cgt gct ggt ctg att ccg gag gat      528
Ser Thr Ala Tyr Val Cys Gly Glu Arg Ala Gly Leu Ile Pro Glu Asp
                165                 170                 175

tcc agc tct atg gac aaa atg atc aag gaa atg gat aac att gac ttc      576
Ser Ser Ser Met Asp Lys Met Ile Lys Glu Met Asp Asn Ile Asp Phe
            180                 185                 190

gaa aaa gtt gag aag aac ctg gtc aaa gaa aag ctg aat gag ctg aaa      624
Glu Lys Val Glu Lys Asn Leu Val Lys Glu Lys Leu Asn Glu Leu Lys
        195                 200                 205

ggc cag gat gct tca aag gaa gtc gtg acc aac acc atg aaa gac ttt      672
Gly Gln Asp Ala Ser Lys Glu Val Val Thr Asn Thr Met Lys Asp Phe
    210                 215                 220

ggc atc aag cgc gcg cgt ctg tac ggt tgg cca aat acc tat gtg ttc      720
Gly Ile Lys Arg Ala Arg Leu Tyr Gly Trp Pro Asn Thr Tyr Val Phe
225                 230                 235                 240

acc aaa gca atg ggt gaa att ttt ctg cag cgc tcc aag gat aac ctg      768
Thr Lys Ala Met Gly Glu Ile Phe Leu Gln Arg Ser Lys Asp Asn Leu
                245                 250                 255

cct ctg gtg atc gtt cgt ccg acc att gtt acc agc acc tac aaa gag      816
Pro Leu Val Ile Val Arg Pro Thr Ile Val Thr Ser Thr Tyr Lys Glu
            260                 265                 270

ccg ttc cca ggc tgg atc caa ggt ttt cgc acc atc gat tcc gtc att      864
Pro Phe Pro Gly Trp Ile Gln Gly Phe Arg Thr Ile Asp Ser Val Ile
        275                 280                 285

gcc ggc tat tgc aaa ggc aag ctg acc tgt ctg ctg gtt gat cca gct      912
```

-continued

```
Ala Gly Tyr Cys Lys Gly Lys Leu Thr Cys Leu Leu Val Asp Pro Ala
    290                 295                 300

acc gtt ctg gat atg att cct gtt gac atg ctg gtc aat agc atc att      960
Thr Val Leu Asp Met Ile Pro Val Asp Met Leu Val Asn Ser Ile Ile
305                 310                 315                 320

gcc gct atg gtt gtc aac tct tac cag tca tcg ggc aat atc att tat     1008
Ala Ala Met Val Val Asn Ser Tyr Gln Ser Ser Gly Asn Ile Ile Tyr
                325                 330                 335

caa gtg ggt tcc agc tct cgt aac cca ctg aat ttc ttt cag atg cat     1056
Gln Val Gly Ser Ser Ser Arg Asn Pro Leu Asn Phe Phe Gln Met His
            340                 345                 350

gaa ttc atc ttc caa tac ttc acc aag aac ccg tgg gtt aat aag gat     1104
Glu Phe Ile Phe Gln Tyr Phe Thr Lys Asn Pro Trp Val Asn Lys Asp
        355                 360                 365

ggc gag cca gtc atc gtg acc aaa ggt acc att ctg acc act atg gcg     1152
Gly Glu Pro Val Ile Val Thr Lys Gly Thr Ile Leu Thr Thr Met Ala
    370                 375                 380

acc ttc cgc atg tac atg aac atc cgt tat atg ctg cca ctg aaa ggc     1200
Thr Phe Arg Met Tyr Met Asn Ile Arg Tyr Met Leu Pro Leu Lys Gly
385                 390                 395                 400

ctg aag ttt gtc aac aaa gca ttc ggc cag tac ttc caa gat atc tac     1248
Leu Lys Phe Val Asn Lys Ala Phe Gly Gln Tyr Phe Gln Asp Ile Tyr
                405                 410                 415

gtg aac tat agc cgc aag ctg gac ctg gtg atg cgt ctg gtt gaa ctg     1296
Val Asn Tyr Ser Arg Lys Leu Asp Leu Val Met Arg Leu Val Glu Leu
            420                 425                 430

tac gag cct tat atg ctg ttc aaa ggc att ttt gat gac gcg aat acc     1344
Tyr Glu Pro Tyr Met Leu Phe Lys Gly Ile Phe Asp Asp Ala Asn Thr
        435                 440                 445

gaa aag ctg tgg cgc acc gca cgt gaa tct ttt atc gat gtg gag tca     1392
Glu Lys Leu Trp Arg Thr Ala Arg Glu Ser Phe Ile Asp Val Glu Ser
    450                 455                 460

ttc aaa ttt gat gcc acc tgt att gac tgg gaa gat tac att atg cac     1440
Phe Lys Phe Asp Ala Thr Cys Ile Asp Trp Glu Asp Tyr Ile Met His
465                 470                 475                 480

gca cac att cct ggt ctg ctg aaa cac gtt ctg att aaa                 1479
Ala His Ile Pro Gly Leu Leu Lys His Val Leu Ile Lys
                485                 490
```

<210> SEQ ID NO 44
<211> LENGTH: 493
<212> TYPE: PRT
<213> ORGANISM: Fragaria vesca (woodland strawberry

<400> SEQUENCE: 44

```
Met Gly Leu Asp Ser Val Leu Gly Tyr Leu Gln Asn Lys Thr Ile Leu
1               5                   10                  15

Ile Thr Gly Ala Thr Gly Phe Leu Gly Met Val Phe Val Glu Lys Ile
            20                  25                  30

Leu Arg Val Gln Pro Asn Leu Lys Lys Leu Tyr Leu Leu Val Arg Ala
        35                  40                  45

Ser Asp Thr Lys Ser Ala Thr His Arg Met His Asp Glu Ile Ile Gly
    50                  55                  60

Lys Glu Leu Phe Arg Val Leu Arg Gln Lys Trp Gly Thr Asp Phe Asp
65                  70                  75                  80

Ser Phe Ile Ser Glu Lys Val Val Ala Leu Pro Gly Asp Val Thr Ile
                85                  90                  95

Glu Asn Leu Gly Val Ser Glu Pro Arg Leu Met Glu Glu Leu Cys Ser
            100                 105                 110
```

-continued

```
Glu Ile Gln Ile Ile Phe Asn Ser Ala Ala Thr Thr Asn Phe Asp Glu
        115                 120                 125

Arg Tyr Asp Ile Ser Leu Ala Val Asn Thr Phe Gly Thr Leu Arg Val
    130                 135                 140

Leu Ser Phe Ala Lys Lys Cys Leu Lys Leu Gln Met Leu Leu His Val
145                 150                 155                 160

Ser Thr Ala Tyr Val Cys Gly Glu Arg Ala Gly Leu Ile Pro Glu Asp
                165                 170                 175

Ser Ser Ser Met Asp Lys Met Ile Lys Glu Met Asp Asn Ile Asp Phe
            180                 185                 190

Glu Lys Val Glu Lys Asn Leu Val Lys Glu Lys Leu Asn Glu Leu Lys
        195                 200                 205

Gly Gln Asp Ala Ser Lys Glu Val Val Thr Asn Thr Met Lys Asp Phe
    210                 215                 220

Gly Ile Lys Arg Ala Arg Leu Tyr Gly Trp Pro Asn Thr Tyr Val Phe
225                 230                 235                 240

Thr Lys Ala Met Gly Glu Ile Phe Leu Gln Arg Ser Lys Asp Asn Leu
                245                 250                 255

Pro Leu Val Ile Val Arg Pro Thr Ile Val Thr Ser Thr Tyr Lys Glu
            260                 265                 270

Pro Phe Pro Gly Trp Ile Gln Gly Phe Arg Thr Ile Asp Ser Val Ile
        275                 280                 285

Ala Gly Tyr Cys Lys Gly Lys Leu Thr Cys Leu Leu Val Asp Pro Ala
    290                 295                 300

Thr Val Leu Asp Met Ile Pro Val Asp Met Leu Val Asn Ser Ile Ile
305                 310                 315                 320

Ala Ala Met Val Val Asn Ser Tyr Gln Ser Ser Gly Asn Ile Ile Tyr
                325                 330                 335

Gln Val Gly Ser Ser Ser Arg Asn Pro Leu Asn Phe Phe Gln Met His
            340                 345                 350

Glu Phe Ile Phe Gln Tyr Phe Thr Lys Asn Pro Trp Val Asn Lys Asp
        355                 360                 365

Gly Glu Pro Val Ile Val Thr Lys Gly Thr Ile Leu Thr Thr Met Ala
    370                 375                 380

Thr Phe Arg Met Tyr Met Asn Ile Arg Tyr Met Leu Pro Leu Lys Gly
385                 390                 395                 400

Leu Lys Phe Val Asn Lys Ala Phe Gly Gln Tyr Phe Gln Asp Ile Tyr
                405                 410                 415

Val Asn Tyr Ser Arg Lys Leu Asp Leu Val Met Arg Leu Val Glu Leu
            420                 425                 430

Tyr Glu Pro Tyr Met Leu Phe Lys Gly Ile Phe Asp Asp Ala Asn Thr
        435                 440                 445

Glu Lys Leu Trp Arg Thr Ala Arg Glu Ser Phe Ile Asp Val Glu Ser
    450                 455                 460

Phe Lys Phe Asp Ala Thr Cys Ile Asp Trp Glu Asp Tyr Ile Met His
465                 470                 475                 480

Ala His Ile Pro Gly Leu Leu Lys His Val Leu Ile Lys
                485                 490
```

<210> SEQ ID NO 45
<211> LENGTH: 1470
<212> TYPE: DNA
<213> ORGANISM: Fragaria vesca (woodland strawberry)
<220> FEATURE:

-continued

```
<221> NAME/KEY: CDS
<222> LOCATION: (1)..(1470)

<400> SEQUENCE: 45

atg gaa ctg gag tcg ctg ctg gac ttt att caa aac aaa aac atc ctg        48
Met Glu Leu Glu Ser Leu Leu Asp Phe Ile Gln Asn Lys Asn Ile Leu
1               5                   10                  15

gtg acc ggc gcg gcg ggc ttt ctg gca aaa atc ttc gtc gaa aaa att        96
Val Thr Gly Ala Ala Gly Phe Leu Ala Lys Ile Phe Val Glu Lys Ile
            20                  25                  30

ctg cgc gtt cag cct tac gtc aaa aag ctg tat ctg ctg ctg cgt gct       144
Leu Arg Val Gln Pro Tyr Val Lys Lys Leu Tyr Leu Leu Leu Arg Ala
        35                  40                  45

cct gat gca aag acc gct acc caa cgt ctg cac aac gaa atc ctg ggt       192
Pro Asp Ala Lys Thr Ala Thr Gln Arg Leu His Asn Glu Ile Leu Gly
    50                  55                  60

aaa gac ctg ttc cgt gtg tcg cgt gag aag tgg ggt gct cgt atg aat       240
Lys Asp Leu Phe Arg Val Ser Arg Glu Lys Trp Gly Ala Arg Met Asn
65                  70                  75                  80

tcg att gtg tcc gaa aaa ctg act atg gtg ccg ggt gat atc tca aaa       288
Ser Ile Val Ser Glu Lys Leu Thr Met Val Pro Gly Asp Ile Ser Lys
                85                  90                  95

gaa ggc ctg ggt ctg cag gat tca gac ctg cgc gaa gag att ctg tcg       336
Glu Gly Leu Gly Leu Gln Asp Ser Asp Leu Arg Glu Glu Ile Leu Ser
            100                 105                 110

caa gtt gac gtc atc gtg aac ctg gcg gca acc acc aat ttc gat gaa       384
Gln Val Asp Val Ile Val Asn Leu Ala Ala Thr Thr Asn Phe Asp Glu
        115                 120                 125

cgt tac gac gtg gca ctg ggt ctg aac act atg ggc gct aaa tat gtc       432
Arg Tyr Asp Val Ala Leu Gly Leu Asn Thr Met Gly Ala Lys Tyr Val
    130                 135                 140

atg tcc ttt gcg aaa ctg tgc gtg aag ctg gaa gtt ctg gtc cac gtg       480
Met Ser Phe Ala Lys Leu Cys Val Lys Leu Glu Val Leu Val His Val
145                 150                 155                 160

agc acc gca tac gtt tgg ggt gaa aaa gcc ggc ctg ctg cct gag cat       528
Ser Thr Ala Tyr Val Trp Gly Glu Lys Ala Gly Leu Leu Pro Glu His
                165                 170                 175

ccg tgt ctg atg ggc aag agc ctg aac ggt acc cct ggc ctg gat att       576
Pro Cys Leu Met Gly Lys Ser Leu Asn Gly Thr Pro Gly Leu Asp Ile
            180                 185                 190

gaa acc gag atc cgc att gcc aat gaa gag gtc cgc cgt ctg cgt agc       624
Glu Thr Glu Ile Arg Ile Ala Asn Glu Glu Val Arg Arg Leu Arg Ser
        195                 200                 205

gaa cag gct tct gag gcc gct att acc ctg gcg ctg aaa gat ttc ggt       672
Glu Gln Ala Ser Glu Ala Ala Ile Thr Leu Ala Leu Lys Asp Phe Gly
    210                 215                 220

ctg aag cgc gct tct atc tac ggc tgg cca aac acc tat gtt ttt acc       720
Leu Lys Arg Ala Ser Ile Tyr Gly Trp Pro Asn Thr Tyr Val Phe Thr
225                 230                 235                 240

aaa gcg atg ggc gaa atg ctg att ggc gag cac cgc ggc aat ctg cca       768
Lys Ala Met Gly Glu Met Leu Ile Gly Glu His Arg Gly Asn Leu Pro
                245                 250                 255

gtg gtt atc ctg cgt cct acc atc att acc tct acc tac aaa gaa ccg       816
Val Val Ile Leu Arg Pro Thr Ile Ile Thr Ser Thr Tyr Lys Glu Pro
            260                 265                 270

ttc cca ggt tgg gtg gag ggc atc cgc acc att gat tca gtt gca gtc       864
Phe Pro Gly Trp Val Glu Gly Ile Arg Thr Ile Asp Ser Val Ala Val
        275                 280                 285

ggc tat ggt aaa ggc aag ctg acc ttc ttt ctg tgc gac atc gaa gcc       912
Gly Tyr Gly Lys Gly Lys Leu Thr Phe Phe Leu Cys Asp Ile Glu Ala
```

```
    290                 295                 300

att gtc gat atc gtg cca gca gac atg gtc gtg aac gcc atc att gcg      960
Ile Val Asp Ile Val Pro Ala Asp Met Val Val Asn Ala Ile Ile Ala
305                 310                 315                 320

gca atg gcc gct cat gcg aat gaa cca ggt gag gtg atc tac caa gtt     1008
Ala Met Ala Ala His Ala Asn Glu Pro Gly Glu Val Ile Tyr Gln Val
                325                 330                 335

ggc tcc agc gtc cgc aac cct gtg cgt tat aat gat ctg cac gac tac     1056
Gly Ser Ser Val Arg Asn Pro Val Arg Tyr Asn Asp Leu His Asp Tyr
            340                 345                 350

ggt ttc cgc tat ttt acc cgt aaa ccg tgg atc aac aaa gat ggc aag     1104
Gly Phe Arg Tyr Phe Thr Arg Lys Pro Trp Ile Asn Lys Asp Gly Lys
        355                 360                 365

cca gtg acc gtt cat aag tgc acc gtg atg tct tca atg gac tcc ttt     1152
Pro Val Thr Val His Lys Cys Thr Val Met Ser Ser Met Asp Ser Phe
    370                 375                 380

cgc cgt tac atg acc ctg cgc tat ctg ctg ctg ctg aaa ggt ctg gaa     1200
Arg Arg Tyr Met Thr Leu Arg Tyr Leu Leu Leu Leu Lys Gly Leu Glu
385                 390                 395                 400

ctg gct aac att gcg ttc tgt aag tac ttt gag ggc acc tat acc gat     1248
Leu Ala Asn Ile Ala Phe Cys Lys Tyr Phe Glu Gly Thr Tyr Thr Asp
                405                 410                 415

ctg aat cgt aaa atc aag ttc gtt atg cgc ctg gtc gaa ctg tac cgt     1296
Leu Asn Arg Lys Ile Lys Phe Val Met Arg Leu Val Glu Leu Tyr Arg
            420                 425                 430

ccg tac ctg ttc ttc aaa ggc gtt ttt gat gac ctg aat acc gaa aag     1344
Pro Tyr Leu Phe Phe Lys Gly Val Phe Asp Asp Leu Asn Thr Glu Lys
        435                 440                 445

ctg cgc atc gca gtc cgt gaa agc acc acc gag gcc gat atg ttc tat     1392
Leu Arg Ile Ala Val Arg Glu Ser Thr Thr Glu Ala Asp Met Phe Tyr
    450                 455                 460

ttt gac cca aaa atc att gat tgg gaa gac tac ttt atg aat acc cac     1440
Phe Asp Pro Lys Ile Ile Asp Trp Glu Asp Tyr Phe Met Asn Thr His
465                 470                 475                 480

atc tct ggt gtc gtg aaa tac gtg ttt aag                             1470
Ile Ser Gly Val Val Lys Tyr Val Phe Lys
                485                 490


<210> SEQ ID NO 46
<211> LENGTH: 490
<212> TYPE: PRT
<213> ORGANISM: Fragaria vesca (woodland strawberry

<400> SEQUENCE: 46

Met Glu Leu Glu Ser Leu Leu Asp Phe Ile Gln Asn Lys Asn Ile Leu
1               5                   10                  15

Val Thr Gly Ala Ala Gly Phe Leu Ala Lys Ile Phe Val Glu Lys Ile
            20                  25                  30

Leu Arg Val Gln Pro Tyr Val Lys Lys Leu Tyr Leu Leu Leu Arg Ala
        35                  40                  45

Pro Asp Ala Lys Thr Ala Thr Gln Arg Leu His Asn Glu Ile Leu Gly
    50                  55                  60

Lys Asp Leu Phe Arg Val Ser Arg Glu Lys Trp Gly Ala Arg Met Asn
65                  70                  75                  80

Ser Ile Val Ser Glu Lys Leu Thr Met Val Pro Gly Asp Ile Ser Lys
                85                  90                  95

Glu Gly Leu Gly Leu Gln Asp Ser Asp Leu Arg Glu Glu Ile Leu Ser
            100                 105                 110
```

```
Gln Val Asp Val Ile Val Asn Leu Ala Ala Thr Thr Asn Phe Asp Glu
        115                 120                 125

Arg Tyr Asp Val Ala Leu Gly Leu Asn Thr Met Gly Ala Lys Tyr Val
    130                 135                 140

Met Ser Phe Ala Lys Leu Cys Val Lys Leu Glu Val Leu Val His Val
145                 150                 155                 160

Ser Thr Ala Tyr Val Trp Gly Glu Lys Ala Gly Leu Leu Pro Glu His
                165                 170                 175

Pro Cys Leu Met Gly Lys Ser Leu Asn Gly Thr Pro Gly Leu Asp Ile
            180                 185                 190

Glu Thr Glu Ile Arg Ile Ala Asn Glu Glu Val Arg Arg Leu Arg Ser
        195                 200                 205

Glu Gln Ala Ser Glu Ala Ala Ile Thr Leu Ala Leu Lys Asp Phe Gly
    210                 215                 220

Leu Lys Arg Ala Ser Ile Tyr Gly Trp Pro Asn Thr Tyr Val Phe Thr
225                 230                 235                 240

Lys Ala Met Gly Glu Met Leu Ile Gly Glu His Arg Gly Asn Leu Pro
                245                 250                 255

Val Val Ile Leu Arg Pro Thr Ile Ile Thr Ser Thr Tyr Lys Glu Pro
            260                 265                 270

Phe Pro Gly Trp Val Glu Gly Ile Arg Thr Ile Asp Ser Val Ala Val
        275                 280                 285

Gly Tyr Gly Lys Gly Lys Leu Thr Phe Phe Leu Cys Asp Ile Glu Ala
    290                 295                 300

Ile Val Asp Ile Val Pro Ala Asp Met Val Val Asn Ala Ile Ile Ala
305                 310                 315                 320

Ala Met Ala Ala His Ala Asn Glu Pro Gly Glu Val Ile Tyr Gln Val
                325                 330                 335

Gly Ser Ser Val Arg Asn Pro Val Arg Tyr Asn Asp Leu His Asp Tyr
            340                 345                 350

Gly Phe Arg Tyr Phe Thr Arg Lys Pro Trp Ile Asn Lys Asp Gly Lys
        355                 360                 365

Pro Val Thr Val His Lys Cys Thr Val Met Ser Ser Met Asp Ser Phe
    370                 375                 380

Arg Arg Tyr Met Thr Leu Arg Tyr Leu Leu Leu Leu Lys Gly Leu Glu
385                 390                 395                 400

Leu Ala Asn Ile Ala Phe Cys Lys Tyr Phe Glu Gly Thr Tyr Thr Asp
                405                 410                 415

Leu Asn Arg Lys Ile Lys Phe Val Met Arg Leu Val Glu Leu Tyr Arg
            420                 425                 430

Pro Tyr Leu Phe Phe Lys Gly Val Phe Asp Asp Leu Asn Thr Glu Lys
        435                 440                 445

Leu Arg Ile Ala Val Arg Glu Ser Thr Thr Glu Ala Asp Met Phe Tyr
    450                 455                 460

Phe Asp Pro Lys Ile Ile Asp Trp Glu Asp Tyr Phe Met Asn Thr His
465                 470                 475                 480

Ile Ser Gly Val Val Lys Tyr Val Phe Lys
                485                 490
```

<210> SEQ ID NO 47
<211> LENGTH: 1473
<212> TYPE: DNA
<213> ORGANISM: Solanum lycopersicum (tomato)
<220> FEATURE:
<221> NAME/KEY: CDS

```
<222> LOCATION: (1)..(1473)

<400> SEQUENCE: 47

atg gag ctg acc tct gtt ctg aag ttt ctg gaa aat cgt gca atc ctg        48
Met Glu Leu Thr Ser Val Leu Lys Phe Leu Glu Asn Arg Ala Ile Leu
1               5                   10                  15

gtg acc ggc gcg acc ggc ttt ctg gct aaa atc ttc gtc gaa aaa atc        96
Val Thr Gly Ala Thr Gly Phe Leu Ala Lys Ile Phe Val Glu Lys Ile
                20                  25                  30

ctg cgc gtc cag ccg aac gtg aaa aag ctg tac ctg ctg ctg cgc gcg       144
Leu Arg Val Gln Pro Asn Val Lys Lys Leu Tyr Leu Leu Leu Arg Ala
        35                  40                  45

cag gat aac aat gcg gca ctg caa cgt ttc aac aat gag gcc gtg gct       192
Gln Asp Asn Asn Ala Ala Leu Gln Arg Phe Asn Asn Glu Ala Val Ala
    50                  55                  60

aaa gac ctg ttt aag ctg ctg cgc gaa aaa cac ggt gca aac ctg aat       240
Lys Asp Leu Phe Lys Leu Leu Arg Glu Lys His Gly Ala Asn Leu Asn
65                  70                  75                  80

acc ttc att tcc gag cgt acc acc atc att cca ggt gat atc acc att       288
Thr Phe Ile Ser Glu Arg Thr Thr Ile Ile Pro Gly Asp Ile Thr Ile
                85                  90                  95

gaa aac ctg ggc gtg aag gac acc aat ctg ctg gaa gag atg tgg cgc       336
Glu Asn Leu Gly Val Lys Asp Thr Asn Leu Leu Glu Glu Met Trp Arg
            100                 105                 110

gag gtt gat gtg gtt gtc aac ctg gcc gct acc acc aat ttt gat gaa       384
Glu Val Asp Val Val Val Asn Leu Ala Ala Thr Thr Asn Phe Asp Glu
        115                 120                 125

cgt tac gac gtt gcc ctg ggt ctg aac acc ttc ggc gcc atc aac gtc       432
Arg Tyr Asp Val Ala Leu Gly Leu Asn Thr Phe Gly Ala Ile Asn Val
    130                 135                 140

ctg aat ttt gct aaa aag tgc agc aaa ctg aag gtt ctg ctg cat gtc       480
Leu Asn Phe Ala Lys Lys Cys Ser Lys Leu Lys Val Leu Leu His Val
145                 150                 155                 160

tca acc gct tac gtg tcg ggt gaa aaa cgc ggc ctg atc ctg gag acc       528
Ser Thr Ala Tyr Val Ser Gly Glu Lys Arg Gly Leu Ile Leu Glu Thr
                165                 170                 175

cct tat aac ctg ggt gaa acc ctg aat ggt acc tct ggc ctg gat att       576
Pro Tyr Asn Leu Gly Glu Thr Leu Asn Gly Thr Ser Gly Leu Asp Ile
            180                 185                 190

tat acc gaa aag aaa gtg atg gaa gag acc ctg aaa cag ctg cgt gtt       624
Tyr Thr Glu Lys Lys Val Met Glu Glu Thr Leu Lys Gln Leu Arg Val
        195                 200                 205

gaa ggc tcc agc caa gag agc atc acc tct gcg atg aaa gaa ctg ggt       672
Glu Gly Ser Ser Gln Glu Ser Ile Thr Ser Ala Met Lys Glu Leu Gly
    210                 215                 220

ctg cag cgc gcc cgt aag tac ggc tgg ccg aat ccg tac gtg ttc acc       720
Leu Gln Arg Ala Arg Lys Tyr Gly Trp Pro Asn Pro Tyr Val Phe Thr
225                 230                 235                 240

aaa gcg ctg gca gag atg att ctg ggt gat atg aag gaa gac gtg ctg       768
Lys Ala Leu Ala Glu Met Ile Leu Gly Asp Met Lys Glu Asp Val Leu
                245                 250                 255

ctg gtt atc ttc cgc cca acc att gtc acc tct acc ctg cgt gat cct       816
Leu Val Ile Phe Arg Pro Thr Ile Val Thr Ser Thr Leu Arg Asp Pro
            260                 265                 270

ttt ccg ggt tgg gtc gaa ggc atc cgc acc att gac tca ctg gcc gtg       864
Phe Pro Gly Trp Val Glu Gly Ile Arg Thr Ile Asp Ser Leu Ala Val
        275                 280                 285

ggc tat ggt aaa ggc aag ctg acc tgc ttt ctg ggc gat ccg gaa gct       912
Gly Tyr Gly Lys Gly Lys Leu Thr Cys Phe Leu Gly Asp Pro Glu Ala
    290                 295                 300
```

```
atc att gat ctg atc cca gcg gac atg gtg gtt aac gca atg att gtg      960
Ile Ile Asp Leu Ile Pro Ala Asp Met Val Val Asn Ala Met Ile Val
305                 310                 315                 320

acc atg atg gcc cac gct gac cag cgc ggt agc caa atc att tac cat     1008
Thr Met Met Ala His Ala Asp Gln Arg Gly Ser Gln Ile Ile Tyr His
                325                 330                 335

gtg ggc acc tcg gtt tcc aat cca gtc aaa ttc acc tgt cct cag gag     1056
Val Gly Thr Ser Val Ser Asn Pro Val Lys Phe Thr Cys Pro Gln Glu
            340                 345                 350

tat gcg ttc cgt cac ttt aag gaa cat cct tgg atc gat aaa caa ggc     1104
Tyr Ala Phe Arg His Phe Lys Glu His Pro Trp Ile Asp Lys Gln Gly
        355                 360                 365

aag ccg gtc att gtg ggc aaa gtt aac gtc ctg tct tca atg gac tcg     1152
Lys Pro Val Ile Val Gly Lys Val Asn Val Leu Ser Ser Met Asp Ser
    370                 375                 380

ttt cgc cgt tac atg gca ctg cgc tat atg ctg ccg ctg aaa ggc ctg     1200
Phe Arg Arg Tyr Met Ala Leu Arg Tyr Met Leu Pro Leu Lys Gly Leu
385                 390                 395                 400

gag atc gtg aat acc att ctg tgt cag ttc ttt cag gat aag tac tca     1248
Glu Ile Val Asn Thr Ile Leu Cys Gln Phe Phe Gln Asp Lys Tyr Ser
                405                 410                 415

gaa ctg gac cgc aaa atc aag ttc gtc atg cgt ctg att gat ctg tac     1296
Glu Leu Asp Arg Lys Ile Lys Phe Val Met Arg Leu Ile Asp Leu Tyr
            420                 425                 430

gag cca tac ctg ttc ttc aaa ggt gtg tat gat gac atg aac acc gaa     1344
Glu Pro Tyr Leu Phe Phe Lys Gly Val Tyr Asp Asp Met Asn Thr Glu
        435                 440                 445

aaa ctg cgc cgt gcg gca aag gaa tcc ggc atc gag acc gat gtt ttc     1392
Lys Leu Arg Arg Ala Ala Lys Glu Ser Gly Ile Glu Thr Asp Val Phe
    450                 455                 460

aac ttt aat cct aaa agc att aac tgg gaa gac tat ttt atg aac acc     1440
Asn Phe Asn Pro Lys Ser Ile Asn Trp Glu Asp Tyr Phe Met Asn Thr
465                 470                 475                 480

cac att cct ggc gtc gtg aag tac gtt ttt aag                         1473
His Ile Pro Gly Val Val Lys Tyr Val Phe Lys
                485                 490


<210> SEQ ID NO 48
<211> LENGTH: 491
<212> TYPE: PRT
<213> ORGANISM: Solanum lycopersicum (tomato)

<400> SEQUENCE: 48

Met Glu Leu Thr Ser Val Leu Lys Phe Leu Glu Asn Arg Ala Ile Leu
1               5                   10                  15

Val Thr Gly Ala Thr Gly Phe Leu Ala Lys Ile Phe Val Glu Lys Ile
            20                  25                  30

Leu Arg Val Gln Pro Asn Val Lys Lys Leu Tyr Leu Leu Leu Arg Ala
        35                  40                  45

Gln Asp Asn Asn Ala Ala Leu Gln Arg Phe Asn Asn Glu Ala Val Ala
    50                  55                  60

Lys Asp Leu Phe Lys Leu Leu Arg Glu Lys His Gly Ala Asn Leu Asn
65                  70                  75                  80

Thr Phe Ile Ser Glu Arg Thr Thr Ile Ile Pro Gly Asp Ile Thr Ile
                85                  90                  95

Glu Asn Leu Gly Val Lys Asp Thr Asn Leu Leu Glu Glu Met Trp Arg
            100                 105                 110

Glu Val Asp Val Val Val Asn Leu Ala Ala Thr Thr Asn Phe Asp Glu
```

-continued

```
        115                 120                 125

Arg Tyr Asp Val Ala Leu Gly Leu Asn Thr Phe Gly Ala Ile Asn Val
    130                 135                 140

Leu Asn Phe Ala Lys Lys Cys Ser Lys Leu Lys Val Leu Leu His Val
145                 150                 155                 160

Ser Thr Ala Tyr Val Ser Gly Glu Lys Arg Gly Leu Ile Leu Glu Thr
                165                 170                 175

Pro Tyr Asn Leu Gly Glu Thr Leu Asn Gly Thr Ser Gly Leu Asp Ile
            180                 185                 190

Tyr Thr Glu Lys Lys Val Met Glu Glu Thr Leu Lys Gln Leu Arg Val
        195                 200                 205

Glu Gly Ser Ser Gln Glu Ser Ile Thr Ser Ala Met Lys Glu Leu Gly
    210                 215                 220

Leu Gln Arg Ala Arg Lys Tyr Gly Trp Pro Asn Pro Tyr Val Phe Thr
225                 230                 235                 240

Lys Ala Leu Ala Glu Met Ile Leu Gly Asp Met Lys Glu Asp Val Leu
                245                 250                 255

Leu Val Ile Phe Arg Pro Thr Ile Val Thr Ser Thr Leu Arg Asp Pro
            260                 265                 270

Phe Pro Gly Trp Val Glu Gly Ile Arg Thr Ile Asp Ser Leu Ala Val
        275                 280                 285

Gly Tyr Gly Lys Gly Lys Leu Thr Cys Phe Leu Gly Asp Pro Glu Ala
    290                 295                 300

Ile Ile Asp Leu Ile Pro Ala Asp Met Val Val Asn Ala Met Ile Val
305                 310                 315                 320

Thr Met Met Ala His Ala Asp Gln Arg Gly Ser Gln Ile Ile Tyr His
                325                 330                 335

Val Gly Thr Ser Val Ser Asn Pro Val Lys Phe Thr Cys Pro Gln Glu
            340                 345                 350

Tyr Ala Phe Arg His Phe Lys Glu His Pro Trp Ile Asp Lys Gln Gly
        355                 360                 365

Lys Pro Val Ile Val Gly Lys Val Asn Val Leu Ser Ser Met Asp Ser
    370                 375                 380

Phe Arg Arg Tyr Met Ala Leu Arg Tyr Met Leu Pro Leu Lys Gly Leu
385                 390                 395                 400

Glu Ile Val Asn Thr Ile Leu Cys Gln Phe Phe Gln Asp Lys Tyr Ser
                405                 410                 415

Glu Leu Asp Arg Lys Ile Lys Phe Val Met Arg Leu Ile Asp Leu Tyr
            420                 425                 430

Glu Pro Tyr Leu Phe Phe Lys Gly Val Tyr Asp Asp Met Asn Thr Glu
        435                 440                 445

Lys Leu Arg Arg Ala Ala Lys Glu Ser Gly Ile Glu Thr Asp Val Phe
    450                 455                 460

Asn Phe Asn Pro Lys Ser Ile Asn Trp Glu Asp Tyr Phe Met Asn Thr
465                 470                 475                 480

His Ile Pro Gly Val Val Lys Tyr Val Phe Lys
                485                 490
```

<210> SEQ ID NO 49
<211> LENGTH: 1476
<212> TYPE: DNA
<213> ORGANISM: Solanum lycopersicum (tomato)
<220> FEATURE:
<221> NAME/KEY: CDS
<222> LOCATION: (1)..(1476)

```
<400> SEQUENCE: 49

atg gag atg acc tct gtt ctg aac ttt ctg gaa aat cgc acc att ctg        48
Met Glu Met Thr Ser Val Leu Asn Phe Leu Glu Asn Arg Thr Ile Leu
1               5                   10                  15

gtt acc ggc gct acc ggc ttt ctg gct aaa atc ttc gtt gaa aag atc        96
Val Thr Gly Ala Thr Gly Phe Leu Ala Lys Ile Phe Val Glu Lys Ile
            20                  25                  30

ctg cgc gtt cag ccg tac gtc aaa aag ctg tat ctg ctg ctg cgc gcg       144
Leu Arg Val Gln Pro Tyr Val Lys Lys Leu Tyr Leu Leu Leu Arg Ala
        35                  40                  45

gca gat gac aaa tct gcg atg caa cgt ttc aat acc gaa gtg gtt ggt       192
Ala Asp Asp Lys Ser Ala Met Gln Arg Phe Asn Thr Glu Val Val Gly
    50                  55                  60

aaa gac ctg ttc aag gtg ctg cgc gag aaa tgc ggc cct aac ttc acc       240
Lys Asp Leu Phe Lys Val Leu Arg Glu Lys Cys Gly Pro Asn Phe Thr
65                  70                  75                  80

acc ttt gtc tca cag cgt acc acc atc gtg ccg ggt gat att acc tgt       288
Thr Phe Val Ser Gln Arg Thr Thr Ile Val Pro Gly Asp Ile Thr Cys
                85                  90                  95

gaa aac ctg ggc gtg aac gac acc aat ctg ctg gaa caa atg tgg aaa       336
Glu Asn Leu Gly Val Asn Asp Thr Asn Leu Leu Glu Gln Met Trp Lys
            100                 105                 110

gag gtt gac att gtc gtg aat ctg gcc gct acc acc aac ttc gat gaa       384
Glu Val Asp Ile Val Val Asn Leu Ala Ala Thr Thr Asn Phe Asp Glu
        115                 120                 125

cgt tac gac gtc gcc ctg ggt ctg aac acc ttc ggc gcg tcc cac gtg       432
Arg Tyr Asp Val Ala Leu Gly Leu Asn Thr Phe Gly Ala Ser His Val
    130                 135                 140

ctg aat ttt gca aaa aag tgc aac aaa ctg aag gtg ctg ctg cat gtt       480
Leu Asn Phe Ala Lys Lys Cys Asn Lys Leu Lys Val Leu Leu His Val
145                 150                 155                 160

agc acc gct tat gtt tgt ggt gaa aaa gag ggc ctg atg ctg gaa aag       528
Ser Thr Ala Tyr Val Cys Gly Glu Lys Glu Gly Leu Met Leu Glu Lys
                165                 170                 175

cct tac tat atg ggc gag acc ctg aat ggt acc ctg ggc ctg gat atc       576
Pro Tyr Tyr Met Gly Glu Thr Leu Asn Gly Thr Leu Gly Leu Asp Ile
            180                 185                 190

gaa gca gag aaa aag gtc atg gac gaa aaa ctg aag cag ctg aaa gcc       624
Glu Ala Glu Lys Lys Val Met Asp Glu Lys Leu Lys Gln Leu Lys Ala
        195                 200                 205

gaa aac gct tcg gag aag tcc att acc acc gcc atg aaa gaa ctg ggt       672
Glu Asn Ala Ser Glu Lys Ser Ile Thr Thr Ala Met Lys Glu Leu Gly
    210                 215                 220

ctg gag cgc gct cgt aag tac ggc tgg cca aat acc tat gtg ttc acc       720
Leu Glu Arg Ala Arg Lys Tyr Gly Trp Pro Asn Thr Tyr Val Phe Thr
225                 230                 235                 240

aaa gcg atg ggt gaa atg ctg ctg ggc aaa ctg aag gaa gag gtc cct       768
Lys Ala Met Gly Glu Met Leu Leu Gly Lys Leu Lys Glu Glu Val Pro
                245                 250                 255

ctg gtg atc aac cgc ccg acc atc att acc tca acc ttc aaa gaa ccg       816
Leu Val Ile Asn Arg Pro Thr Ile Ile Thr Ser Thr Phe Lys Glu Pro
            260                 265                 270

ttt cca ggt tgg gtg gag ggc atc cgc acc att gat tcg ctg gca gtt       864
Phe Pro Gly Trp Val Glu Gly Ile Arg Thr Ile Asp Ser Leu Ala Val
        275                 280                 285

ggc tac ggc aag ggc cgt atc acc tgc ttt ctg ggt aat cca aaa acc       912
Gly Tyr Gly Lys Gly Arg Ile Thr Cys Phe Leu Gly Asn Pro Lys Thr
    290                 295                 300
```

-continued

```
atc ctg gat gtt att cct gcg gac atg gtt gtc aac tct atg att gtc      960
Ile Leu Asp Val Ile Pro Ala Asp Met Val Val Asn Ser Met Ile Val
305                 310                 315                 320

gca atg atg gcg cac gca gat cag aaa ggc agc gaa acc atc tat caa     1008
Ala Met Met Ala His Ala Asp Gln Lys Gly Ser Glu Thr Ile Tyr Gln
                325                 330                 335

att ggc tcc agc gtt tct aac ccg ctg aat atc acc aac ctg cgc gac     1056
Ile Gly Ser Ser Val Ser Asn Pro Leu Asn Ile Thr Asn Leu Arg Asp
            340                 345                 350

tac ggc ttc aat tat ttt cgt aag aac ccg tgg atc aac aag gtt aac     1104
Tyr Gly Phe Asn Tyr Phe Arg Lys Asn Pro Trp Ile Asn Lys Val Asn
        355                 360                 365

ggc aag cca atc atc gtc ggc aaa gtg aat gtt ctg tct tca atg gat     1152
Gly Lys Pro Ile Ile Val Gly Lys Val Asn Val Leu Ser Ser Met Asp
    370                 375                 380

tcc ttc cag cgc tac atg gcc ctg cat tat atc ctg cca ctg aaa ggt     1200
Ser Phe Gln Arg Tyr Met Ala Leu His Tyr Ile Leu Pro Leu Lys Gly
385                 390                 395                 400

ctg gaa att gtc aac gcg gca ttc tgt cag tac ttt cag ggc aag tac     1248
Leu Glu Ile Val Asn Ala Ala Phe Cys Gln Tyr Phe Gln Gly Lys Tyr
                405                 410                 415

ctg gag ctg tat aaa aag atc aaa ttt gtg atg cgc ctg att gat ctg     1296
Leu Glu Leu Tyr Lys Lys Ile Lys Phe Val Met Arg Leu Ile Asp Leu
            420                 425                 430

tac ggc cca tac ctg ttc ctg aaa gcc gct ttt gat gac ctg aac acc     1344
Tyr Gly Pro Tyr Leu Phe Leu Lys Ala Ala Phe Asp Asp Leu Asn Thr
        435                 440                 445

gaa aaa ctg cgt att ggt gct aag gag agc ggc atc gaa acc gag att     1392
Glu Lys Leu Arg Ile Gly Ala Lys Glu Ser Gly Ile Glu Thr Glu Ile
    450                 455                 460

ttc tat ttt gac cct aaa atc att aac tgg gaa gac tac ttt atg aag     1440
Phe Tyr Phe Asp Pro Lys Ile Ile Asn Trp Glu Asp Tyr Phe Met Lys
465                 470                 475                 480

atc cat ctg cct ggc gtc gtt cgc tac gtg ttc aaa                     1476
Ile His Leu Pro Gly Val Val Arg Tyr Val Phe Lys
                485                 490


<210> SEQ ID NO 50
<211> LENGTH: 492
<212> TYPE: PRT
<213> ORGANISM: Solanum lycopersicum (tomato)

<400> SEQUENCE: 50

Met Glu Met Thr Ser Val Leu Asn Phe Leu Glu Asn Arg Thr Ile Leu
1               5                   10                  15

Val Thr Gly Ala Thr Gly Phe Leu Ala Lys Ile Phe Val Glu Lys Ile
            20                  25                  30

Leu Arg Val Gln Pro Tyr Val Lys Lys Leu Tyr Leu Leu Leu Arg Ala
        35                  40                  45

Ala Asp Asp Lys Ser Ala Met Gln Arg Phe Asn Thr Glu Val Val Gly
    50                  55                  60

Lys Asp Leu Phe Lys Val Leu Arg Glu Lys Cys Gly Pro Asn Phe Thr
65                  70                  75                  80

Thr Phe Val Ser Gln Arg Thr Thr Ile Val Pro Gly Asp Ile Thr Cys
                85                  90                  95

Glu Asn Leu Gly Val Asn Asp Thr Asn Leu Leu Glu Gln Met Trp Lys
            100                 105                 110

Glu Val Asp Ile Val Val Asn Leu Ala Ala Thr Thr Asn Phe Asp Glu
        115                 120                 125
```

```
Arg Tyr Asp Val Ala Leu Gly Leu Asn Thr Phe Gly Ala Ser His Val
    130                 135                 140

Leu Asn Phe Ala Lys Lys Cys Asn Lys Leu Lys Val Leu Leu His Val
145                 150                 155                 160

Ser Thr Ala Tyr Val Cys Gly Glu Lys Glu Gly Leu Met Leu Glu Lys
                165                 170                 175

Pro Tyr Tyr Met Gly Glu Thr Leu Asn Gly Thr Leu Gly Leu Asp Ile
            180                 185                 190

Glu Ala Glu Lys Lys Val Met Asp Glu Lys Leu Lys Gln Leu Lys Ala
        195                 200                 205

Glu Asn Ala Ser Glu Lys Ser Ile Thr Thr Ala Met Lys Glu Leu Gly
    210                 215                 220

Leu Glu Arg Ala Arg Lys Tyr Gly Trp Pro Asn Thr Tyr Val Phe Thr
225                 230                 235                 240

Lys Ala Met Gly Glu Met Leu Leu Gly Lys Leu Lys Glu Glu Val Pro
                245                 250                 255

Leu Val Ile Asn Arg Pro Thr Ile Ile Thr Ser Thr Phe Lys Glu Pro
            260                 265                 270

Phe Pro Gly Trp Val Glu Gly Ile Arg Thr Ile Asp Ser Leu Ala Val
        275                 280                 285

Gly Tyr Gly Lys Gly Arg Ile Thr Cys Phe Leu Gly Asn Pro Lys Thr
    290                 295                 300

Ile Leu Asp Val Ile Pro Ala Asp Met Val Val Asn Ser Met Ile Val
305                 310                 315                 320

Ala Met Met Ala His Ala Asp Gln Lys Gly Ser Glu Thr Ile Tyr Gln
                325                 330                 335

Ile Gly Ser Ser Val Ser Asn Pro Leu Asn Ile Thr Asn Leu Arg Asp
            340                 345                 350

Tyr Gly Phe Asn Tyr Phe Arg Lys Asn Pro Trp Ile Asn Lys Val Asn
        355                 360                 365

Gly Lys Pro Ile Ile Val Gly Lys Val Asn Val Leu Ser Ser Met Asp
    370                 375                 380

Ser Phe Gln Arg Tyr Met Ala Leu His Tyr Ile Leu Pro Leu Lys Gly
385                 390                 395                 400

Leu Glu Ile Val Asn Ala Ala Phe Cys Gln Tyr Phe Gln Gly Lys Tyr
                405                 410                 415

Leu Glu Leu Tyr Lys Lys Ile Lys Phe Val Met Arg Leu Ile Asp Leu
            420                 425                 430

Tyr Gly Pro Tyr Leu Phe Leu Lys Ala Ala Phe Asp Asp Leu Asn Thr
        435                 440                 445

Glu Lys Leu Arg Ile Gly Ala Lys Glu Ser Gly Ile Glu Thr Glu Ile
    450                 455                 460

Phe Tyr Phe Asp Pro Lys Ile Ile Asn Trp Glu Asp Tyr Phe Met Lys
465                 470                 475                 480

Ile His Leu Pro Gly Val Val Arg Tyr Val Phe Lys
                485                 490
```

<210> SEQ ID NO 51
<211> LENGTH: 1479
<212> TYPE: DNA
<213> ORGANISM: Ricinus communis (castor bean)
<220> FEATURE:
<221> NAME/KEY: CDS
<222> LOCATION: (1)..(1479)

<400> SEQUENCE: 51

```
atg gac ctg ggc agc gtc atc gag ttt ctg gat aat aag acc att ctg       48
Met Asp Leu Gly Ser Val Ile Glu Phe Leu Asp Asn Lys Thr Ile Leu
1               5                   10                  15

gtt acc ggc gcg acc ggc tac ctg gca aaa gtg ttc gtg gaa aaa gtc       96
Val Thr Gly Ala Thr Gly Tyr Leu Ala Lys Val Phe Val Glu Lys Val
            20                  25                  30

ctg cgc gtg cag cct aac gtg aaa aag ctg tac ctg ctg ctg cgt gct      144
Leu Arg Val Gln Pro Asn Val Lys Lys Leu Tyr Leu Leu Leu Arg Ala
        35                  40                  45

gca gac gct aac agc gct atg gaa cgt ctg aat aaa gaa gtg atc ggc      192
Ala Asp Ala Asn Ser Ala Met Glu Arg Leu Asn Lys Glu Val Ile Gly
    50                  55                  60

aaa gac ctg ttc aag gtg ctg cgc gag cgt tat ggt gcg tca ctg aat      240
Lys Asp Leu Phe Lys Val Leu Arg Glu Arg Tyr Gly Ala Ser Leu Asn
65                  70                  75                  80

tcg ttt gtg tcc gaa aaa atg acc ccg atc cca ggc gat att tca cgc      288
Ser Phe Val Ser Glu Lys Met Thr Pro Ile Pro Gly Asp Ile Ser Arg
                85                  90                  95

gag gac ctg ggt att aaa gat tcg aac ctg cgt aat gaa atg ctg aag      336
Glu Asp Leu Gly Ile Lys Asp Ser Asn Leu Arg Asn Glu Met Leu Lys
            100                 105                 110

gat atc gac gtg gtt att aac ttc gcc gct acc acc aat ttt gat gaa      384
Asp Ile Asp Val Val Ile Asn Phe Ala Ala Thr Thr Asn Phe Asp Glu
        115                 120                 125

cgc tac gac gtc gcg ctg ggc atc aac acc ctg ggt gcg ctg cac gtg      432
Arg Tyr Asp Val Ala Leu Gly Ile Asn Thr Leu Gly Ala Leu His Val
    130                 135                 140

ctg aat ttc gca aaa aag tgc ctg aaa att cgt atg ctg gtt cat gtc      480
Leu Asn Phe Ala Lys Lys Cys Leu Lys Ile Arg Met Leu Val His Val
145                 150                 155                 160

agc acc gcg tac gtg tgt ggc gaa gac acc ggt ctg atc ctg gag aaa      528
Ser Thr Ala Tyr Val Cys Gly Glu Asp Thr Gly Leu Ile Leu Glu Lys
                165                 170                 175

cct ttt ccg atg ggc gaa ggt aaa aag ggc aac tct aag atc gat atc      576
Pro Phe Pro Met Gly Glu Gly Lys Lys Gly Asn Ser Lys Ile Asp Ile
            180                 185                 190

gaa gaa gaa aag aaa ctg gtt cag gag aaa ctg aac gag ctg gaa agc      624
Glu Glu Glu Lys Lys Leu Val Gln Glu Lys Leu Asn Glu Leu Glu Ser
        195                 200                 205

gag aat gcc tct gaa aaa gag atc acc gct att atg aag gat ttc ggc      672
Glu Asn Ala Ser Glu Lys Glu Ile Thr Ala Ile Met Lys Asp Phe Gly
    210                 215                 220

att gaa cgc gcg cgt gca ctg ggt tgg cca aac acc tac gtg ttt acc      720
Ile Glu Arg Ala Arg Ala Leu Gly Trp Pro Asn Thr Tyr Val Phe Thr
225                 230                 235                 240

aaa gcg atg gcg gag atg ctg ctg gtt cac atg aag gaa aat ctg ccg      768
Lys Ala Met Ala Glu Met Leu Leu Val His Met Lys Glu Asn Leu Pro
                245                 250                 255

ctg ctg atc att cgc cca acc atg atc acc tct acc tac aaa caa cca      816
Leu Leu Ile Ile Arg Pro Thr Met Ile Thr Ser Thr Tyr Lys Gln Pro
            260                 265                 270

ttc cct ggc tgg att gaa ggt gtg cgt acc atc gat tca gtg att gtt      864
Phe Pro Gly Trp Ile Glu Gly Val Arg Thr Ile Asp Ser Val Ile Val
        275                 280                 285

ggc tat ggt aaa cgc aag atc acc tgc ttt gtt tcc agc cct cgt tct      912
Gly Tyr Gly Lys Arg Lys Ile Thr Cys Phe Val Ser Ser Pro Arg Ser
    290                 295                 300

atc ctg gac gtc att ccg gca gat atg gtc gtg aac ggc atc att gtg      960
```

-continued

```
Ile Leu Asp Val Ile Pro Ala Asp Met Val Val Asn Gly Ile Ile Val
305                 310                 315                 320

gcg atg gca acc cgc tac cag aag caa tct tca gaa atc att tat cag      1008
Ala Met Ala Thr Arg Tyr Gln Lys Gln Ser Ser Glu Ile Ile Tyr Gln
                325                 330                 335

atc ggt tcg tcc ctg cgc aac ccg ctg aaa ttc tca aat att cac gac      1056
Ile Gly Ser Ser Leu Arg Asn Pro Leu Lys Phe Ser Asn Ile His Asp
            340                 345                 350

ttc gcc tac cgt tat ttt tcc gct aat ccg tgg att gat aaa gaa ggc      1104
Phe Ala Tyr Arg Tyr Phe Ser Ala Asn Pro Trp Ile Asp Lys Glu Gly
        355                 360                 365

agc cct gtg aaa atc ggc aag ggt att gtt ctg agc tct atg acc agc      1152
Ser Pro Val Lys Ile Gly Lys Gly Ile Val Leu Ser Ser Met Thr Ser
    370                 375                 380

ttt cac atg tat atg gcc gtt tgt ttc caa ctg cca ctg aaa gcg ttt      1200
Phe His Met Tyr Met Ala Val Cys Phe Gln Leu Pro Leu Lys Ala Phe
385                 390                 395                 400

gag ctg gca acc acc ctg gtc ctg aaa gaa tac cag gac aag tat cgc      1248
Glu Leu Ala Thr Thr Leu Val Leu Lys Glu Tyr Gln Asp Lys Tyr Arg
                405                 410                 415

ctg ctg gat cgt aaa gtt aag ctg gtc caa cgc ctg gtg gat ctg tac      1296
Leu Leu Asp Arg Lys Val Lys Leu Val Gln Arg Leu Val Asp Leu Tyr
            420                 425                 430

aag tcg tac ctg ttc ttc gaa ggt atc ttc gat gac acc aac ctg gaa      1344
Lys Ser Tyr Leu Phe Phe Glu Gly Ile Phe Asp Asp Thr Asn Leu Glu
        435                 440                 445

aaa ctg cgt acc gag gct cgc ctg cgt tcc ctg gaa gtt gag gaa atg      1392
Lys Leu Arg Thr Glu Ala Arg Leu Arg Ser Leu Glu Val Glu Glu Met
    450                 455                 460

gac gag ttc aac ttt gat ccg acc aat att gat tgg gaa gat tac atg      1440
Asp Glu Phe Asn Phe Asp Pro Thr Asn Ile Asp Trp Glu Asp Tyr Met
465                 470                 475                 480

atg ggc gtc cac att cct ggt ctg gtg aaa tac acc atg                  1479
Met Gly Val His Ile Pro Gly Leu Val Lys Tyr Thr Met
                485                 490


<210> SEQ ID NO 52
<211> LENGTH: 493
<212> TYPE: PRT
<213> ORGANISM: Ricinus communis (castor bean)

<400> SEQUENCE: 52

Met Asp Leu Gly Ser Val Ile Glu Phe Leu Asp Asn Lys Thr Ile Leu
1               5                   10                  15

Val Thr Gly Ala Thr Gly Tyr Leu Ala Lys Val Phe Val Glu Lys Val
            20                  25                  30

Leu Arg Val Gln Pro Asn Val Lys Lys Leu Tyr Leu Leu Leu Arg Ala
        35                  40                  45

Ala Asp Ala Asn Ser Ala Met Glu Arg Leu Asn Lys Glu Val Ile Gly
    50                  55                  60

Lys Asp Leu Phe Lys Val Leu Arg Glu Arg Tyr Gly Ala Ser Leu Asn
65                  70                  75                  80

Ser Phe Val Ser Glu Lys Met Thr Pro Ile Pro Gly Asp Ile Ser Arg
                85                  90                  95

Glu Asp Leu Gly Ile Lys Asp Ser Asn Leu Arg Asn Glu Met Leu Lys
            100                 105                 110

Asp Ile Asp Val Val Ile Asn Phe Ala Ala Thr Thr Asn Phe Asp Glu
        115                 120                 125
```

```
Arg Tyr Asp Val Ala Leu Gly Ile Asn Thr Leu Gly Ala Leu His Val
    130                 135                 140

Leu Asn Phe Ala Lys Lys Cys Leu Lys Ile Arg Met Leu Val His Val
145                 150                 155                 160

Ser Thr Ala Tyr Val Cys Gly Glu Asp Thr Gly Leu Ile Leu Glu Lys
                165                 170                 175

Pro Phe Pro Met Gly Glu Gly Lys Lys Gly Asn Ser Lys Ile Asp Ile
            180                 185                 190

Glu Glu Glu Lys Lys Leu Val Gln Glu Lys Leu Asn Glu Leu Glu Ser
        195                 200                 205

Glu Asn Ala Ser Glu Lys Glu Ile Thr Ala Ile Met Lys Asp Phe Gly
    210                 215                 220

Ile Glu Arg Ala Arg Ala Leu Gly Trp Pro Asn Thr Tyr Val Phe Thr
225                 230                 235                 240

Lys Ala Met Ala Glu Met Leu Leu Val His Met Lys Glu Asn Leu Pro
                245                 250                 255

Leu Leu Ile Ile Arg Pro Thr Met Ile Thr Ser Thr Tyr Lys Gln Pro
            260                 265                 270

Phe Pro Gly Trp Ile Glu Gly Val Arg Thr Ile Asp Ser Val Ile Val
        275                 280                 285

Gly Tyr Gly Lys Arg Lys Ile Thr Cys Phe Val Ser Ser Pro Arg Ser
    290                 295                 300

Ile Leu Asp Val Ile Pro Ala Asp Met Val Val Asn Gly Ile Ile Val
305                 310                 315                 320

Ala Met Ala Thr Arg Tyr Gln Lys Gln Ser Ser Glu Ile Ile Tyr Gln
                325                 330                 335

Ile Gly Ser Ser Leu Arg Asn Pro Leu Lys Phe Ser Asn Ile His Asp
            340                 345                 350

Phe Ala Tyr Arg Tyr Phe Ser Ala Asn Pro Trp Ile Asp Lys Glu Gly
        355                 360                 365

Ser Pro Val Lys Ile Gly Lys Gly Ile Val Leu Ser Ser Met Thr Ser
    370                 375                 380

Phe His Met Tyr Met Ala Val Cys Phe Gln Leu Pro Leu Lys Ala Phe
385                 390                 395                 400

Glu Leu Ala Thr Thr Leu Val Leu Lys Glu Tyr Gln Asp Lys Tyr Arg
                405                 410                 415

Leu Leu Asp Arg Lys Val Lys Leu Val Gln Arg Leu Val Asp Leu Tyr
            420                 425                 430

Lys Ser Tyr Leu Phe Phe Glu Gly Ile Phe Asp Asp Thr Asn Leu Glu
        435                 440                 445

Lys Leu Arg Thr Glu Ala Arg Leu Arg Ser Leu Glu Val Glu Glu Met
    450                 455                 460

Asp Glu Phe Asn Phe Asp Pro Thr Asn Ile Asp Trp Glu Asp Tyr Met
465                 470                 475                 480

Met Gly Val His Ile Pro Gly Leu Val Lys Tyr Thr Met
                485                 490
```

<210> SEQ ID NO 53
<211> LENGTH: 1479
<212> TYPE: DNA
<213> ORGANISM: Ricinus communis (castor bean)
<220> FEATURE:
<221> NAME/KEY: CDS
<222> LOCATION: (1)..(1479)

<400> SEQUENCE: 53

-continued

```
atg gaa gtg ggt tct atc ctg gag ttt ctg gag aat aag acc atc ctg       48
Met Glu Val Gly Ser Ile Leu Glu Phe Leu Glu Asn Lys Thr Ile Leu
1               5                   10                  15

gct acc ggc gcg acc ggc tac ctg gct aag att ttc gtg gaa aaa gtt       96
Ala Thr Gly Ala Thr Gly Tyr Leu Ala Lys Ile Phe Val Glu Lys Val
            20                  25                  30

ctg cgc gtc cag ccg aac gtc aaa aag ctg tac ctg ctg ctg cgt gcg      144
Leu Arg Val Gln Pro Asn Val Lys Lys Leu Tyr Leu Leu Leu Arg Ala
        35                  40                  45

gca gat gcc gac tct gct atg gag cgc ctg aat cgt gaa gtg att ggt      192
Ala Asp Ala Asp Ser Ala Met Glu Arg Leu Asn Arg Glu Val Ile Gly
    50                  55                  60

aaa gac ctg ttc aag ggc gtt cgc gaa aaa tat ggt tcc agc ctg aac      240
Lys Asp Leu Phe Lys Gly Val Arg Glu Lys Tyr Gly Ser Ser Leu Asn
65                  70                  75                  80

tcc ttc gtt agc gag aag atg acc ccg atc cca ggc gat att tca cgc      288
Ser Phe Val Ser Glu Lys Met Thr Pro Ile Pro Gly Asp Ile Ser Arg
                85                  90                  95

gag gac ctg ggt atc gaa gat ttt aat ctg cgt gac gaa atc ctg aaa      336
Glu Asp Leu Gly Ile Glu Asp Phe Asn Leu Arg Asp Glu Ile Leu Lys
            100                 105                 110

gat att gac gtg gtt atc aac ttc gcc gct acc acc aat ttt gat gag      384
Asp Ile Asp Val Val Ile Asn Phe Ala Ala Thr Thr Asn Phe Asp Glu
        115                 120                 125

cgc tac gac gtt gct ctg ggt gtc aac acc ctg ggt gct ctg aac gtc      432
Arg Tyr Asp Val Ala Leu Gly Val Asn Thr Leu Gly Ala Leu Asn Val
    130                 135                 140

ctg aat ttt gca aaa aag tgc ctg aaa att cgt atg ctg gtt cac gtc      480
Leu Asn Phe Ala Lys Lys Cys Leu Lys Ile Arg Met Leu Val His Val
145                 150                 155                 160

tct acc gcg tat gtg tgt ggc gag gat acc ggc ctg atc ctg gaa aaa      528
Ser Thr Ala Tyr Val Cys Gly Glu Asp Thr Gly Leu Ile Leu Glu Lys
                165                 170                 175

cct ttc ccg atg ggt gaa gca aaa aag ggc aat cgc aag atc gac att      576
Pro Phe Pro Met Gly Glu Ala Lys Lys Gly Asn Arg Lys Ile Asp Ile
            180                 185                 190

gaa gaa gaa aag aaa ctg gtg cag gaa aaa ctg aac gag ctg gaa tct      624
Glu Glu Glu Lys Lys Leu Val Gln Glu Lys Leu Asn Glu Leu Glu Ser
        195                 200                 205

gag aat gcc tca gaa aaa gag atc acc gct att atg aag gat ttc ggc      672
Glu Asn Ala Ser Glu Lys Glu Ile Thr Ala Ile Met Lys Asp Phe Gly
    210                 215                 220

att gaa cgc gcg cgt atg ttt ggt tgg cca aac acc tac gtt ttc acc      720
Ile Glu Arg Ala Arg Met Phe Gly Trp Pro Asn Thr Tyr Val Phe Thr
225                 230                 235                 240

aaa gca atg ggc gaa atg att ctg atg cac atg aaa gaa gat ctg tca      768
Lys Ala Met Gly Glu Met Ile Leu Met His Met Lys Glu Asp Leu Ser
                245                 250                 255

ctg ctg atc att cgc cct acc atg atc acc tcg acc tac cgt gaa cca      816
Leu Leu Ile Ile Arg Pro Thr Met Ile Thr Ser Thr Tyr Arg Glu Pro
            260                 265                 270

ttt cct ggt tgg att gag ggt gct cgt acc gtg gac tcc gtg atc gtt      864
Phe Pro Gly Trp Ile Glu Gly Ala Arg Thr Val Asp Ser Val Ile Val
        275                 280                 285

ggc tat ggt aaa ggc aaa gtg ggc tgc ttc gtt tcg cgt ccg gaa tcc      912
Gly Tyr Gly Lys Gly Lys Val Gly Cys Phe Val Ser Arg Pro Glu Ser
    290                 295                 300

gtg ctg gat gtt atc cca gct gac atg gtc gtg aac ggt atc att gtt      960
Val Leu Asp Val Ile Pro Ala Asp Met Val Val Asn Gly Ile Ile Val
```

-continued 305 310 315 320 gcg atg gca acc cgc gcg cag aag caa gca tcc gaa atc att tac caa 1008
Ala Met Ala Thr Arg Ala Gln Lys Gln Ala Ser Glu Ile Ile Tyr Gln
325 330 335 att ggc tct tca ctg cgc aac cct ctg aaa ctg tcg tcc gtc aat gat 1056
Ile Gly Ser Ser Leu Arg Asn Pro Leu Lys Leu Ser Ser Val Asn Asp
340 345 350 ttc agc tac cgt tat ttt tct gcg aac cct tgg atc aat aaa gaa ggt 1104
Phe Ser Tyr Arg Tyr Phe Ser Ala Asn Pro Trp Ile Asn Lys Glu Gly
355 360 365 gtc ccg gtg aaa acc agc aag gcc atc att ctg agc tct atg acc aag 1152
Val Pro Val Lys Thr Ser Lys Ala Ile Ile Leu Ser Ser Met Thr Lys
370 375 380 ttc tac atc tac atg gct ttc cgc ttc cag ctg cca ctg aaa gcc ctg 1200
Phe Tyr Ile Tyr Met Ala Phe Arg Phe Gln Leu Pro Leu Lys Ala Leu
385 390 395 400 caa gtc gct acc atc ctg gtg ctg aag aac tat cag gat atg tgt acc 1248
Gln Val Ala Thr Ile Leu Val Leu Lys Asn Tyr Gln Asp Met Cys Thr
405 410 415 gtg ctg gac cgc aaa gtc aag ctg gtg atg cgt ctg gtt caa ctg tac 1296
Val Leu Asp Arg Lys Val Lys Leu Val Met Arg Leu Val Gln Leu Tyr
420 425 430 aaa ccg tat gtc ttc ttt gaa ggc tcc ttc gat gac tca aat tcg gag 1344
Lys Pro Tyr Val Phe Phe Glu Gly Ser Phe Asp Asp Ser Asn Ser Glu
435 440 445 aag ctg cgt att gaa gca cgc gag cgt agc ctg gaa ctg aaa gag atg 1392
Lys Leu Arg Ile Glu Ala Arg Glu Arg Ser Leu Glu Leu Lys Glu Met
450 455 460 gat gaa ttc aac ttt gac cca acc gaa att gat tgg gaa aac tac atg 1440
Asp Glu Phe Asn Phe Asp Pro Thr Glu Ile Asp Trp Glu Asn Tyr Met
465 470 475 480 atg agc gtc cac att cct ggt ctg gtg aaa tac gtg atg 1479
Met Ser Val His Ile Pro Gly Leu Val Lys Tyr Val Met
485 490

<210> SEQ ID NO 54
<211> LENGTH: 493
<212> TYPE: PRT
<213> ORGANISM: Ricinus communis (castor bean)

<400> SEQUENCE: 54

Met Glu Val Gly Ser Ile Leu Glu Phe Leu Glu Asn Lys Thr Ile Leu
1 5 10 15

Ala Thr Gly Ala Thr Gly Tyr Leu Ala Lys Ile Phe Val Glu Lys Val
20 25 30

Leu Arg Val Gln Pro Asn Val Lys Lys Leu Tyr Leu Leu Leu Arg Ala
35 40 45

Ala Asp Ala Asp Ser Ala Met Glu Arg Leu Asn Arg Glu Val Ile Gly
50 55 60

Lys Asp Leu Phe Lys Gly Val Arg Glu Lys Tyr Gly Ser Ser Leu Asn
65 70 75 80

Ser Phe Val Ser Glu Lys Met Thr Pro Ile Pro Gly Asp Ile Ser Arg
85 90 95

Glu Asp Leu Gly Ile Glu Asp Phe Asn Leu Arg Asp Glu Ile Leu Lys
100 105 110

Asp Ile Asp Val Val Ile Asn Phe Ala Ala Thr Thr Asn Phe Asp Glu
115 120 125

Arg Tyr Asp Val Ala Leu Gly Val Asn Thr Leu Gly Ala Leu Asn Val

```
    130                 135                 140

Leu Asn Phe Ala Lys Lys Cys Leu Lys Ile Arg Met Leu Val His Val
145                 150                 155                 160

Ser Thr Ala Tyr Val Cys Gly Glu Asp Thr Gly Leu Ile Leu Glu Lys
                165                 170                 175

Pro Phe Pro Met Gly Glu Ala Lys Lys Gly Asn Arg Lys Ile Asp Ile
            180                 185                 190

Glu Glu Glu Lys Lys Leu Val Gln Glu Lys Leu Asn Glu Leu Glu Ser
        195                 200                 205

Glu Asn Ala Ser Glu Lys Glu Ile Thr Ala Ile Met Lys Asp Phe Gly
    210                 215                 220

Ile Glu Arg Ala Arg Met Phe Gly Trp Pro Asn Thr Tyr Val Phe Thr
225                 230                 235                 240

Lys Ala Met Gly Glu Met Ile Leu Met His Met Lys Glu Asp Leu Ser
                245                 250                 255

Leu Leu Ile Ile Arg Pro Thr Met Ile Thr Ser Thr Tyr Arg Glu Pro
            260                 265                 270

Phe Pro Gly Trp Ile Glu Gly Ala Arg Thr Val Asp Ser Val Ile Val
        275                 280                 285

Gly Tyr Gly Lys Gly Lys Val Gly Cys Phe Val Ser Arg Pro Glu Ser
    290                 295                 300

Val Leu Asp Val Ile Pro Ala Asp Met Val Val Asn Gly Ile Ile Val
305                 310                 315                 320

Ala Met Ala Thr Arg Ala Gln Lys Gln Ala Ser Glu Ile Ile Tyr Gln
                325                 330                 335

Ile Gly Ser Ser Leu Arg Asn Pro Leu Lys Leu Ser Ser Val Asn Asp
            340                 345                 350

Phe Ser Tyr Arg Tyr Phe Ser Ala Asn Pro Trp Ile Asn Lys Glu Gly
        355                 360                 365

Val Pro Val Lys Thr Ser Lys Ala Ile Ile Leu Ser Ser Met Thr Lys
    370                 375                 380

Phe Tyr Ile Tyr Met Ala Phe Arg Phe Gln Leu Pro Leu Lys Ala Leu
385                 390                 395                 400

Gln Val Ala Thr Ile Leu Val Leu Lys Asn Tyr Gln Asp Met Cys Thr
                405                 410                 415

Val Leu Asp Arg Lys Val Lys Leu Val Met Arg Leu Val Gln Leu Tyr
            420                 425                 430

Lys Pro Tyr Val Phe Phe Glu Gly Ser Phe Asp Asp Ser Asn Ser Glu
        435                 440                 445

Lys Leu Arg Ile Glu Ala Arg Glu Arg Ser Leu Glu Leu Lys Glu Met
    450                 455                 460

Asp Glu Phe Asn Phe Asp Pro Thr Glu Ile Asp Trp Glu Asn Tyr Met
465                 470                 475                 480

Met Ser Val His Ile Pro Gly Leu Val Lys Tyr Val Met
                485                 490
```

<210> SEQ ID NO 55
<211> LENGTH: 1932
<212> TYPE: DNA
<213> ORGANISM: Vitis vinifera (wine grape)
<220> FEATURE:
<221> NAME/KEY: CDS
<222> LOCATION: (1)..(1932)

<400> SEQUENCE: 55

-continued

```
atg aat agc atg ttt ctg ctg tcg tgg tcc cag tcg tcg gtc atc acc       48
Met Asn Ser Met Phe Leu Leu Ser Trp Ser Gln Ser Ser Val Ile Thr
1               5                   10                  15

tcg ctg ctg caa ctg tcg tgc gaa gtc tcg gat aag gca gat gaa atg       96
Ser Leu Leu Gln Leu Ser Cys Glu Val Ser Asp Lys Ala Asp Glu Met
            20                  25                  30

agc ctg acc ctg ctg cag cca att ctg gcg gca gtg cac ggt cat aaa      144
Ser Leu Thr Leu Leu Gln Pro Ile Leu Ala Ala Val His Gly His Lys
        35                  40                  45

ctg caa cac ttc ctg ctg ggc acc aag acc ccg cca ctg aaa ttc ctg      192
Leu Gln His Phe Leu Leu Gly Thr Lys Thr Pro Pro Leu Lys Phe Leu
    50                  55                  60

gag ttt ggc gat gaa gcc atc att gag ctg aag gct gtt cag aaa tcc      240
Glu Phe Gly Asp Glu Ala Ile Ile Glu Leu Lys Ala Val Gln Lys Ser
65                  70                  75                  80

agc ccg gtc cac cgc aac gat cac ggc tac ggt acc aat att acc acc      288
Ser Pro Val His Arg Asn Asp His Gly Tyr Gly Thr Asn Ile Thr Thr
                85                  90                  95

agc ctg tgg aag cgt aag cat acc ggt atc ttt tgc tgt cag tca ggc      336
Ser Leu Trp Lys Arg Lys His Thr Gly Ile Phe Cys Cys Gln Ser Gly
            100                 105                 110

gag tcg gat cgc gcc ctg atg cag caa tcc aag acc caa aaa gtg cgt      384
Glu Ser Asp Arg Ala Leu Met Gln Gln Ser Lys Thr Gln Lys Val Arg
        115                 120                 125

gcg ctg aag gaa atg gca gtt agc acc acc acc acc cct aac acc tct      432
Ala Leu Lys Glu Met Ala Val Ser Thr Thr Thr Thr Pro Asn Thr Ser
    130                 135                 140

att acc aat ggc ctg ggt atc ctg cag ttc ctg gcc ggt aaa acc tat      480
Ile Thr Asn Gly Leu Gly Ile Leu Gln Phe Leu Ala Gly Lys Thr Tyr
145                 150                 155                 160

ttt att acc ggt gct acc ggt ctg ctg gct aag gca gtg gtt gaa aaa      528
Phe Ile Thr Gly Ala Thr Gly Leu Leu Ala Lys Ala Val Val Glu Lys
                165                 170                 175

atc ctg cgc cgt gcg ccg gat gtc ggc aag atc ttc att ctg atc aaa      576
Ile Leu Arg Arg Ala Pro Asp Val Gly Lys Ile Phe Ile Leu Ile Lys
            180                 185                 190

gca aag aac aaa gag gcc gct gtg gac cgc ctg aaa acc gaa atc att      624
Ala Lys Asn Lys Glu Ala Ala Val Asp Arg Leu Lys Thr Glu Ile Ile
        195                 200                 205

aat tca gag ctg ttc gaa tgc ctg aag cag cgt cac ggt aaa tac tac      672
Asn Ser Glu Leu Phe Glu Cys Leu Lys Gln Arg His Gly Lys Tyr Tyr
    210                 215                 220

caa gat ttc atg ctg agc aaa ctg gcg cca gtc gtg ggt aac ctg tgt      720
Gln Asp Phe Met Leu Ser Lys Leu Ala Pro Val Val Gly Asn Leu Cys
225                 230                 235                 240

gag tcc gat ctg ggc att gac gcg aat ctg att agc gaa atc gca gaa      768
Glu Ser Asp Leu Gly Ile Asp Ala Asn Leu Ile Ser Glu Ile Ala Glu
                245                 250                 255

gag gtc gac gtg atc att aac tcg gcg gca aac acc aat ttt gaa gag      816
Glu Val Asp Val Ile Ile Asn Ser Ala Ala Asn Thr Asn Phe Glu Glu
            260                 265                 270

cgc tac gat gtc tcc ctg cac gcc aat acc atc ggc ccg tgc cgc ctg      864
Arg Tyr Asp Val Ser Leu His Ala Asn Thr Ile Gly Pro Cys Arg Leu
        275                 280                 285

atg gac ttc gct aaa aag tac tgt aaa aac ctg cgt gtc ttt ctg cat      912
Met Asp Phe Ala Lys Lys Tyr Cys Lys Asn Leu Arg Val Phe Leu His
    290                 295                 300

gtg tct acc gcg tat gtt aat ggc gag cgc gaa ggc atg att acc gaa      960
Val Ser Thr Ala Tyr Val Asn Gly Glu Arg Glu Gly Met Ile Thr Glu
305                 310                 315                 320
```

```
aag cca ttc tac atg ggt gaa agc atc gcc cgt gag aaa gtc gct tct     1008
Lys Pro Phe Tyr Met Gly Glu Ser Ile Ala Arg Glu Lys Val Ala Ser
                325                 330                 335

gaa ttt ctg cca ctg tca tat cct gca ctg gat gtg gat gac gaa att     1056
Glu Phe Leu Pro Leu Ser Tyr Pro Ala Leu Asp Val Asp Asp Glu Ile
            340                 345                 350

aag atc gcg ctg gac tcc aaa gtt gca ttc gaa ggc aac ctg gag gat     1104
Lys Ile Ala Leu Asp Ser Lys Val Ala Phe Glu Gly Asn Leu Glu Asp
        355                 360                 365

cag aag atg aaa gaa ctg ggt ctg gag cgc gcg cgt att cac ggc tgg     1152
Gln Lys Met Lys Glu Leu Gly Leu Glu Arg Ala Arg Ile His Gly Trp
    370                 375                 380

cat aac ccg tat gag ttt acc aaa gca atg ggt gaa atg atg att aat     1200
His Asn Pro Tyr Glu Phe Thr Lys Ala Met Gly Glu Met Met Ile Asn
385                 390                 395                 400

agc atg cgc ggc gat atc ccg ctg gtt atc att cgt cca acc gcg atc     1248
Ser Met Arg Gly Asp Ile Pro Leu Val Ile Ile Arg Pro Thr Ala Ile
                405                 410                 415

gaa tct acc ctg gag gat cct ttc ccg ggt tgg att caa ggc aac cgc     1296
Glu Ser Thr Leu Glu Asp Pro Phe Pro Gly Trp Ile Gln Gly Asn Arg
            420                 425                 430

atg ctg gac cca atg atc ctg tca tac ggc aaa ggt aac ctg cct tcg     1344
Met Leu Asp Pro Met Ile Leu Ser Tyr Gly Lys Gly Asn Leu Pro Ser
        435                 440                 445

ttt ctg gtt aat ccg gaa gtt gtc att gat atg atc cct gtc gac atg     1392
Phe Leu Val Asn Pro Glu Val Val Ile Asp Met Ile Pro Val Asp Met
    450                 455                 460

gtg gtt aat gcc atc att gcc gct atg gcg aaa cac ggc att gca ggc     1440
Val Val Asn Ala Ile Ile Ala Ala Met Ala Lys His Gly Ile Ala Gly
465                 470                 475                 480

aag cca ggc atc aaa gtt tat cat gtc ggt tct tca gct gtg aac ctg     1488
Lys Pro Gly Ile Lys Val Tyr His Val Gly Ser Ser Ala Val Asn Leu
                485                 490                 495

ctg cct ctg ggc gac ctg ttc aag tac tcg tat gaa cac ttt att tgc     1536
Leu Pro Leu Gly Asp Leu Phe Lys Tyr Ser Tyr Glu His Phe Ile Cys
            500                 505                 510

tcc ccg atc aat atg gat acc gag ggc aaa acc acc gac atg aag gaa     1584
Ser Pro Ile Asn Met Asp Thr Glu Gly Lys Thr Thr Asp Met Lys Glu
        515                 520                 525

atg aaa ttc ttc tcc agc atg gat gac ttc agc tct cac atg cag acc     1632
Met Lys Phe Phe Ser Ser Met Asp Asp Phe Ser Ser His Met Gln Thr
    530                 535                 540

gaa att gtt cag caa cgc cgt ctg gca atc tcc ggt aac aat gct agc     1680
Glu Ile Val Gln Gln Arg Arg Leu Ala Ile Ser Gly Asn Asn Ala Ser
545                 550                 555                 560

caa cgc ctg gag cgt aag tgt aaa atg att gtc gaa cac gcc atc aac     1728
Gln Arg Leu Glu Arg Lys Cys Lys Met Ile Val Glu His Ala Ile Asn
                565                 570                 575

ctg gct cgc gtg tac cag cca cac atg ttc ttt cgc ggc cgt ttc gat     1776
Leu Ala Arg Val Tyr Gln Pro His Met Phe Phe Arg Gly Arg Phe Asp
            580                 585                 590

aac tct aat acc cat aag atc atg gaa ggc atg tca gaa gag gaa atg     1824
Asn Ser Asn Thr His Lys Ile Met Glu Gly Met Ser Glu Glu Glu Met
        595                 600                 605

aaa cgt ttt ggc ctg gac gtg gag aac gtt gat tgg gaa gac tat gtg     1872
Lys Arg Phe Gly Leu Asp Val Glu Asn Val Asp Trp Glu Asp Tyr Val
    610                 615                 620

acc aac atc cac att cca ggt ctg aag cgt cac gtc atc aaa ggt cgt     1920
Thr Asn Ile His Ile Pro Gly Leu Lys Arg His Val Ile Lys Gly Arg
```

-continued

```
625                 630                 635                 640

ggt atg cca aag                                                 1932
Gly Met Pro Lys


<210> SEQ ID NO 56
<211> LENGTH: 644
<212> TYPE: PRT
<213> ORGANISM: Vitis vinifera (wine grape)

<400> SEQUENCE: 56

Met Asn Ser Met Phe Leu Leu Ser Trp Ser Gln Ser Ser Val Ile Thr
1               5                   10                  15

Ser Leu Leu Gln Leu Ser Cys Glu Val Ser Asp Lys Ala Asp Glu Met
            20                  25                  30

Ser Leu Thr Leu Leu Gln Pro Ile Leu Ala Ala Val His Gly His Lys
        35                  40                  45

Leu Gln His Phe Leu Leu Gly Thr Lys Thr Pro Pro Leu Lys Phe Leu
    50                  55                  60

Glu Phe Gly Asp Glu Ala Ile Ile Glu Leu Lys Ala Val Gln Lys Ser
65                  70                  75                  80

Ser Pro Val His Arg Asn Asp His Gly Tyr Gly Thr Asn Ile Thr Thr
                85                  90                  95

Ser Leu Trp Lys Arg Lys His Thr Gly Ile Phe Cys Cys Gln Ser Gly
            100                 105                 110

Glu Ser Asp Arg Ala Leu Met Gln Gln Ser Lys Thr Gln Lys Val Arg
        115                 120                 125

Ala Leu Lys Glu Met Ala Val Ser Thr Thr Thr Thr Pro Asn Thr Ser
    130                 135                 140

Ile Thr Asn Gly Leu Gly Ile Leu Gln Phe Leu Ala Gly Lys Thr Tyr
145                 150                 155                 160

Phe Ile Thr Gly Ala Thr Gly Leu Leu Ala Lys Ala Val Val Glu Lys
                165                 170                 175

Ile Leu Arg Arg Ala Pro Asp Val Gly Lys Ile Phe Ile Leu Ile Lys
            180                 185                 190

Ala Lys Asn Lys Glu Ala Ala Val Asp Arg Leu Lys Thr Glu Ile Ile
        195                 200                 205

Asn Ser Glu Leu Phe Glu Cys Leu Lys Gln Arg His Gly Lys Tyr Tyr
    210                 215                 220

Gln Asp Phe Met Leu Ser Lys Leu Ala Pro Val Val Gly Asn Leu Cys
225                 230                 235                 240

Glu Ser Asp Leu Gly Ile Asp Ala Asn Leu Ile Ser Glu Ile Ala Glu
                245                 250                 255

Glu Val Asp Val Ile Ile Asn Ser Ala Ala Asn Thr Asn Phe Glu Glu
            260                 265                 270

Arg Tyr Asp Val Ser Leu His Ala Asn Thr Ile Gly Pro Cys Arg Leu
        275                 280                 285

Met Asp Phe Ala Lys Lys Tyr Cys Lys Asn Leu Arg Val Phe Leu His
    290                 295                 300

Val Ser Thr Ala Tyr Val Asn Gly Glu Arg Glu Gly Met Ile Thr Glu
305                 310                 315                 320

Lys Pro Phe Tyr Met Gly Glu Ser Ile Ala Arg Glu Lys Val Ala Ser
                325                 330                 335

Glu Phe Leu Pro Leu Ser Tyr Pro Ala Leu Asp Val Asp Asp Glu Ile
            340                 345                 350
```

```
Lys Ile Ala Leu Asp Ser Lys Val Ala Phe Glu Gly Asn Leu Glu Asp
        355                 360                 365

Gln Lys Met Lys Glu Leu Gly Leu Glu Arg Ala Arg Ile His Gly Trp
    370                 375                 380

His Asn Pro Tyr Glu Phe Thr Lys Ala Met Gly Glu Met Met Ile Asn
385                 390                 395                 400

Ser Met Arg Gly Asp Ile Pro Leu Val Ile Ile Arg Pro Thr Ala Ile
                405                 410                 415

Glu Ser Thr Leu Glu Asp Pro Phe Pro Gly Trp Ile Gln Gly Asn Arg
            420                 425                 430

Met Leu Asp Pro Met Ile Leu Ser Tyr Gly Lys Gly Asn Leu Pro Ser
        435                 440                 445

Phe Leu Val Asn Pro Glu Val Val Ile Asp Met Ile Pro Val Asp Met
    450                 455                 460

Val Val Asn Ala Ile Ile Ala Ala Met Ala Lys His Gly Ile Ala Gly
465                 470                 475                 480

Lys Pro Gly Ile Lys Val Tyr His Val Gly Ser Ser Ala Val Asn Leu
                485                 490                 495

Leu Pro Leu Gly Asp Leu Phe Lys Tyr Ser Tyr Glu His Phe Ile Cys
            500                 505                 510

Ser Pro Ile Asn Met Asp Thr Glu Gly Lys Thr Thr Asp Met Lys Glu
        515                 520                 525

Met Lys Phe Phe Ser Ser Met Asp Asp Phe Ser Ser His Met Gln Thr
    530                 535                 540

Glu Ile Val Gln Gln Arg Arg Leu Ala Ile Ser Gly Asn Asn Ala Ser
545                 550                 555                 560

Gln Arg Leu Glu Arg Lys Cys Lys Met Ile Val Glu His Ala Ile Asn
                565                 570                 575

Leu Ala Arg Val Tyr Gln Pro His Met Phe Phe Arg Gly Arg Phe Asp
            580                 585                 590

Asn Ser Asn Thr His Lys Ile Met Glu Gly Met Ser Glu Glu Glu Met
        595                 600                 605

Lys Arg Phe Gly Leu Asp Val Glu Asn Val Asp Trp Glu Asp Tyr Val
    610                 615                 620

Thr Asn Ile His Ile Pro Gly Leu Lys Arg His Val Ile Lys Gly Arg
625                 630                 635                 640

Gly Met Pro Lys


<210> SEQ ID NO 57
<211> LENGTH: 1818
<212> TYPE: DNA
<213> ORGANISM: Vitis vinifera (wine grape)
<220> FEATURE:
<221> NAME/KEY: CDS
<222> LOCATION: (1)..(1818)

<400> SEQUENCE: 57

atg gca atc ggc acc tcg caa tcg gca atc tcg tcg ttc cct tac gca       48
Met Ala Ile Gly Thr Ser Gln Ser Ala Ile Ser Ser Phe Pro Tyr Ala
1               5                   10                  15

ctg cag ggc atc ggt ctg gat ctg gtt ccg ttt gag gac aag acc ttt       96
Leu Gln Gly Ile Gly Leu Asp Leu Val Pro Phe Glu Asp Lys Thr Phe
            20                  25                  30

gat gtg gtt gaa ctg aaa gcg gtg aaa aag tcc agc cac ctg cat acc      144
Asp Val Val Glu Leu Lys Ala Val Lys Lys Ser Ser His Leu His Thr
        35                  40                  45
```

-continued

```
atc gac cac ggc tac ggt acc aac atc att acc tct ctg tgg gaa cgc      192
Ile Asp His Gly Tyr Gly Thr Asn Ile Ile Thr Ser Leu Trp Glu Arg
    50                  55                  60

aaa aat acc ggt att ttc tgc tgt cag tcc ggc gag agc gat cgt gca      240
Lys Asn Thr Gly Ile Phe Cys Cys Gln Ser Gly Glu Ser Asp Arg Ala
65                  70                  75                  80

ctg atg cag caa agc cgc acc caa aag gtc cgt acc ctg aaa gag atg      288
Leu Met Gln Gln Ser Arg Thr Gln Lys Val Arg Thr Leu Lys Glu Met
                85                  90                  95

gaa gtg agc acc acc acc acc aac acc tct atc acc aat ggc ctg ggt      336
Glu Val Ser Thr Thr Thr Thr Asn Thr Ser Ile Thr Asn Gly Leu Gly
            100                 105                 110

att ctg cag ttc ctg ccg ggt aaa gat tat ttt atc acc ggc ggt acc      384
Ile Leu Gln Phe Leu Pro Gly Lys Asp Tyr Phe Ile Thr Gly Gly Thr
        115                 120                 125

ggc ttc ctg gct aag gca gtc gtg gaa aaa att ctg cgc acc gcg cct      432
Gly Phe Leu Ala Lys Ala Val Val Glu Lys Ile Leu Arg Thr Ala Pro
    130                 135                 140

gac gtc ggc aag atc ttt gtg ctg att aaa gca aag aac aaa gaa gcg      480
Asp Val Gly Lys Ile Phe Val Leu Ile Lys Ala Lys Asn Lys Glu Ala
145                 150                 155                 160

gca atg gat cgc ctg aaa acc gag atc att gac tcc gag ctg ttt gaa      528
Ala Met Asp Arg Leu Lys Thr Glu Ile Ile Asp Ser Glu Leu Phe Glu
                165                 170                 175

tgc ctg aag cag cgt cat ggc aaa tac tat caa gat ttc atc ctg tcg      576
Cys Leu Lys Gln Arg His Gly Lys Tyr Tyr Gln Asp Phe Ile Leu Ser
            180                 185                 190

aaa ctg gcc ccg gtt gtc ggt aac ctg tgt gaa tcc gat ctg ggc att      624
Lys Leu Ala Pro Val Val Gly Asn Leu Cys Glu Ser Asp Leu Gly Ile
        195                 200                 205

gac gcc aat agc atc tct gag att gct gaa gag gtt gat gtc atc att      672
Asp Ala Asn Ser Ile Ser Glu Ile Ala Glu Glu Val Asp Val Ile Ile
    210                 215                 220

aac tcc gcc gct aac acc aat ttc gaa gag cgc tac gat gtg tca ctg      720
Asn Ser Ala Ala Asn Thr Asn Phe Glu Glu Arg Tyr Asp Val Ser Leu
225                 230                 235                 240

tcg acc aat gtt ctg ggc cca cgc cgt ctg atg gac ttt acc aac aag      768
Ser Thr Asn Val Leu Gly Pro Arg Arg Leu Met Asp Phe Thr Asn Lys
                245                 250                 255

tac tgc aaa aat ctg cgc gtg ttc ctg cac gtt tct acc gcg tac gtg      816
Tyr Cys Lys Asn Leu Arg Val Phe Leu His Val Ser Thr Ala Tyr Val
            260                 265                 270

tca ggc gag cgt gaa ggc atg atc atg gaa aag cct ttt cac atg ggc      864
Ser Gly Glu Arg Glu Gly Met Ile Met Glu Lys Pro Phe His Met Gly
        275                 280                 285

gag cgc att gcc cgt gaa aaa gcg gca tca gag ttc ccg cca ctg gct      912
Glu Arg Ile Ala Arg Glu Lys Ala Ala Ser Glu Phe Pro Pro Leu Ala
    290                 295                 300

tac ccg gtg ctg gat gtt gac ggc gag atc gaa att gcc ctg gat agc      960
Tyr Pro Val Leu Asp Val Asp Gly Glu Ile Glu Ile Ala Leu Asp Ser
305                 310                 315                 320

aag gtg gct ttt gaa ggc aac ctg gag gac gaa aag atg aaa gcg ctg     1008
Lys Val Ala Phe Glu Gly Asn Leu Glu Asp Glu Lys Met Lys Ala Leu
                325                 330                 335

ggt ctg gaa cgc gca cgt atc cac ggc tgg cat aac ccg tat gaa ttc     1056
Gly Leu Glu Arg Ala Arg Ile His Gly Trp His Asn Pro Tyr Glu Phe
            340                 345                 350

acc aaa gcg atg ggt gaa atg ctg atc aat agc atg cgc ggc gat att     1104
Thr Lys Ala Met Gly Glu Met Leu Ile Asn Ser Met Arg Gly Asp Ile
        355                 360                 365
```

```
ccg ctg gtc atc att cgt cca acc gcc att ggt tct acc ctg gat gac      1152
Pro Leu Val Ile Ile Arg Pro Thr Ala Ile Gly Ser Thr Leu Asp Asp
    370                 375                 380

cct ttt ccg ggt tgg atc cag ggc aac cgc atg gct gat cca ctg att      1200
Pro Phe Pro Gly Trp Ile Gln Gly Asn Arg Met Ala Asp Pro Leu Ile
385                 390                 395                 400

ctg tcc tat ggc cgt gtt aac ctg cct agc ttc ctg gtt aat ccg gaa      1248
Leu Ser Tyr Gly Arg Val Asn Leu Pro Ser Phe Leu Val Asn Pro Glu
                405                 410                 415

gcg gtc atc gac atg att ccg gtg gtt atg gtc gtg aac gca atc att      1296
Ala Val Ile Asp Met Ile Pro Val Val Met Val Val Asn Ala Ile Ile
            420                 425                 430

gcc gct atg gcg aaa cac ggc atc gca ggc aag cca ggc att aaa gtc      1344
Ala Ala Met Ala Lys His Gly Ile Ala Gly Lys Pro Gly Ile Lys Val
        435                 440                 445

tac cat gtg ggt tct tca gcc gtg aac cca ctg cct ctg ggc gac ctg      1392
Tyr His Val Gly Ser Ser Ala Val Asn Pro Leu Pro Leu Gly Asp Leu
    450                 455                 460

ttc aag cac tcc tac gaa cat ttc atc tgc tcg cca att aat atg gat      1440
Phe Lys His Ser Tyr Glu His Phe Ile Cys Ser Pro Ile Asn Met Asp
465                 470                 475                 480

acc gaa ggt aaa acc gtg gac atg aag gag atg aaa atc ttc agc cct      1488
Thr Glu Gly Lys Thr Val Asp Met Lys Glu Met Lys Ile Phe Ser Pro
                485                 490                 495

atg gat gac ttt tcg tcc cac atg cag acc gaa atc gtt cag caa cgc      1536
Met Asp Asp Phe Ser Ser His Met Gln Thr Glu Ile Val Gln Gln Arg
            500                 505                 510

cgt ctg acc att tcg ggc aac aaa gct tcc caa cgc ctg gaa cgc aag      1584
Arg Leu Thr Ile Ser Gly Asn Lys Ala Ser Gln Arg Leu Glu Arg Lys
        515                 520                 525

tgt aaa atg atc gtt gag cac gcc att aat ctg gct cgc gtc tac cag      1632
Cys Lys Met Ile Val Glu His Ala Ile Asn Leu Ala Arg Val Tyr Gln
    530                 535                 540

ccg tat atg ttc ttt cgc ggt cgt ttt gat aac tct aat acc cat aac      1680
Pro Tyr Met Phe Phe Arg Gly Arg Phe Asp Asn Ser Asn Thr His Asn
545                 550                 555                 560

ctg atg gaa ggc atg tca gaa gag gaa atg aaa cgc ttc cgt ctg gac      1728
Leu Met Glu Gly Met Ser Glu Glu Glu Met Lys Arg Phe Arg Leu Asp
                565                 570                 575

gtt gaa aat gtc gat tgg gag gac tac atc acc aac atc cac atc tcg      1776
Val Glu Asn Val Asp Trp Glu Asp Tyr Ile Thr Asn Ile His Ile Ser
            580                 585                 590

ggt ctg aag aaa cac gtc atg aaa ggt cgc ggt atg cca aag              1818
Gly Leu Lys Lys His Val Met Lys Gly Arg Gly Met Pro Lys
        595                 600                 605
```

<210> SEQ ID NO 58
<211> LENGTH: 606
<212> TYPE: PRT
<213> ORGANISM: Vitis vinifera (wine grape)

<400> SEQUENCE: 58

```
Met Ala Ile Gly Thr Ser Gln Ser Ala Ile Ser Ser Phe Pro Tyr Ala
1               5                   10                  15

Leu Gln Gly Ile Gly Leu Asp Leu Val Pro Phe Glu Asp Lys Thr Phe
            20                  25                  30

Asp Val Val Glu Leu Lys Ala Val Lys Lys Ser Ser His Leu His Thr
        35                  40                  45

Ile Asp His Gly Tyr Gly Thr Asn Ile Ile Thr Ser Leu Trp Glu Arg
```

```
    50                  55                  60

Lys Asn Thr Gly Ile Phe Cys Cys Gln Ser Gly Glu Ser Asp Arg Ala
65                  70                  75                  80

Leu Met Gln Gln Ser Arg Thr Gln Lys Val Arg Thr Leu Lys Glu Met
                85                  90                  95

Glu Val Ser Thr Thr Thr Thr Asn Thr Ser Ile Thr Asn Gly Leu Gly
            100                 105                 110

Ile Leu Gln Phe Leu Pro Gly Lys Asp Tyr Phe Ile Thr Gly Gly Thr
        115                 120                 125

Gly Phe Leu Ala Lys Ala Val Val Glu Lys Ile Leu Arg Thr Ala Pro
    130                 135                 140

Asp Val Gly Lys Ile Phe Val Leu Ile Lys Ala Lys Asn Lys Glu Ala
145                 150                 155                 160

Ala Met Asp Arg Leu Lys Thr Glu Ile Ile Asp Ser Glu Leu Phe Glu
                165                 170                 175

Cys Leu Lys Gln Arg His Gly Lys Tyr Tyr Gln Asp Phe Ile Leu Ser
            180                 185                 190

Lys Leu Ala Pro Val Val Gly Asn Leu Cys Glu Ser Asp Leu Gly Ile
        195                 200                 205

Asp Ala Asn Ser Ile Ser Glu Ile Ala Glu Glu Val Asp Val Ile Ile
    210                 215                 220

Asn Ser Ala Ala Asn Thr Asn Phe Glu Glu Arg Tyr Asp Val Ser Leu
225                 230                 235                 240

Ser Thr Asn Val Leu Gly Pro Arg Arg Leu Met Asp Phe Thr Asn Lys
                245                 250                 255

Tyr Cys Lys Asn Leu Arg Val Phe Leu His Val Ser Thr Ala Tyr Val
            260                 265                 270

Ser Gly Glu Arg Glu Gly Met Ile Met Glu Lys Pro Phe His Met Gly
        275                 280                 285

Glu Arg Ile Ala Arg Glu Lys Ala Ala Ser Glu Phe Pro Pro Leu Ala
    290                 295                 300

Tyr Pro Val Leu Asp Val Asp Gly Glu Ile Glu Ile Ala Leu Asp Ser
305                 310                 315                 320

Lys Val Ala Phe Glu Gly Asn Leu Glu Asp Glu Lys Met Lys Ala Leu
                325                 330                 335

Gly Leu Glu Arg Ala Arg Ile His Gly Trp His Asn Pro Tyr Glu Phe
            340                 345                 350

Thr Lys Ala Met Gly Glu Met Leu Ile Asn Ser Met Arg Gly Asp Ile
        355                 360                 365

Pro Leu Val Ile Ile Arg Pro Thr Ala Ile Gly Ser Thr Leu Asp Asp
    370                 375                 380

Pro Phe Pro Gly Trp Ile Gln Gly Asn Arg Met Ala Asp Pro Leu Ile
385                 390                 395                 400

Leu Ser Tyr Gly Arg Val Asn Leu Pro Ser Phe Leu Val Asn Pro Glu
                405                 410                 415

Ala Val Ile Asp Met Ile Pro Val Val Met Val Val Asn Ala Ile Ile
            420                 425                 430

Ala Ala Met Ala Lys His Gly Ile Ala Gly Lys Pro Gly Ile Lys Val
        435                 440                 445

Tyr His Val Gly Ser Ser Ala Val Asn Pro Leu Pro Leu Gly Asp Leu
    450                 455                 460

Phe Lys His Ser Tyr Glu His Phe Ile Cys Ser Pro Ile Asn Met Asp
465                 470                 475                 480
```

```
Thr Glu Gly Lys Thr Val Asp Met Lys Glu Met Lys Ile Phe Ser Pro
                485                 490                 495

Met Asp Asp Phe Ser Ser His Met Gln Thr Glu Ile Val Gln Gln Arg
            500                 505                 510

Arg Leu Thr Ile Ser Gly Asn Lys Ala Ser Gln Arg Leu Glu Arg Lys
        515                 520                 525

Cys Lys Met Ile Val Glu His Ala Ile Asn Leu Ala Arg Val Tyr Gln
    530                 535                 540

Pro Tyr Met Phe Phe Arg Gly Arg Phe Asp Asn Ser Asn Thr His Asn
545                 550                 555                 560

Leu Met Glu Gly Met Ser Glu Glu Glu Met Lys Arg Phe Arg Leu Asp
                565                 570                 575

Val Glu Asn Val Asp Trp Glu Asp Tyr Ile Thr Asn Ile His Ile Ser
            580                 585                 590

Gly Leu Lys Lys His Val Met Lys Gly Arg Gly Met Pro Lys
        595                 600                 605


<210> SEQ ID NO 59
<211> LENGTH: 1470
<212> TYPE: DNA
<213> ORGANISM: Vitis vinifera (wine grape)
<220> FEATURE:
<221> NAME/KEY: CDS
<222> LOCATION: (1)..(1470)

<400> SEQUENCE: 59

atg gaa ctg ggc agc atc gtg gag ttt ctg gaa aat aag agc atc ctg       48
Met Glu Leu Gly Ser Ile Val Glu Phe Leu Glu Asn Lys Ser Ile Leu
1               5                   10                  15

gtg acc ggc gcg acc ggc ttt ctg gca aaa atc ttc gtc gaa cgc atc       96
Val Thr Gly Ala Thr Gly Phe Leu Ala Lys Ile Phe Val Glu Arg Ile
            20                  25                  30

ctg cgt acc cag ccg aac gtg aaa aag ctg ttc ctg ctg ctg cgc gca      144
Leu Arg Thr Gln Pro Asn Val Lys Lys Leu Phe Leu Leu Leu Arg Ala
        35                  40                  45

ggt gat acc aaa tct gcc acc caa cgt ctg cac aac gaa gtg att ggc      192
Gly Asp Thr Lys Ser Ala Thr Gln Arg Leu His Asn Glu Val Ile Gly
    50                  55                  60

aaa gaa ctg ttt tgg gtt ctg cgc gaa aag tgg gcc tca gac ttc aat      240
Lys Glu Leu Phe Trp Val Leu Arg Glu Lys Trp Ala Ser Asp Phe Asn
65                  70                  75                  80

tcg ttt gtt tcc aaa aag ctg acc ccg gtc cca ggt gat atc tca tgc      288
Ser Phe Val Ser Lys Lys Leu Thr Pro Val Pro Gly Asp Ile Ser Cys
                85                  90                  95

gat gac ctg ggc gtg acc gac tcg aac ctg cgc gaa gag atg tgg cgt      336
Asp Asp Leu Gly Val Thr Asp Ser Asn Leu Arg Glu Glu Met Trp Arg
            100                 105                 110

gaa gtt gat att gtg gtt aac ctg gcg gca acc acc aat ttc gat gag      384
Glu Val Asp Ile Val Val Asn Leu Ala Ala Thr Thr Asn Phe Asp Glu
        115                 120                 125

cgc tac gac gtg gct ctg ggt atc aat gcc ctg ggc gct cgt cac gtc      432
Arg Tyr Asp Val Ala Leu Gly Ile Asn Ala Leu Gly Ala Arg His Val
    130                 135                 140

ctg gac ttt gcg aaa aag tgt gtg aaa att aag atg ctg ctg cat gtc      480
Leu Asp Phe Ala Lys Lys Cys Val Lys Ile Lys Met Leu Leu His Val
145                 150                 155                 160

tcc acc gcg tat gtg gca ggc gag cag agc ggc ctg atc ctg gaa cag      528
Ser Thr Ala Tyr Val Ala Gly Glu Gln Ser Gly Leu Ile Leu Glu Gln
                165                 170                 175
```

```
ccg ttc caa atg ggc gag acc ctg aat ggt acc ttt ggc ctg gat att      576
Pro Phe Gln Met Gly Glu Thr Leu Asn Gly Thr Phe Gly Leu Asp Ile
            180                 185                 190

gaa gaa gaa aag aaa ctg atg gag gaa cgt ctg gac gag ctg cag agc      624
Glu Glu Glu Lys Lys Leu Met Glu Glu Arg Leu Asp Glu Leu Gln Ser
        195                 200                 205

gaa ggt gct acc cgt gaa gca gtt acc ctg gcc atg aaa gat ttc ggt      672
Glu Gly Ala Thr Arg Glu Ala Val Thr Leu Ala Met Lys Asp Phe Gly
    210                 215                 220

atc caa cgc gca aag atg cac ggc tgg cca aac acc tac gtc ttt acc      720
Ile Gln Arg Ala Lys Met His Gly Trp Pro Asn Thr Tyr Val Phe Thr
225                 230                 235                 240

aaa gcg atg ggc gaa atg ctg ctg ggc cat ctg aag gag aat ctg cca      768
Lys Ala Met Gly Glu Met Leu Leu Gly His Leu Lys Glu Asn Leu Pro
                245                 250                 255

ctg gct atc ctg cgt cct acc att gtg tcc agc acc tac aaa gaa cct      816
Leu Ala Ile Leu Arg Pro Thr Ile Val Ser Ser Thr Tyr Lys Glu Pro
            260                 265                 270

ttc ccg ggt tgg gtt gag ggc atc cgc acc att gat tcc ttt gca gtc      864
Phe Pro Gly Trp Val Glu Gly Ile Arg Thr Ile Asp Ser Phe Ala Val
        275                 280                 285

ggc tat ggt aaa ggc cgt ctg acc ttc ttt ctg ggc gac atc gaa gct      912
Gly Tyr Gly Lys Gly Arg Leu Thr Phe Phe Leu Gly Asp Ile Glu Ala
    290                 295                 300

att gtt gat gtc atc cca gcg gac atg gtc gtg aac tct atg att gtt      960
Ile Val Asp Val Ile Pro Ala Asp Met Val Val Asn Ser Met Ile Val
305                 310                 315                 320

gct atg gcc gct cac gcg aat cag ccg tgc gaa gtt atc tat caa gtc     1008
Ala Met Ala Ala His Ala Asn Gln Pro Cys Glu Val Ile Tyr Gln Val
                325                 330                 335

ggt tct tca gtg aaa aac cca gtt cgc tac tcc aat ctg cag gat ttc     1056
Gly Ser Ser Val Lys Asn Pro Val Arg Tyr Ser Asn Leu Gln Asp Phe
            340                 345                 350

ggc ctg cgt tac ttc acc aag aac cct tgg atc aac aaa gac ggc aag     1104
Gly Leu Arg Tyr Phe Thr Lys Asn Pro Trp Ile Asn Lys Asp Gly Lys
        355                 360                 365

gcg gtg aaa gtt ggc aag gtc acc gtg ctg agc act atg gat tct ttc     1152
Ala Val Lys Val Gly Lys Val Thr Val Leu Ser Thr Met Asp Ser Phe
    370                 375                 380

cat cgc tac atg gca ctg cgt tat ctg ctg ctg ctg aaa ggt ctg cag     1200
His Arg Tyr Met Ala Leu Arg Tyr Leu Leu Leu Leu Lys Gly Leu Gln
385                 390                 395                 400

ttt gtg aac acc gcc ttc tgc caa tac ttt cgc ggc acc tat acc gat     1248
Phe Val Asn Thr Ala Phe Cys Gln Tyr Phe Arg Gly Thr Tyr Thr Asp
                405                 410                 415

ctg aat cgc cgt atc aaa ttc ctg ctg cgt ctg att gaa ctg tac aaa     1296
Leu Asn Arg Arg Ile Lys Phe Leu Leu Arg Leu Ile Glu Leu Tyr Lys
            420                 425                 430

cct tac ctg ttc ttc aag ggt gtc ttt gat gac atg aac acc gaa aaa     1344
Pro Tyr Leu Phe Phe Lys Gly Val Phe Asp Asp Met Asn Thr Glu Lys
        435                 440                 445

ctg cgt atg gct gtg acc gct tcc ggt gct gag gca gac ctg ttc tac     1392
Leu Arg Met Ala Val Thr Ala Ser Gly Ala Glu Ala Asp Leu Phe Tyr
    450                 455                 460

ttt gac ccg aag tgt att gat tgg gaa gat tac ttt atg aac atc cac     1440
Phe Asp Pro Lys Cys Ile Asp Trp Glu Asp Tyr Phe Met Asn Ile His
465                 470                 475                 480

att cct ggt gca gtg aaa tac gtt ttt aag                             1470
Ile Pro Gly Ala Val Lys Tyr Val Phe Lys
```

485 490

<210> SEQ ID NO 60
<211> LENGTH: 490
<212> TYPE: PRT
<213> ORGANISM: Vitis vinifera (wine grape)

<400> SEQUENCE: 60

```
Met Glu Leu Gly Ser Ile Val Glu Phe Leu Glu Asn Lys Ser Ile Leu
1               5                   10                  15

Val Thr Gly Ala Thr Gly Phe Leu Ala Lys Ile Phe Val Glu Arg Ile
            20                  25                  30

Leu Arg Thr Gln Pro Asn Val Lys Lys Leu Phe Leu Leu Arg Ala
        35                  40                  45

Gly Asp Thr Lys Ser Ala Thr Gln Arg Leu His Asn Glu Val Ile Gly
    50                  55                  60

Lys Glu Leu Phe Trp Val Leu Arg Glu Lys Trp Ala Ser Asp Phe Asn
65                  70                  75                  80

Ser Phe Val Ser Lys Lys Leu Thr Pro Val Pro Gly Asp Ile Ser Cys
                85                  90                  95

Asp Asp Leu Gly Val Thr Asp Ser Asn Leu Arg Glu Glu Met Trp Arg
            100                 105                 110

Glu Val Asp Ile Val Val Asn Leu Ala Ala Thr Thr Asn Phe Asp Glu
        115                 120                 125

Arg Tyr Asp Val Ala Leu Gly Ile Asn Ala Leu Gly Ala Arg His Val
    130                 135                 140

Leu Asp Phe Ala Lys Lys Cys Val Lys Ile Lys Met Leu Leu His Val
145                 150                 155                 160

Ser Thr Ala Tyr Val Ala Gly Glu Gln Ser Gly Leu Ile Leu Glu Gln
                165                 170                 175

Pro Phe Gln Met Gly Glu Thr Leu Asn Gly Thr Phe Gly Leu Asp Ile
            180                 185                 190

Glu Glu Glu Lys Lys Leu Met Glu Glu Arg Leu Asp Glu Leu Gln Ser
        195                 200                 205

Glu Gly Ala Thr Arg Glu Ala Val Thr Leu Ala Met Lys Asp Phe Gly
    210                 215                 220

Ile Gln Arg Ala Lys Met His Gly Trp Pro Asn Thr Tyr Val Phe Thr
225                 230                 235                 240

Lys Ala Met Gly Glu Met Leu Leu Gly His Leu Lys Glu Asn Leu Pro
                245                 250                 255

Leu Ala Ile Leu Arg Pro Thr Ile Val Ser Ser Thr Tyr Lys Glu Pro
            260                 265                 270

Phe Pro Gly Trp Val Glu Gly Ile Arg Thr Ile Asp Ser Phe Ala Val
        275                 280                 285

Gly Tyr Gly Lys Gly Arg Leu Thr Phe Phe Leu Gly Asp Ile Glu Ala
    290                 295                 300

Ile Val Asp Val Ile Pro Ala Asp Met Val Val Asn Ser Met Ile Val
305                 310                 315                 320

Ala Met Ala Ala His Ala Asn Gln Pro Cys Glu Val Ile Tyr Gln Val
                325                 330                 335

Gly Ser Ser Val Lys Asn Pro Val Arg Tyr Ser Asn Leu Gln Asp Phe
            340                 345                 350

Gly Leu Arg Tyr Phe Thr Lys Asn Pro Trp Ile Asn Lys Asp Gly Lys
        355                 360                 365
```

```
Ala Val Lys Val Gly Lys Val Thr Val Leu Ser Thr Met Asp Ser Phe
    370                 375                 380

His Arg Tyr Met Ala Leu Arg Tyr Leu Leu Leu Leu Lys Gly Leu Gln
385                 390                 395                 400

Phe Val Asn Thr Ala Phe Cys Gln Tyr Phe Arg Gly Thr Tyr Thr Asp
                405                 410                 415

Leu Asn Arg Arg Ile Lys Phe Leu Leu Arg Leu Ile Glu Leu Tyr Lys
            420                 425                 430

Pro Tyr Leu Phe Phe Lys Gly Val Phe Asp Asp Met Asn Thr Glu Lys
        435                 440                 445

Leu Arg Met Ala Val Thr Ala Ser Gly Ala Glu Ala Asp Leu Phe Tyr
    450                 455                 460

Phe Asp Pro Lys Cys Ile Asp Trp Glu Asp Tyr Phe Met Asn Ile His
465                 470                 475                 480

Ile Pro Gly Ala Val Lys Tyr Val Phe Lys
                485                 490


<210> SEQ ID NO 61
<211> LENGTH: 1470
<212> TYPE: DNA
<213> ORGANISM: Vitis vinifera (wine grape)
<220> FEATURE:
<221> NAME/KEY: CDS
<222> LOCATION: (1)..(1470)

<400> SEQUENCE: 61

atg gag ctg ggt tct atc gtg gag ttt ctg gaa aat aaa tca atc ctg       48
Met Glu Leu Gly Ser Ile Val Glu Phe Leu Glu Asn Lys Ser Ile Leu
1               5                   10                  15

gtg acc ggc gcg acc ggc ttt ctg gca aaa atc ttc gtc gaa aaa atc       96
Val Thr Gly Ala Thr Gly Phe Leu Ala Lys Ile Phe Val Glu Lys Ile
            20                  25                  30

ctg cgc att cag ccg aac gtg aaa aag ctg ttt ctg ctg ctg cgc gcg      144
Leu Arg Ile Gln Pro Asn Val Lys Lys Leu Phe Leu Leu Leu Arg Ala
        35                  40                  45

gca gat acc aaa tcc gcc acc caa cgt ctg cac aat gaa gtc ctg ggc      192
Ala Asp Thr Lys Ser Ala Thr Gln Arg Leu His Asn Glu Val Leu Gly
    50                  55                  60

aag gag ctg ttt cgt gtg ctg aag gat aag tgg ggt tct aac ctg aat      240
Lys Glu Leu Phe Arg Val Leu Lys Asp Lys Trp Gly Ser Asn Leu Asn
65                  70                  75                  80

tcc ttc att agc gaa aaa gtg acc ccg att cca ggc gac atc tca tgt      288
Ser Phe Ile Ser Glu Lys Val Thr Pro Ile Pro Gly Asp Ile Ser Cys
                85                  90                  95

gag aac ctg ggt gtt acc aac ctg aat ctg cgc gaa gag att tgg cgt      336
Glu Asn Leu Gly Val Thr Asn Leu Asn Leu Arg Glu Glu Ile Trp Arg
            100                 105                 110

gaa gtc gat gtg atc ctg aat ctg gcc gct acc acc aaa ttt gat gag      384
Glu Val Asp Val Ile Leu Asn Leu Ala Ala Thr Thr Lys Phe Asp Glu
        115                 120                 125

cgc tac gac gtg gcc ctg ggc att aac acc ctg ggt gct tcg cac gtt      432
Arg Tyr Asp Val Ala Leu Gly Ile Asn Thr Leu Gly Ala Ser His Val
    130                 135                 140

ctg aat ttc tcc aaa aag tgc gtc aaa ctg aag atg ctg ctg cat gtc      480
Leu Asn Phe Ser Lys Lys Cys Val Lys Leu Lys Met Leu Leu His Val
145                 150                 155                 160

tct acc gcg tat gtg tca ggc gaa cgt gag ggt ctg atc ctg gaa tcc      528
Ser Thr Ala Tyr Val Ser Gly Glu Arg Glu Gly Leu Ile Leu Glu Ser
                165                 170                 175
```

-continued

```
cca ctg aaa atg ggc aag gcg ctg aac ggc gca agc ggt ctg gat gtt      576
Pro Leu Lys Met Gly Lys Ala Leu Asn Gly Ala Ser Gly Leu Asp Val
            180                 185                 190

gac aaa gag aaa aag ctg gtc gaa gag ggt ctg aac gaa ctg aat gag      624
Asp Lys Glu Lys Lys Leu Val Glu Glu Gly Leu Asn Glu Leu Asn Glu
        195                 200                 205

ctg cag gca acc gaa gag acc att tcc ctg acc atg aaa gaa ctg ggc      672
Leu Gln Ala Thr Glu Glu Thr Ile Ser Leu Thr Met Lys Glu Leu Gly
    210                 215                 220

atg aag cgc gcc ctg atg tac ggt tgg ccg aac acc tat gtc ttt acc      720
Met Lys Arg Ala Leu Met Tyr Gly Trp Pro Asn Thr Tyr Val Phe Thr
225                 230                 235                 240

aaa gct atg ggc gaa atg ctg ctg ggc cag ttc aag gag aat ctg cct      768
Lys Ala Met Gly Glu Met Leu Leu Gly Gln Phe Lys Glu Asn Leu Pro
                245                 250                 255

ctg gtg atc ctg cgc ccg acc atc att acc tca acc tac atg gaa cca      816
Leu Val Ile Leu Arg Pro Thr Ile Ile Thr Ser Thr Tyr Met Glu Pro
            260                 265                 270

ttt tcg ggc tgg atc gag ggt att cgt acc atc gat aac gtg ctg gcc      864
Phe Ser Gly Trp Ile Glu Gly Ile Arg Thr Ile Asp Asn Val Leu Ala
        275                 280                 285

ggc tat tgc aaa ggc aag ctg acc tgt ctg ctg gcg gac cca gaa tgc      912
Gly Tyr Cys Lys Gly Lys Leu Thr Cys Leu Leu Ala Asp Pro Glu Cys
    290                 295                 300

att ctg gat gca atc cct ggc gac atg gtg gtt aac tgt atg atc gtg      960
Ile Leu Asp Ala Ile Pro Gly Asp Met Val Val Asn Cys Met Ile Val
305                 310                 315                 320

gct atg gtt gcc cat gct aat cag ccg tgc gaa atc att tac caa gtt     1008
Ala Met Val Ala His Ala Asn Gln Pro Cys Glu Ile Ile Tyr Gln Val
                325                 330                 335

ggt tcc agc ctg aaa aat cca ctg aag ctg ctg gat ctg cac gac ttc     1056
Gly Ser Ser Leu Lys Asn Pro Leu Lys Leu Leu Asp Leu His Asp Phe
            340                 345                 350

ttt ttc aag tac ttc cat gaa aac cct tgg att aat aaa gat ggc aag     1104
Phe Phe Lys Tyr Phe His Glu Asn Pro Trp Ile Asn Lys Asp Gly Lys
        355                 360                 365

gcg gtt aaa gtc agc aag ctg atc ctg ttc tct acc acc ttt gtg ttc     1152
Ala Val Lys Val Ser Lys Leu Ile Leu Phe Ser Thr Thr Phe Val Phe
    370                 375                 380

cac ggt tac ctg gca gtt cgc tat atg ctg ccg ctg aaa gtt ctg cag     1200
His Gly Tyr Leu Ala Val Arg Tyr Met Leu Pro Leu Lys Val Leu Gln
385                 390                 395                 400

ttt ctg aac ttc ctg ctg tgt caa att ctg tgc ggc atg tgt acc gat     1248
Phe Leu Asn Phe Leu Leu Cys Gln Ile Leu Cys Gly Met Cys Thr Asp
                405                 410                 415

cat aat cgt aaa atc aag atg ctg atg tac ctg gtc gaa ctg tac aaa     1296
His Asn Arg Lys Ile Lys Met Leu Met Tyr Leu Val Glu Leu Tyr Lys
            420                 425                 430

cca tac ctg ttc ttc aag ggc att ttc gat gac ctg aac acc gac aaa     1344
Pro Tyr Leu Phe Phe Lys Gly Ile Phe Asp Asp Leu Asn Thr Asp Lys
        435                 440                 445

ctg cgt ctg gcg gca acc gag tct tca tcg aaa gct gac ctg ttc tac     1392
Leu Arg Leu Ala Ala Thr Glu Ser Ser Ser Lys Ala Asp Leu Phe Tyr
    450                 455                 460

ttc gac cct aag tgc atc gat tgg gaa gac tac ttt atc aac atc cac     1440
Phe Asp Pro Lys Cys Ile Asp Trp Glu Asp Tyr Phe Ile Asn Ile His
465                 470                 475                 480

att cct ggc gtt ctg aaa tac gtc ctg aag                             1470
Ile Pro Gly Val Leu Lys Tyr Val Leu Lys
                485                 490
```

<210> SEQ ID NO 62
<211> LENGTH: 490
<212> TYPE: PRT
<213> ORGANISM: Vitis vinifera (wine grape)

<400> SEQUENCE: 62

```
Met Glu Leu Gly Ser Ile Val Glu Phe Leu Glu Asn Lys Ser Ile Leu
1               5                   10                  15

Val Thr Gly Ala Thr Gly Phe Leu Ala Lys Ile Phe Val Glu Lys Ile
            20                  25                  30

Leu Arg Ile Gln Pro Asn Val Lys Lys Leu Phe Leu Leu Leu Arg Ala
        35                  40                  45

Ala Asp Thr Lys Ser Ala Thr Gln Arg Leu His Asn Glu Val Leu Gly
    50                  55                  60

Lys Glu Leu Phe Arg Val Leu Lys Asp Lys Trp Gly Ser Asn Leu Asn
65                  70                  75                  80

Ser Phe Ile Ser Glu Lys Val Thr Pro Ile Pro Gly Asp Ile Ser Cys
                85                  90                  95

Glu Asn Leu Gly Val Thr Asn Leu Asn Leu Arg Glu Glu Ile Trp Arg
            100                 105                 110

Glu Val Asp Val Ile Leu Asn Leu Ala Ala Thr Thr Lys Phe Asp Glu
        115                 120                 125

Arg Tyr Asp Val Ala Leu Gly Ile Asn Thr Leu Gly Ala Ser His Val
    130                 135                 140

Leu Asn Phe Ser Lys Lys Cys Val Lys Leu Lys Met Leu Leu His Val
145                 150                 155                 160

Ser Thr Ala Tyr Val Ser Gly Glu Arg Glu Gly Leu Ile Leu Glu Ser
                165                 170                 175

Pro Leu Lys Met Gly Lys Ala Leu Asn Gly Ala Ser Gly Leu Asp Val
            180                 185                 190

Asp Lys Glu Lys Lys Leu Val Glu Glu Gly Leu Asn Glu Leu Asn Glu
        195                 200                 205

Leu Gln Ala Thr Glu Glu Thr Ile Ser Leu Thr Met Lys Glu Leu Gly
    210                 215                 220

Met Lys Arg Ala Leu Met Tyr Gly Trp Pro Asn Thr Tyr Val Phe Thr
225                 230                 235                 240

Lys Ala Met Gly Glu Met Leu Leu Gly Gln Phe Lys Glu Asn Leu Pro
                245                 250                 255

Leu Val Ile Leu Arg Pro Thr Ile Ile Thr Ser Thr Tyr Met Glu Pro
            260                 265                 270

Phe Ser Gly Trp Ile Glu Gly Ile Arg Thr Ile Asp Asn Val Leu Ala
        275                 280                 285

Gly Tyr Cys Lys Gly Lys Leu Thr Cys Leu Leu Ala Asp Pro Glu Cys
    290                 295                 300

Ile Leu Asp Ala Ile Pro Gly Asp Met Val Val Asn Cys Met Ile Val
305                 310                 315                 320

Ala Met Val Ala His Ala Asn Gln Pro Cys Glu Ile Ile Tyr Gln Val
                325                 330                 335

Gly Ser Ser Leu Lys Asn Pro Leu Lys Leu Leu Asp Leu His Asp Phe
            340                 345                 350

Phe Phe Lys Tyr Phe His Glu Asn Pro Trp Ile Asn Lys Asp Gly Lys
        355                 360                 365

Ala Val Lys Val Ser Lys Leu Ile Leu Phe Ser Thr Thr Phe Val Phe
```

```
    370                 375                 380

His Gly Tyr Leu Ala Val Arg Tyr Met Leu Pro Leu Lys Val Leu Gln
385                 390                 395                 400

Phe Leu Asn Phe Leu Leu Cys Gln Ile Leu Cys Gly Met Cys Thr Asp
                405                 410                 415

His Asn Arg Lys Ile Lys Met Leu Met Tyr Leu Val Glu Leu Tyr Lys
            420                 425                 430

Pro Tyr Leu Phe Phe Lys Gly Ile Phe Asp Asp Leu Asn Thr Asp Lys
        435                 440                 445

Leu Arg Leu Ala Ala Thr Glu Ser Ser Ser Lys Ala Asp Leu Phe Tyr
    450                 455                 460

Phe Asp Pro Lys Cys Ile Asp Trp Glu Asp Tyr Phe Ile Asn Ile His
465                 470                 475                 480

Ile Pro Gly Val Leu Lys Tyr Val Leu Lys
                485                 490


<210> SEQ ID NO 63
<211> LENGTH: 1545
<212> TYPE: DNA
<213> ORGANISM: Mus musculus
<220> FEATURE:
<221> NAME/KEY: CDS
<222> LOCATION: (1)..(1545)

<400> SEQUENCE: 63

atg gtt agc atc cct gag tac tac gaa ggc aaa aac atc ctg ctg acc       48
Met Val Ser Ile Pro Glu Tyr Tyr Glu Gly Lys Asn Ile Leu Leu Thr
1               5                   10                  15

ggc gcg acc ggc ttt ctg ggc aaa gtt ctg ctg gaa aaa ctg ctg cgc       96
Gly Ala Thr Gly Phe Leu Gly Lys Val Leu Leu Glu Lys Leu Leu Arg
            20                  25                  30

agc tgc ccg cgt gtg aac tct gtt tac gtc ctg gtg cgt cag aaa gct      144
Ser Cys Pro Arg Val Asn Ser Val Tyr Val Leu Val Arg Gln Lys Ala
        35                  40                  45

ggc cag acc cca caa gaa cgc gtt gaa gag att ctg tcc agc aag ctg      192
Gly Gln Thr Pro Gln Glu Arg Val Glu Glu Ile Leu Ser Ser Lys Leu
    50                  55                  60

ttt gat cgc ctg cgt gac gaa aac cca gat ttc cgc gag aaa atc att      240
Phe Asp Arg Leu Arg Asp Glu Asn Pro Asp Phe Arg Glu Lys Ile Ile
65                  70                  75                  80

gct atc aat tcc gaa ctg acc caa cct aaa ctg gcg ctg agc gaa gag      288
Ala Ile Asn Ser Glu Leu Thr Gln Pro Lys Leu Ala Leu Ser Glu Glu
                85                  90                  95

gac aag gag atc atc atc gat tct acc aac gtt atc ttc cac tgc gcg      336
Asp Lys Glu Ile Ile Ile Asp Ser Thr Asn Val Ile Phe His Cys Ala
            100                 105                 110

gca acc gtc cgt ttc aac gaa aat ctg cgc gac gca gtc cag ctg aat      384
Ala Thr Val Arg Phe Asn Glu Asn Leu Arg Asp Ala Val Gln Leu Asn
        115                 120                 125

gtg att gcc acc cgt caa ctg atc ctg ctg gcc cag caa atg aag aac      432
Val Ile Ala Thr Arg Gln Leu Ile Leu Leu Ala Gln Gln Met Lys Asn
    130                 135                 140

ctg gaa gtt ttt atg cac gtc tcc acc gca tac gcc tat tgt aat cgc      480
Leu Glu Val Phe Met His Val Ser Thr Ala Tyr Ala Tyr Cys Asn Arg
145                 150                 155                 160

aaa cat att gat gaa gtg gtt tac ccg cca cct gtt gac cca aaa aag      528
Lys His Ile Asp Glu Val Val Tyr Pro Pro Pro Val Asp Pro Lys Lys
                165                 170                 175

ctg atc gat tcc ctg gag tgg atg gat gac ggc ctg gtc aac gac att      576
```

-continued

```
Leu Ile Asp Ser Leu Glu Trp Met Asp Asp Gly Leu Val Asn Asp Ile
            180                 185                 190

acc cct aaa ctg atc ggt gat cgt ccg aat acc tac att tat acc aag      624
Thr Pro Lys Leu Ile Gly Asp Arg Pro Asn Thr Tyr Ile Tyr Thr Lys
        195                 200                 205

gct ctg gcg gaa tat gtc gtg cag caa gag ggc gca aaa ctg aac gtg      672
Ala Leu Ala Glu Tyr Val Val Gln Gln Glu Gly Ala Lys Leu Asn Val
    210                 215                 220

gcc att gtt cgc cct tcg atc gtg ggc gct tcc tgg aag gaa ccg ttc      720
Ala Ile Val Arg Pro Ser Ile Val Gly Ala Ser Trp Lys Glu Pro Phe
225                 230                 235                 240

cca ggt tgg atc gat aac ttt aat ggc ccg tct ggt ctg ttc att gcc      768
Pro Gly Trp Ile Asp Asn Phe Asn Gly Pro Ser Gly Leu Phe Ile Ala
                245                 250                 255

gct ggc aaa ggt atc ctg cgc acc atg cgt gcg tca aac aat gca ctg      816
Ala Gly Lys Gly Ile Leu Arg Thr Met Arg Ala Ser Asn Asn Ala Leu
            260                 265                 270

gcc gac ctg gtt ccg gtc gat gtt gtc gtg aac acc tca ctg gcg gca      864
Ala Asp Leu Val Pro Val Asp Val Val Val Asn Thr Ser Leu Ala Ala
        275                 280                 285

gcc tgg tac tcg ggt gtg aac cgc ccg cgt aat att atg gtt tat aac      912
Ala Trp Tyr Ser Gly Val Asn Arg Pro Arg Asn Ile Met Val Tyr Asn
    290                 295                 300

tgc acc acc ggc tcc acc aat cca ttt cac tgg ggt gaa gtg gag tac      960
Cys Thr Thr Gly Ser Thr Asn Pro Phe His Trp Gly Glu Val Glu Tyr
305                 310                 315                 320

cat gtt atc agc acc ttt aaa cgc aac cca ctg gaa cag gca ttc cgc     1008
His Val Ile Ser Thr Phe Lys Arg Asn Pro Leu Glu Gln Ala Phe Arg
                325                 330                 335

cgt cct aac gtc aat ctg acc tca aat cac ctg ctg tac cat tat tgg     1056
Arg Pro Asn Val Asn Leu Thr Ser Asn His Leu Leu Tyr His Tyr Trp
            340                 345                 350

att gcc gtg tcg cac aaa gct cct gcg ttc ctg tac gac atc tat ctg     1104
Ile Ala Val Ser His Lys Ala Pro Ala Phe Leu Tyr Asp Ile Tyr Leu
        355                 360                 365

cgt atg acc ggc cgc tcc ccg cgt atg atg aaa acc att acc cgc ctg     1152
Arg Met Thr Gly Arg Ser Pro Arg Met Met Lys Thr Ile Thr Arg Leu
    370                 375                 380

cat aag gca atg gtg ttc ctg gaa tat ttt acc tct aac tca tgg gtc     1200
His Lys Ala Met Val Phe Leu Glu Tyr Phe Thr Ser Asn Ser Trp Val
385                 390                 395                 400

tgg aat acc gat aac gtg aat atg ctg atg aac cag ctg aat cca gag     1248
Trp Asn Thr Asp Asn Val Asn Met Leu Met Asn Gln Leu Asn Pro Glu
                405                 410                 415

gac aaa aag acc ttt aac att gat gtc cgt caa ctg cac tgg gcc gaa     1296
Asp Lys Lys Thr Phe Asn Ile Asp Val Arg Gln Leu His Trp Ala Glu
            420                 425                 430

tac atc gag aac tat tgt atg ggc acc aaa aag tac gtt ctg aat gaa     1344
Tyr Ile Glu Asn Tyr Cys Met Gly Thr Lys Lys Tyr Val Leu Asn Glu
        435                 440                 445

gag atg agc ggt ctg ccg gct gcg cgc aaa cat ctg aac aag ctg cgc     1392
Glu Met Ser Gly Leu Pro Ala Ala Arg Lys His Leu Asn Lys Leu Arg
    450                 455                 460

aat att cgt tat ggt ttt aac acc atc ctg gtg att ctg atc tgg cgc     1440
Asn Ile Arg Tyr Gly Phe Asn Thr Ile Leu Val Ile Leu Ile Trp Arg
465                 470                 475                 480

att ttc atc gct cgt tct cag atg gcg cgc aat atc tgg tat ttc gtc     1488
Ile Phe Ile Ala Arg Ser Gln Met Ala Arg Asn Ile Trp Tyr Phe Val
                485                 490                 495
```

```
gtc tct ctg tgc tat aaa ttc ctg tcg tac ttt cgt gct tcg tcc acc      1536
Val Ser Leu Cys Tyr Lys Phe Leu Ser Tyr Phe Arg Ala Ser Ser Thr
            500                 505                 510

atg cgc tac                                                          1545
Met Arg Tyr
        515


<210> SEQ ID NO 64
<211> LENGTH: 515
<212> TYPE: PRT
<213> ORGANISM: Mus musculus

<400> SEQUENCE: 64

Met Val Ser Ile Pro Glu Tyr Tyr Glu Gly Lys Asn Ile Leu Leu Thr
1               5                   10                  15

Gly Ala Thr Gly Phe Leu Gly Lys Val Leu Leu Glu Lys Leu Leu Arg
            20                  25                  30

Ser Cys Pro Arg Val Asn Ser Val Tyr Val Leu Val Arg Gln Lys Ala
        35                  40                  45

Gly Gln Thr Pro Gln Glu Arg Val Glu Glu Ile Leu Ser Ser Lys Leu
    50                  55                  60

Phe Asp Arg Leu Arg Asp Glu Asn Pro Asp Phe Arg Glu Lys Ile Ile
65                  70                  75                  80

Ala Ile Asn Ser Glu Leu Thr Gln Pro Lys Leu Ala Leu Ser Glu Glu
                85                  90                  95

Asp Lys Glu Ile Ile Ile Asp Ser Thr Asn Val Ile Phe His Cys Ala
            100                 105                 110

Ala Thr Val Arg Phe Asn Glu Asn Leu Arg Asp Ala Val Gln Leu Asn
        115                 120                 125

Val Ile Ala Thr Arg Gln Leu Ile Leu Leu Ala Gln Gln Met Lys Asn
    130                 135                 140

Leu Glu Val Phe Met His Val Ser Thr Ala Tyr Ala Tyr Cys Asn Arg
145                 150                 155                 160

Lys His Ile Asp Glu Val Val Tyr Pro Pro Pro Val Asp Pro Lys Lys
                165                 170                 175

Leu Ile Asp Ser Leu Glu Trp Met Asp Asp Gly Leu Val Asn Asp Ile
            180                 185                 190

Thr Pro Lys Leu Ile Gly Asp Arg Pro Asn Thr Tyr Ile Tyr Thr Lys
        195                 200                 205

Ala Leu Ala Glu Tyr Val Val Gln Gln Glu Gly Ala Lys Leu Asn Val
    210                 215                 220

Ala Ile Val Arg Pro Ser Ile Val Gly Ala Ser Trp Lys Glu Pro Phe
225                 230                 235                 240

Pro Gly Trp Ile Asp Asn Phe Asn Gly Pro Ser Gly Leu Phe Ile Ala
                245                 250                 255

Ala Gly Lys Gly Ile Leu Arg Thr Met Arg Ala Ser Asn Asn Ala Leu
            260                 265                 270

Ala Asp Leu Val Pro Val Asp Val Val Val Asn Thr Ser Leu Ala Ala
        275                 280                 285

Ala Trp Tyr Ser Gly Val Asn Arg Pro Arg Asn Ile Met Val Tyr Asn
    290                 295                 300

Cys Thr Thr Gly Ser Thr Asn Pro Phe His Trp Gly Glu Val Glu Tyr
305                 310                 315                 320

His Val Ile Ser Thr Phe Lys Arg Asn Pro Leu Glu Gln Ala Phe Arg
                325                 330                 335
```

```
Arg Pro Asn Val Asn Leu Thr Ser Asn His Leu Leu Tyr His Tyr Trp
            340                 345                 350

Ile Ala Val Ser His Lys Ala Pro Ala Phe Leu Tyr Asp Ile Tyr Leu
        355                 360                 365

Arg Met Thr Gly Arg Ser Pro Arg Met Met Lys Thr Ile Thr Arg Leu
    370                 375                 380

His Lys Ala Met Val Phe Leu Glu Tyr Phe Thr Ser Asn Ser Trp Val
385                 390                 395                 400

Trp Asn Thr Asp Asn Val Asn Met Leu Met Asn Gln Leu Asn Pro Glu
                405                 410                 415

Asp Lys Lys Thr Phe Asn Ile Asp Val Arg Gln Leu His Trp Ala Glu
            420                 425                 430

Tyr Ile Glu Asn Tyr Cys Met Gly Thr Lys Lys Tyr Val Leu Asn Glu
        435                 440                 445

Glu Met Ser Gly Leu Pro Ala Ala Arg Lys His Leu Asn Lys Leu Arg
    450                 455                 460

Asn Ile Arg Tyr Gly Phe Asn Thr Ile Leu Val Ile Leu Ile Trp Arg
465                 470                 475                 480

Ile Phe Ile Ala Arg Ser Gln Met Ala Arg Asn Ile Trp Tyr Phe Val
                485                 490                 495

Val Ser Leu Cys Tyr Lys Phe Leu Ser Tyr Phe Arg Ala Ser Ser Thr
            500                 505                 510

Met Arg Tyr
        515


<210> SEQ ID NO 65
<211> LENGTH: 1545
<212> TYPE: DNA
<213> ORGANISM: Mus musculus
<220> FEATURE:
<221> NAME/KEY: CDS
<222> LOCATION: (1)..(1545)

<400> SEQUENCE: 65

atg tca atg atc gcg gct ttc tac tcg aac aag tct att ctg att acc       48
Met Ser Met Ile Ala Ala Phe Tyr Ser Asn Lys Ser Ile Leu Ile Thr
1               5                   10                  15

ggc gca acc ggc ttc ctg ggc aag gtg ctg atg gaa aaa ctg ttc cgc       96
Gly Ala Thr Gly Phe Leu Gly Lys Val Leu Met Glu Lys Leu Phe Arg
            20                  25                  30

acc tca ccg cac ctg aaa gtc atc tac att ctg gtg cgt cca aag tcg      144
Thr Ser Pro His Leu Lys Val Ile Tyr Ile Leu Val Arg Pro Lys Ser
        35                  40                  45

ggc cag acc ctg caa gaa cgc gtc ttc cag atc ctg aac tcc aag ctg      192
Gly Gln Thr Leu Gln Glu Arg Val Phe Gln Ile Leu Asn Ser Lys Leu
    50                  55                  60

ttc gaa aag gtt aaa gaa gtg tgc ccg aat gtg cat gag aag atc cgt      240
Phe Glu Lys Val Lys Glu Val Cys Pro Asn Val His Glu Lys Ile Arg
65                  70                  75                  80

cca att tcc gcg gat ctg aac cag cgc gac ttt gca att tcc aaa gaa      288
Pro Ile Ser Ala Asp Leu Asn Gln Arg Asp Phe Ala Ile Ser Lys Glu
                85                  90                  95

gat gtg caa gag ctg ctg agc tgc acc aat atc att ttc cac tgt gcg      336
Asp Val Gln Glu Leu Leu Ser Cys Thr Asn Ile Ile Phe His Cys Ala
            100                 105                 110

gca acc gtt cgt ttt gac gcg cat ctg cgc gaa gca gtt cag ctg aac      384
Ala Thr Val Arg Phe Asp Ala His Leu Arg Glu Ala Val Gln Leu Asn
        115                 120                 125
```

-continued

```
gtc acc gcc acc cag caa ctg ctg ctg atg gct agc caa atg ccg aaa      432
Val Thr Ala Thr Gln Gln Leu Leu Leu Met Ala Ser Gln Met Pro Lys
    130                 135                 140

ctg gaa gcc ttc atc cac att tcg acc gct ttt tcc aac tgc aat ctg      480
Leu Glu Ala Phe Ile His Ile Ser Thr Ala Phe Ser Asn Cys Asn Leu
145                 150                 155                 160

tct cat atc gat gaa gtg att tat ccg tgt cca gtt gag ccg cgt aag      528
Ser His Ile Asp Glu Val Ile Tyr Pro Cys Pro Val Glu Pro Arg Lys
                165                 170                 175

atc att gac tca atg gaa tgg ctg gat gac tcg atc att gaa gag atc      576
Ile Ile Asp Ser Met Glu Trp Leu Asp Asp Ser Ile Ile Glu Glu Ile
            180                 185                 190

acc cca aaa ctg att ggt gat cgc cct aac acc tac acc tat acc aag      624
Thr Pro Lys Leu Ile Gly Asp Arg Pro Asn Thr Tyr Thr Tyr Thr Lys
        195                 200                 205

gcc ctg ggc gaa atc gtg gtt cag caa gag tct ggt aac ctg aat gtg      672
Ala Leu Gly Glu Ile Val Val Gln Gln Glu Ser Gly Asn Leu Asn Val
    210                 215                 220

gcg atc gtt cgc ccg tca att gtt ggc gca acc tgg cag gaa cct ttc      720
Ala Ile Val Arg Pro Ser Ile Val Gly Ala Thr Trp Gln Glu Pro Phe
225                 230                 235                 240

ccg ggt tgg gtc gat aac ctg aat ggc cca agc ggt ctg atc att gcc      768
Pro Gly Trp Val Asp Asn Leu Asn Gly Pro Ser Gly Leu Ile Ile Ala
                245                 250                 255

acc ggc aaa ggt ttt ctg cgt tct atc aag gct acc cct atg gcc gtc      816
Thr Gly Lys Gly Phe Leu Arg Ser Ile Lys Ala Thr Pro Met Ala Val
            260                 265                 270

gct gat gtg atc ccg gtt gac acc gtc gtg aat ctg acc att gct gtc      864
Ala Asp Val Ile Pro Val Asp Thr Val Val Asn Leu Thr Ile Ala Val
        275                 280                 285

ggt tgg tac acc gct gtg cac cgt cct aaa tca acc ctg att tat cat      912
Gly Trp Tyr Thr Ala Val His Arg Pro Lys Ser Thr Leu Ile Tyr His
    290                 295                 300

tcc acc agc ggc aac ctg aat ccg tgt aac tgg tac aaa atg ggt ctg      960
Ser Thr Ser Gly Asn Leu Asn Pro Cys Asn Trp Tyr Lys Met Gly Leu
305                 310                 315                 320

cag gtt ctg gcg acc atc gaa aag att cca ttc gag tcc gcg ttt cgc     1008
Gln Val Leu Ala Thr Ile Glu Lys Ile Pro Phe Glu Ser Ala Phe Arg
                325                 330                 335

cgt cct aac gca gat ttc acc acc tcg aat ttt acc acc cac tat tgg     1056
Arg Pro Asn Ala Asp Phe Thr Thr Ser Asn Phe Thr Thr His Tyr Trp
            340                 345                 350

aac acc gtg tcc cat cgt gtt cca gca atc att tac gac ttc tat ctg     1104
Asn Thr Val Ser His Arg Val Pro Ala Ile Ile Tyr Asp Phe Tyr Leu
        355                 360                 365

cgc ctg acc ggt cgc aaa cct cgt atg ctg aag ctg atg aat cgt ctg     1152
Arg Leu Thr Gly Arg Lys Pro Arg Met Leu Lys Leu Met Asn Arg Leu
    370                 375                 380

ctg aaa acc atc agc atg ctg gaa tac ttt att aac cac agc tgg gaa     1200
Leu Lys Thr Ile Ser Met Leu Glu Tyr Phe Ile Asn His Ser Trp Glu
385                 390                 395                 400

tgg tct acc aac aat acc gag atg ctg ctg tct gaa ctg tca ccg gag     1248
Trp Ser Thr Asn Asn Thr Glu Met Leu Leu Ser Glu Leu Ser Pro Glu
                405                 410                 415

gat cag cgt gtt ttc aat ttt gac gtc cgc caa ctg aac tgg ctg gaa     1296
Asp Gln Arg Val Phe Asn Phe Asp Val Arg Gln Leu Asn Trp Leu Glu
            420                 425                 430

tac atc gag aat tat gtc ctg ggc gtg aaa aag tac ctg ctg aaa gaa     1344
Tyr Ile Glu Asn Tyr Val Leu Gly Val Lys Lys Tyr Leu Leu Lys Glu
        435                 440                 445
```

```
gat ctg gcc ggt atc cca aaa gct aag cag cac ctg cgc cgt ctg cgc      1392
Asp Leu Ala Gly Ile Pro Lys Ala Lys Gln His Leu Arg Arg Leu Arg
    450                 455                 460

aac att cat tac ctg ttc aat acc gcg ctg ttt ctg atc att tgg cgc      1440
Asn Ile His Tyr Leu Phe Asn Thr Ala Leu Phe Leu Ile Ile Trp Arg
465                 470                 475                 480

ctg ctg att gcg cgt tct caa atg gca cgc aac gtg tgg ttc ttt atc      1488
Leu Leu Ile Ala Arg Ser Gln Met Ala Arg Asn Val Trp Phe Phe Ile
                485                 490                 495

gtg agc ttc tgt tac aag ttc atc tcc tat ttt cgt gca tca tcc acc      1536
Val Ser Phe Cys Tyr Lys Phe Ile Ser Tyr Phe Arg Ala Ser Ser Thr
            500                 505                 510

ctg aaa gtg                                                          1545
Leu Lys Val
        515


<210> SEQ ID NO 66
<211> LENGTH: 515
<212> TYPE: PRT
<213> ORGANISM: Mus musculus

<400> SEQUENCE: 66

Met Ser Met Ile Ala Ala Phe Tyr Ser Asn Lys Ser Ile Leu Ile Thr
1               5                   10                  15

Gly Ala Thr Gly Phe Leu Gly Lys Val Leu Met Glu Lys Leu Phe Arg
            20                  25                  30

Thr Ser Pro His Leu Lys Val Ile Tyr Ile Leu Val Arg Pro Lys Ser
        35                  40                  45

Gly Gln Thr Leu Gln Glu Arg Val Phe Gln Ile Leu Asn Ser Lys Leu
    50                  55                  60

Phe Glu Lys Val Lys Glu Val Cys Pro Asn Val His Glu Lys Ile Arg
65                  70                  75                  80

Pro Ile Ser Ala Asp Leu Asn Gln Arg Asp Phe Ala Ile Ser Lys Glu
                85                  90                  95

Asp Val Gln Glu Leu Leu Ser Cys Thr Asn Ile Ile Phe His Cys Ala
            100                 105                 110

Ala Thr Val Arg Phe Asp Ala His Leu Arg Glu Ala Val Gln Leu Asn
        115                 120                 125

Val Thr Ala Thr Gln Gln Leu Leu Leu Met Ala Ser Gln Met Pro Lys
    130                 135                 140

Leu Glu Ala Phe Ile His Ile Ser Thr Ala Phe Ser Asn Cys Asn Leu
145                 150                 155                 160

Ser His Ile Asp Glu Val Ile Tyr Pro Cys Pro Val Glu Pro Arg Lys
                165                 170                 175

Ile Ile Asp Ser Met Glu Trp Leu Asp Asp Ser Ile Ile Glu Glu Ile
            180                 185                 190

Thr Pro Lys Leu Ile Gly Asp Arg Pro Asn Thr Tyr Thr Tyr Thr Lys
        195                 200                 205

Ala Leu Gly Glu Ile Val Val Gln Gln Glu Ser Gly Asn Leu Asn Val
    210                 215                 220

Ala Ile Val Arg Pro Ser Ile Val Gly Ala Thr Trp Gln Glu Pro Phe
225                 230                 235                 240

Pro Gly Trp Val Asp Asn Leu Asn Gly Pro Ser Gly Leu Ile Ile Ala
                245                 250                 255

Thr Gly Lys Gly Phe Leu Arg Ser Ile Lys Ala Thr Pro Met Ala Val
            260                 265                 270
```

-continued

Ala Asp Val Ile Pro Val Asp Thr Val Val Asn Leu Thr Ile Ala Val
275 280 285

Gly Trp Tyr Thr Ala Val His Arg Pro Lys Ser Thr Leu Ile Tyr His
290 295 300

Ser Thr Ser Gly Asn Leu Asn Pro Cys Asn Trp Tyr Lys Met Gly Leu
305 310 315 320

Gln Val Leu Ala Thr Ile Glu Lys Ile Pro Phe Glu Ser Ala Phe Arg
325 330 335

Arg Pro Asn Ala Asp Phe Thr Thr Ser Asn Phe Thr Thr His Tyr Trp
340 345 350

Asn Thr Val Ser His Arg Val Pro Ala Ile Ile Tyr Asp Phe Tyr Leu
355 360 365

Arg Leu Thr Gly Arg Lys Pro Arg Met Leu Lys Leu Met Asn Arg Leu
370 375 380

Leu Lys Thr Ile Ser Met Leu Glu Tyr Phe Ile Asn His Ser Trp Glu
385 390 395 400

Trp Ser Thr Asn Asn Thr Glu Met Leu Leu Ser Glu Leu Ser Pro Glu
405 410 415

Asp Gln Arg Val Phe Asn Phe Asp Val Arg Gln Leu Asn Trp Leu Glu
420 425 430

Tyr Ile Glu Asn Tyr Val Leu Gly Val Lys Lys Tyr Leu Leu Lys Glu
435 440 445

Asp Leu Ala Gly Ile Pro Lys Ala Lys Gln His Leu Arg Arg Leu Arg
450 455 460

Asn Ile His Tyr Leu Phe Asn Thr Ala Leu Phe Leu Ile Ile Trp Arg
465 470 475 480

Leu Leu Ile Ala Arg Ser Gln Met Ala Arg Asn Val Trp Phe Phe Ile
485 490 495

Val Ser Phe Cys Tyr Lys Phe Ile Ser Tyr Phe Arg Ala Ser Ser Thr
500 505 510

Leu Lys Val
515

<210> SEQ ID NO 67
<211> LENGTH: 699
<212> TYPE: DNA
<213> ORGANISM: Nostoc punctiform
<220> FEATURE:
<221> NAME/KEY: CDS
<222> LOCATION: (1)..(699)

<400> SEQUENCE: 67 atg cag cag ctt aca gac caa tct aaa gaa tta gat ttc aag agc gaa 48
Met Gln Gln Leu Thr Asp Gln Ser Lys Glu Leu Asp Phe Lys Ser Glu
1 5 10 15 aca tac aaa gat gct tat agc cgg att aat gcg atc gtg att gaa ggg 96
Thr Tyr Lys Asp Ala Tyr Ser Arg Ile Asn Ala Ile Val Ile Glu Gly
20 25 30 gaa caa gaa gcc cat gaa aat tac atc aca cta gcc caa ctg ctg cca 144
Glu Gln Glu Ala His Glu Asn Tyr Ile Thr Leu Ala Gln Leu Leu Pro
35 40 45 gaa tct cat gat gaa ttg att cgc cta tcc aag atg gaa agc cgc cat 192
Glu Ser His Asp Glu Leu Ile Arg Leu Ser Lys Met Glu Ser Arg His
50 55 60 aag aaa gga ttt gaa gct tgt ggg cgc aat tta gct gtt acc cca gat 240
Lys Lys Gly Phe Glu Ala Cys Gly Arg Asn Leu Ala Val Thr Pro Asp
65 70 75 80

```
ttg caa ttt gcc aaa gag ttt ttc tcc ggc cta cac caa aat ttt caa      288
Leu Gln Phe Ala Lys Glu Phe Phe Ser Gly Leu His Gln Asn Phe Gln
                85                  90                  95

aca gct gcc gca gaa ggg aaa gtg gtt act tgt ctg ttg att cag tct      336
Thr Ala Ala Ala Glu Gly Lys Val Val Thr Cys Leu Leu Ile Gln Ser
            100                 105                 110

tta att att gaa tgt ttt gcg atc gca gca tat aac att tac atc ccc      384
Leu Ile Ile Glu Cys Phe Ala Ile Ala Ala Tyr Asn Ile Tyr Ile Pro
        115                 120                 125

gtt gcc gac gat ttc gcc cgt aaa att act gaa gga gta gtt aaa gaa      432
Val Ala Asp Asp Phe Ala Arg Lys Ile Thr Glu Gly Val Val Lys Glu
    130                 135                 140

gaa tac agc cac ctc aat ttt gga gaa gtt tgg ttg aaa gaa cac ttt      480
Glu Tyr Ser His Leu Asn Phe Gly Glu Val Trp Leu Lys Glu His Phe
145                 150                 155                 160

gca gaa tcc aaa gct gaa ctt gaa ctt gca aat cgc cag aac cta ccc      528
Ala Glu Ser Lys Ala Glu Leu Glu Leu Ala Asn Arg Gln Asn Leu Pro
                165                 170                 175

atc gtc tgg aaa atg ctc aac caa gta gaa ggt gat gcc cac aca atg      576
Ile Val Trp Lys Met Leu Asn Gln Val Glu Gly Asp Ala His Thr Met
            180                 185                 190

gca atg gaa aaa gat gct ttg gta gaa gac ttc atg att cag tat ggt      624
Ala Met Glu Lys Asp Ala Leu Val Glu Asp Phe Met Ile Gln Tyr Gly
        195                 200                 205

gaa gca ttg agt aac att ggt ttt tcg act cgc gat att atg cgc ttg      672
Glu Ala Leu Ser Asn Ile Gly Phe Ser Thr Arg Asp Ile Met Arg Leu
    210                 215                 220

tca gcc tac gga ctc ata ggt gct taa                                  699
Ser Ala Tyr Gly Leu Ile Gly Ala
225                 230
```

<210> SEQ ID NO 68
<211> LENGTH: 232
<212> TYPE: PRT
<213> ORGANISM: Nostoc punctiform

<400> SEQUENCE: 68

```
Met Gln Gln Leu Thr Asp Gln Ser Lys Glu Leu Asp Phe Lys Ser Glu
1               5                   10                  15

Thr Tyr Lys Asp Ala Tyr Ser Arg Ile Asn Ala Ile Val Ile Glu Gly
            20                  25                  30

Glu Gln Glu Ala His Glu Asn Tyr Ile Thr Leu Ala Gln Leu Leu Pro
        35                  40                  45

Glu Ser His Asp Glu Leu Ile Arg Leu Ser Lys Met Glu Ser Arg His
    50                  55                  60

Lys Lys Gly Phe Glu Ala Cys Gly Arg Asn Leu Ala Val Thr Pro Asp
65                  70                  75                  80

Leu Gln Phe Ala Lys Glu Phe Phe Ser Gly Leu His Gln Asn Phe Gln
                85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160
```

-continued

```
Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
    210                 215                 220

Ser Ala Tyr Gly Leu Ile Gly Ala
225                 230


<210> SEQ ID NO 69
<211> LENGTH: 133
<212> TYPE: DNA
<213> ORGANISM: Artificial Sequence
<220> FEATURE:
<223> OTHER INFORMATION: Synthetic DNA

<400> SEQUENCE: 69

taccatgggc atacatatgg ccatcataac ggttctggca aatattctga aatgagctgt      60

tgacaattaa tcatcggctc gtataatgtg tggaattgtg agcggataac aatttcacac     120

aaggagatat acg                                                        133
```